US007572806B2

(12) United States Patent
Arnold et al.

(10) Patent No.: US 7,572,806 B2
(45) Date of Patent: Aug. 11, 2009

(54) PPAR ACTIVE COMPOUNDS

(75) Inventors: James Arnold, West Chester, PA (US); Dean R. Artis, Kensington, CA (US); Clarence R. Hurt, San Ramon, CA (US); Prabha N. Ibrahim, Mountain View, CA (US); Heike Krupka, Hayward, CA (US); Jack Lin, Hercules, CA (US); Michael V. Milburn, Emerville, CA (US); Weiru Wang, Lafayette, CA (US); Chao Zhang, Moraga, CA (US)

(73) Assignee: Plexxikon, Inc., Berkeley, CA (US)

( * ) Notice: Subject to any disclaimer, the term of this patent is extended or adjusted under 35 U.S.C. 154(b) by 0 days.

(21) Appl. No.: 12/001,026

(22) Filed: Dec. 7, 2007

(65) Prior Publication Data
US 2008/0096913 A1 Apr. 24, 2008

Related U.S. Application Data

(60) Division of application No. 10/937,791, filed on Sep. 8, 2004, now Pat. No. 7,348,338, which is a continuation-in-part of application No. 10/893,134, filed on Jul. 16, 2004, now Pat. No. 7,202,266.

(60) Provisional application No. 60/488,523, filed on Jul. 17, 2003, provisional application No. 60/552,994, filed on Mar. 12, 2004.

(51) Int. Cl.
*A61K 31/44* (2006.01)
*A61K 31/4725* (2006.01)
*A61K 31/404* (2006.01)

(52) U.S. Cl. .................. 514/300; 514/310; 514/313; 514/339; 514/415

(58) Field of Classification Search .................. 514/300, 514/310, 313, 339, 415
See application file for complete search history.

(56) References Cited

U.S. PATENT DOCUMENTS

| 3,489,767 | A | 1/1970 | Yamamoto et al. |
| 3,511,841 | A | 5/1970 | Archer et al. |
| 5,075,313 | A | 12/1991 | Yu et al. |
| 6,329,389 | B1 | 12/2001 | Suzuki et al. |
| 6,395,768 | B1 | 5/2002 | Pappolla et al. |
| 6,635,655 | B1 | 10/2003 | Jayyosi et al. |
| 7,348,338 | B2 * | 3/2008 | Arnold et al. ............... 514/300 |
| 7,476,746 | B2 * | 1/2009 | Artis et al. .................. 548/469 |
| 2005/0004115 | A1 | 1/2005 | Sharma et al. |
| 2006/0111426 | A1 | 5/2006 | Bonnert et al. |
| 2007/0149603 | A1 | 6/2007 | Arnold et al. |
| 2008/0045581 | A1 | 2/2008 | Arnold et al. |

FOREIGN PATENT DOCUMENTS

| EP | 0620214 | 10/1994 |
| EP | 1285908 | 2/2003 |
| EP | 1219595 | 1/2006 |
| GB | 1128607 | 9/1968 |
| GB | 2407318 | 4/2005 |
| WO | WO 00/64876 | 11/2000 |
| WO | WO 01/38305 | 5/2001 |
| WO | WO 02/30863 | 4/2002 |
| WO | WO 2005/009958 | 2/2005 |
| WO | WO 2005/037763 | 4/2005 |
| WO | WO 2005/040112 | 5/2005 |
| WO | WO 2005/054176 | 6/2005 |

OTHER PUBLICATIONS

Seehra et al., Preparation of indole derivatives as phospholipase enzyme inhibitors for treatment of inflammatory conditions. CAPLUS, 2003:1275.
Guo et al., A new total synthesis of chuangxinmycin and the study of its stereoisomers. CAPLUS, 1988:454536.
Lala et al, Role of nitric oxide in tumor progression: Lessons from experimental tumors. Cancer and Metastasis Reviews, 17(1): 91-106, 1998.
Golub et al., Molecular classification of cancer: Class discovery and class prediction by gene expression monitoring. Science, 286: 531-537, 1999.
U.S. Appl. No. 11/289,781, filed Nov. 29, 2005, Lin et al.
U.S. Appl. No. 11/517,573, filed Sep. 6, 2006, Lin et al.
U.S. Appl. No. 11/679,738, filed Feb. 27, 2007, Artis et al.
U.S. Appl. No. 11/679,777, filed Feb. 27, 2007, Artis et al.
U.S. Appl. No. 11/679,792, filed Feb. 27, 2007, Arnold et al.
Cancer (online), retrieved from http://www.nim.nih.gov/medlineplus/cancer.html (retrieved Jul. 6, 2007).
Cancer (online), retrieved from http://en.wikipedia.org/wiki/Cancer (retrieved Jul. 6, 2007).
Eczema (online), retrieved from http://www.nim.nih.gov/medlineplus/eczema.html (retrieved Dec. 19, 2007).
Colitis (online), retrieved from http://www.nim.nih.gov/medlineplus.colitis.html (retrieved Dec. 19, 2007).
Diabetes Mellitus (online), retrieved from http://www.merck.com/mmpe/print/sec12/ch128b.html (retrieved Apr. 17, 2007).
FDA Clinical Trials [online], [retrieved on Mar. 13, 2008]. Retrieved from the Internet, URL: http://www.fda.gov/oashi/clinicaltrials/default.htm.
Ulcerative Colitis [online], [retrieved on Mar. 13, 2008]. Retrieved from the Internet, URL: http://www.nlm. nih.gov/medlineplus/ulcerativecolitis.html.
Colitis [online], [retrieved on Mar. 13, 2008]. Retrieved from the Internet, URL: http://www.nlm. nih.gov/medlineplus/ency/article/000259.htm.

(Continued)

*Primary Examiner*—Golam M. M. Shameem
*Assistant Examiner*—Susannah Chung
(74) *Attorney, Agent, or Firm*—Foley & Lardner LLP

(57) ABSTRACT

Compounds are described that are active on PPARs, including pan-active compounds. Also described are methods for developing or identifying compounds having a desired selectivity profile.

5 Claims, No Drawings

OTHER PUBLICATIONS

Collagenous Colitis [online], [retrieved on Mar. 13, 2008]. Retrieved from the Internet, URL: http://digestive. niddk.nih.gov/ddiseases/pubs/collagenouscolitis/index.htm.

Basanagoudar and Siddappa, Synthesis of indole-3-propionic acids and 3-(3-aminopropyl) indoles., Journal of the Karnatak University, 17:33-42, 1972. Abstract, XP-002483945.

Collot et al., Heck cross-coupling reaction of 3-iodoindazoles with methyl acrylate: a mild and flexible strategy to design 2-azatryptamines. Tetrahedron Letters, 41(22): 4363-4366, 2000. Abstract, XP-002483946.

Ketcha et al., Synthesis of alkyl-substituted N-protected indoles via acylation and reductive deoxygenation, J.Org.Chem., 54:4350-4356, 1989.

Kuwano et al., Highly enantioselective synthesis of chiral 3-substitued indulines by catalytic asymmetric hydrogenation of indoles. Organic Letters, 6(13): 2213-2215, 2004. XP-002483944.

Trost and Quayle, 2-Alkoxybenzo-1,3-dithiole 1,1,3,3-Tetraoxide, a carbonyl 1,1-Dipole Synthon. J.Am.Chem.Soc., 106:2469-2471, 1984.

Yato et al., Reduction of carboxylic esters to ethers with triethyl silane in the combined use of titanium tetrachloride and trimethylsilyl trifluoromethanesulfonate. Tetrahedron, 57:5353-5359, 2001.

Partial European Search Report for EPO Patent Application No. EP 04 77 8641.

Patent Opposition for Costa Rica Patent Application No. 9869.

Silverman et al., "Drug Discovery, Design and Development." Chapter 2 in *The Organic Chemistry of Drug Design and Drug Action*, San Diego: Academic Press, 1992, p. 4-51.

Partial European Search Report for EPO Patent Application No. EP 04 77 8641, 2008.

Patent Opposition for Costa Rica Patent Application No. 9869, 2005.

* cited by examiner

PPAR ACTIVE COMPOUNDS

CROSS-REFERENCE TO RELATED PATENT APPLICATIONS

This application is a Divisional of U.S. application Ser. No. 10/937,791, filed Sep. 8, 2004, which is a CIP of U.S. application Ser. No. 10/893,134, filed Jul. 16, 2004, which claims the benefit of U.S. Provisional Application No. 60/488,523, filed Jul. 17, 2003, and U.S. Provisional Application No. 60/552,994, filed Mar. 12, 2004, all entitled PPAR Active Compounds, and all of which are incorporated herein by reference in their entireties.

BACKGROUND OF THE INVENTION

The present invention relates to the field of agonists for the family of nuclear receptors identified as peroxisome proliferator-activated receptors.

The following description is provided solely to assist the understanding of the reader. None of the references cited or information provided is admitted to be prior art to the present invention. Each of the references cited herein is incorporated by reference in its entirety, to the same extent as if each reference were individually indicated to be incorporated herein in its entirety.

The peroxisome proliferator-activated receptors (PPARs) form a subfamily in the nuclear receptor superfamily. Three isoforms, encoded by separate genes, have been identified thus far: PPARγ, PPARα, and PPARδ.

There are two PPARγ isoforms expressed at the protein level in mouse and human, γ1 and γ2. They differ only in that the latter has 30 additional amino acids at its N terminus due to differential promoter usage within the same gene, and subsequent alternative RNA processing. PPARγ2 is expressed primarily in adipose tissue, while PPARγ1 is expressed in a broad range of tissues.

Murine PPARα was the first member of this nuclear receptor subclass to be cloned; it has since been cloned from humans. PPARα is expressed in numerous metabolically active tissues, including liver, kidney, heart, skeletal muscle, and brown fat. It is also present in monocytes, vascular endothelium, and vascular smooth muscle cells. Activation of PPARα induces hepatic peroxisome proliferation, hepatomegaly, and hepatocarcinogenesis in rodents. These toxic effects are lost in humans, although the same compounds activate PPARα across species.

Human PPARδ was cloned in the early 1990s and subsequently cloned from rodents. PPARδ is expressed in a wide range of tissues and cells with the highest levels of expression found in digestive tract, heart, kidney, liver, adipose, and brain. Thus far, no PPARδ-specific gene targets have been identified.

The PPARs are ligand-dependent transcription factors that regulate target gene expression by binding to specific peroxisome proliferator response elements (PPREs) in enhancer sites of regulated genes. PPARs possess a modular structure composed of functional domains that include a DNA binding domain (DBD) and a ligand binding domain (LBD). The DBD specifically binds PPREs in the regulatory region of PPAR-responsive genes. The DBD, located in the C-terminal half of the receptor contains the ligand-dependent activation domain, AF-2. Each receptor binds to its PPRE as a heterodimer with a retinoid X receptor (RXR). Upon binding an agonist, the conformation of a PPAR is altered and stabilized such that a binding cleft, made up in part of the AF-2 domain, is created and recruitment of transcriptional coactivators occurs. Coactivators augment the ability of nuclear receptors to initiate the transcription process. The result of the agonist-induced PPAR-coactivator interaction at the PPRE is an increase in gene transcription. Downregulation of gene expression by PPARs appears to occur through indirect mechanisms. (Bergen & Wagner, 2002, *Diabetes Tech. & Ther.*, 4:163-174).

The first cloning of a PPAR(PPARα) occurred in the course of the search for the molecular target of rodent hepatic peroxisome proliferating agents. Since then, numerous fatty acids and their derivatives including a variety of eicosanoids and prostaglandins have been shown to serve as ligands of the PPARs. Thus, these receptors may play a central role in the sensing of nutrient levels and in the modulation of their metabolism. In addition, PPARs are the primary targets of selected classes of synthetic compounds that have been used in the successful treatment of diabetes and dyslipidemia. As such, an understanding of the molecular and physiological characteristics of these receptors has become extremely important to the development and utilization of drugs used to treat metabolic disorders. In addition, due to the great interest within the research community, a wide range of additional roles for the PPARs have been discovered; PPARα and PPARγ may play a role in a wide range of events involving the vasculature, including atherosclerotic plaque formation and stability, thrombosis, vascular tone, angio-genesis, and cancer.

Among the synthetic ligands identified for PPARs are Thiazolidinediones (TZDs). These compounds were originally developed on the basis of their insulin-sensitizing effects in animal pharmacology studies. Subsequently, it was found that TZDs induced adipocyte differentiation and increased expression of adipocyte genes, including the adipocyte fatty acid-binding protein aP2. Independently, it was discovered that PPARγ interacted with a regulatory element of the aP2 gene that controlled its adipocyte-specific expression. On the basis of these seminal observations, experiments were performed that determined that TZDs were PPARγ ligands and agonists and demonstrate a definite correlation between their in vitro PPARγ activities and their in vivo insulin-sensitizing actions. (Bergen & Wagner, 2002, *Diabetes Tech. & Ther.*, 4:163-174).

Several TZDs, including troglitazone, rosiglitazone, and pioglitazone, have insulin-sensitizing and anti-diabetic activity in humans with type 2 diabetes and impaired glucose tolerance. Farglitazar is a very potent non-TZD PPAR-γ-selective agonist that was recently shown to have antidiabetic as well as lipid-altering efficacy in humans. In addition to these potent PPARγ ligands, a subset of the non-steroidal antiinflammatory drugs (NSAIDs), including indomethacin, fenoprofen, and ibuprofen, have displayed weak PPARγ and PPARα activities. (Bergen & Wagner, 2002, *Diabetes Tech. & Ther.*, 4:163-174).

The fibrates, amphipathic carboxylic acids that have been proven useful in the treatment of hypertriglyceridemia, are PPARα ligands. The prototypical member of this compound class, clofibrate, was developed prior to the identification of PPARs, using in vivo assays in rodents to assess lipid-lowering efficacy. (Bergen & Wagner, 2002, *Diabetes Tech. & Ther.*, 4:163-174).

Fu et al., *Nature*, 2003, 425:9093, demonstrated that the PPARα binding compound, oleylethanolamide, produces satiety and reduces body weight gain in mice.

Clofibrate and fenofibrate have been shown to activate PPARα with a 10-fold selectivity over PPARγ. Bezafibrate acted as a pan-agonist that showed similar potency on all three PPAR isoforms. Wy-14643, the 2-arylthioacetic acid analogue of clofibrate, was a potent murine PPARα agonist as well as a weak PPARγ agonist. In humans, all of the fibrates must be used at high doses (200-1,200 mg/day) to achieve efficacious lipid-lowering activity.

TZDs and non-TZDs have also been identified that are dual PPARγ/α agonists. By virtue of the additional PPARα agonist activity, this class of compounds has potent lipid-altering efficacy in addition to antihyperglycemic activity in animal models of diabetes and lipid disorders. KRP-297 is an example of a TZD dual PPARγ/α agonist (Fajas, 1997, *J. Biol. Chem.*, 272:18779-18789) DRF-2725 and AZ-242 are non-TZD dual PPARγ/α agonists. (Lohray, et al., 2001, *J. Med. Chem.*, 44:2675-2678; Cronet, et al., 2001, Structure (Camb.) 9:699-706).

In order to define the physiological role of PPARδ, efforts have been made to develop novel compounds that activate this receptor in a selective manner. Amongst the α-substituted carboxylic acids previously described, the potent PPARδ ligand L-165041 demonstrated approximately 30-fold agonist selectivity for this receptor over PPARγ, it was inactive on murine PPARα (Liebowitz, et al., 2000, *FEBS Lett.*, 473:333-336). This compound was found to increase high-density lipoprotein levels in rodents. It was also reported that GW501516 was a potent, highly-selective PPARδ agonist that produced beneficial changes in serum lipid parameters in obese, insulin-resistant rhesus monkeys. (Oliver et al., 2001, *Proc. Natl. Acad. Sci.*, 98:5306-5311).

In addition to the compounds above, certain thiazole derivatives active on PPARs have been described. (Cadilla et al., Internat. Appl. PCT/US01/149320, Internat. Publ. W) 02/062774, incorporated herein by reference in its entirety.)

Some tricyclic-α-alkyloxyphenylpropionic acids were described as dual PPARα/γ agonists. Sauerberg et al., 2002, *J. Med. Chem.* 45:789-804.)

A group of compounds that were stated to have equal activity on PPARα/γ/δ was described in Morgensen et al., 2002, *Bioorg. & Med. Chem. Lett.* 13:257-260.

Oliver et al., described a selective PPARδ agonist that promotes reverse cholesterol transport. (Oliver et al., 2001, *PNAS* 98:5306-5311.)

Yamamoto et al., U.S. Pat. No. 3,489,767 describes "1-(phenylsulfonyl)-indolyl aliphatic acid derivatives" that are stated to have "antiphlogistic, analgesic and antipyretic actions." (Col. 1, lines 16-19.)

Kato et al., European patent application 94101551.3, Publication No. 0 610 793 A1, describes the use of 3-(5-methoxy-1-p-toluenesulfonylindol-3-yl)propionic acid (page 6) and 1-(2,3,6-triisopropylphenylsulfonyl)-indole-3-propionic acid (page 9) as intermediates in the synthesis of particular tetracyclic morpholine derivatives.

SUMMARY OF THE INVENTION

In the present invention, compounds were identified that were only weakly active on PPARs. Identification of such compounds led to the identification of molecular scaffolds that allows for convenient ligand development utilizing structural information about the PPARS, and the preparation of compounds based on that scaffold that have greatly enhanced activity on PPARs as compared to the compounds initially identified. Included are compounds that have significant pan-activity across the PPARs, PPARα, PPARδ, and PPARγ, as well as compounds that have significant specificity (at least 5-, 10-, or 20-fold greater activity) on a single PPAR, or on two of the three PPARs.

A molecular scaffold is represented below by the structure of Formula I, but with n=1, Y═CH, the R substituents except for $R^1$ as H, and with $R^1$ as —COOH. Similar scaffolds with each of the alternate selections for the indicated moieties (e.g., Y═N and/or n=0 or 2 and/or $R^1$ as one of the other indicated substituents) are also provided. The present invention concerns molecular scaffolds of Formula I and the use of such molecular scaffolds, and the use of compounds with the structure of Formula I as modulators of the PPARs, PPARα, PPARδ, and PPARγ, where Formula I is:

Formula I

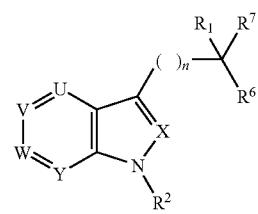

where:

U, V, W, X, and Y are independently substituted N or $CR^8$, where there are no more than 4, and preferably no more than 3, nitrogens in the bicyclic ring structure shown in Formula I, and there are no more than 2 nitrogens in either of the rings;

$R^1$ is a carboxyl group (or ester thereof) or a carboxylic acid isostere such as optionally substituted thiazolidine dione, optionally substituted hydroxamic acid, optionally substituted acyl-cyanamide, optionally substituted tetrazole, optionally substituted isoxazole, optionally substituted sulphonate, optionally substituted sulfonamide, and optionally substituted acylsulphonamide;

$R^2$ is hydrogen, optionally substituted lower alkyl, —$CH_2$—$CR^{12}$═$CR^{13}R^{14}$, —$CH_2$—C≡$CR^5$, optionally substituted cycloalkyl, optionally substituted heterocycloalkyl, optionally substituted aryl, optionally substituted aralkyl, optionally substituted heteroaryl, optionally substituted heteroaralkyl, —C(Z)$NR^{10}R^{11}$, —C(Z)$R^{20}$, —$S(O)_2$$NR^{10}R^{11}$; or —$S(O)_2R^{21}$;

$R^6$ and $R^7$ are independently hydrogen, optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl, or $R^6$ and $R^7$ combine to form a mono-carbocyclic or mono-heterocyclic 5- or 6-membered ring system;

$R^8$ is hydrogen, halo, optionally substituted lower alkyl, —$CH_2$—$CR^{12}$═$CR^{13}R^{14}$, optionally substituted cycloalkyl, optionally substituted monofluoroalkyl, optionally substituted difluoroalkyl, optionally substituted trifluoroalkyl, trifluoromethyl, —$CH_2$—C≡$CR^{15}$, optionally substituted heterocycloalkyl, optionally substituted aryl, optionally substituted aralkyl, optionally substituted heteroaryl, optionally substituted heteroaralkyl, —$OR^9$, —$SR^9$, —$NR^{10}R^{11}$, —C(Z)$NR^{10}R^{11}$, —C(Z)$R^{20}$, —$S(O)_2NR^{10}R^{11}$, or —$S(O)_2R^{21}$;

$R^9$ is optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl;

$R^{10}$ and $R^{11}$ are independently hydrogen, optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl, or $R^{10}$ and $R^{11}$ combine to form a mono-carbocyclic or mono-heterocyclic 5- or 6-membered ring system;

$R^{12}$, $R^{13}$, $R^{14}$, and $R^{15}$ are independently optionally substituted lower alkyl, optionally substituted cycloalkyl, optionally substituted monofluoroalkyl, trifluoromethyl, optionally substituted difluoroalkyl, optionally substituted heterocycloalkyl, optionally substituted aryl, optionally substituted aralkyl, optionally substituted heteroaryl, or optionally substituted heteroaralkyl;

$R^{20}$ is optionally substituted monofluoroalkyl, trifluoromethyl, optionally substituted difluoroalkyl, —$CH_2$—$CR^{12}$=$CR^{13}R^{14}$, —$CH_2$—C≡$CR^{15}$, optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl;

$R^{21}$ is optionally substituted lower alkoxy, —$CH_2$—$CR^{12}$=$CR^{13}R^{14}$, —$CH_2$—C≡$CR^{15}$, optionally substituted cycloalkyl, optionally substituted heterocycloalkyl, optionally substituted aryl, optionally substituted aralkyl, optionally substituted heteroaryl, or optionally substituted heteroaralkyl;

Z is O or S; and n=0, 1, or 2.

In specifying a compound or compounds of Formula I, unless clearly indicated to the contrary, specification of such compound(s) includes pharmaceutically acceptable salts of the compound(s).

In connection with compounds of Formula I, various chemical structures and moieties have the following meanings.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl, or cycloalkyl. In many embodiments, an alkyl is a straight or branched alkyl group containing from 1-15, 1 to 8, 1-6, 1-4, or 1-2, carbon atoms, such as methyl, ethyl, propyl, isopropyl, butyl, t-butyl and the like. The term "lower alkyl" is used herein to describe the straight chain alkyl groups of 1-6, 1-4, or 1-2 carbon atoms. Preferably, cycloalkyl groups are monocyclic, bicyclic or tricyclic ring systems of 3-8, more preferably 3-6, ring members per ring, such as cyclopropyl, cyclopentyl, cyclohexyl, and the like, but can also include larger ring structures such as adamantyl. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bond. In the case of a cycloalkenyl group, conjugation of more than one carbon to carbon double bond is not such as to confer aromaticity to the ring. Carbon to carbon double bonds may be either contained within a cycloalkenyl portion, with the exception of cyclopropenyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2-20, preferably 2-17, more preferably 2-10, even more preferably 2-8, most preferably 2-4, carbon atoms containing at least one, preferably one, carbon to carbon triple bond. Examples of alkynyl groups include ethynyl, propynyl, butynyl and the like. A substituted alkynyl refers to the straight chain alkynyl or branched alkynyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'"R"", where R is lower alkylene, or substituted lower alkylene, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RCCR' where R is lower alkylene or substituted lower alkylene, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" or "thioalkoxy" denotes the group —SR, —$S(O)_{n=1\text{-}2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl, substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" or substituted amine denotes the group —NRR', where R and R' may independently by hydrogen, lower alkyl, substituted lower alkyl, aryl, substituted aryl, hetaryl, or substituted heteroaryl as defined herein, acyl or sulfonyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

The term "carboxylic acid isostere" refers to a group selected from optionally substituted thiazolidine dione, optionally substituted hydroxamic acid, optionally substituted acyl-cyanamide, optionally substituted tetrazole, optionally substituted isoxazole, optionally substituted sulphonate, optionally substituted sulfonamide, and optionally substituted acylsulphonamide "Carbocyclic" refers to a saturated, unsaturated, or aromatic group having a single ring (e.g., phenyl) or multiple condensed rings where all ring atoms are carbon atoms, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Aryl"—alone or in combination means phenyl or naphthyl optionally carbocyclic fused with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, heteroaryl, substituted heteroaryl, nitro, cyano, thiol, sulfamido and the like.

"Heterocycle" refers to a saturated, unsaturated, or aromatic group having a single ring (e.g., morpholino, pyridyl or furyl) or multiple condensed rings (e.g., naphthpyridyl, quinoxalyl, quinolinyl, indolizinyl or benzo[b]thienyl) and having carbon atoms and at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5-6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted heterocyclyl group contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkylene group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R is lower alkylene or substituted lower alkylene. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkylene or substituted lower alkylene. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkylene or substituted lower alkylene. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

In certain embodiments involving compounds of Formula I, the compounds have a structure of Formula I in which the bicyclic core shown for Formula I has one of the following structures:

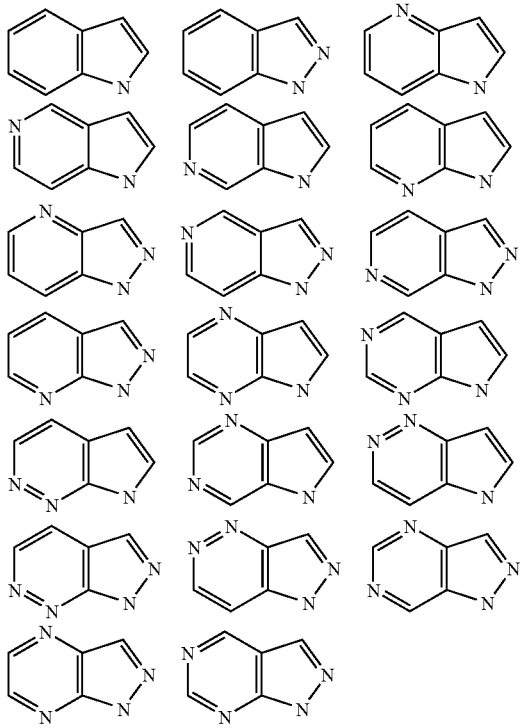

Thus, in particular embodiments involving compounds of Formula I, the compound includes a bicyclic core as shown above. Such compounds can include substitutents as described for Formula I, with the understanding that ring nitrogens other than the nitrogen corresponding to position 1 of the indole structure are unsubstituted. In particular embodiments, the compounds have one of the bicyclic cores shown above and substitution selections as shown herein for compounds having an indolyl core; the compounds have one of the bicyclic cores above, and the substituents shown at the 5-position are instead attached at the 6-position.

In certain embodiments involving compounds of Formula I, the compounds have a structure of Formula I-1, namely

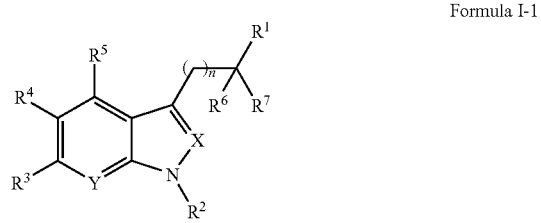

Formula I-1 where:

$R^3$, $R^4$, and $R^5$ are independently hydrogen, halo, trifluoromethyl, optionally substituted lower alkyl, —CH$_2$—CR$^{12}$=CR$^{13}$R$^{14}$, optionally substituted monofluoroalkyl, optionally substituted difluoroalkyl, optionally substituted trifluoroalkyl, —CH$_2$—C≡CR$^{15}$, optionally substituted cycloalkyl, optionally substituted heterocycloalkyl, optionally substituted aryl, optionally substituted aralkyl, optionally substituted heteroaryl, optionally substituted heteroaralkyl, —OR$^9$, —SR$^9$, —NR$^{10}$R$^{11}$, —C(Z)NR$^{10}$R$^{11}$, —C(Z)R$^{20}$, —S(O)$_2$NR$^{10}$R$^{11}$, or —S(O)$_2$R$^{21}$.

In particular embodiments of the different aspects of the invention, including in certain embodiments, the compounds of Formula I are compounds of Formulas Ia, Ib, Ic, Id, X, or XIV as shown in the Detailed Description. Also in particular embodiments, such compounds are compounds of Formula I with Y=N; with Y=CR$^8$; with Y=CH; with all R substituents other than R$^1$, R$^2$, and R$^4$ as H (for each of X as N, X as CH, and X as CR$^8$); with R$^6$ and R$^7$ as H (for each of X as N, X as CH, and X as CR$^8$).

In certain embodiments, n=1; n=1 and X and/or Y is CH; n=1, X and/or Y is CH, and R$^6$ and R$^7$ are H; n=1 and X and/or Y=CR$^8$.

In certain embodiments, n=1, R$^2$ is —S(O)$_2$R$^{21}$, with R$^{21}$ being optionally substituted aryl or optionally substituted heteroaryl. In certain embodiments, in which n=1, and R$^2$ is —S(O)$_2$R$^{21}$, with R$^{21}$ being optionally substituted aryl or optionally substituted heteroaryl, the aryl group is a 5- or 6-membered ring; the aryl group is a 6-membered ring; in further embodiments in which the aryl group is a 6-membered ring, the ring is substituted with one or two groups independently selected from halo, alkoxy, cycloalkyl, aryl, aryloxy, heteroaryl, heteroaryloxy, aryl or heteroaryl substituted alkyl, and aryl or heteroaryl substituted alkoxy; in further embodiments in which a 6-membered ring is substituted with halo or alkoxy, the ring is substituted at the 3-position (meta), 4-position (para), or 3- and 4-positions (meta and para); in further embodiments in which a 6-membered ring is substituted at the 4-position, or 3- and 4-positions, the 4-position substituent is lower alkyl, the 4-position substituent is not alkyl, the 4-position substituent is halo (e.g., fluoro or chloro), the 3- and 4-position substituents are fluoro, the 3- and 4-position substitutents are chloro, one of the 3- and 4-position substituents is fluoro and the other is chloro, the 3-position is halo (e.g., fluoro or chloro) and the 4-position is alkoxy (e.g., methoxy or ethoxy), the 3-position is alkoxy (e.g., methoxy or ethoxy) and the 4-position is halo (e.g., fluoro or chloro), the 3-position is chloro and the 4-position is alkoxy, the 3-position is alkoxy and the 4-position is chloro; the 6-membered ring is fused with a second 5- or 6-membered aromatic or non-aromatic carbocyclic or heterocyclic ring. In further embodiments in which the aryl group is a 5-membered ring, the ring is substituted with one or two groups located at ring positions not adjacent to the ring atom linked to the —S(O)$_2$— group; the 5-membered ring is substituted with one or two ring substituents selected from the group consisting of halo, alkoxy, cycloalkyl, aryl, aryloxy, heteroaryl, heteroaryloxy, aryl or heteroaryl substituted alkyl, and aryl or heteroaryl substituted alkoxy; the ring is substituted with chloro; the ring is substituted with alkoxy; the ring is substituted with alkyl; the ring is substituted with optionally substituted aryl or heteroaryl; the ring is substituted with optionally substituted aryloxy or heteroaryloxy; the 5-membered ring is fused with a second 5- or 6-membered aromatic or non-aromatic carbocyclic or heterocyclic ring.

In certain embodiments in which n=1, and R$^2$ is —S(O)$_2$R$^{21}$, with R$^{21}$ being optionally substituted aryl or optionally substituted heteroaryl, R$^4$ is different from H and alkoxy, or R$^4$ is different from H and OR$^9$.

In certain embodiments, n=2; n=2 and X and/or Y is CH; n=2, X and/or Y is CH, and R$^6$ and R$^7$ are H; n=2 and X and/or Y is CR$^8$; n=2 and X and/or Y is N.

In certain embodiments in which n=2, R$^4$ is different from H, halo, alkyl, alkoxy, alkylthio; R$^4$ is different from H, halo, C$_{1-3}$ alkyl, C$_{1-3}$ alkoxy, C$_{1-3}$ alkylthio; R$^4$ is different from C$_{1-3}$ alkoxy; R$^4$ is not methoxy.

In certain embodiments, n=2, R$^2$ is —S(O)$_2$R$^{21}$, with R$^{21}$ being optionally substituted aryl or optionally substituted heteroaryl. In certain embodiments, in which n=2, and R$^2$ is —S(O)$_2$R$^{21}$, with R$^{21}$ being optionally substituted aryl or optionally substituted heteroaryl, the aryl group is a 5- or 6-membered ring; the aryl group is a 6-membered ring; in further embodiments in which the aryl group is a 6-membered ring, the ring is substituted with one or two groups independently selected from halo, alkyl, cycloalkyl, aryl, aryloxy, heteroaryl, heteroaryloxy, aryl or heteroaryl substituted alkyl, and aryl or heteroaryl substituted alkoxy; in further embodiments in which a 6-membered ring is substituted with halo or alkoxy, the ring is substituted at the 3-position (meta), 4-position (para), or 3- and 4-positions (meta and para); in further embodiments in which a 6-membered ring is substituted at the 4-position, or 3- and 4-positions, the 4-position substitutent is lower alkyl, the 4-position substituent is not alkyl, the 4-position substituent is halo (e.g., fluoro or chloro), the 3- and 4-position substituents are fluoro, the 3- and 4-position substitutents are chloro, one of the 3- and 4-position substituents is fluoro and the other is chloro, the 3-position is halo (e.g., fluoro or chloro) and the 4-position is alkoxy (e.g., methoxy or ethoxy), the 3-position is alkoxy (e.g., methoxy or ethoxy) and the 4-position is halo (e.g., fluoro or chloro), the 3-position is chloro and the 4-position is alkoxy, the 3-position is alkoxy and the 4-position is chloro; the 6-membered ring is fused with a second 5- or 6-membered aromatic or non-aromatic carbocyclic or heterocyclic ring. In further embodiments in which the aryl group is a 5-membered ring, the ring is substituted with one or two groups located at ring positions not adjacent to the ring atom linked to the —S(O)$_2$— group; the 5-membered ring is substituted with one or two ring substituents selected from the group consisting of halo, alkoxy, cycloalkyl, aryl, aryloxy, heteroaryl, heteroaryloxy, aryl or heteroaryl substituted alkyl, and aryl or heteroaryl substituted alkoxy; the ring is substituted with chloro; the ring is substituted with alkoxy; the ring is substituted with alkyl; the ring is substituted with optionally substituted aryl or heteroaryl; the ring is substituted with optionally substituted aryloxy or heteroaryloxy; the 5-membered ring is fused with a second 5- or 6-membered aromatic or non-aromatic carbocyclic or heterocyclic ring.

In certain embodiments, in which n=2, and R$^2$ is —S(O)$_2$R$^{21}$, with R$^{21}$ being a substituted aryl group with a 6-membered, the substitution on the aryl group is not methoxy, the substitution on the aryl group is not alkoxy; the substitution on the aryl group is not alkoxy; R$^4$ and the substitution on the aryl group are not both alkoxy; R$^4$ and the substitution on the aryl group are not both methoxy; R$^4$ is not alkoxy; R$^4$ is not methoxy.

Certain further embodiments include compounds described for corresponding embodiments as described above for both n=1 and n=2.

In certain embodiments, compounds of Formula I have a structure of Formula Ie as shown below:

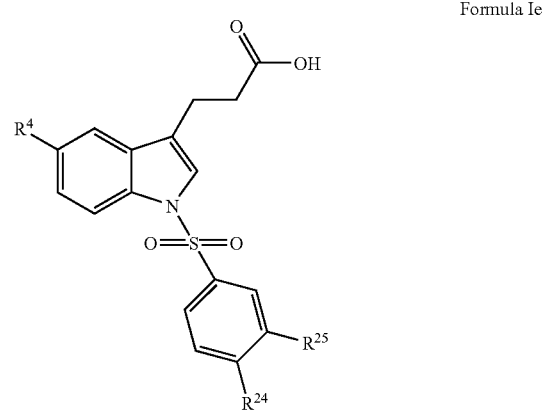

Formula Ie where

R$^4$ is hydrogen, halo, optionally substituted lower alkyl, optionally substituted cycloalkyl, optionally substituted heterocycloalkyl, optionally substituted aryl, optionally substituted aralkyl, optionally substituted heteroaryl, optionally substituted heteroaralkyl, —OR$^9$ (e.g., optionally substituted alkoxy, for example, methoxy, ethoxy)-SR$^9$, —NR$^{10}$R$^{11}$, —C(Z)NR$^{10}$R$^{11}$, —C(Z)R$^{20}$, —S(O)$_2$NR$^{10}$R$^{11}$, or —S(O)$_2$R$^{21}$;

R$^{24}$ is H, halo, optionally substituted alkyl, optionally substituted alkoxy, or optionally substituted aryloxy, or optionally substituted aralkoxy (e.g., Aryl-O(CH$_2$)$_p$O—, where p is 1-4);

R$^{15}$ is H, halo, optionally substituted alkyl, optionally substituted alkoxy, optionally substituted aryloxy, or R$^{24}$ and R$^{25}$ together form a fused ring with the phenyl group, e.g., benzofuran.

In particular embodiments, R$^4$ is optionally substituted alkoxy (e.g., methoxy, ethoxy, propoxy, isopropoxy), optionally substituted aryloxy, optionally substituted heteroaryloxy, optionally substituted alkyl (e.g., methyl or ethyl), optionally substituted cycloalkyl, optionally substituted cycloheteroalkyl, optionally substituted aryl, optionally substituted heteroaryl, or halo.

In particular embodiments, R$^4$ is optionally substituted alkoxy (e.g., methoxy, ethoxy, propoxy, isopropoxy), optionally substituted alkyl (e.g., methyl or ethyl), optionally substituted aryl, optionally substituted heteroaryl, or halo.

In particular embodiments, compounds of Formula I can be as specified for Formula Ie, but with the phenyl ring to which R$^{24}$ and R$^{25}$ are attached as a heteroaryl ring. If the heteroaryl ring is a 5-membered ring, R$^{24}$ and R$^{25}$ are attached at the ring positions that are not adjacent to the atom linking to the sulfonyl group shown in Formula Ie.

In particular embodiments of compounds of Formula Ie, $R^4$ is alkoxy and $R^{24}$ and $R^{25}$ are chloro; $R^4$ is alkoxy and $R^{24}$ and $R^{25}$ are fluoro; $R^4$ is alkoxy and $R^{24}$ is alkoxy; $R^4$ is alkoxy and $R^{24}$ is alkyl; $R^4$ is methoxy or ethoxy and $R^{24}$ and $R^{25}$ are chloro; $R^4$ is methoxy or ethoxy and $R^{24}$ is alkoxy; $R^4$ is methoxy or ethoxy and $R^{24}$ is alkyl.

In particular embodiments of compounds of Formula Ie, both of $R^{24}$ and $R^{25}$ are not alkyl; neither of $R^{24}$ and $R^{25}$ are alkyl; with R as H, $R^{25}$ is not alkyl; with $R^{25}$ as H $R^{24}$ is not alkyl.

Exemplary compounds include those listed in Table 1 and in Table 4. Reference to compounds of Formula I herein includes specific reference to sub-groups and species of compounds of Formula I described herein (e.g., particular embodiments as described above) unless indicated to the contrary.

In particular embodiments, any one or more of the subgroups of compounds of Formula I or any one or more of the exemplary compounds is excluded from one of the specified compound groups or sub-groups of Formula I that would otherwise include such sub-group or sub-groups.

In particular embodiments of aspects involving compounds of Formula I, the compound is specific for PPARα; specific for PPARδ; specific for PPARγ; specific for PPARα and PPARδ; specific for PPARα, and PPARγ; specific for PPARδ and PPARγ. Such specificity means that the compound has at least 5-fold greater activity (preferably at least 1-, 20-, 50-, or 100-fold or more greater activity) on the specific PPAR(s) than on the other PPAR(s), where the activity is determined using a biochemical assay suitable for determining PPAR activity, e.g., an assay as described herein.

As used herein in connection with PPAR modulating compound, binding compounds or ligands, the term "specific for PPAR" and terms of like import mean that a particular compound binds to a PPAR to a statistically greater extent than to other biomolecules that may be present in a particular organism, e.g., at least 2, 3, 4, 5, 10, 20, 50, 100, or 1000-fold. Also, where biological activity other than binding is indicated, the term "specific for PPAR" indicates that a particular compound has greater biological activity associated with binding a PPAR than to other biomolecules (e.g., at a level as indicated for binding specificity). Similarly, the specificity can be for a specific PPAR with respect to other PPARs that may be present from an organism.

As used herein, the terms "ligand" and "modulator" are used equivalently to refer to a compound that modulates the activity of a target biomolecule, e.g., a PPAR. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by a person for a particular biological system or therapeutic use. In terms of the development of ligands from scaffolds, a ligand is a derivative of a molecular scaffold that has been chemically modified at one or more chemically tractable structures to bind to the target molecule with altered or changed binding affinity or binding specificity relative to the molecular scaffold. The ligand can bind with a greater specificity or affinity for a member of the molecular family relative to the molecular scaffold. A ligand binds non-covalently to a target molecule, which can preferably be a protein or enzyme.

In the context of binding compounds, molecular scaffolds, and ligands, the term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

Thus, the term "parent compound" refers to a reference compound for another compound, having structural features continued in the derivative compound. Often but not always, a parent compound has a simpler chemical structure than the derivative.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. In some cases, the specificity is with reference to a limited set of other biomolecules, e.g., in the case of PPARs, in some cases the reference may be other receptors, or for a particular PPAR, it may be other PPARs. In particular embodiments, the greater specificity is at least 2, 3, 4, 5, 8, 10, 50, 100, 200, 400, 500, or 1000-fold greater specificity.

A first aspect of the invention concerns novel compounds of Formula I and sub-groups of Formula I, e.g., as described above or otherwise described herein.

A related aspect of this invention concerns pharmaceutical compositions that include a compound of Formula I and at least one pharmaceutically acceptable carrier, excipient, or diluent. The composition can include a plurality of different pharmacalogically active compounds.

As used herein, the term "pharmaceutical composition" refers to a preparation that includes a therapeutically significant quantity of an active agent, that is prepared in a form adapted for administration to a subject. Thus, the preparation does not include any component or components in such quantity that a reasonably prudent medical practitioner would find the preparation unsuitable for administration to a normal subject. In many cases, such a pharmaceutical composition is a sterile preparation.

In a related aspect, the invention provides kits that include a pharmaceutical composition as described herein. In particular embodiments, the pharmaceutical composition is packaged, e.g., in a vial, bottle, flask, which may be further packaged, e.g., within a box, envelope, or bag; the pharmaceutical composition is approved by the U.S. Food and Drug Administration or similar regulatory agency for administration to a mammal, e.g., a human; the pharmaceutical composition is approved for administration to a mammal, e.g., a human for a PPAR-mediated disease or condition; the kit includes written instructions or other indication that the composition is suitable or approved for administration to a mammal, e.g., a human, for a PPAR-mediated disease or condition; the pharmaceutical composition is packaged in unit does or single dose form, e.g., single dose pills, capsules, or the like.

In another related aspect, compounds of Formula I can be used in the preparation of a medicament for the treatment of a PPAR-mediated disease or condition or a disease or condition in which modulation of a PPAR provides a therapeutic benefit.

In another aspect, the invention concerns a method of treating or prophylaxis of a disease or condition in a mammal, e.g., a PPAR-mediated disease or condition or a disease or condition in which modulation of a PPAR provides a therapeutic benefit, by administering to the mammal a therapeutically effective amount of a compound of Formula I, a prodrug of such compound, or a pharmaceutically acceptable salt of such compound or prodrug. The compound can be alone or can be part of a pharmaceutical composition.

In aspects and embodiments involving treatment or prophylaxis of a disease or conditions, the disease or condition is obesity, overweight condition, hyperlipidemia, dyslipidemia including associated diabetic dyslipidemia and mixed dyslipidemia, hypoalphalipoproteinemia, Syndrome X, Type II diabetes mellitus, Type I diabetes, hyperinsulinemia, impaired glucose tolerance, insulin resistance, a diabetic complication (e.g., neuropathy, nephropathy, retinopathy or cataracts), hypertension, coronary heart disease, heart failure, hypercholesterolemia, inflammation, thrombosis, congestive heart failure, cardiovascular disease (including atherosclerosis, arteriosclerosis, and hypertriglyceridemia), epithelial hyperproliferative diseases (such as eczema and psoriasis), cancer, and conditions associated with the lung and gut and regulation of appetite and food intake in subjects suffering from disorders such as obesity, anorexia bulimia and anorexia nervosa.

As used herein, the term "PPAR-mediated" disease or condition and like terms refer to a disease or condition in which the biological function of a PPAR affects the development and/or course of the disease or condition, and/or in which modulation of PPAR alters the development, course, and/or symptoms of the disease or condition. Similarly, the phrase "PPAR modulation provides a therapeutic benefit" indicates that modulation of the level of activity of PPAR in a subject indicates that such modulation reduces the severity and/or duration of the disease, reduces the likelihood or delays the onset of the disease or condition, and/or causes an improvement in one or more symptoms of the disease or condition. In some cases the disease or condition may be mediated by one of the PPAR isoforms, e.g., PPARγ, PPARα, and PPARδ.

In the present context, the term "therapeutically effective" indicates that the materials or amount of material is effective to prevent, alleviate, or ameliorate one or more symptoms of a disease or medical condition, and/or to prolong the survival of the subject being treated.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

"A pharmaceutically acceptable salt" is intended to mean a salt that retains the biological effectiveness of the free acids and bases of the specified compound and that is not biologically or otherwise unacceptable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sodium, chloride, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma.-hydroxybutyrates, glycollates, tartrates, methane-sulfonates, propanesulfonates, naphthalene-1-sulfonates, naphthalene-2-sulfonates, and mandelates.

The term "pharmaceutically acceptable metabolite" refers to a pharmacologically acceptable product, which may be an active product, produced through metabolism of a specified compound (or salt thereof) in the body of a subject or patient. Metabolites of a compound may be identified using routine techniques known in the art, and their activities determined using tests such as those described herein. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

The identification of compounds of Formula I active on PPARs also provides a method for identifying or developing additional compounds active on PPARs, e.g., improved modulators, by determining whether any of a plurality of test compounds of Formula I active on at least one PPAR provides an improvement in one or more desired pharmacologic properties relative to a reference compound active on such PPAR, and selecting a compound If any, that has an improvement in the desired pharmacologic property, thereby providing an improved modulator.

In particular embodiments of aspects of modulator development, the desired pharmacologic property is PPAR pan-activity, PPAR selectivity for any individual PPAR (PPARα, PPARδ, or PPARγ), selectivity on any two PPARs (PPARα and PPARδ, PPARα and PPARγ, or PPARδ and PPARγ), serum half-life longer than 2 hr or longer than 4 hr or longer than 8 hr, aqueous solubility, oral bioavailability more than 10%, oral bioavailability more than 20%.

Also in particular embodiments of aspects of modulator development, the reference compound is a compound of Formula I. The process can be repeated multiple times, i.e., multiple rounds of preparation of derivatives and/or selection of additional related compounds and evaluation of such further derivatives of related compounds, e.g., 1, 2, 3, 4, 5, 6, 7, 8, 9, 10 or more additional rounds.

In additional aspects, structural information about one or more of the PPARs is utilized, e.g., in conjunction with compounds of Formula I or a molecular scaffold or scaffold core of Formula I.

Thus, in another aspect, the invention provides a method of designing a ligand that binds to at least one member of the PPAR protein family (PPARα, PPARδ, and PPARγ), by identifying as molecular scaffolds one or more compounds that bind to a binding site of a PPAR with low affinity; determining the orientation of the one or more molecular scaffolds at the binding site of the PPAR by obtaining co-crystal structures of the molecular scaffolds in the binding site; identifying one or more structures of at least one scaffold molecule that, when modified, provide a ligand having altered binding affinity or binding specificity or both for binding to the PPAR as compared to the binding of the scaffold molecule. The designed ligand(s) can then be provided, e.g., by synthesizing or otherwise obtaining the ligand(s). In particular embodiments, the molecular scaffold is a compound of Formula I, or contains a bicyclic core as shown above for Formula I.

In particular embodiments, a plurality of distinct compounds are assayed for binding to the binding site of the PPAR; co-crystals of the molecular scaffolds bound to the PPAR are isolated, and the orientation of the molecular scaffold is determined by performing X-ray crystallography on the co-crystals; the method further involves identifying common chemical structures of the molecular scaffolds, placing the molecular scaffolds into groups based on having at least one common chemical structure, and determining the orientation of the one or more molecular scaffolds at the binding site of the PPAR for at least one representative compound from a plurality of groups; the ligand binds to the target molecule with greater binding affinity or greater binding specificity or both than the molecular scaffold; the orientation of the molecular scaffold is determined by nuclear magnetic resonance in co-crystal structure determination; the plurality of distinct compounds are each assayed for binding to a plurality of members of the PPAR family.

Also in particular embodiments, after the identification of common chemical structures of the distinct compounds that bind, the compounds are grouped into classes based on common chemical structures and a representative compound from a plurality of the classes is selected for performing X-ray crystallography on co-crystals of the compound and target molecule; the distinct compounds are selected based on criteria selected from molecular weight, clogP, and the number of hydrogen bond donors and acceptors; the clog P is less than 2, and the number of hydrogen bond donors and acceptors is less than 5.

In certain embodiments, the distinct compounds have a molecular weight of from about 100 to about 350 daltons, or more preferably from about 150 to about 350 daltons or from 150 to 300 daltons, or from 200 to 300 daltons. The distinct compounds can be of a variety of structures. In some embodiments, the distinct compounds can have a ring structure, either a carbocyclic or heterocyclic ring, such as for example, a phenyl ring, a pyrrole, imidazole, pyridine, purine, or any ring structure.

In various embodiments, a compound or compounds binds with extremely low affinity, very low affinity, low affinity, moderate affinity, or high affinity; at least about 5% of the binding compounds bind with low affinity (and/or has low activity), or at least about 10%, 15%, or 20% of the compounds bind with low affinity (or very low or extremely low). After the identification of common chemical structures of the distinct compounds that bind, the compounds can be grouped into classes based on common chemical structures and at least one representative compound from at least one, or preferably a plurality, of the classes selected for performing orientation determination, e.g., by X-ray crystallography and/or NMR analysis.

In selecting the distinct compounds for assay in the present invention, the selection can be based on various criteria appropriate for the particular application, such as molecular weight, clogP (or other method of assessing lipophilicity), Polar Surface Area (PSA) (or other indicator of charge and polarity or related properties), and the number of hydrogen bond donors and acceptors. Compounds can also be selected using the presence of specific chemical moieties which, based on information derived from the molecular family, might be indicated as having predisposing some affinity for members of the family. Compounds with highly similar structures and/ or properties can be identified and grouped using computational techniques to facilitate the selection of a representative subset of the group. As indicated above, in preferred embodiments, the molecular weight is from about 150 to about 350 daltons, more preferably from 150 to 300 daltons. The clog P is preferably less than 2, the number of hydrogen bond donors and acceptors is preferably less than 5 and the PSA less than 100. Compounds can be selected that include chemical structures of drugs having acceptable pharmacalogical properties and/or lacking chemical structures that are known to result in undesirable pharmacological properties, e.g., excessive toxicity and lack of solubility.

In some embodiments, the assay is an enzymatic assay, and the number of groups of molecular scaffolds formed can conveniently be about 500. In some embodiments, the assay is a competition assay, e.g., a binding competition assay. Cell-based assays can also be used. As indicated above, compounds can be used that have low, very low, or extremely low activity in a biochemical or cell-based assay.

The modification of a molecular scaffold can be the addition, subtraction, or substitution of a chemical group. The modification may desirably cause the scaffold to be actively transported to or into particular cells and/or a particular organ. In various embodiments, the modification of the compound includes the addition or subtraction of a chemical atom, substituent or group, such as, for example, a hydrogen, alkyl, alkoxy, phenoxy, alkenyl, alkynyl, phenylalkyl, hydroxyalkyl, haloalkyl, aryl, arylalkyl, alkyloxy, alkylthio, alkenylthio, phenyl, phenylalkyl, phenylalkylthio, hydroxyalkyl-thio, alkylthiocarbbamylthio, cyclohexyl, pyridyl, piperidinyl, alkylamino, amino, nitro, mercapto, cyano, hydroxyl, a halogen atom, halomethyl, an oxygen atom (e.g., forming a ketone, ether or N-oxide), and a sulphur atom (e.g., forming a thiol, thione, sulfonamide or di-alkylsulfoxide (sulfone)).

In certain embodiments, the information provided by performing X-ray crystallography on the co-crystals is provided to a computer program, wherein the computer program provides a measure of the interaction between the molecular scaffold and the protein and a prediction of changes in the interaction between the molecular scaffold and the protein that result from specific modifications to the molecular scaffold, and the molecular scaffold is chemically modified based on the prediction of the biochemical result. The computer program can provide the prediction based on a virtual assay such as, for example, virtual docking of the compound to the protein, shape-based matching, molecular dynamics simulations, free energy perturbation studies, and similarity to a three-dimensional pharmacophore. A variety of such programs are well-known in the art.

Chemical modification of a chemically tractable structure can result, or be selected to provide one or more physical changes, e.g., to result, in a ligand that fills a void volume in the protein-ligand complex, or in an attractive polar interaction being produced in the protein-ligand complex. The modification can also result in a sub-structure of the ligand being present in a binding pocket of the protein binding site when the protein-ligand complex is formed. After common chemical structures of the compounds that bind are identified, the compounds can be grouped based on having a common chemical sub-structure and a representative compound from each group (or a plurality of groups) can be selected for co-crystallization with the protein and performance of the X-ray crystallography. The X-ray crystallography is preferably performed on the co-crystals under at least 20, 30, 40, or 50 distinct environmental conditions, or more preferably under about 96 distinct environmental conditions. The X-ray crystallography and the modification of a chemically tractable structure of the compound can each be performed a plurality of times, e.g., 2, 3, 4, or more rounds of crystallization and modification.

Also in certain embodiments, one or more molecular scaffolds are selected to have binding to a plurality of members of the PPAR family.

The method can also include the identification of conserved residues in a binding site(s) of a PPAR protein that interact with a molecular scaffold, ligand or other binding compound. Conserved residues can, for example, be identified by sequence alignment of different members of the PPAR family, and identifying binding site residues that are the same or at least similar between multiple member of the family. Interacting residues can be characterized as those within a selected distance from the binding compound(s), e.g., 3, 3.5, 4, 4.5, or 5 angstroms.

As used in connection with binding of a compound with a target, the term "interact" indicates that the distance from a bound compound to a particular amino acid residue will be 5.0 angstroms or less. In particular embodiments, the distance from the compound to the particular amino acid residue is 4.5 angstroms or less, 4.0 angstroms or less, or 3.5 angstroms or less. Such distances can be determined, for example, using co-crystallography, or estimated using computer fitting of a compound in an active site.

In a related aspect, the invention provides a method of designing a ligand that binds to at least one PPAR that is a member of the PPAR family, by identifying as molecular scaffolds one or more compounds that bind to binding sites of a plurality of members of the PPAR family, determining the orientation of one or more molecular scaffolds at the binding site of a PPAR(s) to identify chemically tractable structures of the scaffold(s) that, when modified, alter the binding affinity or binding specificity between the scaffold(s) and the PPAR(s), and synthesizing a ligand wherein one or more of the chemically tractable structures of the molecular scaffold(s) is modified to provide a ligand that binds to the PPAR with altered binding affinity or binding specificity.

Particular embodiments include those described for the preceding aspect.

The invention also provides a method to identify properties that a likely binding compound will possess, thereby allowing, for example, more efficient selection of compounds for structure activity relationship determinations and/or for selection for screening. Thus, another aspect concerns a method for identifying binding characteristics of a ligand of a PPAR protein, by identifying at least one conserved interacting residue in the PPAR that interacts with at least two binding molecules; and identifying at least one common interaction property of those binding molecules with the conserved residue(s). The interaction property and location with respect to the structure of the binding compound defines the binding characteristic.

In various embodiments, the identification of conserved interacting residues involves comparing (e.g., by sequence alignment) a plurality of amino acid sequences in the PPAR family and identifying binding site residues conserved in that family; identification of binding site residues by determining a co-crystal structure; identifying interacting residues (preferably conserved residues) within a selected distance of the binding compounds, e.g., 3, 3.5, 4, 4.5, or 5 angstroms; the interaction property involves hydrophobic interaction, charge-charge interaction, hydrogen bonding, charge-polar interaction, polar-polar interaction, or combinations thereof.

Another related aspect concerns a method for developing ligands for a PPAR using a set of scaffolds. The method involves selecting a PPAR or plurality of PPARs, selecting a molecular scaffold, or a compound from a scaffold group, from a set of at least 3 scaffolds or scaffold groups where each of the scaffolds or compounds from each scaffold group are known to bind to the target. In particular embodiments, the set of scaffolds or scaffold groups is at least 4, 5, 6, 7, 8, or even more scaffolds or scaffold groups.

Another aspect concerns a method for identifying structurally and energetically allowed sites on a binding compound for attachment of an additional component(s) by analyzing the orientation of the binding compound(s) in a PPAR binding site (e.g., by analyzing co-crystal structures), thereby identifying accessible sites on the compound for attachment of the separate component. In particular embodiments, the binding compound is a compound of Formula I.

In various embodiments, the method involves calculating the change in binding energy on attachment of the separate component at one or more of the accessible sites; the orientation is determined by co-crystallography; the separate component includes a linker, a label such as a fluorophore, a solid phase material such as a gel, bead, plate, chip, or well.

In a related aspect, the invention provides a method for attaching a PPAR binding compound to an attachment component(s), by identifying energetically allowed sites for attachment of such an attachment component on a binding compound (e.g., as described for the preceding aspect), and attaching the compound or derivative thereof to the attachment component(s) at the energetically allowed site(s). In particular embodiments, the binding compound is a compound of Formula I.

In various embodiments, the attachment component is a linker (which can be a traceless linker) for attachment to a solid phase medium, and the method also involves attaching the compound or derivative to a solid phase medium through the linker attached at the energetically allowed site; the binding compound or derivative thereof is synthesized on a linker attached to the solid phase medium; a plurality of compounds or derivatives are synthesized in combinatorial synthesis; the attachment of the compound(s) to the solid phase medium provides an affinity medium A related aspect concerns a method for making an affinity matrix for a PPAR, where the method involves identifying energetically allowed sites on a PPAR binding compound for attachment to a solid phase matrix; and attaching the PPAR binding compound to the solid phase matrix through the energetically allowed site. In particular embodiments, the binding compound is a compound of Formula I.

Various embodiments are as described for attachment of a separate component above; identifying energetically allowed sites for attachment to a solid phase matrix is performed for at least 5, 10, 20, 30, 50, 80, or 100 different compounds; identifying energetically allowed sites is performed for molecular scaffolds or other PPAR binding compounds having different core ring structures.

As used herein the term "PPAR" refers to a peroxisome proliferator-activated receptor as recognized in the art. As indicated above, the PPAR family includes PPARα (also referred to as PPARa or PPARalpha), PPARδ (also referred to as PPARd or PPARdelta), and PPARγ (also referred to as PPARg or PPARgamma). The individual PPARs can be identified by their sequences, where exemplary reference sequence accession numbers are: NM_005036 (cDNA sequence for hPPARa), NP_005027 (protein sequence for hPPARa), NM_015869 (cDNA sequence for hPPARg isoform 2), NP_056953 (protein sequence for hPPARg isoform 2), NM_006238 (cDNA sequence for hPPARd), and NP_006229 (protein sequence for hPPARd). One of ordinary skill in the art will recognize that sequence differences will exist due to allelic variation, and will also recognize that other animals, particularly other mammals have corresponding PPARs, which have been identified or can be readily identified using sequence alignment and confirmation of activity, can also be used. One of ordinary skill in the art will also recognize that modifications can be introduced in a PPAR sequence without destroying PPAR activity. Such modified PPARs can also be used in the present invention, e.g., if the modifications do not alter the binding site conformation to the extent that the modified PPAR lacks substantially normal ligand binding.

As used herein in connection with the design or development of ligands, the term "bind" and "binding" and like terms refer to a non-covalent energetically favorable association between the specified molecules (i.e., the bound state has a lower free energy than the separated state, which can be measured calorimetrically). For binding to a target, the binding is at least selective, that is, the compound binds preferentially to a particular target or to members of a target family at a binding site, as compared to non-specific binding to unrelated proteins not having a similar binding site. For example, BSA is often used for evaluating or controlling for non-specific binding. In addition, for an association to be regarded as binding, the decrease in free energy going from a separated state to the bound state must be sufficient so that the association is detectable in an biochemical assay suitable for the molecules involved.

By "assaying" is meant the creation of experimental conditions and the gathering of data regarding a particular result of the experimental conditions. For example, enzymes can be assayed based on their ability to act upon a detectable substrate. Likewise, for example, a compound or ligand can be assayed based on its ability to bind to a particular target molecule or molecules and/or to modulate an activity of a target molecule.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

When a decision is described as "based on" particular criteria, it is meant that the criteria selected are parameters of the decision and guide its outcome. A substantial change in the parameters is likely to result in a change in the decision.

By "binding site" is meant an area of a target molecule to which a ligand can bind non-covalently. Binding sites embody particular shapes and often contain multiple binding pockets present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume within a binding site. A binding pocket is a particular space within a binding site at least partially bounded by target molecule atoms. Thus a binding pocket is a particular shape, indentation, or cavity in the binding site. Binding pockets can contain particular chemical groups or structures that are important in the non-covalent binding of another molecule such as, for example, groups that contribute to ionic, hydrogen bonding, van der Waals, or hydrophobic interactions between the molecules.

By "chemical structure" or "chemical substructure" is meant any definable atom or group of atoms that constitute a part of a molecule. Normally, chemical substructures of a scaffold or ligand can have a role in binding of the scaffold or ligand to a target molecule, or can influence the three-dimensional shape, electrostatic charge, and/or conformational properties of the scaffold or ligand.

By "orientation", in reference to a binding compound bound to a target molecule is meant the spatial relationship of the binding compound and at least some of its constituent atoms to the binding pocket and/or atoms of the target molecule at least partially defining the binding pocket.

In the context of target molecules in the present invention, the term "crystal" refers to an ordered complex of target molecule, such that the complex produces an X-ray diffraction pattern when placed in an X-ray beam. Thus, a "crystal" is distinguished from a disordered or partially ordered complex or aggregate of molecules that do not produce such a diffraction pattern. Preferably a crystal is of sufficient order and size to be useful for X-ray crystallography. A crystal may be formed only of target molecule (with solvent and ions) or may be a co-crystal of more than one molecule, for example, as a co-crystal of target molecule and binding compound, and/or of a complex of proteins (such as a holoenzyme).

In the context of this invention, unless otherwise specified, by "co-crystals" is meant an ordered complex of the compound, molecular scaffold, or ligand bound non-covalently to the target molecule that produces a diffraction pattern when placed in an X-ray beam. Preferably the co-crystal is in a form appropriate for analysis by X-ray or protein crystallography. In preferred embodiments the target molecule-ligand complex can be a protein-ligand complex.

By "clog P" is meant the calculated log P of a compound, "P" referring to the partition coefficient of the compound between a lipophilic and an aqueous phase, usually between octanol and water.

By "chemically tractable structures" is meant chemical structures, sub-structures, or sites on a molecule that can be covalently modified to produce a ligand with a more desirable property. The desirable property will depend on the needs of the particular situation. The property can be, for example, that the ligand binds with greater affinity to a target molecule, binds with more specificity, or binds to a larger or smaller number of target molecules in a molecular family, or other desirable properties as needs require.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

By "designing a ligand," "preparing a ligand," "discovering a ligand," and like phrases is meant the process of considering relevant data (especially, but not limited to, any individual or combination of binding data, X-ray co-crystallography data, molecular weight, clogP, and the number of hydrogen bond donors and acceptors) and making decisions about advantages that can be achieved with resort to specific structural modifications to a molecule, and implementing those decisions. This process of gathering data and making decisions about structural modifications that can be advantageous, implementing those decisions, and determining the result can be repeated as many times as necessary to obtain a ligand with desired properties.

By "docking" is meant the process of attempting to fit a three-dimensional configuration of a binding pair member into a three-dimensional configuration of the binding site or binding pocket of the partner binding pair member, which can be a protein, and determining the extent to which a fit is obtained. The extent to which a fit is obtained can depend on the amount of void volume in the resulting binding pair complex (or target molecule-ligand complex). The configuration can be physical or a representative configuration of the binding pair member, e.g., an in silico representation or other model.

By binding with "low affinity" is meant binding to the target molecule with a dissociation constant ($k_d$) of greater than 1 µM under standard conditions. In particular cases, low affinity binding is in a range of 1 µM-10 mM, 1 µM-1 mM, 1 µM-500 µM, 1 µM-200 µM, 1 µM-100 µM. By binding with "very low affinity" is meant binding with a $k_d$ of above about 100 µM under standard conditions, e.g., in a range of 10 µM-1 mM, 100 µM-500 µM, 100 µM-200 µM. By binding with "extremely low affinity" is meant binding at a $k_d$ of above about 1 mM under standard conditions. By "moderate affinity" is meant binding with a $k_d$ of from about 200 nM to about 1 µM under standard conditions. By "moderately high affinity" is meant binding at a $k_d$ of from about 1 nM to about 200 nM. By binding at "high affinity" is meant binding at a $k_d$ of below about 1 nM under standard conditions. For example, low affinity binding can occur because of a poorer fit into the binding site of the target molecule or because of a smaller number of non-covalent bonds, or weaker covalent bonds present to cause binding of the scaffold or ligand to the binding site of the target molecule relative to instances where higher affinity binding occurs. The standard conditions for binding are at pH 7.2 at 37° C. for one hour. For example, 1001/well can be used in HEPES 50 mM buffer at pH 7.2, NaCl 15 mM, ATP 2 µM, and bovine serum albumin 1 µg/well, 37° C. for one hour.

Binding compounds can also be characterized by their effect on the activity of the target molecule. Thus, a "low activity" compound has an inhibitory concentration ($IC_{50}$) (for inhibitors or antagonists) or effective concentration ($EC_{50}$) (applicable to agonists) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured. For PPAR agonists, activities can be determined as described in the Examples, or using other such assay methods known in the art.

By "molecular scaffold" or "scaffold" is meant a small target binding molecule to which one or more additional chemical moieties can be covalently attached, modified, or eliminated to form a plurality of molecules with common structural elements. The moieties can include, but are not limited to, a halogen atom, a hydroxyl group, a methyl group, a nitro group, a carboxyl group, or any other type of molecular group including, but not limited to, those recited in this application. Molecular scaffolds bind to at least one target molecule with low or very low affinity and/or bind to a plurality of molecules in a target family (e.g., protein family), and the target molecule is preferably an enzyme, receptor, or other protein. Preferred characteristics of a scaffold include molecular weight of less than about 350 daltons; binding at a target molecule binding site such that one or more substituents on the scaffold are situated in binding pockets in the target molecule binding site; having chemically tractable structures that can be chemically modified, particularly by synthetic reactions, so that a combinatorial library can be easily constructed; having chemical positions where moieties can be attached that do not interfere with binding of the scaffold to a protein binding site, such that the scaffold or library members can be modified to form ligands, to achieve additional desirable characteristics, e.g., enabling the ligand to be actively transported into cells and/or to specific organs, or enabling the ligand to be attached to a chromatography column for additional analysis. Thus, a molecular scaffold is a small, identified target binding molecule prior to modification to improve binding affinity and/or specificity, or other pharmacalogic properties.

The term "scaffold core" refers to the core structure of a molecular scaffold onto which various substituents can be attached. Thus, for a number of scaffold molecules of a particular chemical class, the scaffold core is common to all the scaffold molecules. In many cases, the scaffold core will consist of or include one or more ring structures.

The term "scaffold group" refers to a set of compounds that share a scaffold core and thus can all be regarded as derivatives of one scaffold molecule.

By "molecular family" is meant groups of molecules classed together based on structural and/or functional similarities. Examples of molecular families include proteins, enzymes, polypeptides, receptor molecules, oligosaccharides, nucleic acids, DNA, RNA, etc. Thus, for example, a protein family is a molecular family. Molecules can also be classed together into a family based on, for example, homology. The person of ordinary skill in the art will realize many other molecules that can be classified as members of a molecular family based on similarities in chemical structure or biological function.

By "protein-ligand complex" or "co-complex" is meant a protein and ligand bound non-covalently together.

By "protein" is meant a polymer of amino acids. The amino acids can be naturally or non-naturally occurring. Proteins can also contain adaptations, such as being glycosylated, phosphorylated, or other common modifications.

By "protein family" is meant a classification of proteins based on structural and/or functional similarities. For example, kinases, phosphatases, proteases, and similar groupings of proteins are protein families. Proteins can be grouped into a protein family based on having one or more protein folds in common, a substantial similarity in shape among folds of the proteins, homology, or based on having a common function. In many cases, smaller families will be specified, e.g., the PPAR family.

"Protein folds" are 3-dimensional shapes exhibited by the protein and defined by the existence, number, and location in the protein of alpha helices, beta-sheets, and loops, i.e., the basic secondary structures of protein molecules. Folds can be, for example, domains or partial domains of a particular protein.

By "ring structure" is meant a molecule having a chemical ring or sub-structure that is a chemical ring. In most cases, ring structures will be carbocyclic or heterocyclic rings. The chemical ring may be, but is not limited to, a phenyl ring, aryl ring, pyrrole ring, imidazole, pyridine, purine, or any ring structure.

By "specific biochemical effect" is meant a therapeutically significant biochemical change in a biological system causing a detectable result. This specific biochemical effect can be, for example, the inhibition or activation of an enzyme, the inhibition or activation of a protein that binds to a desired target, or similar types of changes in the body's biochemistry. The specific biochemical effect can cause alleviation of symptoms of a disease or condition or another desirable effect. The detectable result can also be detected through an intermediate step.

By "standard conditions" is meant conditions under which an assay is performed to obtain scientifically meaningful data. Standard conditions are dependent on the particular assay, and can be generally subjective. Normally the standard conditions of an assay will be those conditions that are optimal for obtaining useful data from the particular assay. The standard conditions will generally minimize background signal and maximize the signal sought to be detected.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667$$

By a "set" of compounds is meant a collection of compounds. The compounds may or may not be structurally related.

In the context of this invention, by "target molecule" is meant a molecule that a compound, molecular scaffold, or ligand is being assayed for binding to. The target molecule has an activity that binding of the molecular scaffold or ligand to the target molecule will alter or change. The binding of the compound, scaffold, or ligand to the target molecule can preferably cause a specific biochemical effect when it occurs in a biological system. A "biological system" includes, but is not limited to, a living system such as a human, animal, plant, or insect. In most but not all cases, the target molecule will be a protein or nucleic acid molecule.

By "pharmacophore" is meant a representation of molecular features that are considered to be responsible for a desired activity, such as interacting or binding with a receptor. A pharmacophore can include 3-dimensional (hydrophobic groups, charged/ionizable groups, hydrogen bond donors/acceptors), 2D (substructures), and 1D (physical or biological) properties.

As used herein in connection with numerical values, the terms "approximately" and "about" mean ±10% of the indicated value.

Additional embodiments will be apparent from the Detailed Description and from the claims.

DETAILED DESCRIPTION OF THE PREFERRED EMBODIMENTS

As indicated in the Summary above, the present invention concerns the peroxisome proliferator-activated receptors (PPARs), which have been identified in humans and other mammals. A group of compounds have been identified, corresponding to Formula I, that are active on one or more of the PPARs, in particular compounds that are active one or more human PPARs.

The identification of these compound provides compounds that can be used as agonists on PPARs, as well as for identification or development of additional active compounds, for example, compounds within Formula I.

I. Applications of PPAR Agonists

The PPARs have been recognized as suitable targets for a number of different disease and conditions. Some of those applications are described briefly below. Additional applications are known and the present compounds can also be used for those diseases and conditions.

(a) Insulin resistance and diabetes: In connection with insulin resistance and diabetes, PPARγ is necessary and sufficient for the differentiation of adipocytes in vitro and in vivo. In adipocytes, PPARγ increases the expression of numerous genes involved in lipid metabolism and lipid uptake. In contrast, PPARγ down-regulates leptin, a secreted, adipocyte-selective protein that has been shown to inhibit feeding and augment catabolic lipid metabolism. This receptor activity could explain the increased caloric uptake and storage noted in vivo upon treatment with PPARγ agonists. Clinically, TZDs, including troglitazone, rosiglitazone, and pioglitazone, and non-TZDs, including farglitazar, have insulin-sensitizing and antidiabetic activity. (Berger et al., 2002, *Diabetes Tech. And Ther.* 4:163-174.)

PPARγ has been associated with several genes that affect insulin action. TNFα, a proinflammatory cytokine that is expressed by adipocytes, has been associated with insulin resistance. PPARγ agonists inhibited expression of TNFβ in adipose tissue of obese rodents, and ablated the actions of TNFα in adipocytes in vitro. PPARγ agonists were shown to inhibit expression of 11β-hydroxysteroid dehydrogenase 1 (11β-HSD-1), the enzyme that converts cortisone to the glucocorticoid agonist cortisol, in adipocytes and adipose tissue of type 2 diabetes mouse models. This is noteworthy since hypercortico-steroidism exacerbates insulin resistance. Adipocyte Complement-Related Protein of 30 kDa (Acrp30 or adiponectin) is a secreted adipocyte-specific protein that decreases glucose, triglycerides, and free fatty acids. In comparison to normal human subjects, patients with type 2 diabetes have reduced plasma levels of Acrp30. Treatment of diabetic mice and nondiabetic human subjects with PPAR-γ agonists increased plasma levels of Acrp30. Induction of Acrp30 by PPARγ agonists might therefore also play a key role in the insulin-sensitizing mechanism of PPARγ agonists in diabetes. (Berger et al., 2002, *Diabetes Tech. And Ther.* 4:163-174.)

PPARγ is expressed predominantly in adipose tissue. Thus, it is believed that the net in vivo efficacy of PPARγ agonists involves direct actions on adipose cells with secondary effects in key insulin responsive tissues such as skeletal muscle and liver. This is supported by the lack of glucose-lowering efficacy of rosiglitazone in a mouse model of severe insulin resistance where white adipose tissue was essentially absent. Furthermore, in vivo treatment of insulin resistant rats produces acute (<24 h) normalization of adipose tissue insulin action whereas insulin-mediated glucose uptake in muscle was not improved until several days after the initiation of therapy. This is consistent with the fact that PPARγ agonists can produce an increase in adipose tissue insulin action after direct in vitro incubation, whereas no such effect could be demonstrated using isolated in vitro incubated skeletal muscles. The beneficial metabolic effects of PPARγ agonists on muscle and liver may be mediated by their ability to (a) enhance insulin-mediated adipose tissue uptake, storage (and potentially catabolism) of free fatty acids; (b) induce the production of adipose-derived factors with potential insulin sensitizing activity (e.g., Acrp30); and/or (c) suppress the circulating levels and/or actions of insulin resistance-causing adipose-derived factors such as TNFα or resistin. (Berger et al., 2002, *Diabetes Tech. And Ther.* 4:163-174.)

(b) Dyslipidemia and atherosclerosis: In connection with dyslipidemia and atherosclerosis, PPARα has been shown to play a critical role in the regulation of cellular uptake, activation, and β-oxidation of fatty acids. Activation of PPARα induces expression of fatty acid transport proteins and enzymes in the peroxisomal β-oxidation pathway. Several mitochondrial enzymes involved in the energy-harvesting catabolism of fatty acids are robustly upregulated by PPARα agonists. Peroxisome proliferators also activate expression of the CYP4As, a subclass of cytochrome P450 enzymes that catalyze the ω-hydroxylation of fatty acids, a pathway that is particularly active in the fasted and diabetic states. In sum, it is clear that PPARα is an important lipid sensor and regulator of cellular energy-harvesting metabolism. (Berger et al., 2002, *Diabetes Tech. And Ther.* 4:163-174.)

Atherosclerosis is a very prevalent disease in Westernized societies. In addition to a strong association with elevated LDL cholesterol, "dyslipidemia" characterized by elevated triglyceride-rich particles and low levels of HDL cholesterol is commonly associated with other aspects of a metabolic syndrome that includes obesity, insulin resistance, type 2 diabetes, and an increased risk of coronary artery disease. Thus, in 8,500 men with known coronary artery disease, 38% were found to have low HDL (<35 mg/dL) and 33% had elevated triglycerides (>200 mg/dL). In such patients, treatment with fibrates resulted in substantial triglyceride lowering and modest HDL-raising efficacy. More importantly, a recent large prospective trial showed that treatment with gemfibrozil produced a 22% reduction in cardiovascular events or death. Thus PPARα agonists can effectively improve cardiovascular risk factors and have a net benefit to improve cardiovascular outcomes. In fact, fenofibrate was recently approved in the United States for treatment of type IIA and IIB hyperlipidemia. Mechanisms by which PPARα activation cause triglyceride lowering are likely to include the effects of agonists to suppress hepatic apo-CIII gene expression while also stimulating lipoprotein lipase gene expression. Dual PPARγ/α agonists, including KRP-297 and DRF 2725, possess potent lipid-altering efficacy in addition to antihyperglycemic activity in animal models of diabetes and lipid disorders.

The presence of PPARα and/or PPARγ expression in vascular cell types, including macrophages, endothelial cells, and vascular smooth muscle cells, suggests that direct vascular effects might contribute to potential antiatherosclerosis efficacy. PPARα and PPARα activation have been shown to inhibit cytokine-induced vascular cell adhesion and to suppress monocyte-macrophage migration. Several additional studies have also shown that PPARγ-selective compounds have the capacity to reduce arterial lesion size and attenuate monocyte-macrophage homing to arterial lesions in animal models of atherosclerosis. In addition, two recent studies have suggested that either PPARα or PPARγ activation in macrophages can induce the expression of a cholesterol efflux "pump" protein.

It has been found that relatively selective PPARδ agonists produce minimal, if any, glucose- or triglyceride-lowering activity in murine models of type 2 diabetes in comparison with efficacious PPARγ or PPARα agonists. Subsequently, a modest increase in HDL-cholesterol levels was detected with PPARδ agonists in db/db mice. Recently, Oliver et al. reported that a potent, selective PPARδ agonist could induce a substantial increase in HDL-cholesterol levels while reducing triglyceride levels and insulin resistance in obese rhesus monkeys.

Thus, via multifactorial mechanisms that include improvements in circulating lipids, systemic and local antiinflammatory effects, and, inhibition of vascular cell proliferation, PPARα, PPARγ, and PPARδ agonists can be used in the treatment or prevention of atherosclerosis. (Berger et al., 2002, *Diabetes Tech. And Ther.* 4:163-174.)

(c) Inflammation: Monocytes and macrophages are known to play an important part in the inflammatory process through the release of inflammatory cytokines and the production of nitric oxide by inducible nitric oxide synthase. Rosiglitazone has been shown to induce apoptosis of macrophages at concentrations that paralleled its affinity for PPARγ. This ligand has also been show to block inflammatory cytokine synthesis in colonic cell lines. This latter observation suggests a mechanistic explanation for the observed anti-inflammatory actions of TZDs in rodent models of colitis.

Anti-inflammatory actions have been described for PPARα ligands that can be important in the maintenance of vascular health. Treatment of cytokine-activated human macrophages with PPARα agonists induced apoptosis of the cells. It was reported that PPARα agonists inhibited activation of aortic smooth muscle cells in response to inflammatory stimuli. (Staels et al., 1998, *Nature* 393:790-793.) In hyperlipidemic patients, fenofibrate treatment decreased the plasma concentrations of the inflammatory cytokine interleukin-6.

(d) Hypertension: Hypertension is a complex disorder of the cardiovascular system that has been shown to be associated with insulin resistance. Type 2 diabetes patients demonstrate a 1.5-2-fold increase in hypertension in comparison with the general population. Troglitazone, rosiglitazone, and pioglitazone therapy have been shown to decrease blood pressure in diabetic patients as well as troglitazone therapy in obese, insulin-resistant subjects. Since such reductions in blood pressure were shown to correlate with decreases in insulin levels, they can be mediated by an improvement in insulin sensitivity. However, since TZDs also lowered blood pressure in one-kidney one-clip Sprague Dawley rats, which are not insulin resistant, it was proposed that the hypotensive action of PPARγ agonists is not exerted solely through their ability to improve insulin sensitivity. Other mechanisms that have been invoked to explain the antihypertensive effects of PPARγ agonists include their ability to (a) downregulate expression of peptides that control vascular tone such as PAI-I, endothelin, and type-c natriuretic peptide C or (b) alter calcium concentrations and the calcium sensitivity of vascular cells. (Berger et al., 2002, *Diabetes Tech. And Ther.* 4:163-174.)

In accordance with the description above, isoforms of the PPAR family of nuclear receptors are clearly involved in the systemic regulation of lipid metabolism and serve as "sensors" for fatty acids, prostanoid metabolites, eicosanoids and related molecules. These receptors function to regulate a broad array of genes in a coordinate fashion. Important biochemical pathways that regulate insulin action, lipid oxidation, lipid synthesis, adipocyte differentiation, peroxisome function, cell apoptosis, and inflammation can be modulated through the individual PPAR isoforms. Strong therapeutic effects of PPARα and PPARγ agonists to favorably influence systemic lipid levels, glucose homeostasis, and atherosclerosis risk (in the case of PPARα activation in humans) have recently been discovered. PPARα and PPARγ agonists are presently used clinically to favorably alter systemic lipid levels and glucose homeostasis, respectively. Recent observations made using PPARS ligands suggest that this isoform is also an important therapeutic target for dyslipidemia and insulin resistance, as well.

Thus, PPAR agonists, such as those described herein, can be used in the prophylaxix and/or therapteutic treatment of a variety of different disease and conditions, such as obesity, overweight condition, hyperlipidemia, dyslipidemia including associated diabetic dyslipidemia and mixed dyslipidemia, hypoalphalipoproteinemia, Syndrome X, Type II diabetes mellitus, Type I diabetes, hyperinsulinemia, impaired glucose tolerance, insulin resistance, a diabetic complication (e.g., neuropathy, nephropathy, retinopathy or cataracts), hypertension, coronary heart disease, heart failure, hypercholesterolemia, inflammation, thrombosis, congestive heart failure, cardiovascular disease (including atherosclerosis, arteriosclerosis, and hypertriglyceridemia), epithelial hyperproliferative diseases (such as eczema and psoriasis), and conditions associated with the lung and gut and regulation of appetite and food intake in subjects suffering from disorders such as obesity, anorexia bulimia and anorexia nervosa.

(e) Cancer: PPAR modulation has also been correlated with cancer treatment. (Burstein et al.; *Breast Cancer Res. Treat.* 2003 79(3):391-7; Alderd et al.; *Oncogene,* 2003, 22(22): 3412-6).

(f) Weight Control: Administration of PPARα agonists can induce satiety, and thus are useful in weight loss or maintenance. Such PPARα agonists can act preferentially on PPARα, or can also act on another PPAR, or can be PPAR pan-agonists. Thus, the satiety inducing effect of PPARα agonists can be used for weight control or loss.

II. PPAR Active Compounds

As indicated in the Summary and in connection with applicable diseases and conditions, a number of different PPAR agonists have been identified. In addition, the present invention provides PPAR agonist compounds described by Formula I as provided in the Summary above. Included within Formula I are sub-groups of compounds, for example, subgroups shown by the structures Ia, Ib, Ic, Id, X, and XIV as shown in the synthetic schemes below. Included within such compounds of Formula I, are exemplary compounds provided in Table 1 below. Additional compounds within Formula I can also be prepared and tested to confirm activity using conventional methods and the guidance provided herein.

III. Development of PPAR Active Compounds

A. Modulator Identification and Design

A large number of different methods can be used to identify modulators and to design improved modulators. Some useful methods involve structure-based design.

Structure-based modulator design and identification methods are powerful techniques that can involve searches of computer databases containing a wide variety of potential modulators and chemical functional groups. The computerized design and identification of modulators is useful as the computer databases contain more compounds than the chemical libraries, often by an order of magnitude. For reviews of structure-based drug design and identification (see Kuntz et al. (1994), *Acc. Chem. Res.* 27:117; Guida (1994) *Current Opinion in Struc. Biol.* 4: 777; Colman (1994) *Current Opinion in Struc. Biol.* 4: 868).

The three dimensional structure of a polypeptide defined by structural coordinates can be utilized by these design methods, for example, the structural coordinates of a PPAR. In addition, the three dimensional structures of PPARs determined by the homology, molecular replacement, and NMR techniques can also be applied to modulator design and identification methods.

For identifying modulators, structural information for a PPAR, in particular, structural information for the active site of the PPAR can be used. However, it may be advantageous to utilize structural information from one or more co-crystals of the PPAR with one or more binding compounds. It can also be advantageous if the binding compound has a structural core in common with test compounds.

Such modulator identification and design can, for example, be used to identify and/or develop additional active compounds within Formula I (a sub-group thereof).

1. Design by Searching Molecular Data Bases

One method of rational design searches for modulators by docking the computer representations of compounds from a database of molecules. Publicly available databases include, for example:
  a) ACD from Molecular Designs Limited
  b) NCI from National Cancer Institute
  c) CCDC from Cambridge Crystallographic Data Center
  d) CAST from Chemical Abstract Service
  e) Derwent from Derwent Information Limited
  f) Maybridge from Maybridge Chemical Company LTD
  g) Aldrich from Aldrich Chemical Company
  h) Directory of Natural Products from Chapman & Hall One such data base (ACD distributed by Molecular Designs Limited Information Systems) contains compounds that are synthetically derived or are natural products. Methods available to those skilled in the art can convert a data set represented in two dimensions to one represented in three dimensions. These methods are can be carried out using such computer programs as CONCORD from Tripos Associates or DE-Converter from Molecular Simulations Limited.

Multiple methods of structure-based modulator design are known to those in the art. (Kuntz et al., (1982), *J. Mol. Biol.* 162: 269; Kuntz et aZ., (1994), *Acc. Chem. Res.* 27: 117; Meng et al., (1992), *J. Compt. Chem.* 13: 505; Bohm, (1994), *J. Comp. Aided Molec. Design* 8: 623.)

A computer program widely utilized by those skilled in the art of rational modulator design is DOCK from the University of California in San Francisco. The general methods utilized by this computer program and programs like it are described in three applications below. More detailed information regarding some of these techniques can be found in the Accelerys User Guide, 1995. A typical computer program used for this purpose can perform a processes comprising the following steps or functions:
  (a) remove the existing compound from the protein;
  (b) dock the structure of another compound into the active-site using the computer program (such as DOCK) or by interactively moving the compound into the active-site;
  (c) characterize the space between the compound and the active-site atoms;
  (d) search libraries for molecular fragments which (i) can fit into the empty space between the compound and the active-site, and (ii) can be linked to the compound; and
  (e) link the fragments found above to the compound and evaluate the new modified compound.

Part (c) refers to characterizing the geometry and the complementary interactions formed between the atoms of the active site and the compounds. A favorable geometric fit is attained when a significant surface area is shared between the compound and active-site atoms without forming unfavorable steric interactions. One skilled in the art would note that the method can be performed by skipping parts (d) and (e) and screening a database of many compounds.

Structure-based design and identification of modulators of PPAR function can be used in conjunction with assay screening. As large computer databases of compounds (around 10,000 compounds) can be searched in a matter of hours or even less, the computer-based method can narrow the compounds tested as potential modulators of PPAR function in biochemical or cellular assays.

The above descriptions of structure-based modulator design are not all encompassing and other methods are reported in the literature and can be used, e.g.:

(1) CAVEAT: Bartlett et al., (1989), in Chemical and Biological Problems in Molecular Recognition, Roberts, S. M.; Ley, S. V.; Campbell, M. M. eds.; *Royal Society of Chemistry*: Cambridge, pp. 182-196.

(2) FLOG: Miller et al., (1994), *J. Comp. Aided Molec. Design* 8:153.

(3) PRO Modulator: Clark et al., (1995), *J. Comp. Aided Molec. Design* 9:13.

(4) MCSS: Miranker and Karplus, (1991), *Proteins: Structure, Function, and Genetics* 11:29.

(5) AUTODOCK: Goodsell and Olson, (1990), *Proteins: Structure, Function, and Genetics* 8:195.

(6) GRID: Goodford, (1985), *J. Med. Chem.* 28:849.

2. Design by Modifying Compounds in Complex with a PPAR

Another way of identifying compounds as potential modulators is to modify an existing modulator in the polypeptide active site. For example, the computer representation of modulators can be modified within the computer representation of a PPAR active site. Detailed instructions for this technique can be found, for example, in the Accelerys User Manual, 1995 in LUDI. The computer representation of the modulator is typically modified by the deletion of a chemical group or groups or by the addition of a chemical group or groups.

Upon each modification to the compound, the atoms of the modified compound and active site can be shifted in conformation and the distance between the modulator and the active-site atoms may be scored along with any complementary interactions formed between the two molecules. Scoring can be complete when a favorable geometric fit and favorable complementary interactions are attained. Compounds that have favorable scores are potential modulators.

3. Design by Modifying the Structure of Compounds that Bind a PPAR

A third method of structure-based modulator design is to screen compounds designed by a modulator building or modulator searching computer program. Examples of these types of programs can be found in the Molecular Simulations Package, Catalyst. Descriptions for using this program are documented in the Molecular Simulations User Guide (1995). Other computer programs used in this application are ISIS/HOST, ISIS/BASE, ISIS/DRAW) from Molecular Designs Limited and UNITY from Tripos Associates.

These programs can be operated on the structure of a compound that has been removed from the active site of the three dimensional structure of a compound-PPAR complex. Operating the program on such a compound is preferable since it is in a biologically active conformation.

A modulator construction computer program is a computer program that may be used to replace computer representations of chemical groups in a compound complexed with a PPAR or other biomolecule with groups from a computer database. A modulator searching computer program is a computer program that may be used to search computer representations of compounds from a computer data base that have similar three dimensional structures and similar chemical groups as compound bound to a particular biomolecule.

A typical program can operate by using the following general steps:

(a) map the compounds by chemical features such as by hydrogen bond donors or acceptors, hydrophobic/lipophilic sites, positively ionizable sites, or negatively ionizable sites;

(b) add geometric constraints to the mapped features; and (c) search databases with the model generated in (b).

Those skilled in the art also recognize that not all of the possible chemical features of the compound need be present in the model of (b). One can use any subset of the model to generate different models for data base searches.

B. Identification of Active Compounds Using PPAR Structure and Molecular Scaffolds In addition to the methods described above that are normally applied based on screening hits that have a substantial level of activity, the availability of crystal structures that include ligand binding sites for the various PPARs provides application of a scaffold method for identifying and developing additional PPAR active compounds. As an example, such a scaffold method can be applied using molecular scaffolds within Formula I, or having a scaffold core of Formula I, but can also be applied to other molecular scaffolds that are identified.

Thus, the present invention also concerns methods for designing ligands active on PPARs by using structural information about the ligand binding sites and identified PPAR binding compounds. While such methods can be implemented in many ways (e.g., as described above), highly preferably the process utilizes molecular scaffolds. Such development processes and related methods are described generally below, and can, as indicated by applied to the PPARs, individually and/or in any pair, or as a family.

Molecular scaffolds are low molecular weight molecules that bind with low or very low affinity to the target and typically have low or very low activity on that target and/or act broadly across families of target molecules. The ability of a scaffold or other compound to act broadly across multiple members of a target family is advantageous in developing ligands. For example, a scaffold or set of scaffolds can serve as starting compounds for developing ligands with desired specificity or with desired cross-activity on a selected subset of members of a target family. Further, identification of a set of scaffolds that each bind with members of a target family provides an advantageous basis for selecting a starting point for ligand development for a particular target or subset of targets. In many cases, the ability of a scaffold to bind to and/or have activity on multiple members of a target family is related to active site or binding site homology that exists across the target family.

A scaffold active across multiple members of the target family interacts with surfaces or residues of relatively high homology, i.e., binds to conserved regions of the binding pockets. Scaffolds that bind with multiple members can be modified to provide greater specificity or to have a particular cross-reactivity, e.g., by exploiting differences between target binding sites to provide specificity, and exploiting similarities to design in cross-reactivities. Adding substituents that provide attractive interactions with the particular target typically increases the binding affinity, often increasing the activity. The various parts of the ligand development process are described in more detail in following sections, but the following describes an advantageous approach for scaffold-based ligand development.

Scaffold-based ligand development (scaffold-based drug discovery) can be implemented in a variety of ways, but large scale expression of protein is useful to provide material for crystallization, co-crystallization, and biochemical screening (e.g., binding and activity assays). For crystallization, crystallization conditions can be established for apo protein and a structure determined from those crystals. For screening, preferably a biased library selected for the particular target family is screening for binding and/or activity on the target. Highly preferably a plurality of members from the target family is screened. Such screening, whether on a single target or on multiple members of a target family provides screening hits. Low affinity and/or low activity hits are selected. Such low affinity hits can either identify a scaffold molecule, or allow identification of a scaffold molecule by analyzing common features between binding molecules. Simpler molecules containing the common features can then be tested to determine if they retain binding and/or activity, thereby allowing identification of a scaffold molecule.

When multiple members of a particular target family are used for screening, the overlap in binding and/or activity of compounds can provide a useful selection for compounds that will be subjected to crystallization. For example, for 3 target molecules from a target family, if each target has about 200-500 hits in screening of a particular library, much smaller subsets of those hits will be common to any 2 of the 3 targets, and a still smaller subset will be common to all 3 targets, e.g., 100-300. In many cases, compounds in the subset common to all 3 targets will be selected for co-crystallography, as they provide the broadest potential for ligand development.

Once compounds for co-crystallography are selected, conditions for forming co-crystals are determined, allowing determination of co-crystal structure and the orientation of binding compound in the binding site of the target is determined by solving the structure (this can be highly assisted if an apo protein crystal structure has been determined or if the structure of a close homolog is available for use in a homology model. Preferably the co-crystals are formed by direct co-crystallization rather than by soaking the compound into crystals of apo protein.

From the co-crystals and knowledge of the structure of the binding compounds, additional selection of scaffolds or other binding compounds can be made by applying selection filters, e.g., for (1) binding mode, (2) multiple sites for substitution, and/or (3) tractable chemistry. A binding mode filter can, for example, be based on the demonstration of a dominant binding mode. That is, a scaffold or compounds of a scaffold group bind with a consistent orientation, preferably a consistent orientation across multiple members of a target family. Filtering scaffolds for multiple sites for substitution provides greater potential for developing ligands for specific targets due to the greater capacity for appropriately modifying the structure of the scaffold. Filtering for tractable chemistry also facilitates preparation of ligands derived from a scaffold because the synthetic paths for making derivative compounds are available. Carrying out such a process of development provides scaffolds, preferably of divergent structure.

In some cases, it may be impractical or undesirable to work with a particular target for some or all of the development process. For example, a particular target may be difficult to express, by easily degraded, or be difficult to crystallize. In these cases, a surrogate target from the target family can be used. It is desirable to have the surrogate be as similar as possible to the desired target, thus a family member that has high homology in the binding site should be used, or the binding site can be modified to be more similar to that of the desired target, or part of the sequence of the desired target can be inserted in the family member replacing the corresponding part of the sequence of the family member.

Once one or more scaffolds are identified for a target family, the scaffolds can be used to develop multiple products directed at specific members of the family, or at specific subsets of family members. Thus, starting from a scaffold that acts on multiple member of the target family, derivative compounds (ligands) can be designed and tested that have increasing selectivity. In addition, such ligands are typically developed to have greater activity, and will also typically have greater binding affinity. In this process, starting with the broadly acting scaffold, ligands are developed that have improved selectivity and activity profiles, leading to identification of lead compounds for drug development, leading to drug candidates, and final drug products.

C. Scaffolds

Typically it is advantageous to select scaffolds (and/or compound sets or libraries for scaffold or binding compound identification) with particular types of characteristics, e.g., to select compounds that are more likely to bind to a particular target and/or to select compounds that have physical and/or synthetic properties to simplify preparation of derivatives, to be drug-like, and/or to provide convenient sites and chemistry for modification or synthesis.

Useful chemical properties of molecular scaffolds can include one or more of the following characteristics, but are not limited thereto: an average molecular weight below about 350 daltons, or between from about 150 to about 350 daltons, or from about 150 to about 300 daltons; having a clogP below 3; a number of rotatable bonds of less than 4; a number of hydrogen bond donors and acceptors below 5 or below 4; a Polar Surface Area of less than 100 $Å^2$; binding at protein binding sites in an orientation so that chemical substituents from a combinatorial library that are attached to the scaffold can be projected into pockets in the protein binding site; and possessing chemically tractable structures at its substituent attachment points that can be modified, thereby enabling rapid library construction.

The term "Molecular Polar Surface Area (PSA)" refers to the sum of surface contributions of polar atoms (usually oxygens, nitrogens and attached hydrogens) in a molecule. The polar surface area has been shown to correlate well with drug transport properties, such as intestinal absorption, or blood-brain barrier penetration.

Additional useful chemical properties of distinct compounds for inclusion in a combinatorial library include the ability to attach chemical moieties to the compound that will not interfere with binding of the compound to at least one protein of interest, and that will impart desirable properties to the library members, for example, causing the library members to be actively transported to cells and/or organs of interest, or the ability to attach to a device such as a chromatography column (e.g., a streptavidin column through a molecule such as biotin) for uses such as tissue and proteomics profiling purposes.

A person of ordinary skill in the art will realize other properties that can be desirable for the scaffold or library members to have depending on the particular requirements of the use, and that compounds with these properties can also be sought and identified in like manner. Methods of selecting compounds for assay are known to those of ordinary skill in the art, for example, methods and compounds described in U.S. Pat. Nos. 6,288,234, 6,090,912, 5,840,485, each of which is hereby incorporated by reference in its entirety, including all charts and drawings.

In various embodiments, the present invention provides methods of designing ligands that bind to a plurality of members of a molecular family, where the ligands contain a common molecular scaffold. Thus, a compound set can be assayed for binding to a plurality of members of a molecular family, e.g., a protein family. One or more compounds that bind to a plurality of family members can be identified as molecular scaffolds. When the orientation of the scaffold at the binding site of the target molecules has been determined and chemically tractable structures have been identified, a set of ligands can be synthesized starting with one or a few molecular scaffolds to arrive at a plurality of ligands, wherein each ligand binds to a separate target molecule of the molecular family with altered or changed binding affinity or binding specificity relative to the scaffold. Thus, a plurality of drug lead molecules can be designed to individually target members of a molecular family based on the same molecular scaffold, and act on them in a specific manner.

D. Binding Assays

1. Use of Binding Assays

The methods of the present invention can involve assays that are able to detect the binding of compounds to a target molecule at a signal of at least about three times the standard deviation of the background signal, or at least about four times the standard deviation of the background signal. The assays can also include assaying compounds for low affinity binding to the target molecule. A large variety of assays indicative of binding are known for different target types and can be used for this invention. Compounds that act broadly across protein families are not likely to have a high affinity against individual targets, due to the broad nature of their binding. Thus, assays (e.g., as described herein) highly preferably allow for the identification of compounds that bind with low affinity, very low affinity, and extremely low affinity. Therefore, potency (or binding affinity) is not the primary, nor even the most important, indicia of identification of a potentially useful binding compound. Rather, even those compounds that bind with low affinity, very low affinity, or extremely low affinity can be considered as molecular scaffolds that can continue to the next phase of the ligand design process.

As indicated above, to design or discover scaffolds that act broadly across protein families, proteins of interest can be assayed against a compound collection or set. The assays can preferably be enzymatic or binding assays. In some embodiments it may be desirable to enhance the solubility of the compounds being screened and then analyze all compounds that show activity in the assay, including those that bind with low affinity or produce a signal with greater than about three times the standard deviation of the background signal. These assays can be any suitable assay such as, for example, binding assays that measure the binding affinity between two binding partners. Various types of screening assays that can be useful in the practice of the present invention are known in the art, such as those described in U.S. Pat. Nos. 5,763,198, 5,747, 276, 5,877,007, 6,243,980, 6,294,330, and 6,294,330, each of which is hereby incorporated by reference in its entirety, including all charts and drawings.

In various embodiments of the assays at least one compound, at least about 5%, at least about 10%, at least about 15%, at least about 20%, or at least about 25% of the compounds can bind with low affinity. In many cases, up to about 20% of the compounds can show activity in the screening assay and these compounds can then be analyzed directly with high-throughput co-crystallography, computational analysis to group the compounds into classes with common structural properties (e.g., structural core and/or shape and polarity characteristics), and the identification of common chemical structures between compounds that show activity.

The person of ordinary skill in the art will realize that decisions can be based on criteria that are appropriate for the needs of the particular situation, and that the decisions can be made by computer software programs. Classes can be created containing almost any number of scaffolds, and the criteria selected can be based on increasingly exacting criteria until an arbitrary number of scaffolds is arrived at for each class that is deemed to be advantageous.

2. Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., BIAcore® analysis to test phosphopeptide-SH2 domain interactions, *Methods in Molecular Biology.* 121: 313-21, 2000; Liparoto et al., Biosensor analysis of the interleukin-2 receptor complex, *Journal of Molecular Recognition.* 12:316-21, 1999; Lipschultz et al., Experimental design for analysis of complex kinetics using surface plasmon resonance, *Methods.* 20(3):310-8, 2000; Malmqvist., BIACORE: an affinity biosensor system for characterization of biomolecular interactions, Biochemical Society Transactions 27:335-40, 1999; Alfthan, Surface plasmon resonance biosensors as a tool in antibody engineering, *Biosensors & Bioelectronics.* 13:653-63, 1998; Fivash et al., BIAcore for macromolecular interaction, Current Opinion in Biotechnology. 9:97-101, 1998; Price et al.; Summary report on the ISOBM TD-4 Workshop: analysis of 56 monoclonal antibodies against the MUC1 mucin. *Tumour Biology* 19 Suppl 1:1-20, 1998; Malmqvist et al, Biomolecular interaction analysis: affinity biosensor technologies for functional analysis of proteins, *Current Opinion in Chemical Biology.* 1:378-83, 1997; O'Shannessy et al., Interpretation of deviations from pseudo-first-order kinetic behavior in the characterization of ligand binding by biosensor technology, *Analytical Biochemistry.* 236:275-83, 1996; Malmborg et al., BIAcore as a tool in antibody engineering, *Journal of Immunological Methods.* 183:7-13, 1995; Van Regenmortel, Use of biosensors to characterize recombinant proteins, *Developments in Biological Standardization.* 83:143-51, 1994; and O'Shannessy, Determination of kinetic rate and equilibrium binding constants for macromolecular interactions: a critique of the surface plasmon resonance literature, *Current Opinions in Biotechnology.* 5:65-71, 1994.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

E. High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator. Similarly, when ligands to a target are sought, known ligands of the target can be present in control/calibration assay wells.

F. Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., *The Chemist's Companion: A Handbook Of Practical Data, Techniques, And References*, John Wiley and Sons, N.Y., 1972, Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., *Spectrophotometry and Spectrofluorometry: A Practical Approach*, pp. 91-114, IRL Press Ltd. (1987); and Bell, *Spectroscopy In Biochemistry*, Vol. 1, pp. 155-194, CRC Press (1981).

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., Application of Fluorescence Polarization Assays in High-Throughput Screening, *Genetic Engineering News*, 17:27, 1997.

FP is particularly desirable since its readout is independent of the emission intensity (Checovich, W. J., et al., *Nature* 375:254-256, 1995; Dandliker, W. B., et al., *Methods in Enzymology* 74:3-28, 1981) and is thus insensitive to the presence of colored compounds that quench fluorescence emission. FP and FRET (see below) are well-suited for identifying compounds that block interactions between sphingolipid receptors and their ligands. See, for example, Parker et al., Development of high throughput screening assays using fluorescence polarization: nuclear receptor-ligand-binding and kinase/phosphatase assays, J Biomol Screen 5:77-88, 2000.

Fluorophores derived from sphingolipids that may be used in FP assays are commercially available. For example, Molecular Probes (Eugene, Oreg.) currently sells sphingomyelin and one ceramide fluorophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan A G, Hombrechtikon, Switzerland). General multi-well plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., Curr. Biol. 6:178-182, 1996; Mitra et al., Gene 173:13-17 1996; and Selvin et al., Meth. Enzymol. 246:300-345, 1995. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a FMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., J. Lipid Res. 38:2365-2373 (1997); Kahl et al., Anal. Biochem. 243:282-283 (1996); Undenfriend et al., Anal. Biochem. 161:494-500 (1987)). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., Anal. Biochem. 257:112-119, 1998).

Additionally, the assay can utilize AlphaScreen (amplified luminescent proximity homogeneous assay) format, e.g., AlphaScreening system (Packard BioScience). AlphaScreen is generally described in Seethala and Prabhavathi, Homogenous Assays: AlphaScreen, Handbook of Drug Screening, Marcel Dekkar Pub. 2001, pp. 106-110. Applications of the technique to PPAR receptor ligand binding assays are described, for example, in Xu et al., 2002, Nature 415:813-817.

G. Assay Compounds and Molecular Scaffolds

As described above, preferred characteristics of a scaffold include being of low molecular weight (e.g., less than 350 Da, or from about 100 to about 350 daltons, or from about 150 to about 300 daltons). Preferably clog P of a scaffold is from −1 to 8, more preferably less than 6, 5, or 4, most preferably less than 3. In particular embodiments the clogP is in a range −1 to an upper limit of 2, 3, 4, 5, 6, or 8; or is in a range of 0 to an upper limit of 2, 3, 4, 5, 6, or 8. Preferably the number of rotatable bonds is less than 5, more preferably less than 4. Preferably the number of hydrogen bond donors and acceptors is below 6, more preferably below 5. An additional criterion that can be useful is a Polar Surface Area of less than 100. Guidance that can be useful in identifying criteria for a particular application can be found in Lipinski et al., Advanced Drug Delivery Reviews 23 (1997) 3-25, which is hereby incorporated by reference in its entirety.

A scaffold will preferably bind to a given protein binding site in a configuration that causes substituent moieties of the scaffold to be situated in pockets of the protein binding site. Also, possessing chemically tractable groups that can be chemically modified, particularly through synthetic reactions, to easily create a combinatorial library can be a preferred characteristic of the scaffold. Also preferred can be having positions on the scaffold to which other moieties can be attached, which do not interfere with binding of the scaffold to the protein(s) of interest but do cause the scaffold to achieve a desirable property, for example, active transport of the scaffold to cells and/or organs, enabling the scaffold to be attached to a chromatographic column to facilitate analysis, or another desirable property. A molecular scaffold can bind to a target molecule with any affinity, such as binding with an affinity measurable as about three times the standard deviation of the background signal, or at high affinity, moderate affinity, low affinity, very low affinity, or extremely low affinity.

Thus, the above criteria can be utilized to select many compounds for testing that have the desired attributes. Many compounds having the criteria described are available in the commercial market, and may be selected for assaying depending on the specific needs to which the methods are to be applied. In some cases sufficiently large numbers of compounds may meet specific criteria that additional methods to group similar compounds may be helpful. A variety of methods to assess molecular similarity, such as the Tanimoto coefficient have been used, see Willett et al, Journal of Chemical Information and Computer Science 38 (1998), 983-996. These can be used to select a smaller subset of a group of highly structurally redundant compounds. In addition, cluster analysis based on relationships between the compounds, or structural components of the compound, can also be carried out to the same end; see Lance and Williams *Computer Journal* 9 (1967) 373-380, Jarvis and Patrick *IEEE Transactions in Computers* C-22 (1973) 1025-1034 for clustering algorithms, and Downs et al. *Journal of Chemical Information and Computer Sciences* 34 (1994) 1094-1102 for a review of these methods applied to chemical problems. One method of deriving the chemical components of a large group of potential scaffolds is to virtually break up the compound at rotatable bonds so as to yield components of no less than 10 atoms. The resulting components may be clustered based on some measure of similarity, e.g. the Tanimoto coefficient, to yield the common component groups in the original collection of compounds. For each component group, all compounds containing that component may be clustered, and the resulting clusters used to select a diverse set of compounds containing a common chemical core structure. In this fashion, a useful library of scaffolds may be derived even from millions of commercial compounds.

A "compound library" or "library" is a collection of different compounds having different chemical structures. A compound library is screenable, that is, the compound library members therein may be subject to screening assays. In preferred embodiments, the library members can have a molecular weight of from about 100 to about 350 daltons, or from about 150 to about 350 daltons.

Libraries can contain at least one compound that binds to the target molecule at low affinity. Libraries of candidate compounds can be assayed by many different assays, such as those described above, e.g., a fluorescence polarization assay. Libraries may consist of chemically synthesized peptides, peptidomimetics, or arrays of combinatorial chemicals that are large or small, focused or nonfocused. By "focused" it is meant that the collection of compounds is prepared using the structure of previously characterized compounds and/or pharmacophores.

Compound libraries may contain molecules isolated from natural sources, artificially synthesized molecules, or molecules synthesized, isolated, or otherwise prepared in such a manner so as to have one or more moieties variable, e.g., moieties that are independently isolated or randomly synthesized. Types of molecules in compound libraries include but are not limited to organic compounds, polypeptides and nucleic acids as those terms are used herein, and derivatives, conjugates and mixtures thereof.

Compound libraries useful for the invention may be purchased on the commercial market or prepared or obtained by any means including, but not limited to, combinatorial chemistry techniques, fermentation methods, plant and cellular extraction procedures and the like (see, e.g., Cwirla et al., *Biochemistry* 1990, 87, 6378-6382; Houghten et al., *Nature* 1991, 354, 84-86; Lam et al., *Nature* 1991, 354, 82-84; Brenner et al., *Proc. Natl. Acad. Sci. USA* 1992, 89, 5381-5383; R. A. Houghten, *Trends Genet.* 1993, 9, 235-239; E. R. Felder, Chimia 1994, 48, 512-541; Gallop et al., *J. Med. Chem.* 1994, 37, 1233-1251; Gordon et al., *J. Med. Chem.* 1994, 37, 1385-1401; Carell et al., *Chem. Biol.* 1995, 3, 171-183; Madden et al., *Perspectives in Drug Discovery and Design* 2, 269-282; Lebl et al., *Biopolymers* 1995, 37 177-198); small molecules assembled around a shared molecular structure; collections of chemicals that have been assembled by various commercial and noncommercial groups, natural products; extracts of marine organisms, fungi, bacteria, and plants.

Preferred libraries can be prepared in a homogenous reaction mixture, and separation of unreacted reagents from members of the library is not required prior to screening. Although many combinatorial chemistry approaches are based on solid state chemistry, liquid phase combinatorial chemistry is capable of generating libraries (Sun C M., Recent advances in liquid-phase combinatorial chemistry, *Combinatorial Chemistry & High Throughput Screening*. 2:299-318, 1999).

Libraries of a variety of types of molecules are prepared in order to obtain members therefrom having one or more preselected attributes that can be prepared by a variety of techniques, including but not limited to parallel array synthesis (Houghton, *Annu Rev Pharmacol Toxicol* 2000 40:273-82, Parallel array and mixture-based synthetic combinatorial chemistry; solution-phase combinatorial chemistry (Merritt, *Comb Chem High Throughput Screen* 1998 1(2):57-72, Solution phase combinatorial chemistry, Coe et al., Mol Divers 1998-99; 4(1):31-8, Solution-phase combinatorial chemistry, Sun, *Comb Chem High Throughput Screen* 1999 2(6):299-318, Recent advances in liquid-phase combinatorial chemistry); synthesis on soluble polymer (Gravert et al., *Curr Opin Chem Biol* 1997 1(1):107-13, Synthesis on soluble polymers: new reactions and the construction of small molecules); and the like. See, e.g., Dolle et al., *J Comb Chem* 1999 1(4):235-82, Comprehensive survey of cominatorial library synthesis: 1998. Freidinger R M., Nonpeptidic ligands for peptide and protein receptors, Current Opinion in Chemical Biology; and Kundu et al., *Prog Drug Res* 1999; 53:89-156, Combinatorial chemistry: polymer supported synthesis of peptide and non-peptide libraries). Compounds may be clinically tagged for ease of identification (Chabala, *Curr Opin Biotechnol* 1995 6(6):633-9, Solid-phase combinatorial chemistry and novel tagging methods for identifying leads).

The combinatorial synthesis of carbohydrates and libraries containing oligosaccharides have been described (Schweizer et al., *Curr Opin Chem Biol* 1999 3(3):291-8, Combinatorial synthesis of carbohydrates). The synthesis of natural-product based compound libraries has been described (Wessjohann, *Curr Opin Chem Biol* 2000 4(3):303-9, Synthesis of natural-product based compound libraries).

Libraries of nucleic acids are prepared by various techniques, including by way of non-limiting example the ones described herein, for the isolation of aptamers. Libraries that include oligonucleotides and polyaminooligonucleotides (Markiewicz et al., Synthetic oligonucleotide combinatorial libraries and their applications, *Farmaco*. 55:174-7, 2000) displayed on streptavidin magnetic beads are known. Nucleic acid libraries are known that can be coupled to parallel sampling and be deconvoluted without complex procedures such as automated mass spectrometry (Enjalbal C. Martinez J. Aubagnac J L, Mass spectrometry in combinatorial chemistry, *Mass Spectrometry Reviews*. 19:139-61, 2000) and parallel tagging. (Perrin D M., Nucleic acids for recognition and catalysis: landmarks, limitations, and looking to the future, *Combinatorial Chemistry & High Throughput Screening* 3:243-69).

Peptidomimetics are identified using combinatorial chemistry and solid phase synthesis (Kim H O. Kahn M., A merger of rational drug design and combinatorial chemistry: development and application of peptide secondary structure mimetics, Combinatorial Chemistry & High Throughput Screening 3:167-83, 2000; al-Obeidi, *Mol Biotechnol* 1998 9(3):205-23, Peptide and peptidomimetric libraries. Molecular diversity and drug design). The synthesis may be entirely random or based in part on a known polypeptide.

Polypeptide libraries can be prepared according to various techniques. In brief, phage display techniques can be used to produce polypeptide ligands (Gram H., Phage display in proteolysis and signal transduction, Combinatorial Chemistry & High Throughput Screening. 2:19-28, 1999) that may be used as the basis for synthesis of peptidomimetics. Polypeptides, constrained peptides, proteins, protein domains, antibodies, single chain antibody fragments, antibody fragments, and antibody combining regions are displayed on filamentous phage for selection.

Large libraries of individual variants of human single chain Fv antibodies have been produced. See, e.g., Siegel R W. Allen B. Pavlik P. Marks J D. Bradbury A., Mass spectral analysis of a protein complex using single-chain antibodies selected on a peptide target: applications to functional genomics, *Journal of Molecular Biology* 302:285-93, 2000; Poul M A. Becerril B. Nielsen U B. Morisson P. Marks J D., Selection of tumor-specific internalizing human antibodies from phage libraries. Source *Journal of Molecular Biology.* 301:1149-61, 2000; Amersdorfer P. Marks J D., Phage libraries for generation of anti-botulinum scFv antibodies, *Methods in Molecular Biology.* 145:219-40, 2001; Hughes-Jones N C. Bye J M. Gorick B D. Marks J D. Ouwehand W H., Synthesis of Rh Fv phage-antibodies using VH and VL germline genes, *British Journal of Haematology.* 105:811-6, 1999; McCall A M. Amoroso A R. Sautes C. Marks J D. Weiner L M., Characterization of anti-mouse Fc gamma RII single-chain Fv fragments derived from human phage display libraries, *Immunotechnology.* 4:71-87, 1998; Sheets M D. Amersdorfer P. Finnern R. Sargent P. Lindquist E. Schier R. Hemingsen G. Wong C. Gerhart J C. Marks J D. Lindquist E., Efficient construction of a large nonimmune phage antibody library: the production of high-affinity human single-chain antibodies to protein antigens (published erratum appears in *Proc Natl Acad Sci USA* 1999 96:795), *Proc Natl Acad Sci USA* 95:6157-62, 1998).

Focused or smart chemical and pharmacophore libraries can be designed with the help of sophisticated strategies involving computational chemistry (e.g., Kundu B. Khare S K. Rastogi S K., Combinatorial chemistry: polymer supported synthesis of peptide and non-peptide libraries, *Progress in Drug Research* 53:89-156, 1999) and the use of structure-based ligands using database searching and docking, de novo drug design and estimation of ligand binding affinities (Joseph-McCarthy D., Computational approaches to structure-based ligand design, *Pharmacology & Therapeutics* 84:179-91, 1999; Kirkpatrick D L. Watson S. Ulhaq S., Structure-based drug design: combinatorial chemistry and molecular modeling, *Combinatorial Chemistry & High Throughput Screening.* 2:211-21, 1999; Eliseev A V. Lehn J M., Dynamic combinatorial chemistry: evolutionary formation and screening of molecular libraries, *Current Topics in Microbiology & Immunology* 243:159-72, 1999; Bolger et al., *Methods Enz.* 203:21-45, 1991; Martin, *Methods Enz.* 203:587-613, 1991; Neidle et al., *Methods Enz.* 203:433-458, 1991; U.S. Pat. No. 6,178,384).

Selecting a library of potential scaffolds and a set of assays measuring binding to representative target molecules which are in a particular protein family thus allows the creation of a data set profiling binding of the library to the target protein family. Groups of scaffolds with different sets of binding properties can be identified using the information within this dataset. Thus, groups of scaffolds binding to one, two or three members of the family may be selected for particular applications.

In many cases, a group of scaffolds exhibiting binding to two or more members of a target protein family will contain scaffolds with a greater likelihood that such binding results from specific interactions with the individual target proteins. This would be expected to substantially reduce the effect of so-called "promiscuous inhibitors" which severely complicate the interpretation of screening assays (see McGovern et al *Journal of Medicinal Chemistry* 45:1712-22, 2002). Thus, in many preferred applications the property of displaying binding to multiple target molecules in a protein family may be used as a selection criteria to identify molecules with desirable properties. In addition, groups of scaffolds binding to specific subsets of a set of potential target molecules may be selected. Such a case would include the subset of scaffolds that bind to any two of three or three of five members of a target protein family.

Such subsets may also be used in combination or opposition to further define a group of scaffolds that have additional desirable properties. This would be of significant utility in cases where inhibiting some members of a protein family had known desirable effects, such as inhibiting tumor growth, whereas inhibiting other members of the protein family which were found to be essential for normal cell function would have undesirable effects. A criteria that would be useful in such a case includes selecting the subset of scaffolds binding to any two of three desirable target molecules and eliminating from this group any that bound to more than one of any three undesirable target molecules.

H. Crystallography

After binding compounds have been determined, the orientation of compound bound to target is determined. Preferably this determination involves crystallography on co-crystals of molecular scaffold compounds with target. Most protein crystallographic platforms can preferably be designed to analyze up to about 500 co-complexes of compounds, ligands, or molecular scaffolds bound to protein targets due to the physical parameters of the instruments and convenience of operation.

If the number of scaffolds that have binding activity exceeds a number convenient for the application of crystallography methods, the scaffolds can be placed into groups based on having at least one common chemical structure or other desirable characteristics, and representative compounds can be selected from one or more of the classes. Classes can be made with increasingly exacting criteria until a desired number of classes (e.g., 10, 20, 50, 100, 200, 300, 400, 500) is obtained. The classes can be based on chemical structure similarities between molecular scaffolds in the class, e.g., all possess a pyrrole ring, benzene ring, or other chemical feature. Likewise, classes can be based on shape characteristics, e.g., space-filling characteristics.

The co-crystallography analysis can be performed by co-complexing each scaffold with its target, e.g., at concentrations of the scaffold that showed activity in the screening assay. This co-complexing can, for example, be accomplished with the use of low percentage organic solvents with the target molecule and then concentrating the target with each of the scaffolds. In preferred embodiments these solvents are less than 5% organic solvent such as dimethyl sulfoxide (DMSO), ethanol, methanol, or ethylene glycol in water or another aqueous solvent.

Each scaffold complexed to the target molecule can then be screened with a suitable number of crystallization screening conditions at appropriate temperature, e.g., both 4 and 20 degrees. In preferred embodiments, about 96 crystallization screening conditions can be performed in order to obtain sufficient information about the co-complexation and crystallization conditions, and the orientation of the scaffold at the binding site of the target molecule. Crystal structures can then be analyzed to determine how the bound scaffold is oriented physically within the binding site or within one or more binding pockets of the molecular family member.

It is desirable to determine the atomic coordinates of the compounds bound to the target proteins in order to determine which is a most suitable scaffold for the protein family. X-ray crystallographic analysis is therefore most preferable for determining the atomic coordinates. Those compounds selected can be further tested with the application of medicinal chemistry. Compounds can be selected for medicinal chemistry testing based on their binding position in the target molecule. For example, when the compound binds at a binding site, the compound's binding position in the binding site of the target molecule can be considered with respect to the chemistry that can be performed on chemically tractable structures or sub-structures of the compound, and how such modifications on the compound are expected to interact with structures or sub-structures on the binding site of the target. Thus, one can explore the binding site of the target and the chemistry of the scaffold in order to make decisions on how to modify the scaffold to arrive at a ligand with higher potency and/or selectivity.

The structure of the target molecule bound to the compound may also be superimposed or aligned with other structures of members of the same protein family. In this way modifications of the scaffold can be made to enhance the binding to members of the target family in general, thus enhancing the utility of the scaffold library. Different useful alignments may be generated, using a variety of criteria such as minimal RMSD superposition of alpha-carbons or backbone atoms of homologous or structurally related regions of the proteins.

These processes allow for more direct design of ligands, by utilizing structural and chemical information obtained directly from the co-complex, thereby enabling one to more efficiently and quickly design lead compounds that are likely to lead to beneficial drug products. In various embodiments it may be desirable to perform co-crystallography on all scaffolds that bind, or only those that bind with a particular affinity, for example, only those that bind with high affinity, moderate affinity, low affinity, very low affinity, or extremely low affinity. It may also be advantageous to perform co-crystallography on a selection of scaffolds that bind with any combination of affinities.

Standard X-ray protein diffraction studies such as by using a Rigaku RU-200® (Rigaku, Tokyo, Japan) with an X-ray imaging plate detector or a synchrotron beam-line can be performed on co-crystals and the diffraction data measured on a standard X-ray detector, such as a CCD detector or an X-ray imaging plate detector.

Performing X-ray crystallography on about 200 co-crystals should generally lead to about 50 co-crystal structures, which should provide about 10 scaffolds for validation in chemistry, which should finally result in about 5 selective leads for target molecules.

Additives that promote co-crystallization can of course be included in the target molecule formulation in order to enhance the formation of co-crystals. In the case of proteins or enzymes, the scaffold to be tested can be added to the protein formulation, which is preferably present at a concentration of approximately 1 mg/ml. The formulation can also contain between 0%-10% (v/v) organic solvent, e.g. DMSO, methanol, ethanol, propane diol, or 1,3 dimethyl propane diol (MPD) or some combination of those organic solvents. Compounds are preferably solubilized in the organic solvent at a concentration of about 10 mM and added to the protein sample at a concentration of about 100 mM. The protein-compound complex is then concentrated to a final concentration of protein of from about 5 to about 20 mg/ml. The complexation and concentration steps can conveniently be performed using a 96 well formatted concentration apparatus (e.g., Amicon Inc., Piscataway, N.J.). Buffers and other reagents present in the formulation being crystallized can contain other components that promote crystallization or are compatible with crystallization conditions, such as DTT, propane diol, glycerol.

The crystallization experiment can be set-up by placing small aliquots of the concentrated protein-compound complex (e.g., 1 μl) in a 96 well format and sampling under 96 crystallization conditions. (Other formats can also be used, for example, plates with fewer or more wells.) Crystals can typically be obtained using standard crystallization protocols that can involve the 96 well crystallization plate being placed at different temperatures. Co-crystallization varying factors other than temperature can also be considered for each protein-compound complex if desirable. For example, atmospheric pressure, the presence or absence of light or oxygen, a change in gravity, and many other variables can all be tested. The person of ordinary skill in the art will realize other variables that can advantageously be varied and considered. Conveniently, commercially available crystal screening plates with specified conditions in individual wells can be utilized.

I. Virtual Assays

As described above, virtual assays or compound design techniques are useful for identification and design of modulators; such techniques are also applicable to a molecular scaffold method. Commercially available software that generates three-dimensional graphical representations of the complexed target and compound from a set of coordinates provided can be used to illustrate and study how a compound is oriented when bound to a target. (e.g., InsightII®, Accelerys, San Diego, Calif.; or Sybyl®, Tripos Associates, St. Louis, Mo.). Thus, the existence of binding pockets at the binding site of the targets can be particularly useful in the present invention. These binding pockets are revealed by the crystallographic structure determination and show the precise chemical interactions involved in binding the compound to the binding site of the target. The person of ordinary skill will realize that the illustrations can also be used to decide where chemical groups might be added, substituted, modified, or deleted from the scaffold to enhance binding or another desirable effect, by considering where unoccupied space is located in the complex and which chemical substructures might have suitable size and/or charge characteristics to fill it. The person of ordinary skill will also realize that regions within the binding site can be flexible and its properties can change as a result of scaffold binding, and that chemical groups can be specifically targeted to those regions to achieve a desired effect. Specific locations on the molecular scaffold can be considered with reference to where a suitable chemical substructure can be attached and in which conformation, and which site has the most advantageous chemistry available.

An understanding of the forces that bind the compounds to the target proteins reveals which compounds can most advantageously be used as scaffolds, and which properties can most effectively be manipulated in the design of ligands. The person of ordinary skill will realize that steric, ionic, polar, hydrogen bond, and other forces can be considered for their contribution to the maintenance or enhancement of the target-compound complex. Additional data can be obtained with automated computational methods, such as docking and/or molecular dynamics simulations, which can afford a measure of the energy of binding. In addition, to account for other effects such as entropies of binding and desolvation penalties, methods which provide a measure of these effects can be integrated into the automated computational approach. The compounds selected can be used to generate information about the chemical interactions with the target or for elucidating chemical modifications that can enhance selectivity of binding of the compound.

An exemplary calculation of binding energies between protein-ligand complexes can be obtained using the FlexX score (an implementation of the Bohm scoring function) within the Tripos software suite (Tripos Associates, St. Louis, Mo.). The form for that equation is shown below:

$$\Delta G_{bind} = \Delta G_{tr} + \Delta G_{hb} + \Delta G_{ion} + \Delta G_{lipo} + \Delta G_{arom} + \Delta G_{rot}$$

where: $\Delta G_{tr}$ is a constant term that accounts for the overall loss of rotational and translational entropy of the ligand, $\Delta G_{hb}$ accounts for hydrogen bonds formed between the ligand and protein, $\Delta G_{ion}$ accounts for the ionic interactions between the ligand and protein, $\Delta G_{lipo}$ accounts for the lipophilic interaction that corresponds to the protein-ligand contact surface, $\Delta G_{arom}$ accounts for interactions between aromatic rings in the protein and ligand, and $\Delta G_{rot}$ accounts for the entropic penalty of restricting rotatable bonds in the ligand upon binding. The calculated binding energy for compounds that bind strongly to a given target will likely be lower than −25 kcal/mol, while the calculated binding affinity for a good scaffold or an unoptimized compound will generally be in the range of −15 to −20. The penalty for restricting a linker such as the ethylene glycol or hexatriene is estimated as typically being in the range of +5 to +15.

This method estimates the free energy of binding that a lead compound should have to a target protein for which there is a crystal structure, and it accounts for the entropic penalty of flexible linkers. It can therefore be used to estimate the penalty incurred by attaching linkers to molecules being screened and the binding energy that a lead compound must attain in order to overcome the penalty of the linker. The method does not account for solvation, and the entropic penalty is likely overestimated when the linkers are bound to the solid phase through an additional binding complex, e.g., a biotin:streptavidin complex.

Another exemplary method for calculating binding energies is the MM-PBSA technique (Massova and Kollman, *Journal of the American Chemical Society* 121:8133-43, 1999; Chong et al, *Proceedings of the National Academy of sciences* 96:14330-5,1999; Donini and Kollman, *Journal of Medicinal Chemistry* 43:4180-8, 2000). This method uses a Molecular Dynamics approach to generate many sample configurations of the compound and complexed target molecule, then calculates an interaction energy using the well-known AMBER force field (Cornell, et al *Journal of the American Chemical Society* 117:5179-97 1995) with corrections for desolvation and entropy of binding from the ensemble.

Use of this method yields binding energies highly correlated with those found experimentally. The absolute binding energies calculated with this method are reasonably accurate, and the variation of binding energies is approximately linear with a slope of 1+/−0.5. Thus, the binding energies of compounds interacting strongly with a given target will be lower than about −8 kcal/mol, while a binding energy of a good scaffold or unoptimized compound will be in the range of −3 to −7 kcal/mol.

Computer models, such as homology models (i.e., based on a known, experimentally derived structure) can be constructed using data from the co-crystal structures. A computer program such as Modeller (Accelrys, San Diego Calif.) may be used to assign the three dimensional coordinates to a protein sequence using an alignment of sequences and a set or sets of template coordinates. When the target molecule is a protein or enzyme, preferred co-crystal structures for making homology models contain high sequence identity in the binding site of the protein sequence being modeled, and the proteins will preferentially also be within the same class and/or fold family. Knowledge of conserved residues in active sites of a protein class can be used to select homology models that accurately represent the binding site. Homology models can also be used to map structural information from a surrogate protein where an apo or co-crystal structure exists to the target protein.

Virtual screening methods, such as docking, can also be used to predict the binding configuration and affinity of scaffolds, compounds, and/or combinatorial library members to homology models. Using this data, and carrying out "virtual experiments" using computer software can save substantial resources and allow the person of ordinary skill to make decisions about which compounds can be suitable scaffolds or ligands, without having to actually synthesize the ligand and perform co-crystallization. Decisions thus can be made about which compounds merit actual synthesis and co-crystallization. An understanding of such chemical interactions aids in the discovery and design of drugs that interact more advantageously with target proteins and/or are more selective for one protein family member over others. Thus, applying these principles, compounds with superior properties can be discovered.

J. Ligand Design and Preparation

The design and preparation of ligands can be performed with or without structural and/or co-crystallization data by considering the chemical structures in common between the active scaffolds of a set. In this process structure-activity hypotheses can be formed and those chemical structures found to be present in a substantial number of the scaffolds, including those that bind with low affinity, can be presumed to have some effect on the binding of the scaffold. This binding can be presumed to induce a desired biochemical effect when it occurs in a biological system (e.g., a treated mammal). New or modified scaffolds or combinatorial libraries derived from scaffolds can be tested to disprove the maximum number of binding and/or structure-activity hypotheses. The remaining hypotheses can then be used to design ligands that achieve a desired binding and biochemical effect.

But in many cases it will be preferred to have co-crystallography data for consideration of how to modify the scaffold to achieve the desired binding effect (e.g., binding at higher affinity or with higher selectivity). Using the case of proteins and enzymes, co-crystallography data shows the binding pocket of the protein with the molecular scaffold bound to the binding site, and it will be apparent that a modification can be made to a chemically tractable group on the scaffold. For example, a small volume of space at a protein binding site or pocket might be filled by modifying the scaffold to include a small chemical group that fills the volume. Filling the void volume can be expected to result in a greater binding affinity, or the loss of undesirable binding to another member of the protein family. Similarly, the co-crystallography data may show that deletion of a chemical group on the scaffold may decrease a hindrance to binding and result in greater binding affinity or specificity.

Various software packages have implemented techniques which facilitate the identification and characterization of interactions of potential binding sites from complex structure, or from an apo structure of a target molecule, i.e. one without a compound bound (e.g. SiteID, Tripos Associates, St. Louis Mo. and SiteFinder, Chemical Computing Group, Montreal Canada, GRID, Molecular Discovery Ltd., London UK). Such techniques can be used with the coordinates of a complex between the scaffold of interest and a target molecule, or these data in conjunction with data for a suitably aligned or superimposed related target molecule, in order to evaluate changes to the scaffold that would enhance binding to the desired target molecule structure or structures. Molecular Interaction Field-computing techniques, such as those implemented in the program GRID, result in energy data for particular positive and negative binding interactions of different computational chemical probes being mapped to the vertices of a matrix in the coordinate space of the target molecule. These data can then be analyzed for areas of substitution around the scaffold binding site which are predicted to have a favorable interaction for a particular target molecule. Compatible chemical substitution on the scaffold e.g. a methyl, ethyl or phenyl group in a favorable interaction region computed from a hydrophobic probe, would be expected to result in an improvement in affinity of the scaffold. Conversely, a scaffold could be made more selective for a particular target molecule by making such a substitution in a region predicted to have an unfavorable hydrophobic interaction in a second, related undesirable target molecule.

It can be desirable to take advantage of the presence of a charged chemical group located at the binding site or pocket of the protein. For example, a positively charged group can be complemented with a negatively charged group introduced on the molecular scaffold. This can be expected to increase binding affinity or binding specificity, thereby resulting in a more desirable ligand. In many cases, regions of protein binding sites or pockets are known to vary from one family member to another based on the amino acid differences in those regions. Chemical additions in such regions can result in the creation or elimination of certain interactions (e.g., hydrophobic, electrostatic, or entropic) that allow a compound to be more specific for one protein target over another or to bind with greater affinity, thereby enabling one to synthesize a compound with greater selectivity or affinity for a particular family member. Additionally, certain regions can contain amino acids that are known to be more flexible than others. This often occurs in amino acids contained in loops connecting elements of the secondary structure of the protein, such as alpha helices or beta strands. Additions of chemical moieties can also be directed to these flexible regions in order to increase the likelihood of a specific interaction occurring between the protein target of interest and the compound. Virtual screening methods can also be conducted in silico to assess the effect of chemical additions, subtractions, modifications, and/or substitutions on compounds with respect to members of a protein family or class.

The addition, subtraction, or modification of a chemical structure or sub-structure to a scaffold can be performed with any suitable chemical moiety. For example the following moieties, which are provided by way of example and are not intended to be limiting, can be utilized: hydrogen, alkyl, alkoxy, phenoxy, alkenyl, alkynyl, phenylalkyl, hydroxyalkyl, haloalkyl, aryl, arylalkyl, alkyloxy, alkylthio, alkenylthio, phenyl, phenylalkyl, phenylalkylthio, hydroxyalkyl-thio, alkylthiocarbbamylthio, cyclohexyl, pyridyl, piperidinyl, alkylamino, amino, nitro, mercapto, cyano, hydroxyl, a halogen atom, halomethyl, an oxygen atom (e.g., forming a ketone or N-oxide) or a sulphur atom (e.g., forming a thiol, thione, di-alkylsulfoxide or sulfone) are all examples of moieties that can be utilized.

Additional examples of structures or sub-structures that may be utilized are an aryl optionally substituted with one, two, or three substituents independently selected from the group consisting of alkyl, alkoxy, halogen, trihalomethyl, carboxylate, nitro, and ester moieties; an amine of formula —$NX_2X_3$, where $X_2$ and $X_3$ are independently selected from the group consisting of hydrogen, saturated or unsaturated alkyl, and homocyclic or heterocyclic ring moieties; halogen or trihalomethyl; a ketone of formula —$COX_4$, where $X_4$ is selected from the group consisting of alkyl and homocyclic or heterocyclic ring moieties; a carboxylic acid of formula —$(X_5)_n COOH$ or ester of formula $(X_6)_n COOX_7$, where $X_5$, $X_6$, and $X_7$ and are independently selected from the group consisting of alkyl and homocyclic or heterocyclic ring moieties and where n is 0 or 1; an alcohol of formula $(X_8)_n OH$ or an alkoxy moiety of formula —$(X_8)_n OX_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; an amide of formula $NHCOX_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; $SO_2$, $NX_{11}X_{12}$, where $X_{11}$ and $X_{12}$ are selected from the group consisting of hydrogen, alkyl, and homocyclic or heterocyclic ring moieties; a homocyclic or heterocyclic ring moiety optionally substituted with one, two, or three substituents independently selected from the group consisting of alkyl, alkoxy, halogen, trihalomethyl, carboxylate, nitro, and ester moieties; an aldehyde of formula —COH; a sulfone of formula —$SO_2X_{13}$, where $X_{13}$ is selected from the group consisting of saturated or unsaturated alkyl and homocyclic or heterocyclic ring moieties; and a nitro of formula —$NO_2$.

K. Identification of Binding Characteristics of Binding Compounds

It can also be beneficial in selecting compounds for testing to first identify binding characteristics that a ligand should advantageously possess. This can be accomplished by analyzing the interactions that a plurality of different binding compounds have with a particular target, e.g., interactions with one or more conserved residues in the binding site. These interactions are identified by considering the nature of the interacting moieties. In this way, atoms or groups that can participate in hydrogen bonding, polar interactions, charge-charge interactions, and the like are identified based on known structural and electronic factors.

L. Identification of Energetically Allowed Sites for Attachment

In addition to the identification and development of ligands, determination of the orientation of a molecular scaffold or other binding compound in a binding site allows identification of energetically allowed sites for attachment of the binding molecule to another component. For such sites, any free energy change associated with the presence of the attached component should not destablize the binding of the compound to the target to an extent that will disrupt the binding. Preferably, the binding energy with the attachment should be at least 4 kcal/mol., more preferably at least 6, 8, 10, 12, 15, or 20 kcal/mol. Preferably, the presence of the attachment at the particular site reduces binding energy by no more than 3, 4, 5, 8, 10, 12, or 15 kcal/mol.

In many cases, suitable attachment sites will be those that are exposed to solvent when the binding compound is bound in the binding site. In some cases, attachment sites can be used that will result in small displacements of a portion of the enzyme without an excessive energetic cost. Exposed sites can be identified in various ways. For example, exposed sites can be identified using a graphic display or 3-dimensional model. In a grahic display, such as a computer display, an image of a compound bound in a binding site can be visually inspected to reveal atoms or groups on the compound that are exposed to solvent and oriented such that attachment at such atom or group would not preclude binding of the enzyme and binding compound. Energetic costs of attachment can be calculated based on changes or distortions that would be caused by the attachment as well as entropic changes.

Many different types of components can be attached. Persons with skill are familiar with the chemistries used for various attachments. Examples of components that can be attached include, without limitation: solid phase components such as beads, plates, chips, and wells; a direct or indirect label; a linker, which may be a traceless linker; among others. Such linkers can themselves be attached to other components, e.g., to solid phase media, labels, and/or binding moieties.

The binding energy of a compound and the effects on binding energy for attaching the molecule to another component can be calculated approximately by manual calculation, or by using any of a variety of available computational virtual assay techniques, such as docking or molecular dynamics simulations. A virtual library of compounds derived from the attachment of components to a particular scaffold can be assembled using a variety of software programs (such as Afferent, MDL Information Systems, San Leandro, Calif. or CombiLibMaker, Tripos Associates, St. Louis, Mo.). This virtual library can be assigned appropriate three dimensional coordinates using software programs (such as Concord, Tripos Associates, St. Louis, Mo. or Omega, Openeye Scientific Software, Santa Fe, N. Mex.). These structures may then be submitted to the appropriate computational technique for evaluation of binding energy to a particular target molecule. This information can be used for purposes of prioritizing compounds for synthesis, for selecting a subset of chemically tractable compounds for synthesis, and for providing data to correlate with the experimentally determined binding energies for the synthesized compounds.

The crystallographic determination of the orientation of the scaffold in the binding site specifically enables more productive methods of assessing the likelihood of the attachment of a particular component resulting in an improvement in binding energy. Such an example is shown for a docking-based strategy in Haque et al *Journal of Medicinal Chemistry* 42:1428-40, 1999, wherein an "Anchor and Grow" technique which relied on a crystallographically determined fragment of a larger molecule, potent and selective inhibitors were rapidly created. The use of a crystallographically characterized small molecule fragment in guiding the selection of productive compounds for synthesis has also been demonstrated in Boehm et al, *Journal of Medicinal Chemistry* 43:2664-74, 2000. An illustration of the use of crystallographic data and molecular dynamics simulations in the prospective assessment of inhibitor binding energies can be found in Pearlman and Charifson, *Journal of Medicinal Chemistry* 44, 3417-23, 2001. Another important class of techniques which rely on a well defined structural starting point for computational design is the combinatorial growth algorithm based systems, such as the GrowMol program (Bohacek and McMartin, *Journal of the American Chemical Society* 116:5560-71, 1994. These techniques have been used to enable the rapid computational evolution of virtual inhibitor computed binding energies, and directly led to more potent synthesized compounds whose binding mode was validated crystallographically (see Organic Letters (2001) 3(15):2309-2312).

(1) Linkers

Linkers suitable for use in the invention can be of many different types. Linkers can be selected for particular applications based on factors such as linker chemistry compatible for attachment to a binding compound and to another component utilized in the particular application. Additional factors can include, without limitation, linker length, linker stability, and ability to remove the linker at an appropriate time. Exemplary linkers include, but are not limited to, hexyl, hexatrienyl, ethylene glycol, and peptide linkers. Traceless linkers can also be used, e.g., as described in Plunkett, M. J., and Ellman, J. A., 1995, *J. Org. Chem.*, 60:6006.

Typical functional groups, that are utilized to link binding compound(s), include, but not limited to, carboxylic acid, amine, hydroxyl, and thiol. (Examples can be found in Solid-supported combinatorial and parallel synthesis of small molecular weight compound libraries; Tetrahedron organic chemistry series Vol. 17; Pergamon, 1998; p85).

(2) Labels

As indicated above, labels can also be attached to a binding compound or to a linker attached to a binding compound. Such attachment may be direct (attached directly to the binding compound) or indirect (attached to a component that is directly or indirectly attached to the binding compound). Such labels allow detection of the compound either directly or indirectly. Attachment of labels can be performed using conventional chemistries. Labels can include, for example, fluorescent labels, radiolabels, light scattering particles, light absorbent particles, magnetic particles, enzymes, and specific binding agents (e.g., biotin or an antibody target moiety).

(3) Solid Phase Media

Additional examples of components that can be attached directly or indirectly to a binding compound include various solid phase media. Similar to attachment of linkers and labels, attachment to solid phase media can be performed using conventional chemistries. Such solid phase media can include, for example, small components such as beads, nanoparticles, and fibers (e.g., in suspension or in a gel or chromatographic matrix). Likewise, solid phase media can include larger objects such as plates, chips, slides, and tubes. In many cases, the binding compound will be attached in only a portion of such an objects, e.g., in a spot or other local element on a generally flat surface or in a well or portion of a well.

IV. Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of a biomolecular function may take a chemical form that is not predictable. A wide array of organic synthetic techniques exist in the art to meet the challenge of constructing these potential modulators. Many of these organic synthetic methods are described in detail in standard reference sources utilized by those skilled in the art. One example of suh a reference is March, 1994, *Advanced Organic Chemistry, Reactions, Mechanisms and Structure*, New York, McGraw Hill. Thus, the techniques useful to synthesize a potential modulator of biomolecular function identified by computer-based methods are readily available to those skilled in the art of organic chemical synthesis.

V. Isomers, Prodrugs, and Active Metabolites

The present compounds are described herein with generic formulas and specific compounds. In addition, the present compounds may exist in a number of different forms or derivatives, all within the scope of the present invention. These include, for example, tautomers, enantiomers, stereoisomers, racemic mixtures, regioisomers, salts, prodrugs (e.g., carboxylic acid esters), solvated forms, different crystal forms or polymorphs, and active metabolites

A. Tautomers, Stereoisomers, Regioisomers, and Solvated Forms

It is understood that certain compounds may exhibit tautomerism. In such cases, the formula drawings within this specification expressly depict only one of the possible tautomeric forms. It is therefore to be understood that within the invention the formulas are intended to represent any tautomeric form of the depicted compounds and are not to be limited merely to the specific tautomeric form depicted by the formula drawings.

Likewise, some of the present compounds may contain one or more chiral centers, and therefore, may exist in two or more stereoisomeric forms. Thus, such compounds may be present as single stereoisomers (i.e., essentially free of other stereoisomers), racemates, and/or mixtures of enantiomers and/or diastereomers. All such single stereoisomers, racemates and mixtures thereof are intended to be within the scope of the present invention. Unless specified to the contrary, all such steroisomeric forms are included within the formulas provided herein.

In certain embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In certain embodiments, the compound is present in optically pure form.

For compounds is which synthesis involves addition of a single group at a double bond, particularly a carbon-carbon double bond, the addition may occur at either of the double bond-linked atoms. For such compounds, the present invention includes both such regioisomers.

Additionally, the formulas are intended to cover solvated as well as unsolvated forms of the identified structures. For example, the indicated structures include both hydrated and non-hydrated forms. Other examples of solvates include the structures in combination with isopropanol, ethanol, methanol, DMSO, ethyl acetate, acetic acid, or ethanol amine.

B. Prodrugs and Metabolites

In addition to the present formulas and compounds described herein, the invention also includes prodrugs (generally pharmaceutically acceptable prodrugs), active metabolic derivatives (active metabolites), and their pharmaceutically acceptable salts.

In this context, prodrugs are compounds that may be converted under physiological conditions or by solvolysis to the specified compound or to a pharmaceutically acceptable salt of such a compound. A common example is an alkyl ester of a carboxylic acid.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

Reductive reactions, such as reduction of carbonyl groups, reduction of alcoholic groups and carbon-carbon double bonds, reduction of nitrogen-containing functions groups, and other reduction reactions.

Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety in intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent publ. 20040077595, application Ser. No. 10/656,838, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Wermuth, Academic Press, San Diego, Calif., 2001.

Prodrugs may proceed from prodrug form to active form in a single step or may have one or more intermediate forms which may themselves have activity or may be inactive.

Metabolites, e.g., active metabolites overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject or patient. Of these, active metabolites are such pharmacologically active derivative compounds. For prodrugs, the prodrug compounds is generally inactive or of lower activity than the metabolic product. For active metabolites, the parent compound may be either an active compound or may be an inactive prodrug.

Prodrugs and active metabolites may be identified using routine techniques know in the art. See, e.g., Bertolini et al, 1997, *J Med Chem* 40:2011-2016; Shan et al., *J Pharm Sci* 86:756-757; Bagshawe, 1995, *Drug Dev Res* 34:220-230; Wermuth, The *Practice of Medicinal Chemistry*, Ch. 31-32, Academic Press, San Diego, Calif., 2001.

C. Pharmaceutically Acceptable Salts

Compounds can be formulated as or be in the form of pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

D. Polymorphic Forms

In the case of agents that are solids, it is understood by those skilled in the art that the compounds and salts may exist in different crystal or polymorphic forms, all of which are intended to be within the scope of the present invention and specified formulas.

VI. Administration

The methods and compounds will typically be used in therapy for human patients. However, they may also be used to treat similar or identical diseases in other vertebrates, e.g., mammals such as other primates, sports animals, bovines, equines, porcines, ovines, and pets such as dogs and cats.

Suitable dosage forms, in part, depend upon the use or the route of administration, for example, oral, transdermal, transmucosal, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in *Remington's Pharmaceutical Sciences*, 18$^{th}$ ed., Mack Publishing Co., Easton, Pa., 1990 (hereby incorporated by reference herein).

Carriers or excipients can be used to produce pharmaceutical compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, or transdermal. Oral administration is preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/orsubcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The amounts of various compound to be administered can be determined by standard procedures taking into account factors such as the compound $IC_{50}$, the biological half-life of the compound, the age, size, and weight of the patient, and the disorder associated with the patient. The importance of these and other factors are well known to those of ordinary skill in the art. Generally, a dose will be between about 0.01 and 50 mg/kg, preferably 0.1 and 20 mg/kg of the patient being treated. Multiple doses may be used.

VII. Synthesis of Compounds of Formula I

Compounds with the chemical structure of Formula I can be prepared in a number of different synthetic routes, including, for example, the synthetic schemes described herein for groups of compounds within Formula I. Additional synthetic routes can be utilized by one skilled in chemical synthesis.

Certain of the syntheses can utilize key intermediate II in the synthesis. Key intermediate II can be prepared as follows:

Synthesis of Key Intermediate II

One synthetic route for Intermediate II compounds is shown below. In these compounds, Y and Z (as well as U, V, and W) can be C as in indole, or can be other heteroatoms as specified for Formula I, and $R^3$, $R^4$, and $R^5$ are as specified for Formula I or a sub-generic description within Formula I. In synthetic Scheme 1a and other synthetic schemes described herein for groups of compounds, it should be understood that generic formulas in the schemes (e.g., Formula III in Scheme 1a) describe a set of compounds, but are referenced in the text description of the synthesis in the singular.

Scheme 1a:

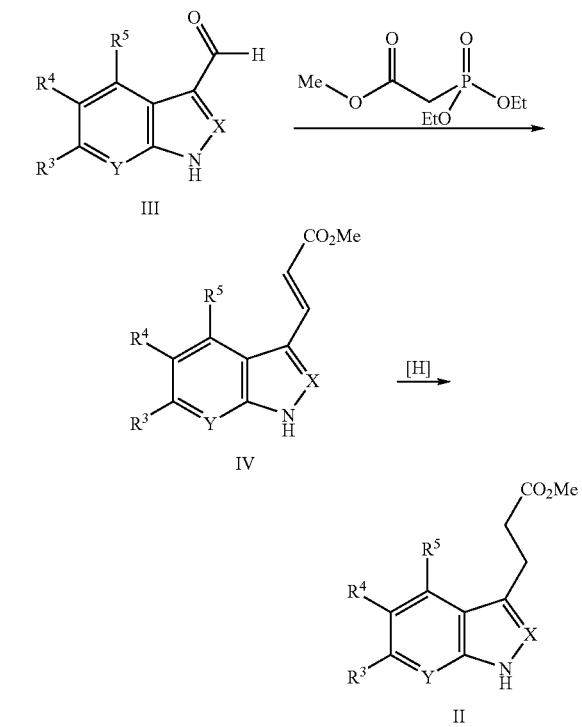

Step 1—Preparation of Compound of Formula IV

Compound IV was prepared by reacting commercially available aldehyde III with an activated phosphonate ester in an inert solvent (e.g. tetrahydrofuran) under reflux conditions, typically for 16-24 h, as described by Garuti et al in *Arch. Pharm*, 1988, 321, 377-83). Compound III, in turn, can be prepared by reacting compound V under Vilsmeier ($POCl_3$ and DMF) conditions as described by in *March's Advanced Organic Chemstry, $5^{th}$ Edition*, p. 715.

Step 2—Preparation of Intermediate II

Key intermediate II was prepared by the reduction of IV in an inert solvent (i.e. tetrahydrofuran) by catalytic hydrogenation (typically 10% palladium on activated carbon and atmospheric hydrogen) as described by Garuti et al in *Arch. Pharm*, 1988, 321, 377-83).

Scheme 1b:

Key Intermediate II compounds can also be prepared in accordance with Scheme 1b as shown below.

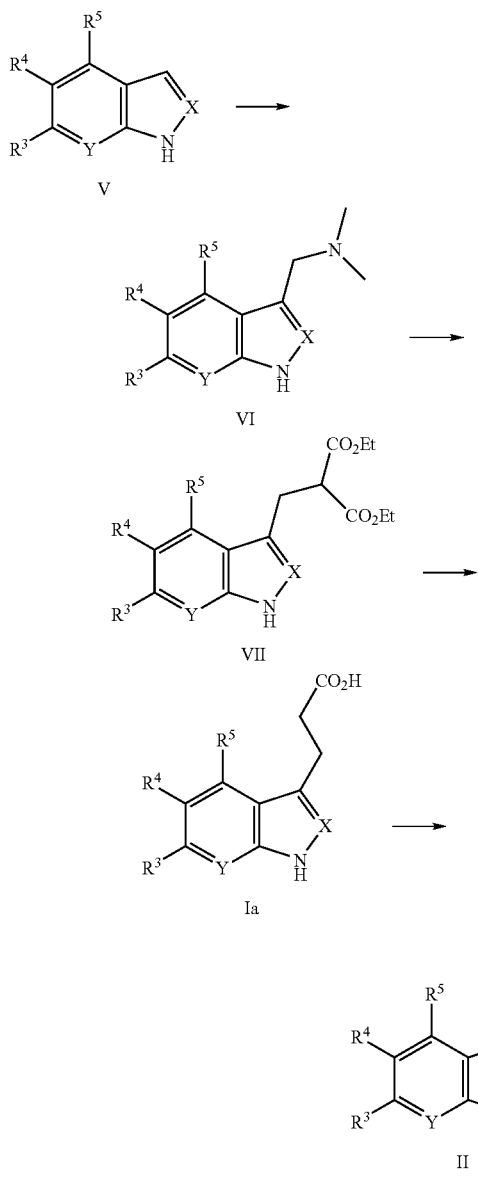

Step 1—Preparation of Formula VI

Compound VI was prepared conventionally by a reacting commercially available compound of formula V with an N,N-dialkyl amine hydrochloride in a polar solvent (e.g. i-Propanol), in the presence of formaldehyde and heated, typically near 90° C., typically for 24 h, as described by Snyder et al, *JACS*, 73, 970.

Step 2—Preparation of Formula VII

Compound of formula VII was prepared by heating compound VI with diethyl malonate and a catalytic amount of sodium metal, typically at 120° C. as described by Robinson et. al, *JACS*, 78, 1247, followed by flash chromatography purification.

Step 3—Preparation of Formula Ia

Compound of formula Ia was prepared by hydrolyzing compound VII using aqueous base (e.g. NaOH) followed by the decarboxylation under reflux conditions (*JACS*, 78, 1247).

Step 4—Preparation of Intermediate II

Intermediate II was prepared by Fisher esterification of compound Ia with alcohol (e.g. Methanol) and catalytic amount of an acid (e.g. HCl) under reflux, typically for 16-24 h.

Scheme 1c:

Compounds of Key Intermediate II can also be prepared according to Scheme 1c as shown below.

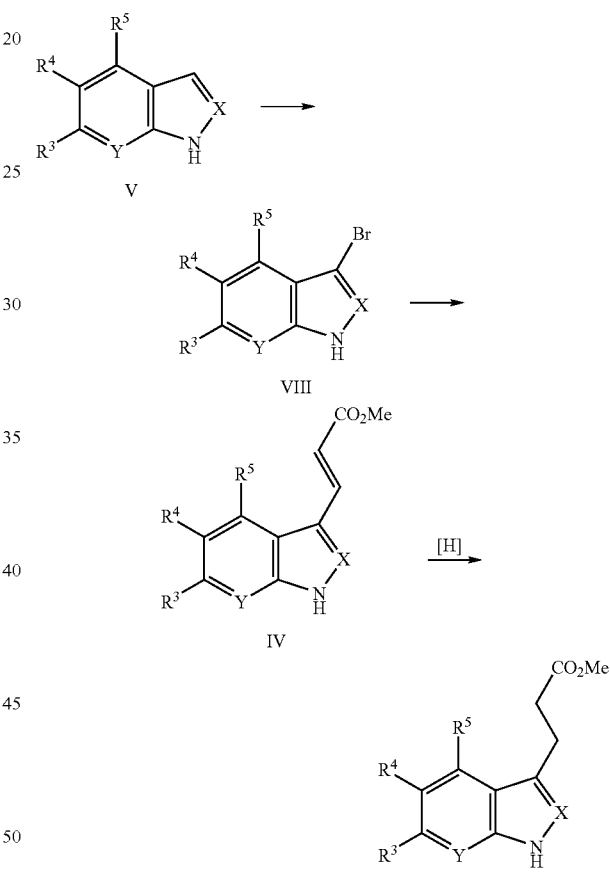

Step 1—Preparation of Formula VIII

Compound VIII can be prepared by a reacting commercially available of a compound of formula V with bromine in an inert solvent (e.g. DMF) (Bocchi and Palla; *Synthesis*, 1982, p1096).

Step 2—Preparation of Formula IV

Compound IV can be prepared by a reacting compound of formula VIII with methacrylate under Heck coupling conditions as described by Sznaidman et. al, in *Bioorg. Med. Chem. Lett.*, 13, 2003, 1517.

Step 3—Preparation of Intermediate II

Key intermediate II was prepared by the reduction of IV in an inert solvent (i.e. tetrahydrofuran) by catalytic hydrogenation (typically 10% palladium on activated carbon and atmospheric hydrogen) as described by Aaruti et. al in *Arch. Pharm,* 321, 1988, 377-83.

Synthesis of Compound Ia

Compounds of Formula Ia can be prepared by hydrolysis of Key Intermediate II as shown in Scheme 2.

Scheme 2

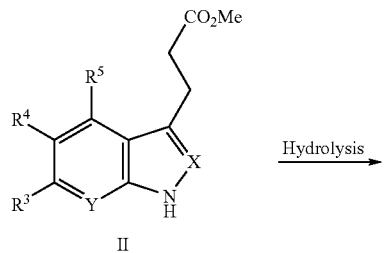

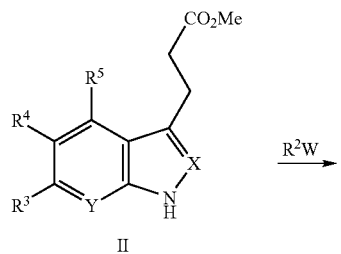

Compound of formula Ia was prepared by the hydrolysis of key intermediate of formula II with aqueous base (e.g. aq. NaOH), typically for 6-15 h and isolating the product by conventional methods (e.g. aqueous work up and purification by chromatography) *Jerry March in March's Advanced Organic Chemstry,* 5$^{th}$ Edition, p. 715.

Synthesis of Compound Ib

Compounds of Formula Ib, in which the indole ring is substituted at the 3-position (or corresponding position of the other bi-cyclic rings of Formula I), can be prepared according to Scheme 3.

Scheme 3

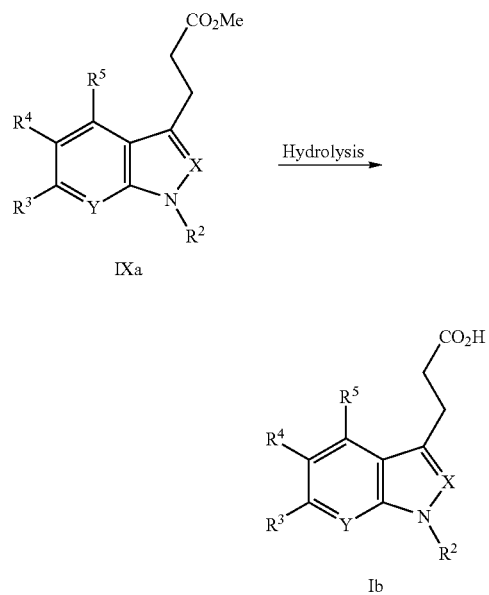

Step 1—Preparation of Compound of Formula IXa

Compound of formula IXa was prepared by treating intermediate of formula II with a base (e.g. sodium hydride) in an inert solvent N,N-Dimethylformamide, followed by the addition of R$^2$W, where "W" is a leaving group (e.g. chloro, bromo), and stirring at RT, typically for 16 to 24 h (*Jerry March in March's Advanced Organic Chemstry,* 5$^{th}$ Edition, p576). The product was obtained by column chromatography (e.g. silica gel) after workup using conventional methods.

Step 2—Preparation of Compound of Formula Ib

Compound of formula Ib was prepared by the hydrolysis of compound of formula V with aqueous base (e.g. aq. NaOH), typically for 6-15 h and isolating the product by conventional methods (e.g. aqueous work up and purification by chromatography).

Synthesis of Compound Ic

Compounds of Formula Ic, in which R$^2$ is R$^{10}$R$^{11}$NCZ, can be prepared according to Scheme 4.

Scheme - 4

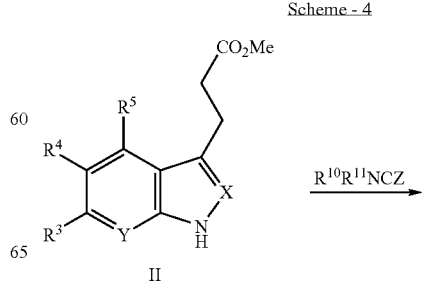

-continued

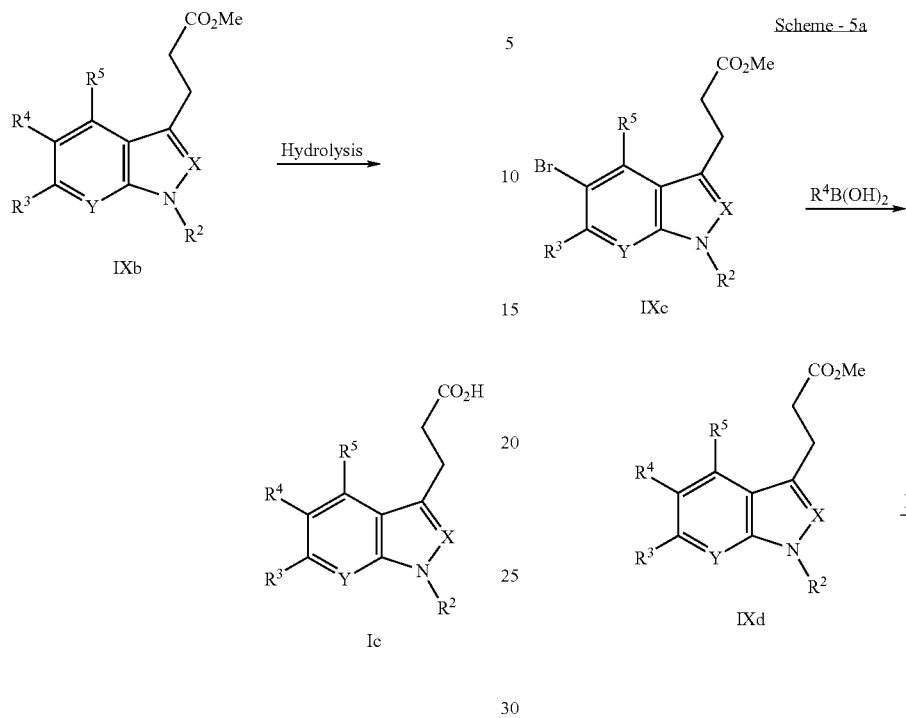

Step 1—Preparation of Compound of Formula IXb

Compound of formula IXb was prepared by treating intermediate of formula II with a base (e.g. sodium hydride) in an inert solvent (DMF) followed by the addition of $R^{16}NCZ$, where "Z" is oxygen or sulfur, and stirring at RT, typically for 16 to 24 h (*Jerry March in March's Advanced Organic Chemstry, 5th Edition*, p1191). The product was obtained by column chromatography (e.g. silica gel) after workup using conventional methods.

Compound of formula IXb can also be prepared by treating intermediate of formula II with $R^{16}NCZ$, where "Z" is oxygen or sulfur, in an inert solvent (THF) followed by the addition of catalytic amount of DMAP (N,N,-dimethylaminopyridine) and stirring at RT, typically for 16 to 24 h. The product can be obtained by column chromatography (e.g. silica gel) after workup using conventional methods.

Step 2—Preparation of Compound of Formula Ic

Compound of formula Ic was prepared by the hydrolysis of compound of formula IXb with aqueous base (e.g. aq. NaOH), typically for 6-15 h and isolating the product by conventional methods (e.g. aqueous work up and purification by chromatography).

In compound of formula Ic, substituent $R^2$ would then be $R^{10}R^{11}NCZ$.

Synthesis of Compound Id

Compounds of Formula Id can be prepared according to Scheme 5a.

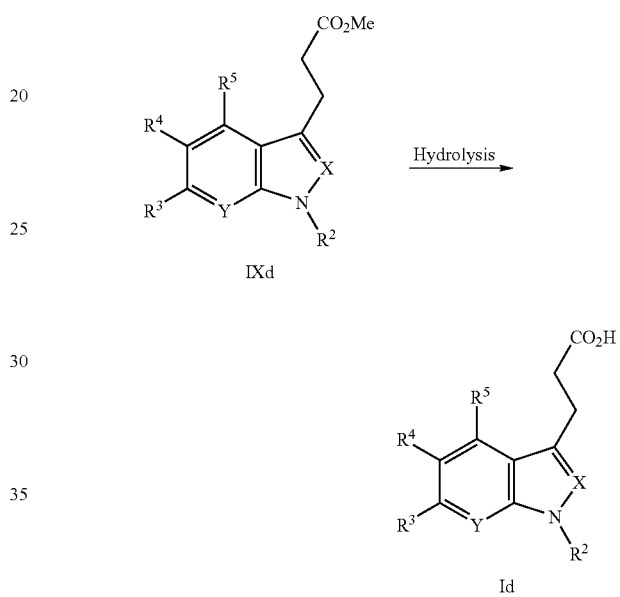

Step 1—Preparation of Compound of Formula IXd

Compound of formula IXd was prepared from compound of formula IXc by reacting it with aryl boronic acids under Suzuki reaction conditions (*March's Advanced Organic Chemistry, 5th Edition*, p8) and heating the reaction mixture, typically 90° C., for 24 and isolating the product by conventional methods (e.g. aqueous work up and purification by chromatography).

Compound of formula IXc was in turn prepared from commercially available compound of formula V, where "$R^4$" is bromine, using the synthetic steps described in Scheme 1b, followed by the reaction with "$R^{16}W$" as described in step 1 of synthetic Scheme 3, where "$R^4$" is bromine.

Step 2—Preparation of Compound of Formula Id

Compound of formula Id was prepared by the hydrolysis of compound of formula IXd with aqueous base (e.g. aq. NaOH), typically for 6-15 h and isolating the product by conventional methods (e.g. aqueous work up and purification by chromatography).

Scheme 5b

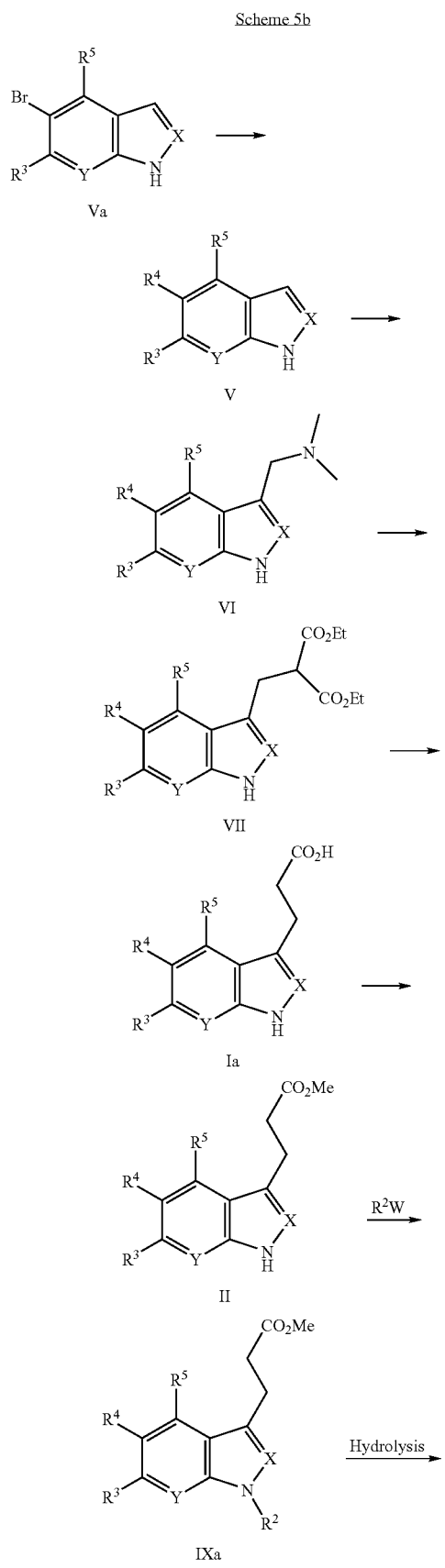

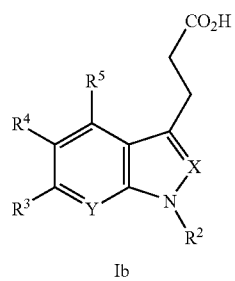

Ib

Step 1—Preparation of Compound of Formula V

Compound of formula V was prepared from commercially available compound of formula Va by reacting it with aryl boronic acids under Kumada reaction conditions as described by Hayashi et. al, *JACS,* 106 (1984), 158-163, and heating the reaction mixture, typically 90° C., for 24 and isolating the product by conventional methods (e.g. aqueous work up and purification by chromatography).

Step 2—Preparation of Formula VI

Compound VI was prepared conventionally by a reacting commercially available compound of formula V with an N,N-dialkyl amine hydrochloride in a polar solvent (e.g. i-Propanol), in the presence of formaldehyde and heated, typically near 90° C., typically for 24 h, as described previously for compound VI.

Step 3—Preparation of Formula VII

Compound of formula VII was prepared by heating compound V1 with diethyl malonate and a catalytic amount of sodium metal, typically at 120° C. as described previously, followed by flash chromatography purification.

Step 4—Preparation of Formula Ia

Compound of formula Ia was prepared by hydrolyzing compound VII using aqueous base (e.g. NaOH) followed by the decarboxylation under reflux conditions as described previously.

Step 5—Preparation of Intermediate II

Intermediate II was prepared by Fisher esterification of compound Ia with alcohol (e.g. Methanol) and catalytic amount of an acid (e.g. HCl) under reflux, typically for 16-24 h.

Step 6—Preparation of Compound of Formula IXa

Compound of formula IXa was prepared by treating intermediate of formula II with a base (e.g. sodium hydride, NaH) in an inert solvent (DMF) followed by the addition of "$R^2W$", where "W" is a leaving group (e.g. chloro, bromo), and stirring at RT, typically for 16 to 24 h. The product was obtained by column chromatography (e.g. silica gel) after workup using conventional methods.

Step 7—Preparation of Compound of Formula Ib

Compound of formula Ib was prepared by the hydrolysis of compound of formula IXa with aqueous base (e.g. aq.

NaOH), typically for 6-15 h and isolating the product by conventional methods (e.g. aqueous work up and purification by chromatography).

Synthesis of Compound X

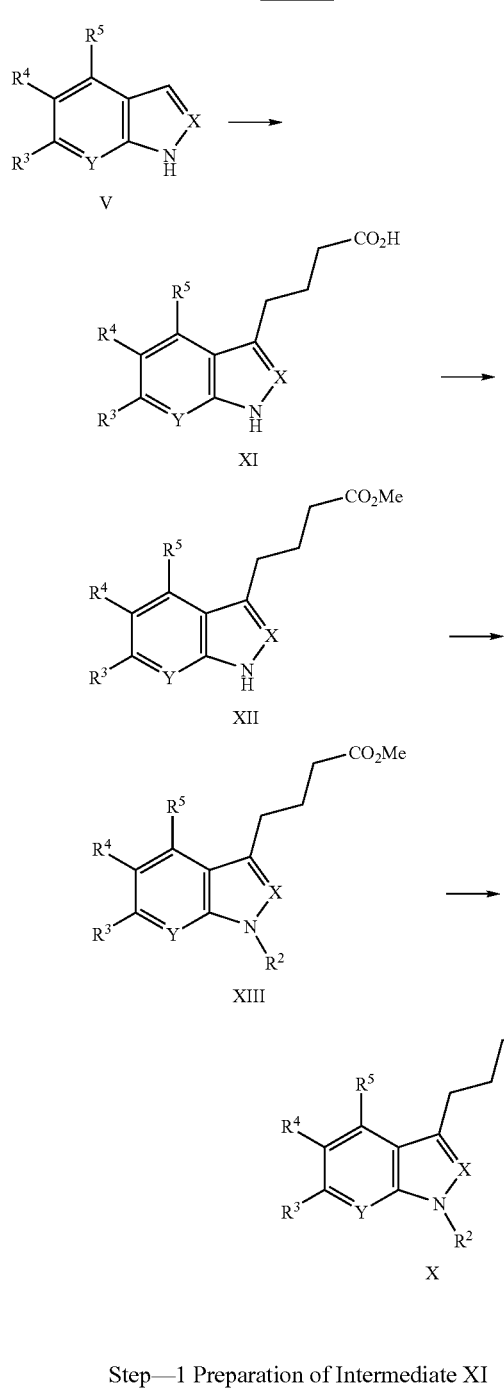

Step—1 Preparation of Intermediate XI

Compound XI was prepared from the compound V reacting with γ-butyrolatone in an inert solvent with potassium hydroxide under reflux conditions, usually 4 to 24 hours, as described by Fritz et al, (*J. Org. Chem.*, 1963, 28, 1384-1385).

Step 2—Preparation of Intermediate XII

Compound XII was prepared by the carboxylic acid $X_1$ reacting in either a catalytic amount of sulfuric acid in methanol under reflux conditions, or activated methylene moiety such as diazomethane.

Step 3—Preparation of Intermediate XIII

Compound XIII was prepared by treating intermediate of formula XII with a base (e.g. sodium hydride) in an inert solvent (DMF) followed by the addition of $R^2W$, where "W" is a leaving group (e.g. chloro, bromo), and stirring at RT, typically for 16 to 24 h (*Jerry March in March's Advanced Organic Chemstry, 5$^{th}$* Edition, p576). The product was obtained by column chromatography (e.g. silica gel) after workup using conventional methods.

Step 4—Preparation of Intermediate X

Compound of formula X was prepared by the hydrolysis of compound of formula XIII with aqueous base (e.g. aq. NaOH), typically for 6-15 h and isolating the product by conventional methods (e.g. aqueous work up and purification by chromatography).

Synthesis of compound XIV

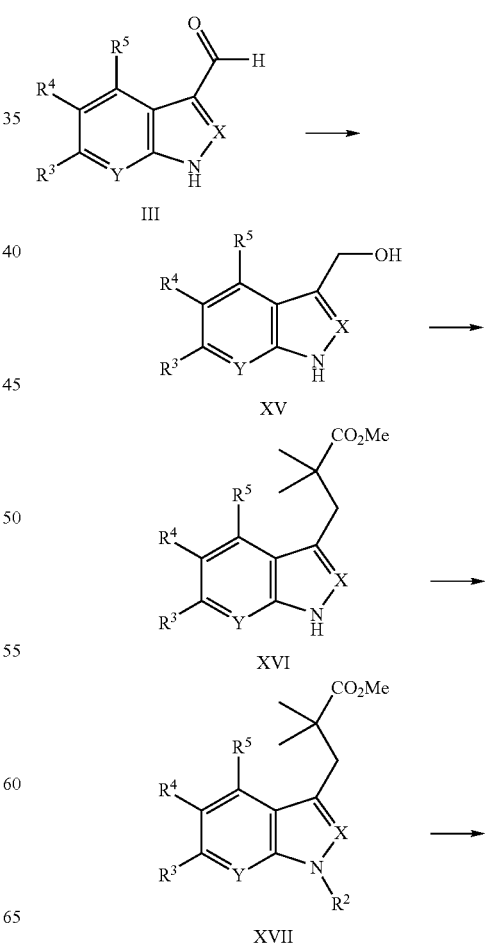

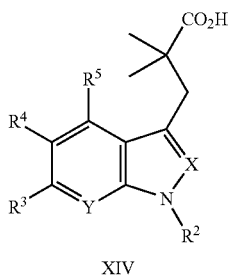

XIV

Step 1: Preparation of Intermediate XV

Compound XV can be prepared from the corresponding aldehyde III reacting with a reducing agent such as sodium borohydride in an inert solvent (e.g. tetrahydrofuran).

Step 2: Preparation of Intermediate XVI

Compound XVI can be prepared by reacting the methanol XV with silyl ketene acetal in presence of a catalyst such as magnesium triflimide or perchlorate at ambient temperature for 1-2 hours as described by Grieco et al in *Tetrahdron Letts* (1997, 38, 2645-2648).

Step 3: Preparation of Intermediate XVII

Compound XVII was prepared by treating intermediate of formula XVI with a base (e.g. sodium hydride) in an inert solvent (DMF) followed by the addition of $R^2W$, where "W" is a leaving group (e.g. chloro, bromo), and stirring at RT, typically for 16 to 24 h (*Jerry March in March's Advanced Organic Chemistry, 5th Edition*, p576). The product was obtained by column chromatography (e.g. silica gel) after workup using conventional methods.

Step 4 Preparation of Intermediate XIV

Compound of formula XIV was prepared by the hydrolysis of compound of formula XVII with aqueous base (e.g. aq. NaOH), typically for 6-15 h and isolating the product by conventional methods (e.g. aqueous work up and purification by chromatography).

Using the synthetic schemes described above, a set of exemplary compound was prepared. Those compounds include those listed below, which are also listed in Table 1 along with the chemical structures, along with additional exemplary compounds.

3-[5-Methoxy-1-(4-methoxy-benzenesulfonyl)-1H-indol-3-yl]-propionic acid,
3-[5-ethyl-1-(4-methoxy-benzenesulfonyl)-1H-indol-3-yl]-propionic acid,
Indazole-3-propionic acid, 5-isopropoxy-3-(1-Benzene-sulfonyl-indol-3-yl)-propionic acid, Indole-3-propionic acid,
3-(1-Benzenesulfonyl-5-methoxy-1H-indol-3-yl)-propionic acid,
3-[5-Methoxy-1-(3-methoxy-benzyl)-1H-indol-3-yl]-propionic acid,
3-[1-(3-Chloro-benzyl)-5-methoxy-1H-indol-3-yl]-propionic acid,
3-[1-(4-Fluoro-benzyl)-5-methoxy-1H-indol-3-yl]-propionic acid,
3-[1-(4-Chloro-benzyl)-5-methoxy-1H-indol-3-yl]-propionic acid,
3-[5-Methoxy-1-(2-methoxy-benzyl)-1H-indol-3-yl]-propionic acid,
3-[5-Methoxy-1-(2-trifluoromethoxy-benzyl)-1H-indol-3-yl]-propionic acid,
3-[5-Methoxy-1-(3-trifluoromethoxy-benzyl)-1H-indol-3-yl]-propionic acid,
3-(1-Ethylthiocarbamoyl-5-methoxy-1H-indol-3-yl)-propionic acid,
3-[5-Methoxy-1-(toluene-4-sulfonyl)-1H-indol-3-yl]-propionic acid,
3-(1-Benzenesulfonyl-1H-indazol-3-yl)-propionic acid,
3-[1-(4-Isopropyl-benzenesulfonyl)-5-methoxy-1H-indol-3-yl]-propionic acid methyl ester,
3-[1-(4-Isopropyl-benzenesulfonyl)-5-methoxy-1H-indol-3-yl]-propionic acid,
3-[1-(4-Butoxy-benzenesulfonyl)-5-methoxy-1H-indol-3-yl]-propionic acid methyl ester,
3-[1-(4-Butoxy-benzenesulfonyl)-5-methoxy-1H-indol-3-yl]-propionic acid,
3-[5-Methoxy-1-(4-trifluoromethoxy-benzenesulfonyl)-1H-indol-3-yl]-propionic acid methyl ester,
3-[5-Methoxy-1-(4-trifluoromethoxy-benzenesulfonyl)-1H-indol-3-yl]-propionic acid,
3-[5-Methoxy-1-(4-phenoxy-benzenesulfonyl)-1H-indol-3-yl]-propionic acid methyl ester,
3-[5-Methoxy-1-(4-phenoxy-benzenesulfonyl)-1H-indol-3-yl]-propionic acid,
3-[1-(4-Chloro-benzenesulfonyl)-5-methoxy-1H-indol-3-yl]-propionic acid methyl ester,
3-[1-(4-Chloro-benzenesulfonyl)-5-methoxy-1H-indol-3-yl]-propionic acid,
3-[1-(4-Cyano-benzenesulfonyl)-5-methoxy-1H-indol-3-yl]-propionic acid methyl ester,
3-[1-(4-Cyano-benzenesulfonyl)-5-methoxy-1H-indol-3-yl]-propionic acid,
3-[1-(3,4-Dichloro-benzenesulfonyl)-5-methoxy-1H-indol-3-yl]-propionic acid methyl ester,
3-[1-(3,4-Dichloro-benzenesulfonyl)-5-methoxy-1H-indol-3-yl]-propionic acid,
3-[5-Methoxy-1-(4-trifluoromethyl-benzenesulfonyl)-1H-indol-3-yl]-propionic acid methyl ester,
3-[5-Methoxy-1-(4-trifluoromethyl-benzenesulfonyl)-1H-indol-3-yl]-propionic acid,
3-[1-(4-Fluoro-benzenesulfonyl)-5-methoxy-1H-indol-3-yl]-propionic acid methyl ester,
3-[1-(4-Fluoro-benzenesulfonyl)-5-methoxy-1H-indol-3-yl]-propionic acid,
3-[5-Methoxy-1-(3-phenoxy-benzenesulfonyl)-1H-indol-3-yl]-propionic acid methyl ester,
3-[5-Methoxy-1-(3-phenoxy-benzenesulfonyl)-1H-indol-3-yl]-propionic acid,
3-[1-(3-Fluoro-benzenesulfonyl)-5-methoxy-1H-indol-3-yl]-propionic acid methyl ester,
3-[1-(3-Fluoro-benzenesulfonyl)-5-methoxy-1H-indol-3-yl]-propionic acid,
3-[5-Methoxy-1-(toluene-3-sulfonyl)-1H-indol-3-yl]-propionic acid methyl ester,
3-[5-Methoxy-1-(toluene-3-sulfonyl)-1H-indol-3-yl]-propionic acid,
3-[1-(3-Chloro-benzenesulfonyl)-5-methoxy-1H-indol-3-yl]-propionic acid methyl ester,
3-[1-(3-Chloro-benzenesulfonyl)-5-methoxy-1H-indol-3-yl]-propionic acid,
3-[5-Methoxy-1-(3-methoxy-benzenesulfonyl)-1H-indol-3-yl]-propionic acid methyl ester, 3-[5-Methoxy-1-(3-methoxy-benzenesulfonyl)-1H-indol-3-yl]-propionic acid,
3-[5-Methoxy-1-(3-trifluoromethyl-benzenesulfonyl)-1H-indol-3-yl]-propionic acid methyl ester,
3-[5-Methoxy-1-(3-trifluoromethyl-benzenesulfonyl)-1H-indol-3-yl]-propionic acid,
3-(1-Benzyl-5-methoxy-1H-indol-3-yl)-propionic acid methyl ester,
3-(1-Benzyl-5-methoxy-1H-indol-3-yl)-propionic acid,
3-[5-Methoxy-1-(thiophene-2-sulfonyl)-1H-indol-3-yl]-propionic acid methyl ester,
3-[5-Methoxy-1-(thiophene-2-sulfonyl)-1H-indol-3-yl]-propionic acid,
3-(5-Methoxy-1-phenylthiocarbamoyl-1H-indol-3-yl)-propionic acid methyl ester,
3-(5-Methoxy-1-phenylthiocarbamoyl-1H-indol-3-yl)-propionic acid,
3-[1-(4-Butyl-benzenesulfonyl)-5-methoxy-1H-indol-3-yl]-propionic acid methyl ester,
3-[1-(4-Butyl-benzenesulfonyl)-5-methoxy-1H-indol-3-yl]-propionic acid,
3-[5-Methoxy-1-(3-trifluoromethoxy-benzenesulfonyl)-1H-indol-3-yl]-propionic acid methyl ester,
3-[5-Methoxy-1-(3-trifluoromethoxy-benzenesulfonyl)-1H-indol-3-yl]-propionic acid,
3-(1-Benzoyl-5-methoxy-1H-indol-3-yl)-propionic acid methyl ester,
3-(1-Benzoyl-5-methoxy-1H-indol-3-yl)-propionic acid,
3-(1-Benzenesulfonyl-5-ethoxy-1H-indol-3-yl)-propionic acid,
3-[1-(4-Isopropoxy-benzenesulfonyl)-5-methoxy-1H-indol-3-yl]-propionic acid,
3-(5-Methoxy-1-phenylcarbamoyl-1H-indol-3-yl)-propionic acid methyl ester,
3-(5-Methoxy-1-phenylcarbamoyl-1H-indol-3-yl)-propionic acid,
3-[1-(4-Ethyl-benzenesulfonyl)-5-methoxy-1H-indol-3-yl]-propionic acid,
3-(5-bromo-1H-indol-3-yl)-propionic acid, 3-(5-Bromo-1H-indol-3-yl)-propionic acid methyl ester,
3-(1-Benzenesulfonyl-5-bromo-1H-indol-3-yl)-propionic acid methyl ester,
3-(1-Benzenesulfonyl-5-bromo-1H-indol-3-yl)-propionic acid methyl ester,
3-(Benzenesulfonyl-5-thiophen-3-yl-1H-indol-3-yl)-propionic acid methyl ester,
3-(Benzenesulfonyl-5-thiophen-3-yl-1H-indol-3-yl)-propionic acid,
3-(1-Benzenesulfonyl-5-pheyl-1H-indol-3-yl) propionic acid methyl ester,
3-(1-Benzenesulfonyl-5-pheyl-1H-indol-3-yl) propionic acid,
Preparation of 3-(1H-Pyrrolo[2,3-b]pyridine-3-yl)-propionic acid,
3-(5-Methoxy-1H-Indol-3-yl)-propionic acid,
3-(1-Benzenesulfonyl-1H-indol-3-yl)-propionic acid,
3-(1-Benzenesulfonyl-5-methoxy-1H-indol-3-yl)-propionic acid methyl ester,
3-[5-Methoxy-1-(thiophene-3-sulfonyl)-1H-indol-3-yl]-propionic acid,
(1-Benzenesulfonyl-5-methoxy-1H-indol-3-yl)-acetic acid.

EXAMPLES

Example 1

Bio-chemical Screening

The homogenous Alpha screen assay was used in the agonist mode to determine the ligand dependent interaction of the PPARs (α,δ,γ) with the coactivator peptides (SRC or DRIP205). Briefly 15 ul of the reaction mix (50 mM Tris pH 7.5, 50 mM Kcl, 0.05% Tween 20, 1 mM DTT, 0.1% BSA and 10 nM-200 nMPPAR and 10 mM-200 nM coactivator peptide) was added to the test compound (1 ul compound in DMSO) and preincubated for 1-6 hr. Next, 5 ul of the Alpha screen beads were added. The reactions were incubated for 2 hrs before taking the reading in the Fusion alpha instrument. In the antagonist mode compounds were assayed for inhibition of the co-activator binding signal caused by the control agonists for each receptor.

The controls agonists used were WY-14643(PPAR(α), farglitazar (PPAR(γ)) and bezafibrate (PPAR(δ)).

Using the assay above, compounds from Table 1 were analyzed for activity. Results for exemplary compounds are shown in Table 2. The data reported in Table 2 was generated via the alpha screen assay and expressed in μMol/L. The data points from the Fusion alpha instrument were transferred to Assay Explorer® (MDL) to generate a curve and calculate the inflection point of the curve as $EC_{50}$.

Among those compounds, several have notable pan-activity at low micromolar or even sub-micromolar levels, for example, compounds 29, 43, and 53. In contrast, compound 6 is selective for PPARγ, with activity on PPARγ of approximately 8 micromolar and activity on PPARα and δ of at least 200 micromolar.

Example 2

Co-transfection Assay 293T cells were transfected for 4-5 hr in serum free DMEM media using cell fectin reagent. Each well was transfected with 1 ug each of the reporter plasmid (pFR-Luc from stratagene) and PPAR constructs (Gal-4-PPAR-LBD). After 24 hrs of recovery in serum medium the cells were treated with compounds for 48 hrs then assayed for luciferase activity using luciferase reporter gene assay kit (Roche).

This assay serves to confirm the observed biochemical activity on the modulation of intended target molecule(s) at the cellular level.

Example 3

Synthesis of 3-[5-methoxy-1-(4-methoxy-benzenesulfonyl)-1H-indol-3-yl]-propionic acid 1

Indole-3-propionic acid 1 was synthesized from the commercially available 5-methoxyindole-3-carboxaldehyde in four steps as shown in Scheme 7.

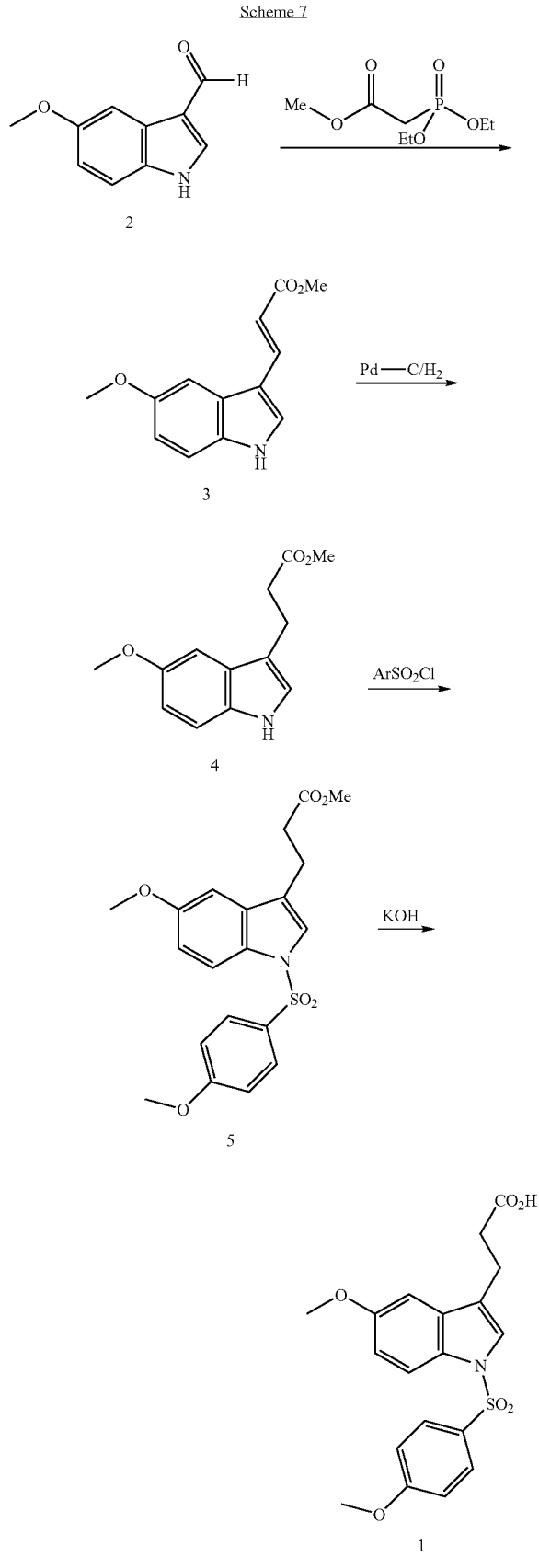

Scheme 7

Step 1—Preparation of 3-(5-Methoxy-1H-indol-3-yl)-acrylic acid methyl ester 3

To a cold solution (ice bath) of methyl phosphonoacetate (13.74 g, 0.065 mol) in tetrahydrofuran (120 mL) under nitrogen, was added sodium hydride (2.6 g, 0.065 mol, 60%) in one portion, and stirred until hydrogen evolution ceased. A solution of commercially available 5-Methoxyindole-3-carboxyaldehyde 2 (5.2 g, 0.029 mol) in tetrahydrofuran (80 mL) was added, over a period of 60 minutes, to the phosphonate solution. The reaction mixture was heated to 55° C. for 24 h after which the mixture was diluted with dichloromethane (DCM, 500 mL) and washed with water (200 mL; 3×). The organic layer was washed once with brine, dried over anhydrous sodium sulfate, and evaporated under reduced pressure to give yellow-tinted oil and purified by filtering through a silica plug. The filtrate was evaporated to afford 3 as an off white solid (6.2 g; 78% yield; M+1=232.0).

Step 2—Preparation of 3-(5-Methoxy-1H-indol-3-yl)-propionic acid methyl ester 4

To a solution of 3-(5-Methoxy-1H-indol-3-yl)-acrylic acid methyl ester 3 (3 g; 0.013 mol) in tetrahydrofuran (THF, 70 mL) was added palladium on activated carbon (10%; 0.72 g). The solution was deoxygenated under vacuum and hydrogen was introduced to the reaction flask from a balloon filled with hydrogen. The process was repeated three times and the reaction mixture was stirred for 16 h at room temperature. The mixture was filtered through celite and the filtrate was evaporated under reduced pressure to yield ester 4 as a while solid (2.78 g; 92% yield; M+1=234.0).

Step 3—Preparation of 3-[5-Methoxy-1-(4-methoxy-benzenesulfonyl)-1H-indol-3-yl]-propionic acid methyl ester 5

To a cooled solution (0° C.) of indole-3-propionic acid methyl ester 4 (0.797 g, 3.42 mmol) in DMF (20 mL) was added sodium hydride (60%; 0.25 g; 0.0625 mol) was added in one portion and stirred for 30 min followed by the addition of 4-methoxybenzenesulfonyl chloride (1.3 g; 6.31 mmol). The reaction was allowed to warm up to room temperature and stirred for 16 h, subjected to aqueous work up, and product was extracted with ethyl acetate. The ethyl acetate layer was washed with brine, dried over anhydrous sodium sulfate, evaporated under reduced pressure, and purified by flash-chromatography (silica gel; 80% n-hexane-20% ethyl acetate) to afford the ester 5 as a white solid (0.83 g; 61% yield; M+1=404.1).

Step 4—Preparation of 3-[5-Methoxy-1-(4-methoxy-benzenesulfonyl)-1H-indol-3-yl]-propionic acid 1

To a solution of the methyl ester 5 (830 mg, 2.06 mmol) in tetrahydrofuran (15 mL) was added an aqueous solution of potassium hydroxide (5 mL of 1M) and stirred at room temperature for 5 h. The acid 1 was isolated by neutralizing the reaction mixture by aqueous hydrochloric acid, extracting the product with ethyl acetate, drying over anhydrous magnesium sulfate, evaporating under reduced pressure, and purifying using flash chromatography with 5% methanol in dichloromethane to afford a white solid (697.5 mg, 91%; M-1=373.1).

Example 4

Synthesis of 3-[5-ethyl-1-(4-methoxy-benzenesulfonyl)-1H-indol-3-yl]-propionic acid 6

Indole-3-propionic acid 6 was synthesized from the commercially available 5-bromo-indole 7 in eight steps as shown in Scheme 8.

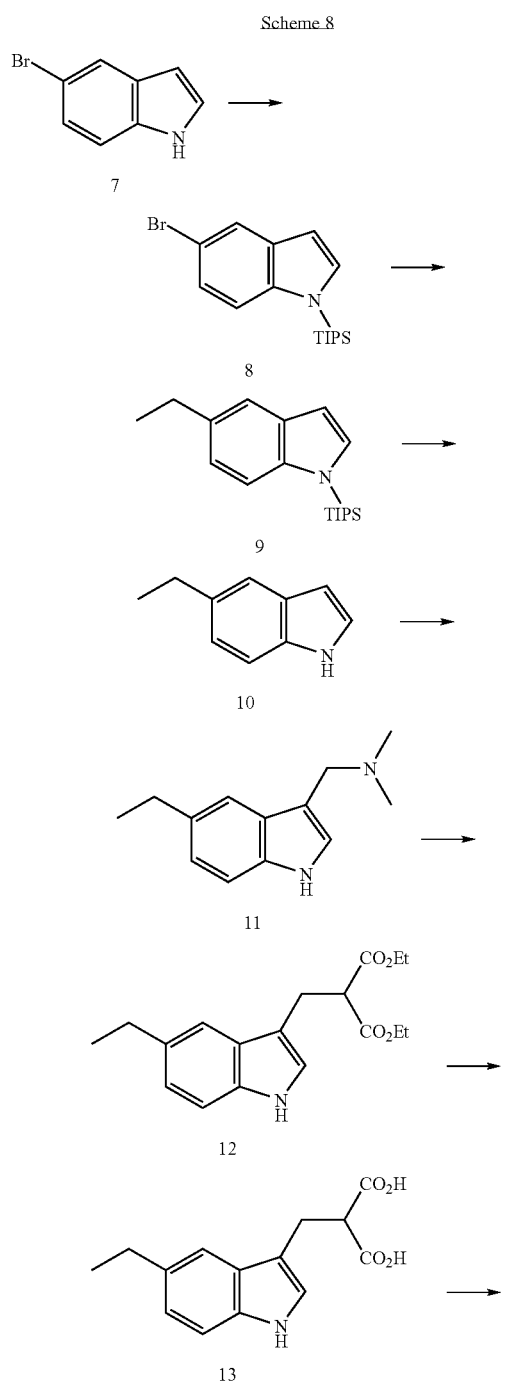

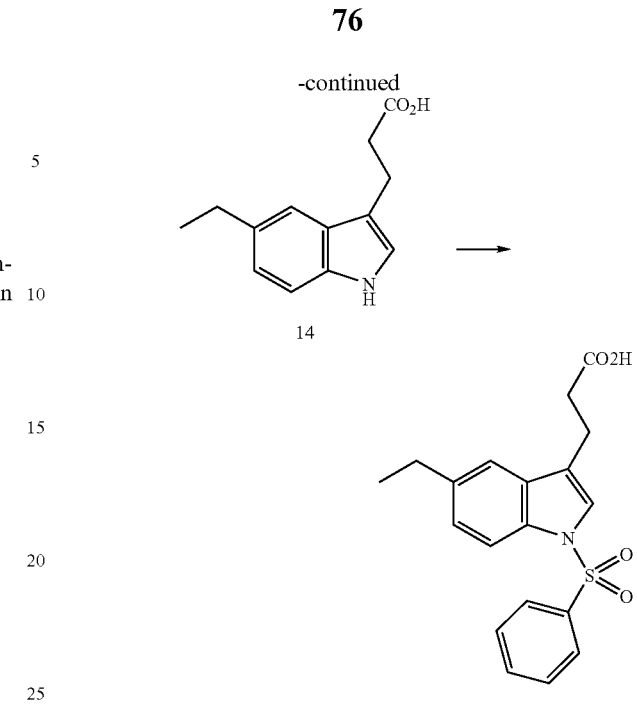

Step 1—Preparation of 5-Bromo-1-triisopropylsilanyl-1H-indole 8

5-Bromoindole (2.5 g, 12.75 mmol) was dissolved in tetrahydrofuran (THF; 50 mL) and cooled to 0° C. and Sodium Hydride NaH (920 mg, 23 mmol, 60%) was added in portions. The mixture was allowed to warm to RT with stirring for 1 hour. The reaction mixture was again cooled to 0° C. and triisopropylsilyl chloride (TIPSCI; 2.78 mL, 13.1 mmol) was added dropwise. The mixture was allowed to warm to room temperature and was stirred overnight. The mixture was washed with 2.0 $NH_3PO_4$, and the organic layer was dried over $MgSO_4$, filtered and evaporated. The residue was purified by flash silica chromatography (100% Hexanes) to give compound 8 as an oil (4.3 g; 96% yield; M+1=353.4)

Step 2—Preparation of 5-Ethyl-1-triisopropylsilanyl-1H-indole 9

The 1-triisopropyl-5-bromoindole (3.0 g, 8.51 mmol) was combined with $PdCl_2$(dppf) at −78° C. and stirred for 5 minutes before Ethylmagnesium bromide (EtMgBr; 12.8 mL, 12.81 mmol) was added. The mixture was allowed to warm to room temperature. Toluene (15 mL) was added to the reaction mixture and heated at reflux for 1 hour. The reaction mixture was allowed to cool to room temperature and was quenched with $2NH_3PO_4$. The mixture was extracted with EtOAc and washed with brine, dried over $MgSO_4$, filtered and evaporated to give compound 9 as an oil (5% EtOAc/Hexanes) to give (2.3 g; 90% yield; M+1=302.5).

Step 3—Preparation of 5-Ethyl-1H-indole 10

The Indole 9 (2.2 g, 7.29 mmol) was dissolved in THF (20 mL) and a solution of ammonium fluoride ($NH_4F$; 1.4 g, 37.8 mmol) in MeOH (20 mL) was added and stirred for 72 hours at room temperature. The solvent was evaporated and the residue was dissolved in ethyl acetate. The organic layer was washed with 2NH₃PO₄, dried over MgSO₄, filtered and evaporated to give compound 10 as an off white solid (1.06 g; M+1-146.2).

Step 4—Preparation of (5-Ethyl-1H-indol-3-ylmethyl)-dimethyl-amine 11

5-Ethylindole 10 (1.0 g, 6.89 mmol) was combined with isopropyl alcohol (200 mL), N,N-dimethylamine hydro chloride (718 mg, 6.95 mmol) and aqueous formaldehyde (37%, 589 mg, 6.95 mmol) and heated at reflux for 2 hours. The reaction mixture was allowed to cool to room temperature, the solvent was evaporated and the resulting residue was dissolved in EtOAc and washed with saturated NaHCO₃. The organic layer was dried over MgSO₄, filtered and evaporated to give compound II as a solid in (1.35 g for a 97% yield; M+1=203.2)

Step 5—Preparation of 2-(5-Ethyl-1H-indol-3-ylmethyl)-malonic acid diethyl ester 12

The 5-Ethylgramine (1.25 g, 6.18 mmol) was combined with diethyl malonate (2.85 mL, 18.54 mmol) and heated to 120° C. until a homogeneous solution was formed. To this mixture was added sodium metal (100 mg, 4.36 mmol) and the mixture was stirred at 120° C. for 24 hours. TLC indicated the completion of the reaction. The reaction was allowed to cool to room temperature and a solution of 5% HCl (aqueous) was slowly added to the mixture and the resulting product was extracted with EtOAc. The organic layer was washed with saturated sodium bicarbonate, dried over anhydrous magnesium sulafate, filtered and evaporated to give compound 12 as a white solid (1.67 g; 85% yield; M+1=318.4). The product was taken into the next step without purification.

Step 6—Preparation of 2-(5-Ethyl-1H-indol-3-ylmethyl)-malonic acid 13

The crude diethyl malonylindole 12 (1.67 g, 5.26 mmol) was dissolved in THF (20 mL) and a solution of NaOH (1.0 g, 25.5 mmol) in H₂O (20 mL) was added. MeOH (5 mL) was also added to the reaction to make the solution homogeneous. The mixture was warmed to 50° C. and stirred overnight. The mixture was allowed to cool to room temperature, the organic layer was evaporated and the residue was acidified with 2N H₃PO₄, and the product was extracted with a mixture of 3:1/CHCl₃:MeOH. The organic layer was washed with brine, dried over MgSO₄, filtered, and evaporated to give the crude diacid as a white solid (1.25 g; M−1=260.2). The product was taken into the next step without purification.

Step 7—Preparation of 3-(5-Ethyl-1H-indol-3-yl)-propionic acid 14

The crude malonic acid 13 (250 mg, 0.957 mmol) was placed in a round bottom flask under vacuum and slowly heated to between 150 and 200° C., as the evolution of CO₂ occurred. As the bubbling ended, the reaction was heated for 2 more additional minutes, then allowed to cool to room temperature. The product was purified by flash chromatography three times using 0 to 10% MeOH in CHCl₃ to give compound 14 as a solid (120 mg; 57.7% yield; M−1=216.3).

Step 8—Preparation of 3-(1-Benzenesulfonyl-5-ethyl-1H-indol-3-yl)-propionic acid 6

The indole propionic acid 14 (100 mg, 0.46 mmol) was dissolved in THF (5.0 mL) and cooled to −78° C. To this solution was added n-butyllithium (n-BuLi; 0.4 mL, 1.0 mmol, 2.4 M in hexanes) dropwise and the mixture was stirred at −78° C. for 1 hour. To this mixture was added benzenesulfonyl chloride (0.13 mL, 1 mmol) and the reaction was allowed to stir overnight and warm to room temperature. The mixture was poured into ice cold H₃PO₄ and extracted with EtOAc. The organic layer was dried over MgSO₄, filtered and evaporated. The residue was purified by flash chromatography (5% MeOH/CHCl₃) to give compound 6 as a white solid (10 mg; M−1=356.4).

Example 5

Synthesis of Indazole-3-propionic acid 16

Indazole-3-propionic acid 16 was prepared from commercially available indazole-3-carboxylic acid 17 in 5 steps as described in Scheme 9.

Scheme 9

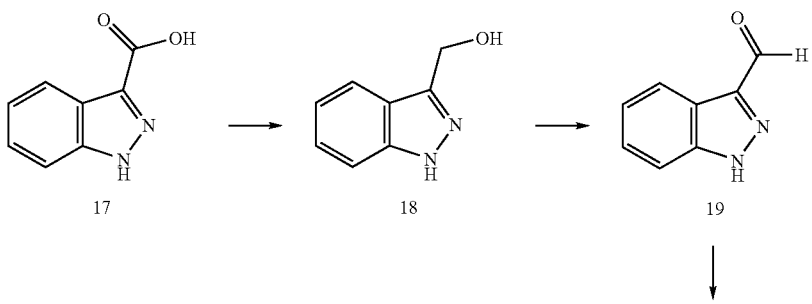

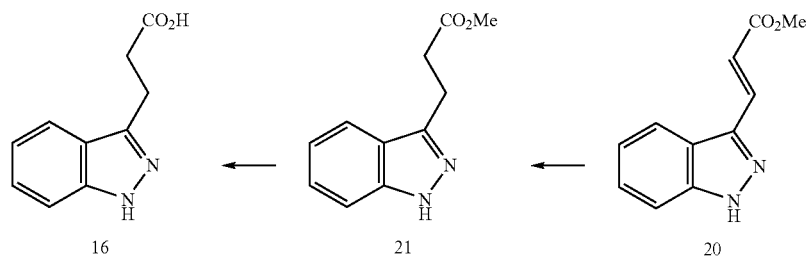

1—Preparation of (1H-Indazo-3-yl)-methanole 18

To a cooled solution of indazole-3-carboxylic acid 17 (3.95 g, 24.4 mmol) in tetrahydrofuran (THF, 300 ml) under nitrogen, lithium aluminum hydride (LAH; 1.9 g, 50.5 mmol) was added in one portion. The resulting alcohol 17 was isolated through quenching the reactive LAH with water, until no hydrogen evolution was observed and the solution was then filtered, washed with THF, and concentrated to give alcohol 18 as a light brown solid (2.63 g, 72%).

Step 2—Preparation of Indazole-3-carboxyaldehyde 19

Manganese (II) oxide (6.4 g, 73 mmol) was added to a solution of (1H-indazol-3-yl)-methanol 18 (1.08 g, 7.4 mmol) in a mixture of DCM (40 ml) and THF (30 ml). The solution stirred for 16 hours at ambient temperature and filtered through celite and concentrated under reduced pressure to yield a white solid (0.65 g, 61%).

Step 3—Preparation of 3-(Indazo-3-yl)-propenoic acid methyl ester 20

3-(Indazo-3-yl)-propenoic acid methyl ester 20 was prepared from aldehyde 19, as described in Step 1, Example 3.

Step 4—Preparation of Indazole-3-propionic acid methyl ester 21

Indazole-3-propionic acid methyl ester was prepared from compound 20 as described in Step 2, Example 3.

5—Preparation of Indazole-3-propionic acid 16

Indazole-3-propionic acid was prepared through saponification of compound 21 as described in Step 4, Example 3 (M−1=197.1).

Example 6

Synthesis of 5-isopropoxy-3-(1-Benzene-sulfonyl-indol-3-yl)-propionic acid 22

Propionic acid 22 was prepared from commercially available 5-hydroxy-indole 23 in 5 steps as shown in Scheme 10.

Scheme 10

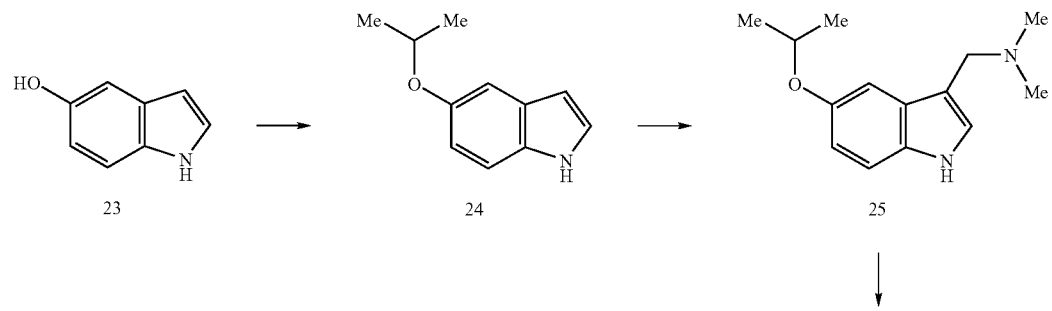

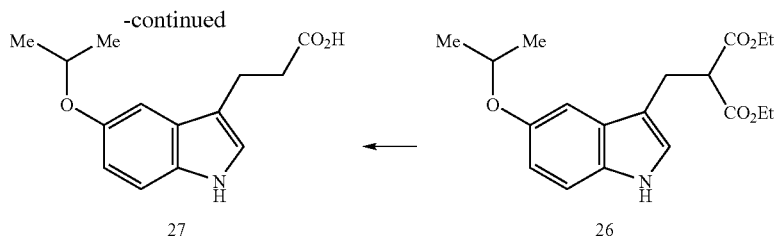

Step 1—Synthesis of 5-Isopropoxy-indole 24

To a solution of 5-hydroxyindole 23 (2.0 g, 0.015 mol) in 20 ml of acetonitrile, anhydrous potassium carbonate (4 grams, 0.028 mol) was added and stirred vigorously before isopropyl iodide (3 grams, 0.018 mol) was added. The reaction was stirred for 2 days at room temperature and the solid was washed with acetonitrile. The filtrate was concentrated and purifed with flash-chromatography (80% n-hexane/20% ethyl acetate) to give the desired product 24 as a light-yellowish oil (1.72 g, 83%; M+1=176.1).

Step 2—Synthesis of 5-Isopropoxy gramine 25

The 5-Isopropoxy gramine 25 was prepared from 5-Isopropoxy-indole 24 as described in Step 2, Example 4 (M+1=233.4).

Step 3—Synthesis of 2-(5-Isopropoxy-1H-Indol-3-ylmethyl)-malonic acid diethyl ester 26

Compound 26 was prepared from 25 as described in Step 3, Example 4 (M+1=348.5).

Step 4—Synthesis of 5-Isopropoxy-indole-3-propionic acid 27

5-Isopropoxy-indole-3-propionic acid 27 was prepared from compound 26 through the same protocol as described in Step 4, Example 4 (M−1=246.2).

Step 5—Synthesis of 5-isopropoxy-3-(1-Benzenesulfonyl-indol-3-yl)-propionic acid 22

To a cooled (−78° C.) solution of propionic acid (27) (96.3 mg, 0.510 mmol) in tetrahydrofuran (10 ml), n-butyl lithium (1.40 ml, 2.24 mol) was added next and stirred for 30 minutes at −78° C. Benzene sulfonyl chloride (277 mg, 1.5 mmol) was added next, and the reaction was stirred for 16-24 hours, allowing temperature to rise from −78° C. to ambient conditions. The reaction was then diluted with ethyl acetate, and 1M HCl was added to adjust the pH to 1-2. The layers were then separated, and the organic layer was placed over magnesium sulfate and concentrated under reduced pressure. The crude material was then purified by flash chromatography with silica, eluting with 5% methanol in dichloromethane to yield the desire product (22) as a white solid. (M−1=386.4)

Example 7

Preparation of Indole-3-propionic acid 28

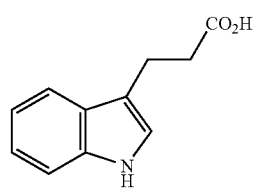

Indole-3-propionic acid 28 was prepared through the commercially available indole-3-carboxyaldehyde as described in Example 3. (M−1, 188.2)

Example 8

Preparation of 3-(1-Benzenesulfonyl-5-methoxy-1H-indol-3-yl)-propionic acid 29

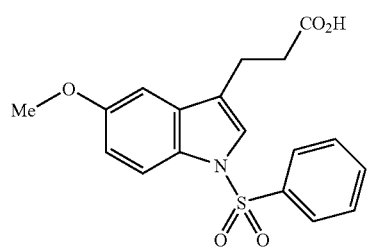

The 3-(1-benzenesulfonyl-5-methoxy-1H-indol-3-yl)-propionic acid 29 was prepared using the same protocol as in example 3, substituting 4-methoxybenzene sulfonyl chloride with benzene sulfonyl chloride, (M−1=358.4)

Example 9

Synthesis of 3-[5-Methoxy-1-(3-methoxy-benzyl)-1H-indol-3-yl]-propionic acid 30

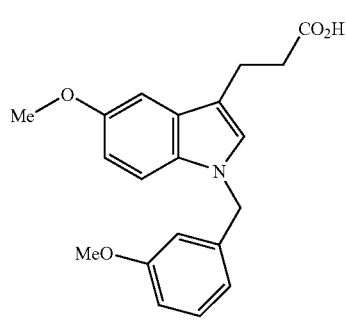

3-[5-Methoxy-1-(3-methoxy-benzyl)-1H-indol-3-yl]-propionic acid 30 was prepared using the same protocol as in example 3, substituting 4-methoxybenzene sulfonyl chloride with 3-methoxybenzyl bromide, (M−1=336.4)

Example 10

Synthesis of 3-[1-(3-Chloro-benzyl)-5-methoxy-1H-indol-3-yl]-propionic acid 31

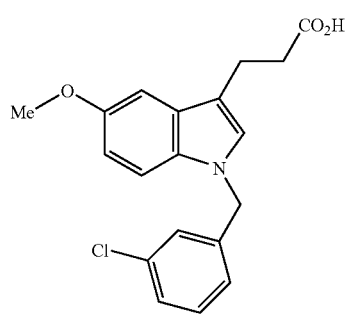

3-[1-(3-Chloro-benzyl)-5-methoxy-1H-indol-3-yl]-propionic acid 31 was prepared using the same protocol as in example 3, substituting 4-methoxybenzene sulfonyl chloride with 3-chlorobenzyl bromide, (M−1=322.4).

Example 11

Synthesis of 3-[1-(4-Fluoro-benzyl)-5-methoxy-1H-indol-3-yl]-propionic acid 32

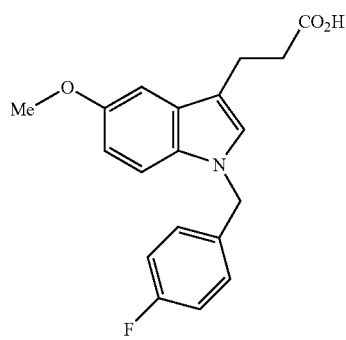

3-[1-(4-Fluoro-benzyl)-5-methoxy-1H-indol-3-yl]-propionic acid 32 was prepared using the same protocol as in example 3, substituting 4-methoxybenzene sulfonyl chloride with 4-fluorobenzyl bromide, (M−1=326.6).

Example 12

Preparation of 3-[1-(4-Chloro-benzyl)-5-methoxy-1H-indol-3-yl]-propionic acid 33

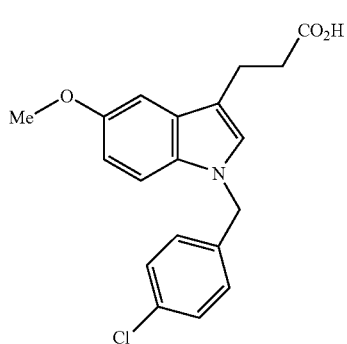

3-[1-(4-Chloro-benzyl)-5-methoxy-1H-indol-3-yl]-propionic acid 33 was prepared using the same protocol as in example 3, substituting 4-methoxybenzene sulfonyl chloride with 4-chlorobenzyl bromide. (M−1=342.8)

Example 13

Synthesis of 3-[5-Methoxy-1-(2-methoxy-benzyl)-1H-indol-3-yl]-propionic acid 34

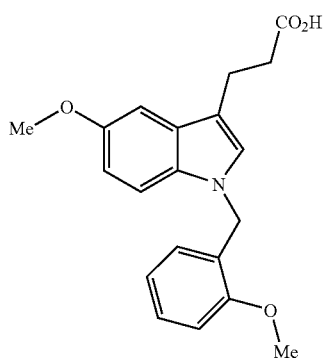

3-[5-Methoxy-1-(2-methoxy-benzyl)-1H-indol-3-yl]-propionic acid 34 was prepared using the same protocol as example 3, substituting 4-methoxybenzene sulfonyl chloride with 2-methoxybenzyl bromide. (M−1=338.4)

Example 14

Synthesis of 3-[5-Methoxy-1-(2-trifluoromethoxy-benzyl)-1H-indol-3-yl]-propionic acid 35

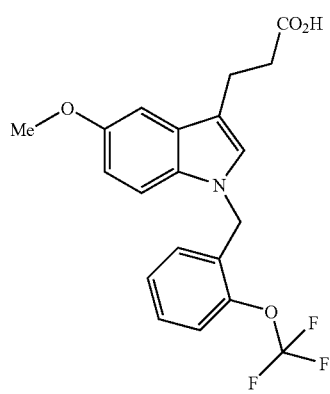

35

3-[5-Methoxy-1-(2-trifluoromethoxy-benzyl)-1H-indol-3-yl]-propionic acid 35 was prepared using the same protocol as in example 3, substituting 4-methoxybenzene sulfonyl chloride with 2-trifluoromethoxybenzyl bromide, (M−1=392.3).

Example 15

Synthesis of 3-[5-Methoxy-1-(3-trifluoromethoxy-benzyl)-1H-indol-3-yl]-propionic acid 36

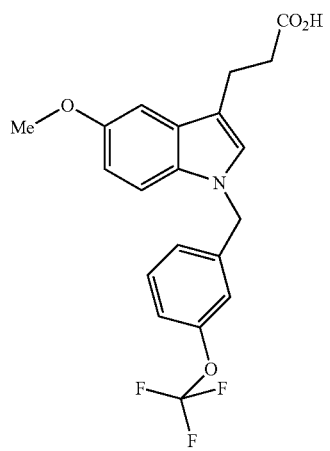

36

3-[5-Methoxy-1-(3-trifluoromethoxy-benzyl)-1H-indol-3-yl]-propionic acid 36 was prepared using the same protocol as in example 3, substituting 4-methoxybenzene sulfonyl chloride with 3-trifluoromethoxybenzyl bromide, (M−1=392.4).

Example 16

Synthesis of 3-(1-Ethylthiocarbamoyl-5-methoxy-1H-indol-3-yl)-propionic acid 37

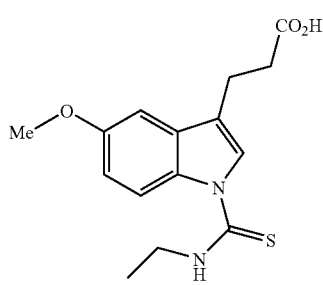

37

3-(1-Ethylthiocarbamoyl-5-methoxy-1H-indol-3-yl)-propionic acid 37 was prepared using the same protocol as in example 3, substituting 4-methoxybenzene sulfonyl chloride with ethyl isothiocyanate, (M−1=305.4).

Example 17

Synthesis of 3-[5-Methoxy-1-(toluene-4-sulfonyl)-1H-indol-3-yl]-propionic acid 38

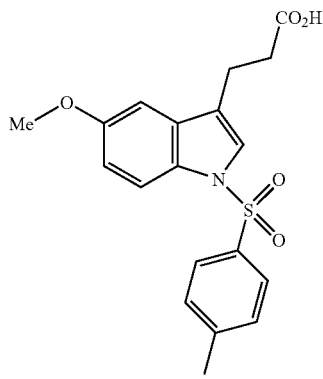

38

3-[5-Methoxy-1-(toluene-4-sulfonyl)-1H-indol-3-yl]-propionic acid 38 was prepared using the same protocol as in example 3, substituting 4-methoxybenzene sulfonyl chloride with 4-tolyl sulfonyl chloride, (M−1=373.4).

Example 18

Synthesis of 3-(1-Benzenesulfonyl-1H-indazol-3-yl)-propionic acid 39

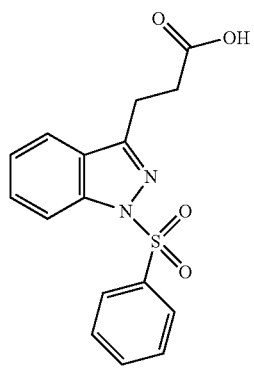

39

3-(1-Benzenesulfonyl-1H-indazol-3-yl)-propionic acid 39 was prepared through the same protocol as in Step 5, Example 6, (M−1=329.4).

Example 19

Synthesis of 3-[1-(4-Isopropyl-benzenesulfonyl)-5-methoxy-1H-indol-3-yl]-propionic acid methyl ester 40

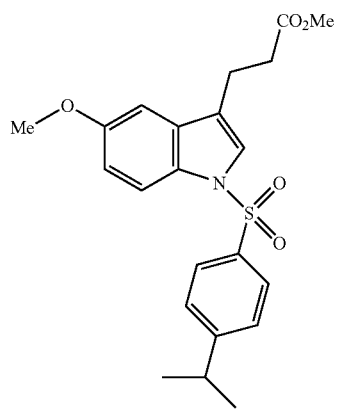

40

3-[1-(4-Isopropyl-benzenesulfonyl)-5-methoxy-1H-indol-3-yl]-propionic acid methyl ester 40 was prepared using the same protocol as in example 3, substituting 4-methoxy-benzenesulfonyl chloride with 4-isopropylbenzenesulfonyl chloride, (M+1=416.6).

Example 20

Synthesis of 3-[1-(4-Isopropyl-benzenesulfonyl)-5-methoxy-1H-indol-3-yl]-propionic acid 41

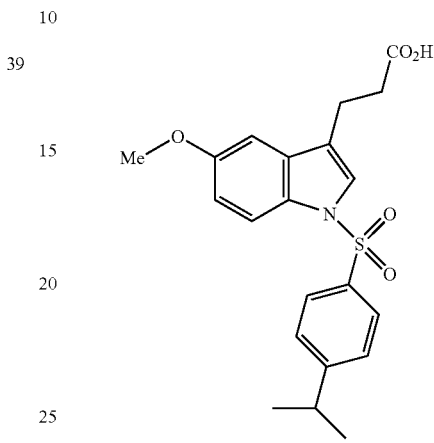

41

3-[1-(4-Isopropyl-benzenesulfonyl)-5-methoxy-1H-indol-3-yl]-propionic acid was prepared through the saponification protocol with 3-[1-(4-Isopropyl-benzenesulfonyl)-5-methoxy-1H-indol-3-yl]-propionic acid methyl ester 41 as described in step 4 of example 3, (M−1=400.5).

Example 21

Synthesis of 3-[1-(4-Butoxy-benzenesulfonyl)-5-methoxy-1H-indol-3-yl]-propionic acid methyl ester 42

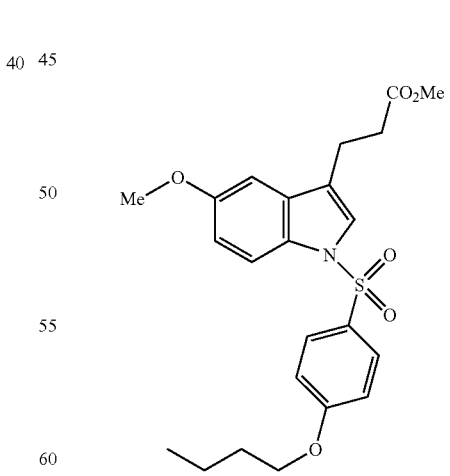

42

3-[1-(4-Butoxy-benzenesulfonyl)-5-methoxy-1H-indol-3-yl]-propionic acid methyl ester 42 was prepared using the same protocol as example 3, substituting 4-methoxybenzenesulfonyl chloride with 4-n-butoxybenzenesulfonyl chloride (M+1=446.5)

Example 22

Synthesis of 3-[1-(4-Butoxy-benzenesulfonyl)-5-methoxy-1H-indol-3-yl]-propionic acid 43

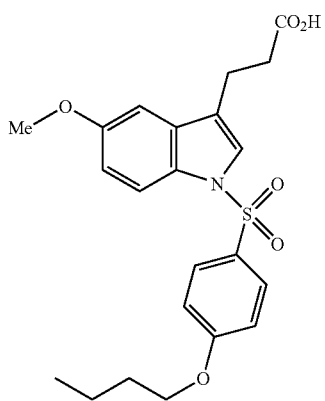

3-[1-(4-Butoxy-benzenesulfonyl)-5-methoxy-1H-indol-3-yl]-propionic acid was prepared through the saponification protocol with -[1-(4-Butoxy-benzenesulfonyl)-5-methoxy-1H-indol-3-yl]-propionic acid methyl ester 42 as described in step 4 of example 3, (M−1=430.5).

Example 23

Synthesis of 3-[5-Methoxy-1-(4-trifluoromethoxy-benzenesulfonyl)-1H-indol-3-yl]-propionic acid methyl ester 44

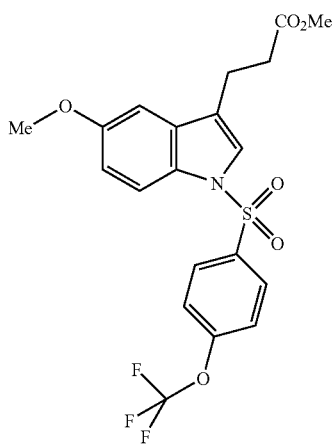

3-[5-Methoxy-1-(4-trifluoromethoxy-benzenesulfonyl)-1H-indol-3-yl]-propionic acid methyl ester was prepared using the same protocol as in example 3, substituting 4-methoxybenzenesulfonyl chloride with 4-trifluoromethoxybenzene sulfonyl chloride, (M+1=457.4).

Example 24

Synthesis of 3-[5-Methoxy-1-(4-trifluoromethoxy-benzenesulfonyl)-1H-indol-3-yl]-propionic acid 45

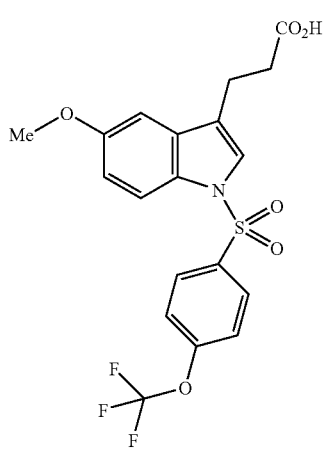

3-[5-Methoxy-1-(4-trifluoromethoxy-benzenesulfonyl)-1H-indol-3-yl]-propionic acid was prepared through the saponification protocol with 3-[5-Methoxy-1-(4-trifluoromethoxy-benzenesulfonyl)-1H-indol-3-yl]-propionic acid methyl ester 45 as described in step 4 of example 3, (M−1=442.4).

Example 25

Synthesis of 3-[5-Methoxy-1-(4-phenoxy-benzenesulfonyl)-1H-indol-3-yl]-propionic acid methyl ester 46

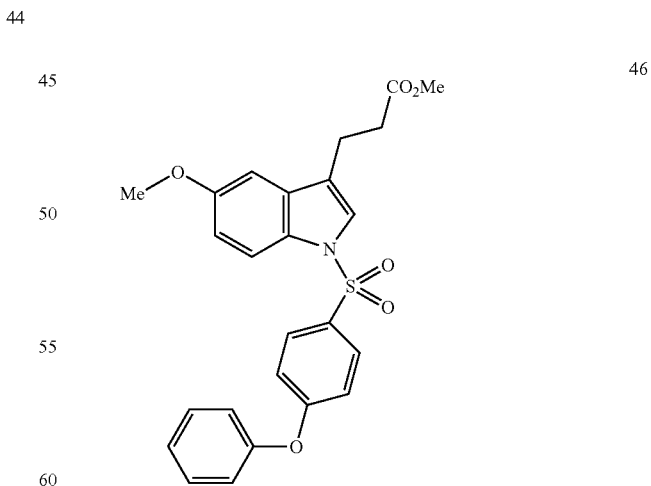

3-[5-Methoxy-1-(4-phenoxy-benzenesulfonyl)-1H-indol-3-yl]-propionic acid methyl ester 45 as prepared using the same protocol as example 3, substituting 4-methoxybenzenesulfonyl chloride with 4-phenoxybenzene sulfonyl chloride, (M+1=466.6).

Example 26

Synthesis of 3-[5-Methoxy-1-(4-phenoxy-benzene-sulfonyl)-1H-indol-3-yl]-propionic acid 47

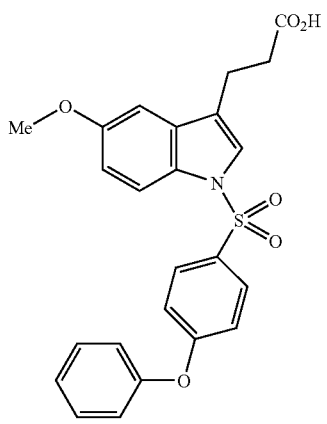

3-[5-Methoxy-1-(4-phenoxy-benzenesulfonyl)-1H-indol-3-yl]-propionic acid was prepared through the saponification protocol with 3-[5-Methoxy-1-(4-phenoxy-benzenesulfonyl)-1H-indol-3-yl]-propionic acid methyl ester 46 as described in step 4 of example 3, (M−1=450.5).

Example 27

Synthesis of 3-[1-(4-Chloro-benzenesulfonyl)-5-methoxy-1H-indol-3-yl]-propionic acid methyl ester 48

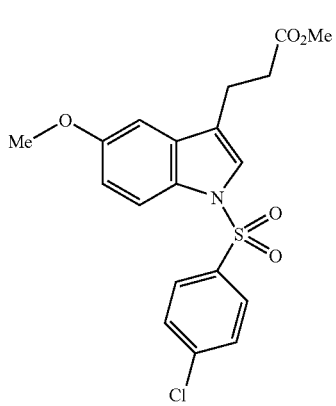

3-[1-(4-Chloro-benzenesulfonyl)-5-methoxy-1H-indol-3-yl]-propionic acid methyl ester 48 was prepared using the same protocol as in example 3, substituting 4-methoxybenzene sulfonyl chloride with 4-chlorobenzene sulfonyl chloride (M+1=406.9).

Example 28

Synthesis of 3-[1-(4-Chloro-benzenesulfonyl)-5-methoxy-1H-indol-3-yl]-propionic acid 49

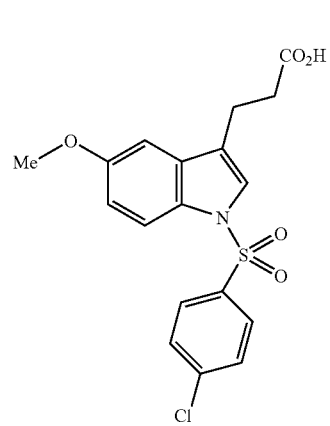

3-[1-(4-Chloro-benzenesulfonyl)-5-methoxy-1H-indol-3-yl]-propionic acid 49 was prepared through the saponification protocol with 3-[1-(4-Chloro-benzenesulfonyl)-5-methoxy-1H-indol-3-yl]-propionic acid methyl ester 48 as described in step 4 of example 3, (M−1=392.9).

Example 29

Synthesis of 3-[1-(4-Cyano-benzenesulfonyl)-5-methoxy-1H-indol-3-yl]-propionic acid methyl ester 50

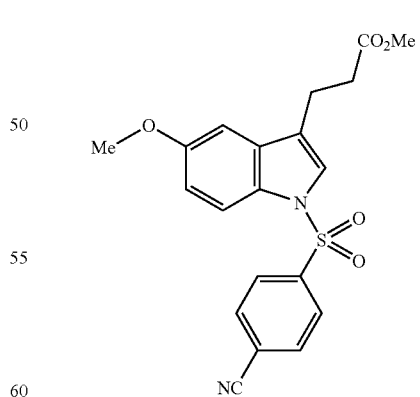

3-[1-(4-Cyano-benzenesulfonyl)-5-methoxy-1H-indol-3-yl]-propionic acid methyl ester 50 was prepared using the same protocol as example 3, substituting 4-methoxybenzene sulfonyl chloride with 4-cyanobenzene sulfonyl chloride. (M+1=399.4)

Example 30

Synthesis of 3-[1-(4-Cyano-benzenesulfonyl)-5-methoxy-1H-indol-3-yl]-propionic acid 51

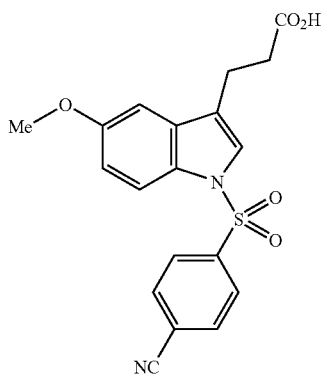

3-[1-(4-Cyano-benzenesulfonyl)-5-methoxy-1H-indol-3-yl]-propionic acid 51 was prepared through the saponification protocol with 3-[1-(4-Cyano-benzenesulfonyl)-5-methoxy-1H-indol-3-yl]-propionic acid methyl ester 50 as described in step 4 of example 3, (M−1=383.4).

Example 31

Synthesis of 3-[1-(3,4-Dichloro-benzenesulfonyl)-5-methoxy-1H-indol-3-yl]-propionic acid methyl ester 52

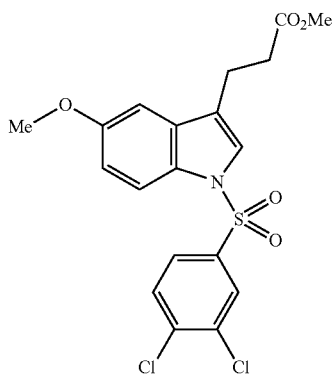

3-[1-(3,4-Dichloro-benzenesulfonyl)-5-methoxy-1H-indol-3-yl]-propionic acid methyl ester 52 was prepared using the same protocol as in example 3, substituting 4-methoxybenzene sulfonyl chloride with 3,4-dichlorobenzene sulfonyl chloride, (M+1=443.3).

Example 32

Synthesis of 3-[1-(3,4-Dichloro-benzenesulfonyl)-5-methoxy-1H-indol-3-yl]-propionic acid 53

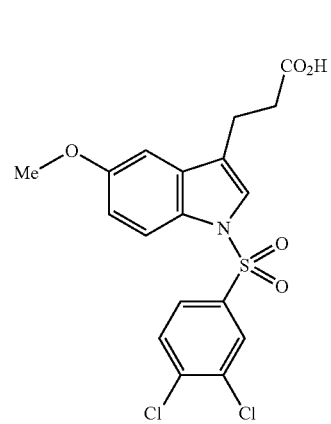

3-[1-(3,4-Dichloro-benzenesulfonyl)-5-methoxy-1H-indol-3-yl]-propionic acid 53 was prepared through the saponification with 3-[1-(3,4-Dichloro-benzenesulfonyl)-5-methoxy-1H-indol-3-yl]-propionic acid methyl ester 52 as described in step 4 of example 3, (M−1=427.3).

Example 33

Synthesis of 3-[5-Methoxy-1-(4-trifluoromethyl-benzenesulfonyl)-1H-indol-3-yl]-propionic acid methyl ester 54

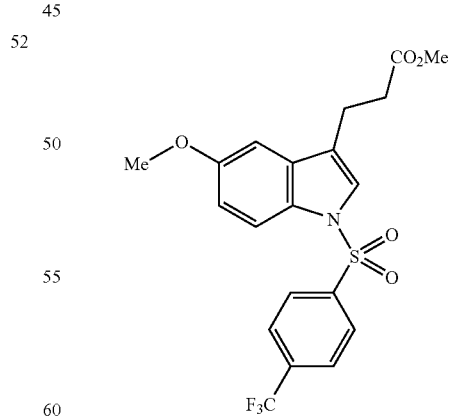

3-[5-Methoxy-1-(4-trifluoromethyl-benzenesulfonyl)-1H-indol-3-yl]-propionic acid methyl ester 54 was prepared using the same protocol as in example 3, substituting 4-methoxybenzenesulfonyl chloride with trifluoromethylbenzene sulfonyl chloride, (M+1=442.4).

Example 34

Synthesis of 3-[5-Methoxy-1-(4-trifluoromethyl-benzenesulfonyl)-1H-indol-3-yl]-propionic acid 55

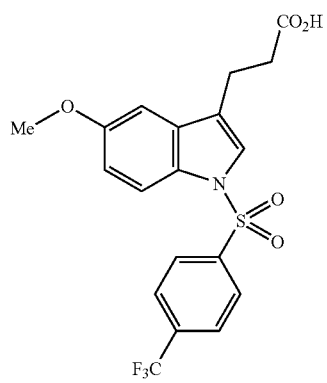

55

3-[5-Methoxy-1-(4-trifluoromethyl-benzenesulfonyl)-1H-indol-3-yl]-propionic acid 55 was prepared through the saponification of 3-[5-Methoxy-1-(4-trifluoromethyl-benzenesulfonyl)-1H-indol-3-yl]-propionic acid methyl ester 54 as described in step 3 of example 3, (M+1=404.5).

Example 35

Synthesis of 3-[1-(4-Fluoro-benzenesulfonyl)-5-methoxy-1H-indol-3-yl]-propionic acid methyl ester 56

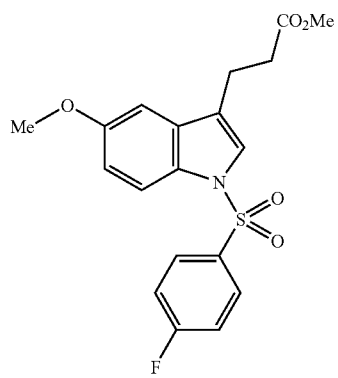

56

3-[1-(4-Fluoro-benzenesulfonyl)-5-methoxy-1H-indol-3-yl]-propionic acid methyl ester 56 was prepared using the same protocol as example 3, substituting 4-methoxybenzene sulfonyl chloride with 4-fluorobenzene sulfonyl chloride, (M+1=392.4).

Example 36

Synthesis of 3-[1-(4-Fluoro-benzenesulfonyl)-5-methoxy-1H-indol-3-yl]-propionic acid 57

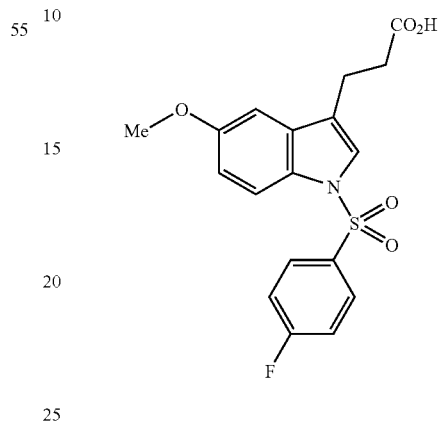

57

3-[1-(4-Fluoro-benzenesulfonyl)-5-methoxy-1H-indol-3-yl]-propionic acid 57 was prepared through the saponification of the 3-[1-(4-Fluoro-benzenesulfonyl)-5-methoxy-1H-indol-3-yl]-propionic acid methyl ester 56 as described in step 4 of example 3, (M−1=376.4).

Example 37

Synthesis of 3-[5-Methoxy-1-(3-phenoxy-benzenesulfonyl)-1H-indol-3-yl]-propionic acid methyl ester 58

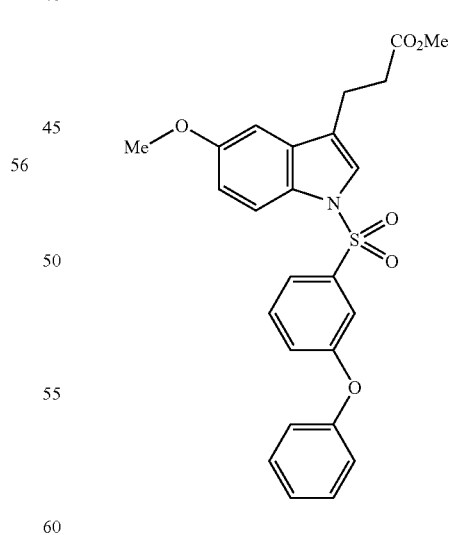

58

3-[5-Methoxy-1-(3-phenoxy-benzenesulfonyl)-1H-indol-3-yl]-propionic acid methyl ester 58 was prepared using the same protocol as in example 3, substituting 4-methoxybenzenesulfonyl chloride with 3-phenoxybenzene sulfonyl chloride, (M+1=466.5).

Example 38

Synthesis of 3-[5-Methoxy-1-(3-phenoxy-benzenesulfonyl)-1H-indol-3-yl]-propionic acid 59

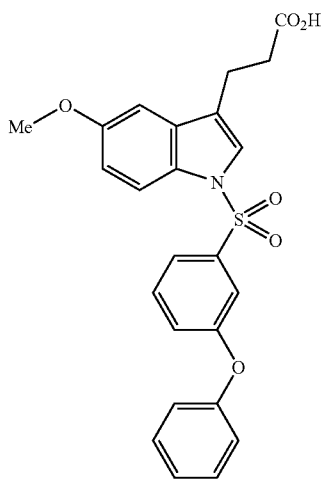

3-[5-Methoxy-1-(3-phenoxy-benzenesulfonyl)-1H-indol-3-yl]-propionic acid 59 was prepared through the saponification of 3-[5-Methoxy-1-(3-phenoxy-benzenesulfonyl)-1H-indol-3-yl]-propionic acid methyl ester 58 as described in step 4 of example 3, (M−1=376.4).

Example 39

Synthesis of 3-[1-(3-Fluoro-benzenesulfonyl)-5-methoxy-1H-indol-3-yl]-propionic acid methyl ester 60

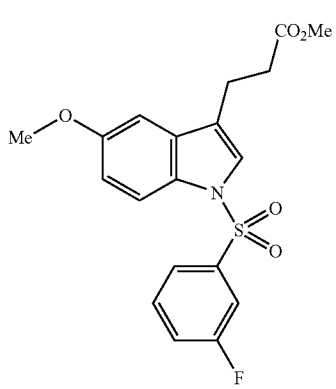

3-[1-(3-Fluoro-benzenesulfonyl)-5-methoxy-1H-indol-3-yl]-propionic acid methyl ester 60 was prepared using the same protocol as in example 3, substituting 4-methoxybenzene sulfonyl chloride with 3-fluorobenzene sulfonyl chloride, (M+1=392.3).

Example 40

Synthesis of 3-[1-(3-Fluoro-benzenesulfonyl)-5-methoxy-1H-indol-3-yl]-propionic acid 61

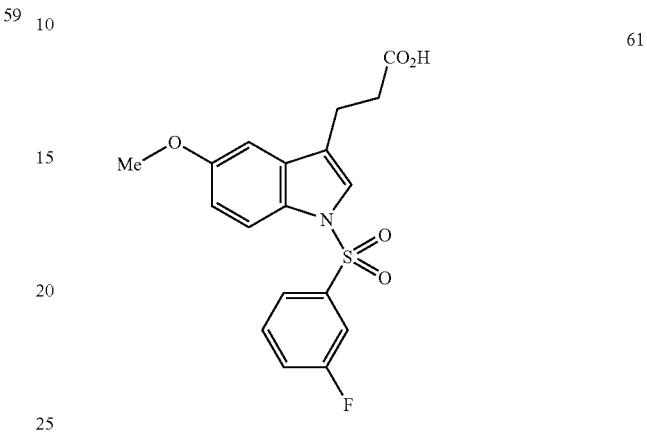

3-[1-(3-Fluoro-benzenesulfonyl)-5-methoxy-1H-indol-3-yl]-propionic acid 61 was prepared through saponification of 3-[1-(3-Fluoro-benzenesulfonyl)-5-methoxy-1H-indol-3-yl]-propionic acid methyl ester 60 as described in step 4 of example 3, (M−1 376.4).

Example 41

Synthesis of 3-[5-Methoxy-1-(toluene-3-sulfonyl)-1H-indol-3-yl]-propionic acid methyl ester 62

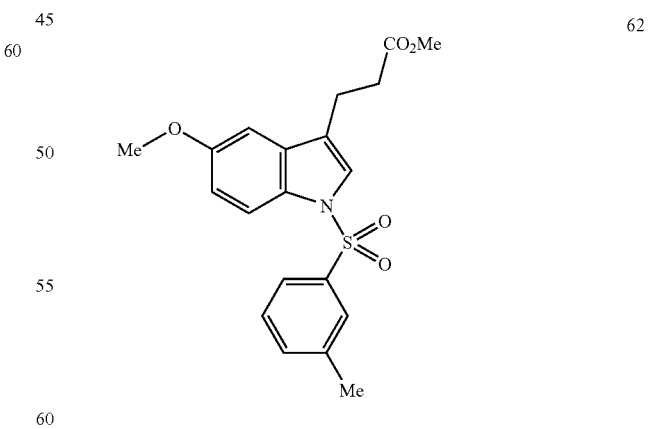

3-[5-Methoxy-1-(toluene-3-sulfonyl)-1H-indol-3-yl]-propionic acid methyl ester was prepared using the same protocol as in example 3, substituting 4-methoxybenzenesulfonyl chloride with 3-tolyl sulfonyl chloride, (M+1=388.5).

Example 42

Synthesis of 3-[5-Methoxy-1-(toluene-3-sulfonyl)-1H-indol-3-yl]-propionic acid 63

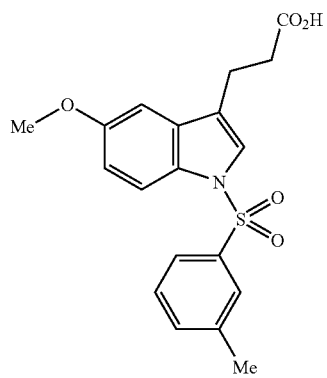

63

3-[5-Methoxy-1-(toluene-3-sulfonyl)-1H-indol-3-yl]-propionic acid 63 was prepared through the saponification of 3-[5-Methoxy-1-(toluene-3-sulfonyl)-1H-indol-3-yl]-propionic acid methyl ester 62 as described in step 4 of example 3, (M−1=372.4).

Example 43

Synthesis of 3-[1-(3-Chloro-benzenesulfonyl)-5-methoxy-1H-indol-3-yl]-propionic acid methyl ester 64

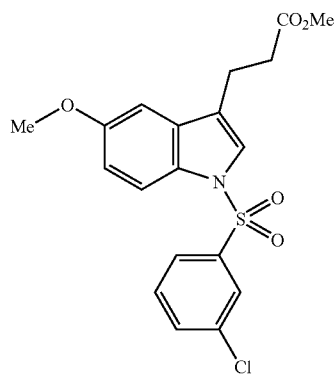

64

3-[1-(3-Chloro-benzenesulfonyl)-5-methoxy-1H-indol-3-yl]-propionic acid methyl ester 64 was prepared using the same protocol as in example 3, substituting 4-methoxybenzenesulfonyl chloride with 3-chlorobenzene sulfonyl chloride, (M+1=408.9).

Example 44

Synthesis of 3-[1-(3-Chloro-benzenesulfonyl)-5-methoxy-1H-indol-3-yl]-propionic acid 65

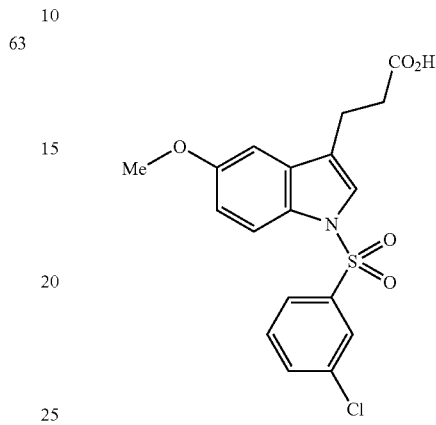

65

3-[1-(3-Chloro-benzenesulfonyl)-5-methoxy-1H-indol-3-yl]-propionic acid 65 was prepared through the saponification of 3-[1-(3-Chloro-benzenesulfonyl)-5-methoxy-1H-indol-3-yl]-propionic acid methyl ester 64 as described in step 4 of example 3, (M−1=392.7).

Example 45

Synthesis of 3-[5-Methoxy-1-(3-methoxy-benzenesulfonyl)-1H-indol-3-yl]-propionic acid methyl ester 66

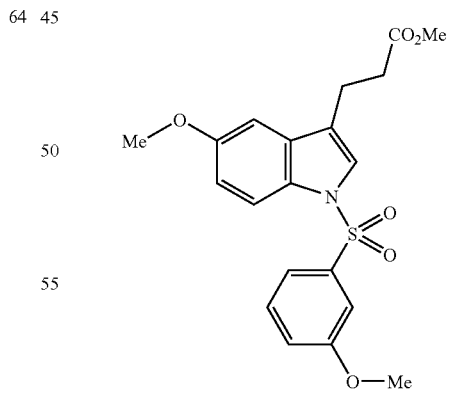

66

3-[5-Methoxy-1-(3-methoxy-benzenesulfonyl)-1H-indol-3-yl]-propionic acid methyl ester 66 was prepared using the same protocol as in example 3, substituting 4-methoxybenzenesulfonyl chloride with 3-methoxybenzene sulfonyl chloride, (M+1=404.5).

Example 46

Synthesis of 3-[5-Methoxy-1-(3-methoxy-benzene-sulfonyl)-1H-indol-3-yl]-propionic acid 67

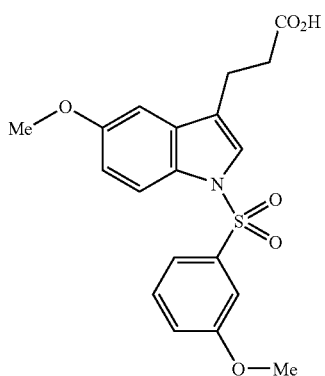

67

3-[5-Methoxy-1-(3-methoxy-benzenesulfonyl)-1H-indol-3-yl]-propionic acid 67 was prepared through the saponification of 3-[5-Methoxy-1-(3-methoxy-benzenesulfonyl)-1H-indol-3-yl]-propionic acid methyl ester 66 as described in step 4 of example 3, (M−1=388.4).

Example 47

Synthesis of 3-[5-Methoxy-1-(3-trifluoromethyl-benzenesulfonyl)-1H-indol-3-yl]-propionic acid methyl ester 68

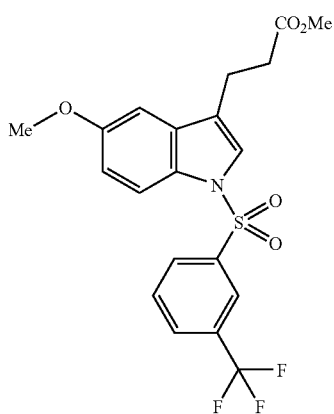

68

3-[5-Methoxy-1-(3-trifluoromethyl-benzenesulfonyl)-1H-indol-3-yl]-propionic acid methyl ester 68 was prepared using the same protocol as in example 3, substituting 4-methoxybenzene sulfonyl chloride with 3-trifluoromethylbenzene sulfonyl chloride, (M+1=442.4).

Example 48

Synthesis of 3-[5-Methoxy-1-(3-trifluoromethyl-benzenesulfonyl)-1H-indol-3-yl]-propionic acid 69

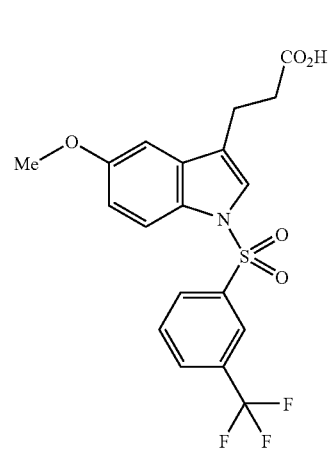

69

3-[5-Methoxy-1-(3-trifluoromethyl-benzenesulfonyl)-1H-indol-3-yl]-propionic acid 69 was prepared through the saponification of 3-[5-Methoxy-1-(3-trifluoromethyl-benzenesulfonyl)-1H-indol-3-yl]-propionic acid methyl ester 68 as described in step 4 of example 3, (M−1=426.4).

Example 49

Synthesis of 3-(1-Benzyl-5-methoxy-1H-indol-3-yl)-propionic acid methyl ester 70

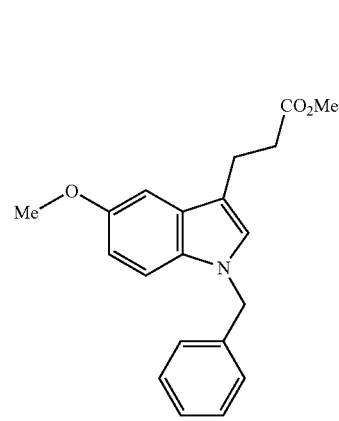

70

3-(1-Benzyl-5-methoxy-1H-indol-3-yl)-propionic acid methyl ester 70 was prepared using the same protocol as example 3, substituting 4-methoxybenzenesulfonyl chloride with benzyl bromide, (M+1=324.4).

Example 50

Synthesis of 3-(1-Benzyl-5-methoxy-1H-indol-3-yl)-propionic acid 71

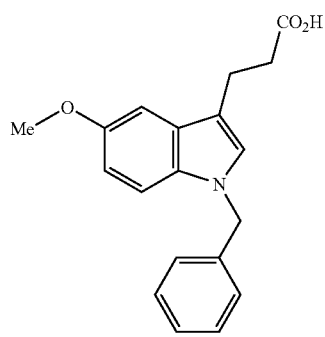

71

3-(1-Benzyl-5-methoxy-1H-indol-3-yl)-propionic acid 71 was prepared through the saponification of 3-(1-Benzyl-5-methoxy-1H-indol-3-yl)-propionic acid methyl ester 70 as described in step 4 of example 3, (M+1=308.3).

Example 51

Synthesis of 3-[5-Methoxy-1-(thiophene-2-sulfonyl)-1H-indol-3-yl]-propionic acid methyl ester 72

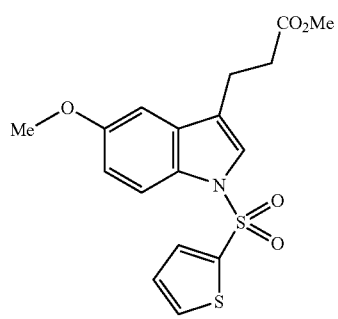

72

3-[5-Methoxy-1-(thiophene-2-sulfonyl)-1H-indol-3-yl]-propionic acid methyl ester 72 was prepared using the same protocol as example 3, substituting 4-methoxybenzene sulfonyl chloride with 2-thiopene sulfonyl chloride, (M+1=380.5).

Example 52

Synthesis of 3-[5-Methoxy-1-(thiophene-2-sulfonyl)-1H-indol-3-yl]-propionic acid 73

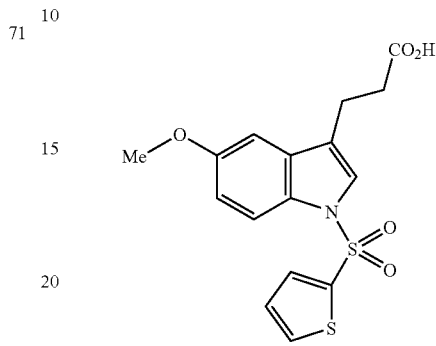

73

3-[5-Methoxy-1-(thiophene-2-sulfonyl)-1H-indol-3-yl]-propionic acid was prepared through the saponification of 3-[5-Methoxy-1-(thiophene-2-sulfonyl)-1H-indol-3-yl]-propionic acid methyl ester as described in step 4 of example 3, (M−1=364.4).

Example 53

Synthesis of 3-(5-Methoxy-1-phenylthiocarbamoyl-1H-indol-3-yl)-propionic acid methyl ester 74

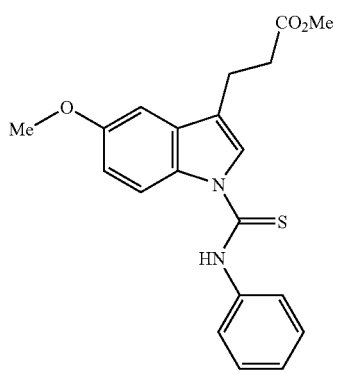

74

3-(5-Methoxy-1-phenylthiocarbamoyl-1H-indol-3-yl)-propionic acid methyl ester 74 was prepared using the same protocol as example 3, substituting 4-methoxybenzene sulfonyl chloride with phenyl isothiocyanate, (M+1=369.5).

Example 54

Synthesis of 3-(5-Methoxy-1-phenylthiocarbamoyl-1H-indol-3-yl)-propionic acid 75

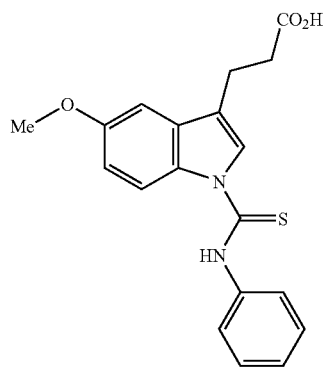

75

3-(5-Methoxy-1-phenylthiocarbamoyl-1H-indol-3-yl)-propionic acid 75 was prepared through the saponification of 3-(5-Methoxy-1-phenylthiocarbamoyl-1H-indol-3-yl)-propionic acid methyl ester 74 as described in step 4 of example 3, (M−1=353.4).

Example 55

Synthesis of 3-[1-(4-Butyl-benzenesulfonyl)-5-methoxy-1H-indol-3-yl]-propionic acid methyl ester 76

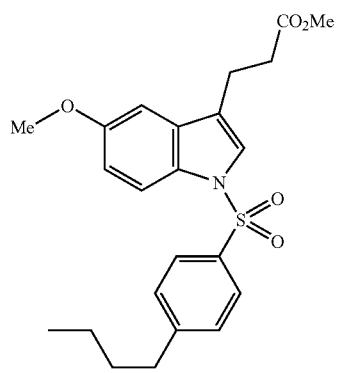

76

3-[1-(4-Butyl-benzenesulfonyl)-5-methoxy-1H-indol-3-yl]-propionic acid methyl ester 76 was prepared using the same protocol as example 3, substituting 4-methoxybenzene sulfonyl chloride with 4-n-butylbenzene sulfonyl chloride, (M+1=430.2).

Example 56

Synthesis of 3-[1-(4-Butyl-benzenesulfonyl)-5-methoxy-1H-indol-3-yl]-propionic acid 77

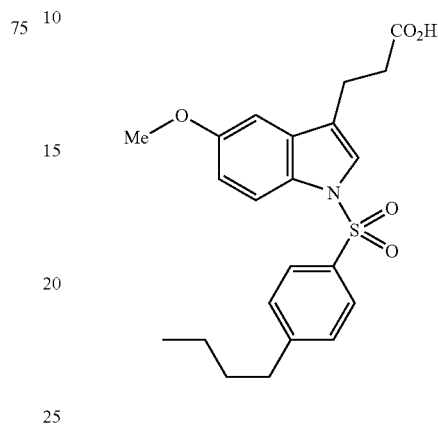

77

3-[1-(4-Butyl-benzenesulfonyl)-5-methoxy-1H-indol-3-yl]-propionic acid 77 was prepared through the saponification of 3-[1-(4-Butyl-benzenesulfonyl)-5-methoxy-1H-indol-3-yl]-propionic acid methyl ester 76 as described in step 4 of example 3, (M−1=414.1).

Example 57

Synthesis of 3-[5-Methoxy-1-(3-trifluoromethoxy-benzenesulfonyl)-1H-indol-3-yl]-propionic acid methyl ester 78

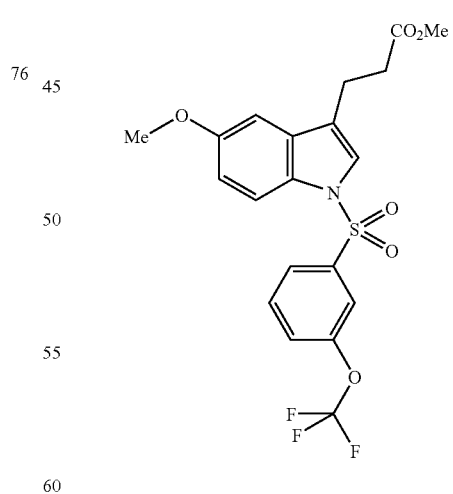

78

3-[5-Methoxy-1-(3-trifluoromethoxy-benzenesulfonyl)-1H-indol-3-yl]-propionic acid methyl ester 78 was prepared using the same protocol as example 3, substituting 4-methoxybenzene sulfonyl chloride with 3-trifluorobenzene sulfonyl chloride (M+1=458.1).

Example 58

Synthesis of 3-[5-Methoxy-1-(3-trifluoromethoxy-benzenesulfonyl)-1H-indol-3-yl]-propionic acid 79

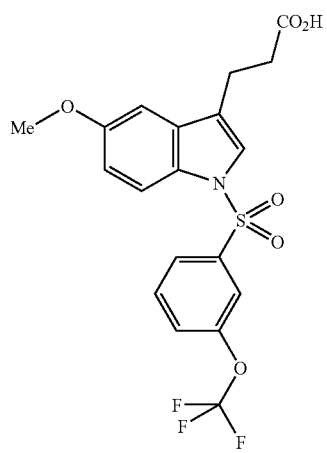

3-[5-Methoxy-1-(3-trifluoromethoxy-benzenesulfonyl)-1H-indol-3-yl]-propionic acid 79 was prepared through the saponification of 3-[5-Methoxy-1-(3-trifluoromethoxy-benzenesulfonyl)-1H-indol-3-yl]-propionic acid methyl ester 4 as described in step 4 of example 3, (M−1=442.0).

Example 59

Synthesis of 3-(1-Benzoyl-5-methoxy-1H-indol-3-yl)-propionic acid methyl ester 80

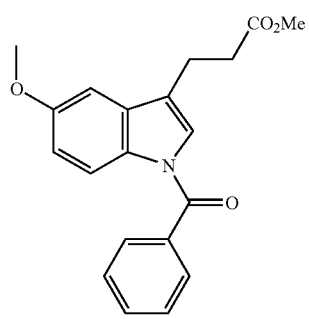

3-(1-Benzoyl-5-methoxy-1H-indol-3-yl)-propionic acid methyl ester 80 was prepared using the same protocol as example 3, substituting 4-methoxybenzene sulfonyl chloride with benzoyl chloride, (M+1=338.1).

Example 60

Synthesis of 3-(1-Benzoyl-5-methoxy-1H-indol-3-yl)-propionic acid 81

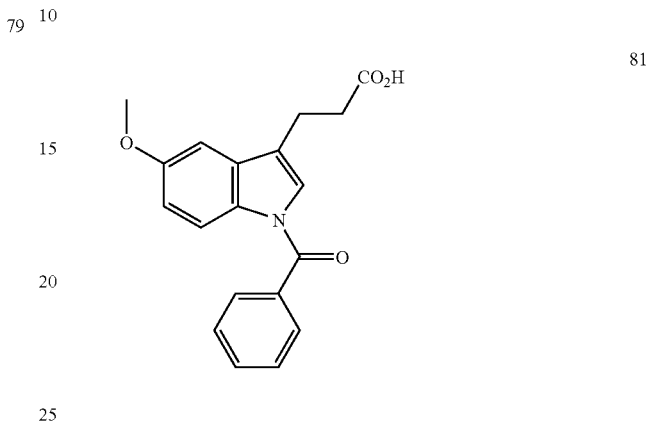

3-(1-Benzoyl-5-methoxy-1H-indol-3-yl)-propionic acid 81 was prepared through the saponification of 3-(1-Benzoyl-5-methoxy-1H-indol-3-yl)-propionic acid methyl ester 80 as described in step 4 of example 3, (M−1=322.1).

Example 61

Synthesis of 3-(1-Benzenesulfonyl-5-ethoxy-1H-indol-3-yl)-propionic acid 82

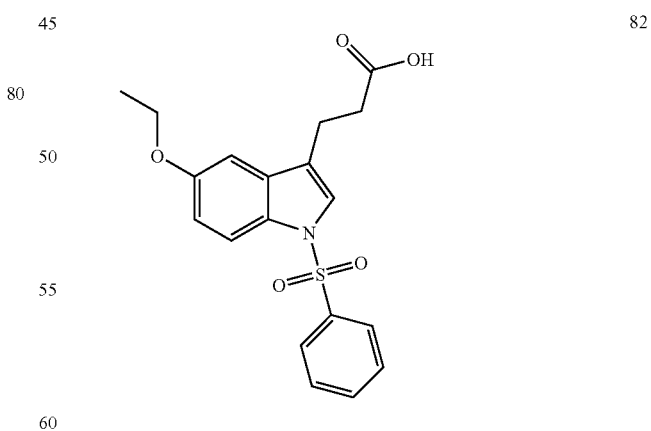

3-(1-Benzenesulfonyl-5-ethoxy-1H-indol-3-yl)-propionic acid 83 was prepared using the same protocol as example 6, substituting 2-propyl iodide with ethyl iodide, (M−1=372.4).

Example 62

Synthesis of 3-[1-(4-Isopropoxy-benzenesulfonyl)-5-methoxy-1H-indol-3-yl]-propionic acid 83

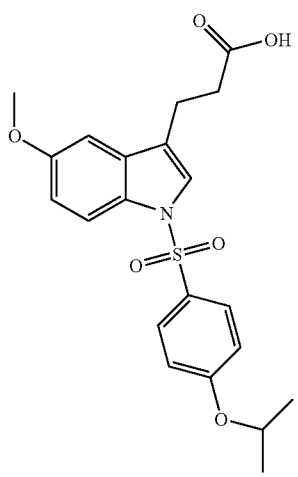

3-[1-(4-Isopropoxy-benzenesulfonyl)-5-methoxy-1H-indol-3-yl]-propionic acid 83 was prepared using the same protocol as example 3, substituting 4-methoxybenzene sulfonyl chloride with 4-isopropoxybenzene sulfonyl chloride, (M−1=416.5).

Example 63

Synthesis of 3-(5-Methoxy-1-phenylcarbamoyl-1H-indol-3-yl)-propionic acid methyl ester 84

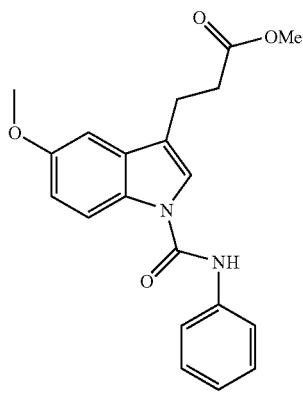

3-(5-Methoxy-1-phenylcarbamoyl-1H-indol-3-yl)-propionic acid methyl ester 84 was prepared using the same protocol as example 3, substituting 4-methoxybenzene sulfonyl chloride with phenyl isocyanate, (M+1=353.4).

Example 64

Synthesis of 3-(5-Methoxy-1-phenylcarbamoyl-1H-indol-3-yl)-propionic acid 85

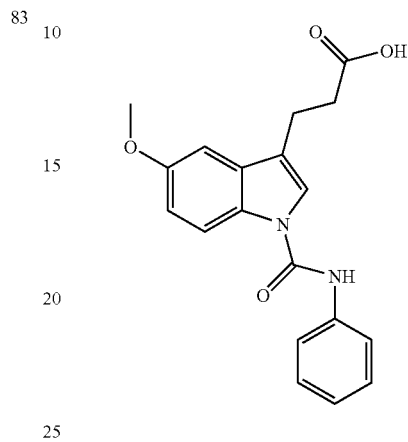

3-(5-Methoxy-1-phenylcarbamoyl-1H-indol-3-yl)-propionic acid 85 was prepared through the saponification of 3-(5-Methoxy-1-phenylcarbamoyl-1H-indol-3-yl)-propionic acid methyl ester 84 as described in step 4 of example 3, (M−1=337.4).

Example 65

Synthesis of 3-[1-(4-Ethyl-benzenesulfonyl)-5-methoxy-1H-indol-3-yl]-propionic acid 86

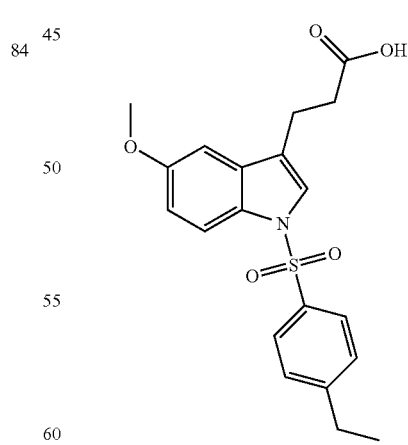

3-[1-(4-Ethyl-benzenesulfonyl)-5-methoxy-1H-indol-3-yl]-propionic acid 86 was prepared using the same protocol as example 3, substituting 4-methoxybenzene sulfonyl chloride with 4-ethylbenzene sulfonyl chloride, (M−1=386.4).

Example 66

Synthesis of 3-(5-bromo-1H-indol-3-yl)-propionic acid 87

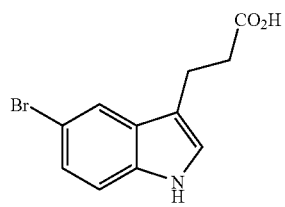

3-(5-bromo-1H-indol-3-yl)-propionic acid 87 was prepared from commercially available 5-Bromoindole using the same protocol as in example 6 to give a beige solid, (M−1=268.0).

Example 67

Synthesis of 3-(5-Bromo-1H-indol-3-yl)-propionic acid methyl ester 88

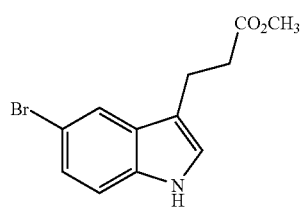

The 5-bromoindole-3-propionic acid 87 (4.0 g, 14.91 mmol) was dissolved in methanol (MeOH, 100 mL) and Trimethylsilyl chloride (TMSCl, 33.0 mL, 32.8 mmol, 1.0 M in CH$_2$Cl$_2$) was added dropwise The mixture was stirred for 24 hours, followed by refluxing for 1 hour. The reaction was allowed to cool to room temperature and the solvent was evaporated to ester as a white solid, (M+1=284).

Example 68

Synthesis of 3-(1-Benzenesulfonyl-5-bromo-1H-indol-3-yl)-propionic acid methyl ester 89

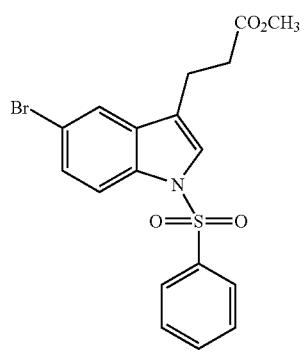

3-(1-Benzenesulfonyl-5-bromo-1H-indol-3-yl)-propionic acid methyl ester 89 prepared as described in step 3 of example 3 by substituting 4-methoxybenzenesulfonyl chloride with benzenesulfonyl chloride, (M+1=424).

Example 69

Synthesis of 3-(1-Benzenesulfonyl-5-bromo-1H-indol-3-yl)-propionic acid methyl ester 90

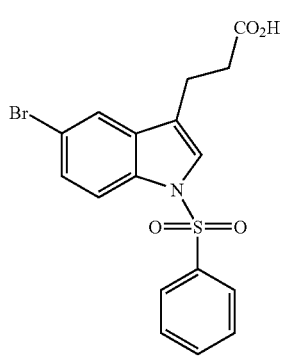

3-(1-Benzenesulfonyl-5-bromo-1H-indol-3-yl)-propionic acid 90 was prepared through the saponification methyl ester 89 using the procedure as described in step 4 of example 3, (M−1=406.0).

Example 70

Synthesis of 3-(Benzenesulfonyl-5-thiophen-3-yl-1H-indol-3-yl)-propionic acid methyl ester 91

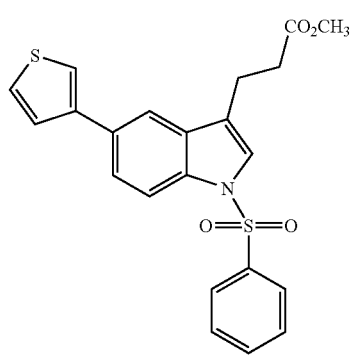

3-(1-Benzenesulfonyl-5-bromo-1H-indol-3-yl)-propionic acid methyl ester 89 (200 mg, 0.474 mmol) was combined with 3-thienyl boronic acid (67.0 mg, 0.52 mmol), triphenylphosphine (9.0 mg, 0.03 mmol), Pd(OAc)$_2$ (4.0 mg, 0.015 mmol), K$_2$CO$_3$ (90 mg, 0.65 mmol), 1,2-Dimethoxyethane (DME, 4.0 mL) and H$_2$O (0.4 mL) and was heated at 90° C. for 48 hours. The reaction was allowed to cool to room temperature and the solvent was evaporated. The resulting residue was dissolved in EtOAc and washed with brine. The organic layer was dried over MgSO$_4$, filtered, and evaporated. The residue was purified with flash silica gel chromatography (20% EtOAc/Hexanes) to obtain the ester 91 as a white solid, (110 mg, M+1=426.1).

Example 71

Synthesis of 3-(Benzenesulfonyl-5-thiophen-3-yl-1H-indol-3-yl)-propionic acid 92

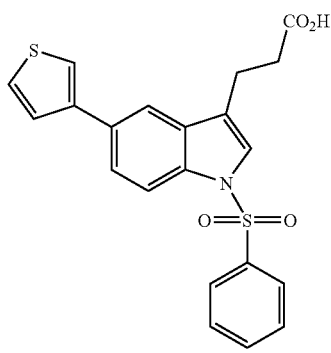

92

3-(Benzenesulfonul-5-thiophen-3-yl-1H-indol-3-yl)-propionic acid 92 was prepared through the saponification of methyl ester 91 as described in step 4 of example 3, (M−1=410.1).

Example 72

Synthesis of 3-(1-Benzenesulfonyl-5-pheyl-1H-indol-3-yl) propionic acid methyl ester 93

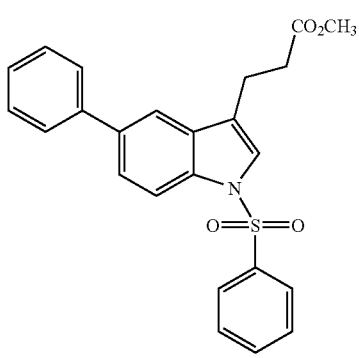

93

The ester 93 was prepared from the methyl ester 89 by following the procedure as described in example 70 by substituting 3-Thienyl boronic acid with Phenyl boronic acid, (M+1=420).

Example 73

Synthesis of 3-(1-Benzenesulfonyl-5-pheyl-1H-indol-3-yl) propionic acid 94

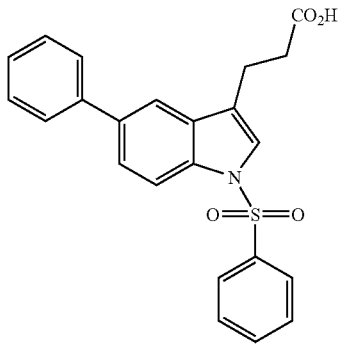

94

3-(1-Benzenesulfonyl-5-pheyl-1H-indol-3-yl) propionic acid 94 was prepared through the saponification of methyl ester 94 as described in step 4 of example 3, (M−1-404.5).

Example 74

Preparation of 3-(1H-Pyrrolo[2,3-b]pyridine-3-yl)-propionic acid 95

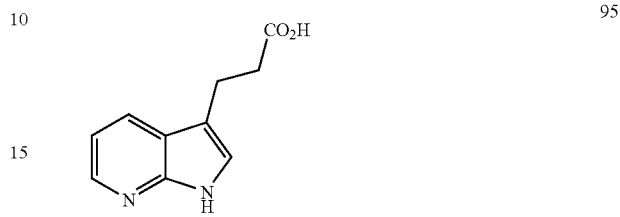

95

3-(1H-Pyrrolo[2,3-b]pyridine-3-yl)-propionic acid 95 was prepared from commercially available 7-azaindole by the same protocol described in steps 4-6 of example 4, (M−1=189.2).

Example 75

Synthesis of 3-(5-Methoxy-1H-Indol-3-yl)-propionic acid 96

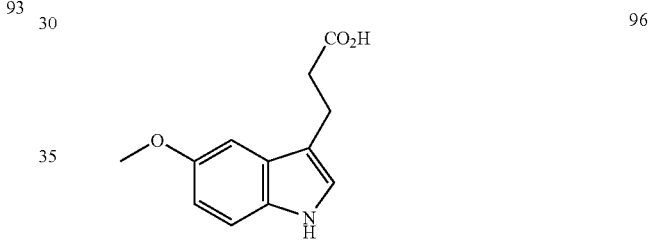

96

3-(5-Methoxy-1H-Indol-3-yl)-propionic acid 96 was prepared from saponification of 3-(5-methoxy-1H-indol-3-yl)-propionic acid methyl ester 4 as described in step 4 of Example 3. (M−1=218.2)

Example 76

Synthesis of 3-(1-Benzenesulfonyl-1H-indol-3-yl)-propionic acid 97

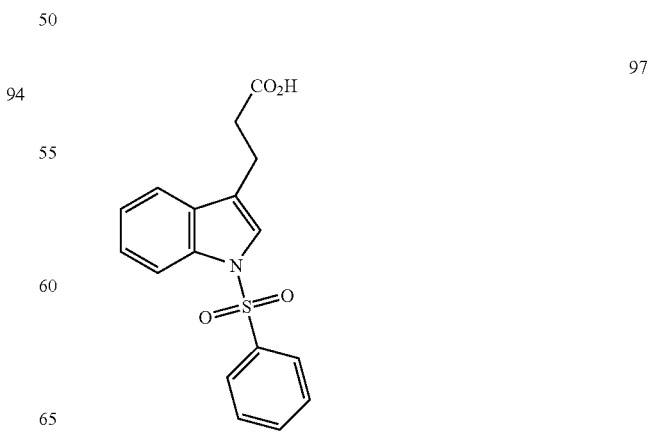

97

3-(1-Benzenesulfonyl-1H-indol-3-yl)-propionic acid 97 was prepared from indole-3-propionic acid 28 using the protocol as described in step 8, Example 4. (M−1=329.4)

Example 77

Synthesis of 3-(1-Benzenesulfonyl-5-methoxy-1H-indol-3-yl)-propionic acid methyl ester 98

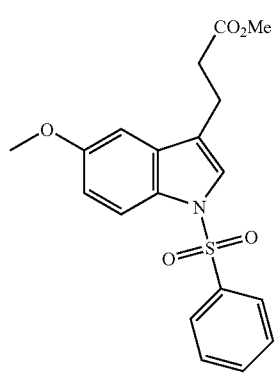

3-(1-Benzenesulfonyl-5-methoxy-1H-indol-3-yl)-propionic acid methyl ester 98 was prepared using the same protocol as example 3, substituting 4-methoxybenzene sulfonyl chloride with benzene sulfonyl chloride. (M+1=374.4)

Example 78

Synthesis of 3-[5-Methoxy-1-(thiophene-3-sulfonyl)-1H-indol-3-yl]-propionic acid 99

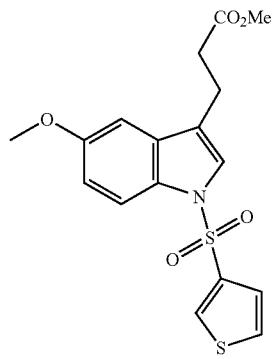

3-[5-Methoxy-1-(thiophene-3-sulfonyl)-1H-indol-3-yl]-propionic acid 99 was prepared from 3-(5-methoxy-1H-indol-3-yl)-propionic acid 96 and 3-thienyl-sulfonyl chloride using the same protocol as described in step 8, Example 4. (M−1, 364.4)

Example 79

Synthesis of (1-Benzenesulfonyl-5-methoxy-1H-indol-3-yl)-acetic acid 100

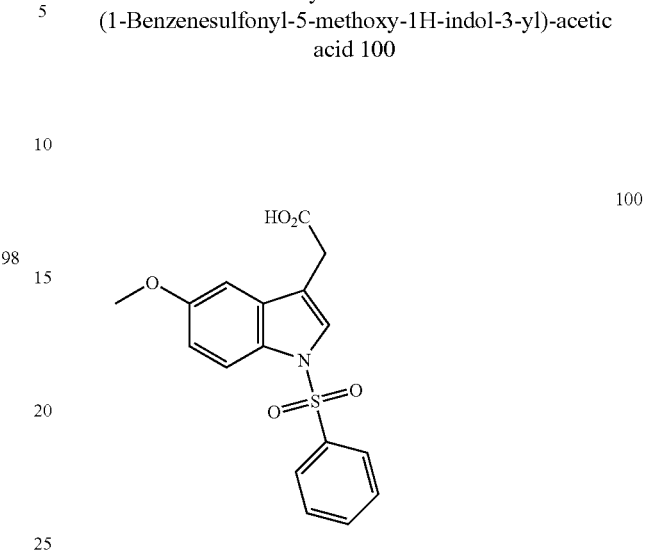

(1-Benzenesulfonyl-5-methoxy-1H-indol-3-yl)-acetic acid 100 was prepared from commercially available (5-methoxy-1H-indol-3-yl)-acetic acid and benzene sulfonyl chloride using the protocol as described in step 8, example 4. (M−1=344.4)

Scheme 11: Alternative synthesis methodology for Compounds of Formula Ib

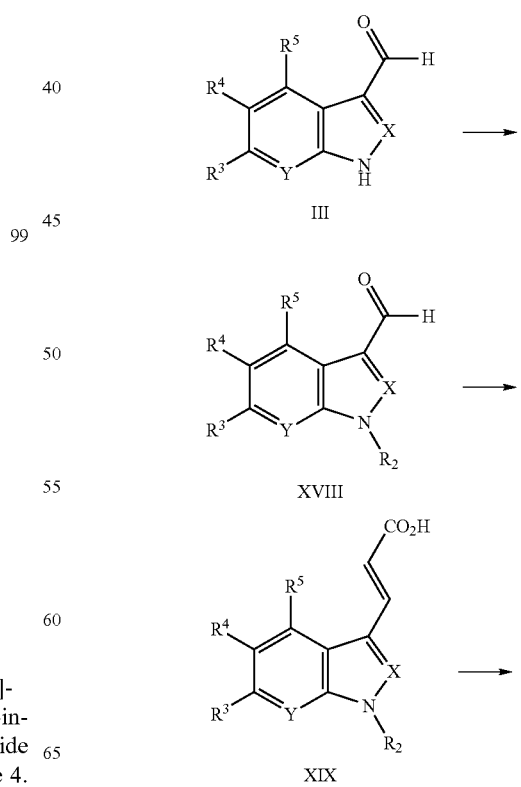

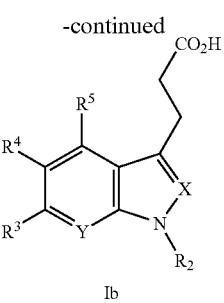

Ib

Step 1—Preparation of Compound of Formula XVIII

Compound XVIII can be prepared through coupling of compound III with benzene sulfonyl chloride in a bi-phasic solvent condition e.g. toluene and water, in presence of a base, e.g. an aqueous potassium hydroxide solution with a phase transfer catalyst, e.g. tetrabutylammonium hydrogen sulfate, similar to conditions as described Gribble et al, in *J. Org. Chem.*, 2002, 63, pg 1001-1003.

Step 2—Preparation of Compound XIX

Compound XIX was prepared through conventionally Knoevenagel reaction reacting compound XVIII with malonic acid piperidine in pyridine at 80° C. for 3-4 hours, as described in Vangvera et al in *J. Med. Chem.*, 1998, 41, pg 4995-5001.

Step 3—Preparation of Compound Ib

Compound Ia was prepared from compound XIX through reduction via catalytic hydrogenation (typically with 10% palladium on activated carbon in an inert solvent (see preparation of intermediate II, vide supra).

Example 80

Alternate synthesis of 3-[5-methoxy-1-(4-methoxy-benzenesulfonyl)-1H-indol-3-yl]-propionic acid 1

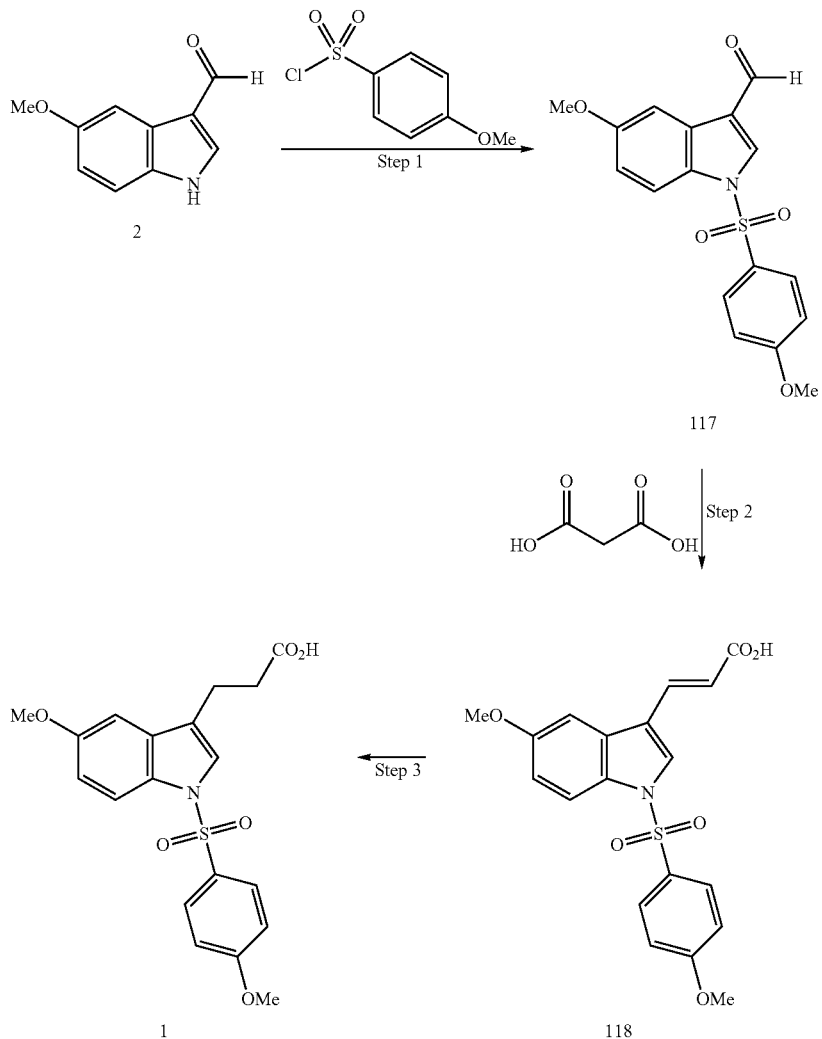

Scheme 12

119

Step 1: Preparation of 1-(4-Methoxy benzenesulfonyl)-5-methoxy-1H-indole-3-carboxyaldehyde)(117)

To a dry round bottom flask, 5-methoxy indole-3-aldehyde 2 (1.0 g, 5.7 mmol) was dissolved with toluene (4 mL). Tetrabutylammonium iodide (10 mg) and 50% KOH solution (2 mL) were added next. After about 5 minutes of stirring, 4-methoxybenzene sulfonyl chloride (1.7 grams, 8.2 mmol) was added. Within 2-3 hours, solid began to precipitate out of the solution. This reaction was allowed to stir at ambient temperature for 2 hours, after which water (50 mL) and ethyl acetate (150 ml) was added to the reaction. The layers were separated; the organic layer was washed with saturated bicarbonate (3×75 mL) and water (4×75 mL) to ensure removal of the hydroxide and sulfonate salt, and washed with brine (1×75 ml) and dried over anhydrous sodium sulfate. Evaporation under reduced pressure afforded 117 as a light brown solid. (1.86 g, 94%) $^1$H NMR (CDCl$_3$) δ 10.0 (s, 1H), 8.20 (s, 1H), 7.92 (d, J=9.2 Hz, 2H), 7.85 (d, J=8.8, 1H), 7.74 (d, J=2.4, 1H), 7.04 (dd, J=2.8 Hz, 9.2 Hz, 1H), 6.97 (d, J=9.2 Hz, 2H), 3.85 (s, 3H).

Step 2: Preparation of 3-[1-(4-Methoxy benzenesulfonyl)-5-methoxy-1H-indol-3-yl]-acrylic acid (118)

To a solution of 1-(4-Methoxybenzenesulfonyl)-5-methoxy-1H-indole-3-carbaldehyde 5 (0.51 g, 1.5 mmol) dissolved in pyridine (10 mL), malonic acid (0.53 g, 5.1 mmol) and piperidine, (1 mL) were combined in a reaction vessel. The yellow solution was heated for 3 hours at 80° C. The reaction was allowed to cool to ambient temperature and diluted with 150 mL of ethyl acetate. The organic layer was washed with 1N HCl (6×50 mL) and saturated sodium chloride solution (1×50 mL). After drying over sodium sulfate, the organic layer was filtered through a pad of sodium sulfate and evaporated under reduced pressure to yield product 118 as an off-white solid. (0.521 g, 90%) $^1$HNMR (CDCl$_3$) δ 7.86 (m, 5H), 7.2 (d, J=2.4 Hz, 1H), 7.0 (dd, J=2.8 Hz, 9.2 Hz, 1H), 6.91 (d, J=8.8 Hz, 2H), 6.46 (d, J=16, 1H), 3.87 (s, 3H, CH$_3$) (M−1=386.2).

Step 3: Preparation of 3-[1-(4-Methoxy benzenesulfonyl)-5-methoxy-1H-indol-3-yl]-propionic acid (1)

To a solution of 3-[1-(4-Methoxy benzenesulfonyl)-5-methoxy-1H-indol-3-yl]-acrylic acid 118 (1.0 g, 2.6 mmol) dissolved in THF (14 mL), Pd/C (67 mg) was added in one portion. The solution was attached to the Parr hydrogenator. The reaction was allowed to proceed overnight at 20-22 psi. The solution was filtered over celite, and the palladium-celite pad was washed with ethyl acetate (40 mL), and methanol (20 mL). The combined washes/solution was evaporated under reduced pressure to afford straw colored oil that solidified after cooling under high vacuum. The crude was triturated with diethyl ether to leave behind off white solid as product 1. (0.620 g, 62%) $^1$H NMR (DMSO) δ 7.86 (d, J=9.2 Hz, 1H), 7.75 (d, J=8.4 Hz, 1H), 6.92 (dd, J=2.4 Hz, 9.2 Hz, 1H), 6.88 (s, 1H), 6.83 (d, J=9.2 Hz, 2H), 3.76 (s, 3H), 2.96 (t, J=7.6 Hz, 14.8 Hz, 2H), 2.74 (t, J=7.6 Hz, 14.8 Hz, 2H) (M−1=388.6).

120

Example 81

Synthesis of 3-[5-Methoxy-1-(4-methoxy-benzenesulfonyl)-1H-indol-3-yl]-2,2-dimethyl-propionic acid 119

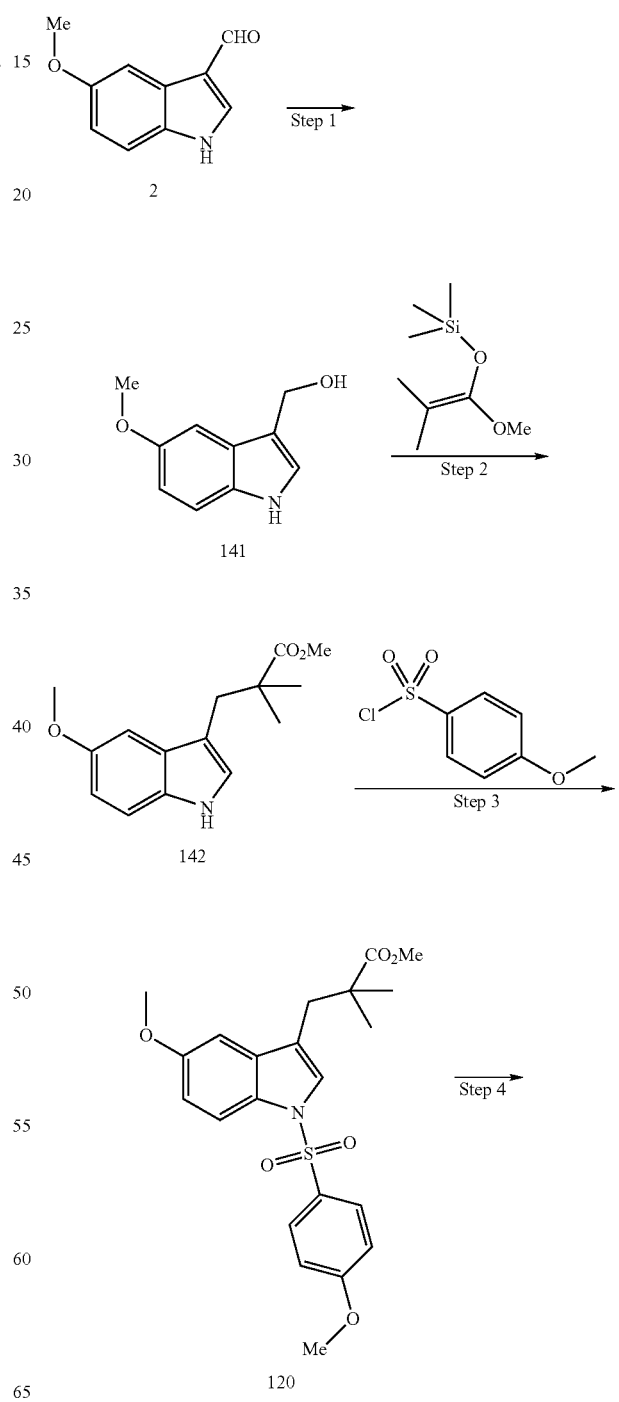

Scheme 13

-continued

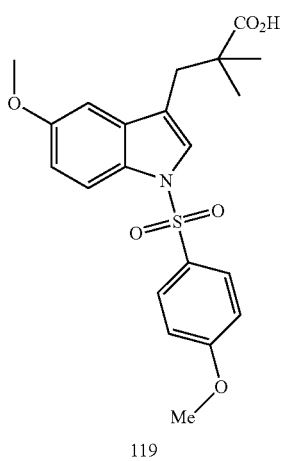

119

Step 1—Synthesis of 5-methoxy-1H-indol-3-yl-methanol 141

To a solution of sodium borohydride (2 grams, 0.05 mol) in methanol (15 ml), a solution of 5-methoxy-1H-indol-3-carboxaldehyde 2 (1 gram, 0.006 mol) dissolved in THF (20 ml) and methanol (15 ml) were combined and stirred at ambient temperature for 16 hours. The reaction was diluted with water and potassium carbonate (to saturation) and stirred to quench unreacted sodium borohydride. Diethyl ether was used to extract the product from the quenched solution. Following layers separation, the aqueous layer was further extracted (2×) with diethyl ether. The combined organic pats were dried over sodium sulfate and evaporated to dryness to yield a light colored solid 141 (736 mg, 70%).

Step 2—Preparation of 3-(5-Methoxy-1H-indol-3-yl)-propionic acid methyl ester 142

To a solution of 5-methoxy-1H-indol-3-yl-methanol 141 (115 mg, 0.643 mmol) dissolved in dichloromethane (3 ml), (1-methoxy-2-methyl-propenyloxy)-trimethylsilane (200 mg, 1 mmol) and magnesium perchlorate (164 mg, 0.74 mmol) were added. The reaction was allowed to stir at ambient temperature for 3-4 hours after after which the mixture was diluted with water (50 ml) and dichloromethane (DCM, 100 mL). The organic layer was separated and washed with water (50 mL; 3×). The organic layer was washed once with brine, dried over anhydrous sodium sulfate, and evaporated under reduced pressure to give an oil and purified with flash chromatography (silica with 80% hexane, 20% ethyl acetate to afford 142 as a light colored oil (150 mg; 88% yield; M+1=262.3).

Step 3—Preparation of 3-[5-Methoxy-1-(4-methoxy-benzenesulfonyl)-1H-indol-3-yl]-propionic acid methyl ester 120

To a cooled solution (0° C.) of indole-3-propionic acid methyl ester 142 (0.110 g, 0.42 mmol) in DMF (3 mL) was added sodium hydride (60%; 0.030 g; 0.75 mmol) was added in one portion and stirred for 30 min followed by the addition of 4-methoxybenzenesulfonyl chloride (0.200 g; 1.0 mmol). The reaction was allowed to warm up to room temperature and stirred for 16 h, subjected to aqueous work up, and product was extracted with ethyl acetate. The ethyl acetate layer was washed with brine, dried over anhydrous sodium sulfate, evaporated under reduced pressure, and purified by flash-chromatography (silica gel; 85% n-hexane-15% ethyl acetate) to afford the methyl ester 120 as an oil (M+1=432.4). The methyl ester 120 was then taken on toward generation of the product.

Step 4—Preparation of 3-[5-Methoxy-1-(4-methoxy-benzenesulfonyl)-1H-indol-3-yl]-2,2-dimethyl-propionic acid 119

To a solution of the methyl ester 120 in tetrahydrofuran (6 mL) was added an aqueous solution of potassium hydroxide (2 mL of 1M) and stirred at room temperature for 5 h. The acid 119 was isolated by neutralizing the reaction mixture by aqueous hydrochloric acid, extracting the product with ethyl acetate, drying over anhydrous magnesium sulfate, evaporating under reduced pressure, and purifying using flash chromatography with 5% methanol in dichloromethane to afford a white solid (80 mg, 46% overall, M−1=416.5).

Example 82

Synthesis of 3-[1-(3,4-Dimethoxy-benzenesulfonyl)-5-methoxy-1H-indol-3-yl]-propionic acid 101

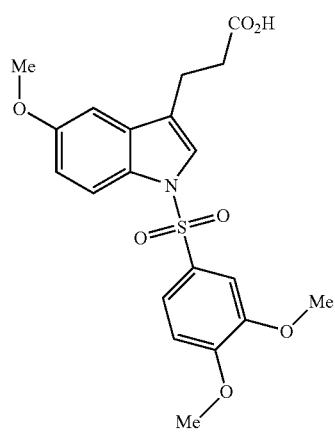

3-[1-(3,4-dimethoxybenzenesulfonyl)-5-methoxy-1H-indol-3-yl]-propionic acid 101 was prepared using the same protocol as in example 3, substituting 4-methoxybenzene sulfonyl chloride with 3,4-dimethoxybenzenesulfonyl chloride, (M−1=418.5).

Example 83

Synthesis of 3-[1-(3,4-Difluoro-benzenesulfonyl)-5-methoxy-1H-indol-3-yl]-propionic acid 102

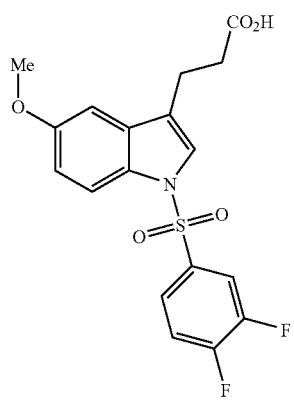

102

3-[1-(3,4-difluorobenzenesulfonyl)-5-methoxy-1H-indol-3-yl]-propionic acid 102 was prepared using the same protocol as in example 3, substituting 4-methoxybenzene sulfonyl chloride with 3,4-difluorobenzenesulfonyl chloride, (M−1=395.3).

Example 84

Synthesis of 3-[1-(3-chloro-4-methyl-benzenesulfonyl)-5-methoxy-1H-indol-3-yl]-propionic acid 103

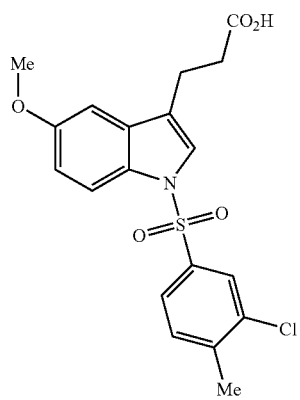

103

3-[1-(3-chloro-4-methyl)-5-methoxy-1H-indol-3-yl]-propionic acid 103 was prepared using the same protocol as in example 3, substituting 4-methoxybenzene sulfonyl chloride with 3-chloro-4-methylbenzenesulfonyl chloride, (M−1=406.8).

Example 85

3-[1-(benzenesulfonyl)-5-fluoro-1H-indol-3-yl]-propionic acid 104

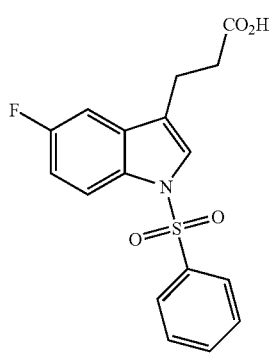

104

3-[1-(benzenesulfonyl)-5-fluoro-1H-indol-3-yl]-propionic acid 104 was prepared using the same protocol as in example 3, substituting 4-methoxybenzene sulfonyl chloride with benzenesulfonyl chloride, (M−1=346.5).

Example 86

Synthesis of 3-[1-(benzenesulfonyl)-5-methyl-1H-indol-3-yl]-propionic acid 105

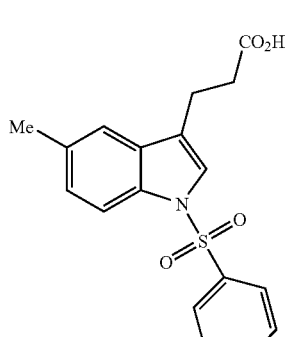

105

3-[1-(benzenesulfonyl)-5-methyl-1H-indol-3-yl]-propionic acid 105 was prepared using the same protocol as in example 3, substituting 4-methoxybenzene sulfonyl chloride with benzenesulfonyl chloride, (M−1=342.2).

Example 87

Synthesis of 3-[1-(benzenesulfonyl)-5-chloro-1H-indol-3-yl]-propionic acid 106

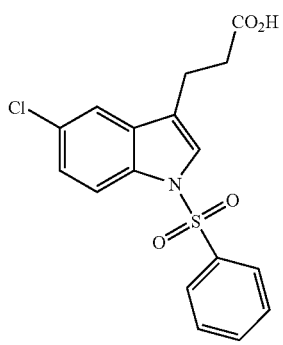

106

3-[1-(benzenesulfonyl)-5-chloro-1H-indol-3-yl]-propionic acid 106 was prepared using the same protocol as in example 3, substituting 4-methoxybenzene sulfonyl chloride with benzenesulfonyl chloride, (M−1=362.7).

Example 88

Synthesis of 3-[1-(3-fluoro-4-methyl-benzenesulfonyl)-5-chloro-1H-indol-3-yl]-propionic acid 107

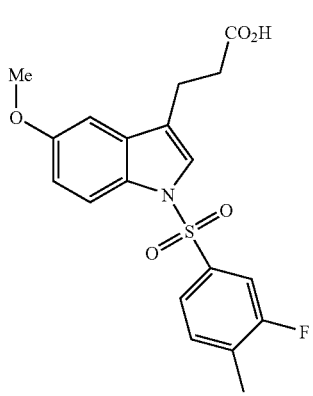

107

3-[1-(3-fluoro-4-methyl-benzenesulfonyl)-5-chloro-1H-indol-3-yl]-propionic acid 107 was prepared using the same protocol as in example 3, substituting 4-methoxybenzene sulfonyl chloride with 3-fluoro-4-methyl-benzenesulfonyl chloride, (M−1=390.3).

Example 89

Synthesis of 3-[1-(2,3-Dihydro-benzofuran-5-sulfonyl)-5-methoxy-1H-indol-3-yl]-propionic acid 108

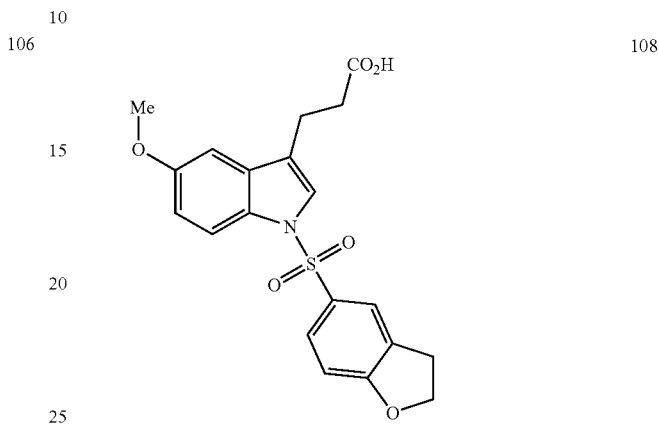

108

3-[1-(2,3-Dihydro-benzofuran-5-sulfonyl)-5-methoxy-1H-indol-3-yl]-propionic acid 108 was prepared using the same protocol as in example 3, substituting 4-methoxybenzene sulfonyl chloride with 2,3-Dihydro-benzofuran-5-sulfonyl chloride, (M−1=400.2).

Example 90

Synthesis of 3-[1-(4-ethyl-benzenesulfonyl)-5-ethoxy-1H-indol-3-yl]-propionic acid 109

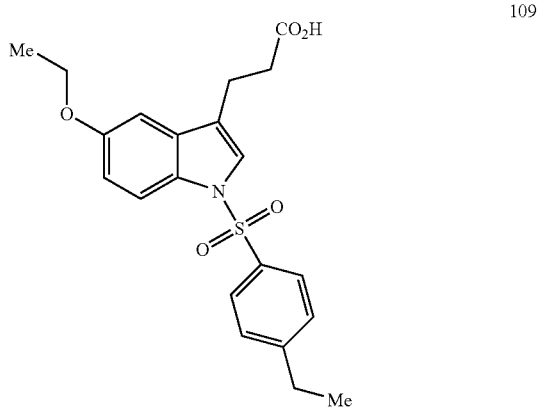

109

3-[1-(4-ethyl-benzenesulfonyl)-5-ethoxy-1H-indol-3-yl]-propionic acid 109 was prepared using the same protocol as in example 3, substituting 4-methoxybenzene sulfonyl chloride with 4-ethyl-benzenesulfonyl chloride, (M−1=400.5).

Example 91

Synthesis of 3-[1-(4-methoxy-benzenesulfonyl)-5-ethoxy-1H-indol-3-yl]propionic acid 110

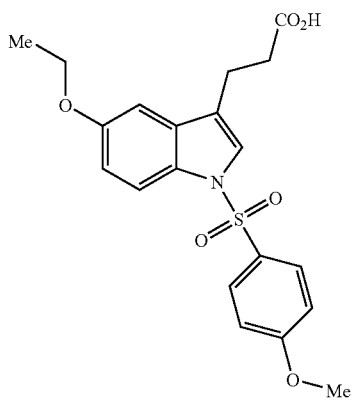

3-[1-(4-methoxy-benzenesulfonyl)-5-ethoxy-1H-indol-3-yl]-propionic acid 110 was prepared using the same protocol as in example 3, (M−1=402.6).

Example 92

Synthesis of 3-[1(3-trifluoromethoxy-benzenesulfonyl)-5-ethoxy-1H-indol-3-yl]-propionic acid 111

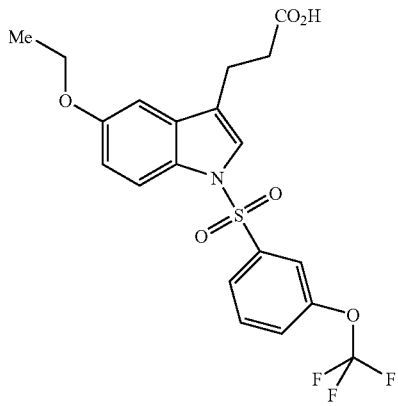

3-[1-(3-trifluoromethoxy-benzenesulfonyl)-5-ethoxy-1H-indol-3-yl]-propionic acid 111 was prepared using the same protocol as in example 3, substituting 4-methoxybenzene sulfonyl chloride with 3-trifluoromethoxy-benzenesulfonyl chloride, (M−1=456.3).

Example 93

Synthesis of 3-[1-(4-butyl-benzenesulfonyl)-5-ethoxy-1H-indol-3-yl]-propionic acid 112

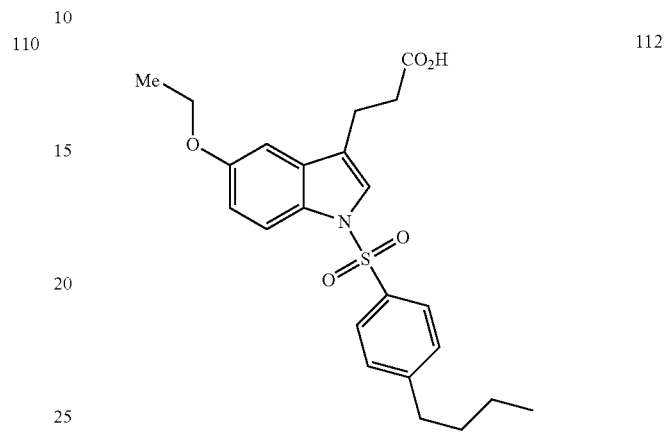

3-[1-(4-butyl-benzenesulfonyl)-5-ethoxy-1H-indol-3-yl]-propionic acid 112 was prepared using the same protocol as in example 3, substituting 4-methoxybenzene sulfonyl chloride 4-butyl-benzenesulfonyl chloride, (M−1=428.4).

Example 94

Synthesis of 3-[1-(4-butoxy-benzenesulfonyl)-5-ethoxy-1H-indol-3-yl]-propionic acid 113

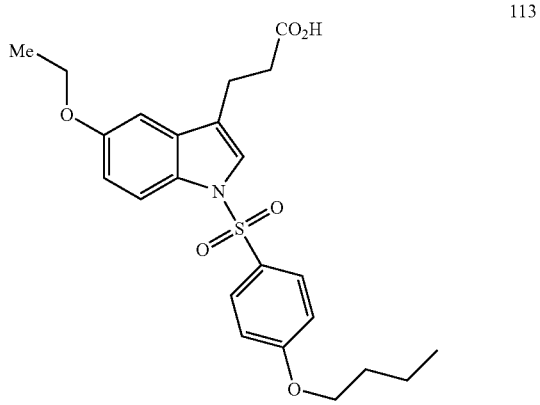

3-[1-(4-butoxy-benzenesulfonyl)-5-ethoxy-1H-indol-3-yl]-propionic acid 113 was prepared using the same protocol as in example 3, substituting 4-methoxybenzene sulfonyl chloride 4-butoxy-benzenesulfonyl chloride, (M−1=444.5).

Example 95

Synthesis of 3-[1-(3,4-dichloro-benzenesulfonyl)-5-ethoxy-1H-indol-3-yl]propionic acid 114

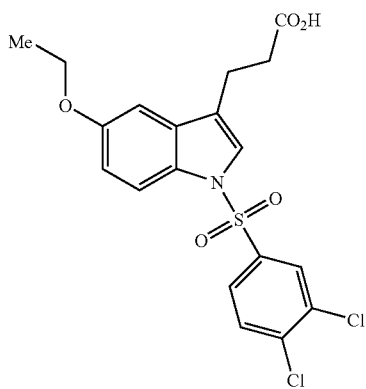

114

3-[1-(3,4-dichloro-benzenesulfonyl)-5-ethoxy-1H-indol-3-yl]-propionic acid 114 was prepared using the same protocol as in example 3, substituting 4-methoxybenzene sulfonyl chloride 3,4-dichloro-benzenesulfonyl chloride, (M−1=441.2).

Example 96

Synthesis of 3-[1-(3-methoxy-benzenesulfonyl)-5-ethoxy-1H-indol-3-yl]propionic acid 115

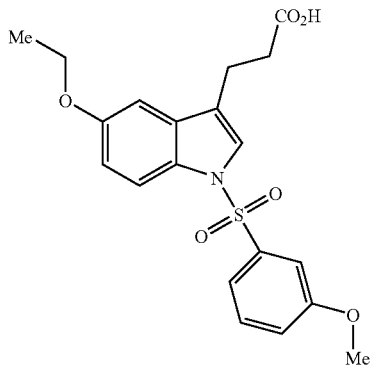

115

3-[1-(3-methoxy-benzenesulfonyl)-5-ethoxy-1H-indol-3-yl]-propionic acid 115 was prepared using the same protocol as in example 3, substituting 4-methoxybenzene sulfonyl chloride 3-methoxy-benzenesulfonyl chloride, (M−1=402.5).

Example 97

Synthesis of 3-[1-(4-phenoxy-benzenesulfonyl)-5-ethoxy-1H-indol-3-yl]-propionic acid 116

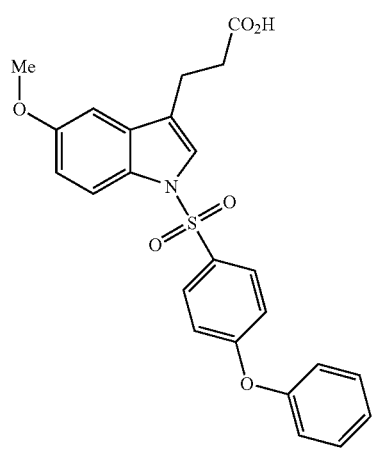

116

3-[1-(4-phenoxy-benzenesulfonyl)-5-ethoxy-1H-indol-3-yl]-propionic acid 116 was prepared using the same protocol as in example 3, substituting 4-methoxybenzene sulfonyl chloride 4-phenoxy-benzenesulfonyl chloride, (M−1=464.3).

Example 98

Synthesis of 3-[1-(3,4-Dichloro-benzenesulfonyl)-5-methoxy-1H-indol-3-yl]-2,2-dimethyl-propionic acid methyl ester 122

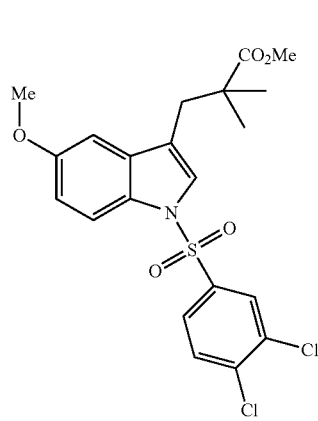

122

3-[1-(3,4-Dichloro-benzenesulfonyl)-5-methoxy-1H-indol-3-yl]-2,2-dimethyl-propionic acid methyl ester 122 was prepared using the same protocol as example 3, step 3, substituting 4-methoxy-benzenesulfonyl chloride with 3,4-dichlorobenzenesulfonyl chloride (M+1=457.2).

Example 99

Synthesis of 3-[1-(3,4-Dichloro-benzenesulfonyl)-5-methoxy-1H-indol-3-yl]-2,2-dimethyl-propionic acid 121

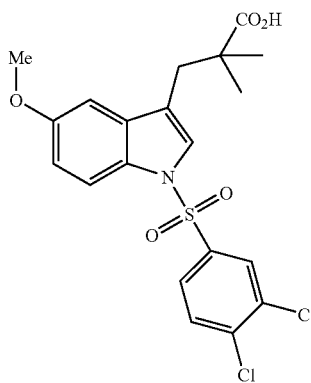

3-[1-(3,4-Dichloro-benzenesulfonyl)-5-methoxy-1H-indol-3-yl]-2,2-dimethyl-propionic acid methyl ester 121 was prepared from the corresponding methyl ester 122, using the same protocol as example 3, step 4, (M+1=469.2).

Example 100

Synthesis of (E)-3-[1-(3,4-Dichloro-benzenesulfonyl)-5-methoxy-1H-indol-3-yl]-acrylic acid 123

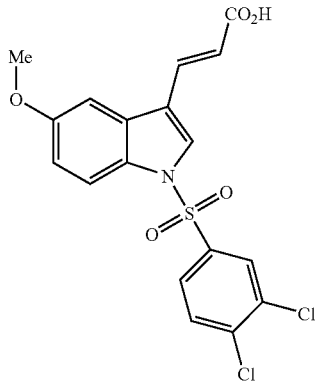

(E)-3-[1-(3,4-Dichloro-benzenesulfonyl)-5-methoxy-1H-indol-3-yl]-acrylic acid 123 was prepared using the same protocol as in Scheme 12, substituting 4-methoxybenzene sulfonyl chloride 3,4-dichlorobenzenesulfonyl chloride in step-1, (M−1=425.2).

Example 101

Synthesis of (E)-3-[1-(4-butyl-benzenesulfonyl)-5-ethoxy-1H-indol-3-yl]acrylic acid 124

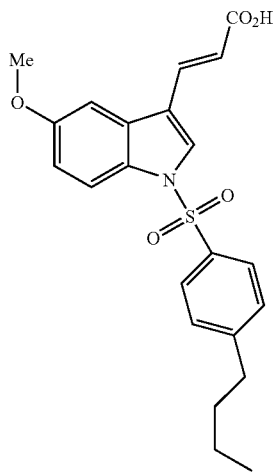

(E)-3-[1-(4-butyl-benzenesulfonyl)-5-ethoxy-1H-indol-3-yl]-acrylic acid 124 was prepared using the same protocol as in Scheme 12, substituting 4-methoxybenzene sulfonyl chloride 4-butylbenzenesulfonyl chloride in step-1, (M−1=426.4).

Example 102

Synthesis of (E)-3-[1-(4-butoxy-benzenesulfonyl)-5-ethoxy-1H-indol-3-yl]-acrylic acid 125

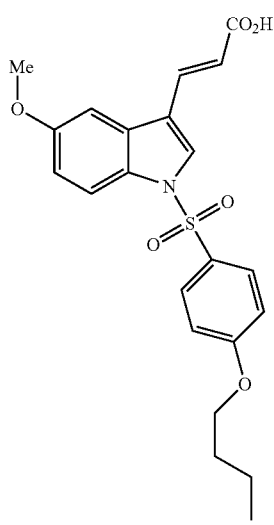

(E)-3-[1-(4-butoxy-benzenesulfonyl)-5-ethoxy-1H-indol-3-yl]-acrylic acid 125 was prepared using the same protocol as in Scheme 12, substituting 4-methoxybenzene sulfonyl chloride in step—1, (M−1=442.4).

Example 103

Synthesis of 3-[1-(3-Chloro-4-methoxy-benzene-sulfonyl)-5-methoxy-1H-indol-3-yl]-propionic acid 126

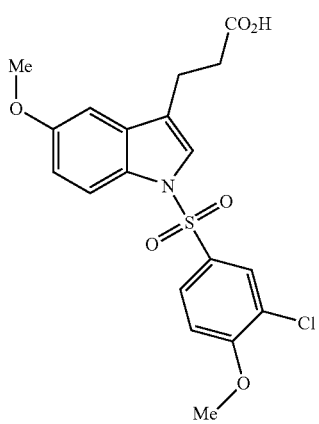

126

3-[1-(3-Chloro-4-methoxy-benzenesulfonyl)-5-methoxy-1H-indol-3-yl]-propionic acid 126 was prepared using the same protocol as in Scheme 12, substituting 4-methoxybenzene sulfonyl chloride 3-chloro-4-methoxy-benzenesulfonyl chloride in step-1, (M−1=423.0). 3-Chloro-4-methoxy-benzenesulfonyl chloride was in turn prepared by reacting 2-chloroanisole with chlorosulfonic acid (neat at 0° C., 4 h) following the literature procedure (Cremlyn, R. J. W.; Hornby, R.; *J. Chem. Soc.* C; 1969; 1341-1345)

Example 104

Synthesis of Synthesis of 3-[1-(4-Methoxy-benzene-sulfonyl)-7-methyl-1H-indol-3-yl]-propionic acid 127

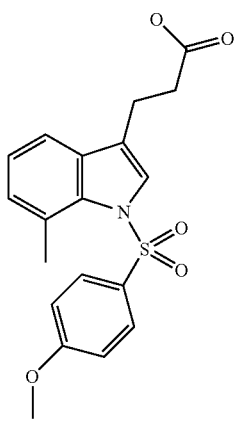

127

Compound 127 is synthesized from commercially available 7-methyl-1indole-3-carboxaldehyde following synthetic steps shown in Scheme 12.

Example 105

Synthesis of 3-[1-(4-Methoxy-benzenesulfonyl)-6-methyl-1H-indol-3-yl]-propionic acid 128

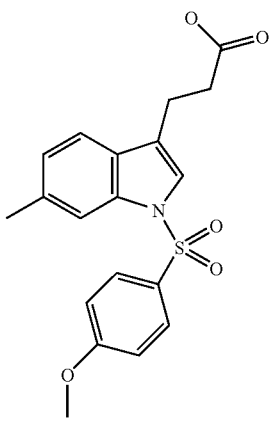

128

Compound 128 is synthesized from commercially available 6-methyl-indole-3-carboxaldehyde following synthetic steps shown in Scheme 12.

Example 106

Synthesis of 3-[1-(4-Methoxy-benzenesulfonyl)-6-fluoro-1H-indol-3-yl]-propionic acid 129

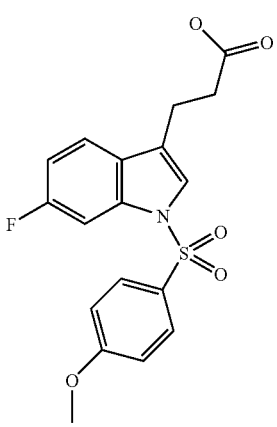

129

Compound 129 is synthesized from commercially available 6-fluoro-indole-3-carboxaldehyde following synthetic steps shown in Scheme 12.

Example 107

Synthesis of 3-[1-(4-Methoxy-benzenesulfonyl)-7-fluoro-1H-indol-3-yl]-propionic acid 130

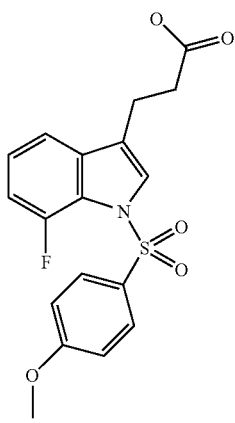

130

Compound 130 is synthesized from commercially available 7-fluoro-indole-3-carboxaldehyde following synthetic steps shown in Scheme 12.

Example 108

Synthesis of 3-[1-(4-Methoxy-benzenesulfonyl)-4-chloro-7-fluoro-1H-indol-3-yl]-propionic acid 131

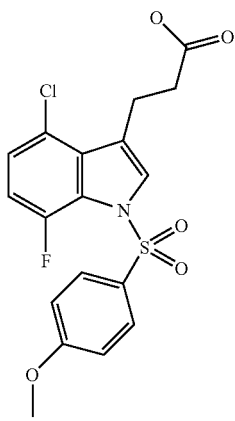

131

Compound 131 is synthesized from commercially available 4-chloro-7-fluoro-indole-3-carboxaldehyde following synthetic steps shown in Scheme 12.

Example 109

Synthesis of 3-[1-(4-Methoxy-benzenesulfonyl)-6-methoxy-1H-indol-3-yl]-propionic acid 132

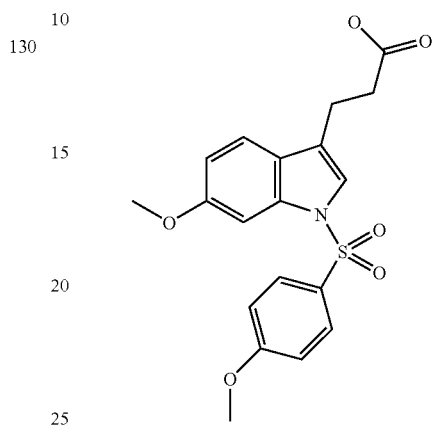

132

Compound 132 is synthesized from 6-methoxy-indole-3-carboxaldehyde, which in turn is synthesized from commercially available 6-methoxy-indole using Vilsmeier-Haack reaction (Advanced organic chemistry, Jerry March, $2^{nd}$ Ed. P715), following synthetic steps shown in Scheme 12.

Example 110

Synthesis of 3-[1-(4-Methoxy-benzenesulfonyl)-5,6-dimethoxy-1H-indol-3-yl]-propionic acid 133

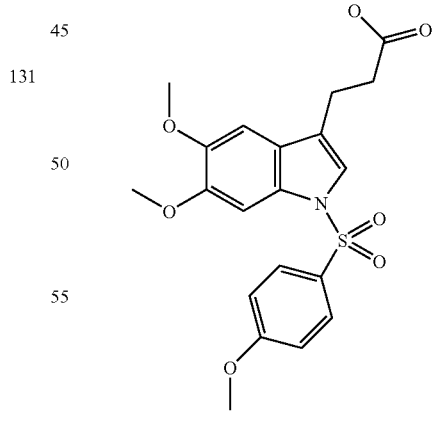

133

Compound 133 is synthesized from 5,6-dimethoxy-indole-3-carboxaldehyde, which in turn is synthesized from commercially available 5,6-dimethoxy-indole using Vilsmeier-Haack reaction (Advanced organic chemistry, Jerry March, $2^{nd}$ Ed. P715), following synthetic steps shown in Scheme 12.

137

Example 111

Synthesis of 3-[1-(4-Methoxy-benzenesulfonyl)-6-bromo-1H-indol-3-yl]-propionic acid 134

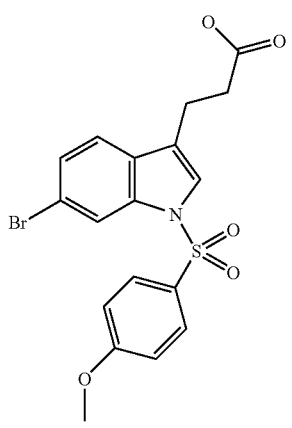

Compound 134 is synthesized from commercially available 6-bromo-indole-3-carboxaldehyde following synthetic steps shown in Scheme 12.

Example 112

Synthesis of 3-[1-(4-Methoxy-benzenesulfonyl)-5-methoxy-1H-indazol-3-yl]-propionic acid 135

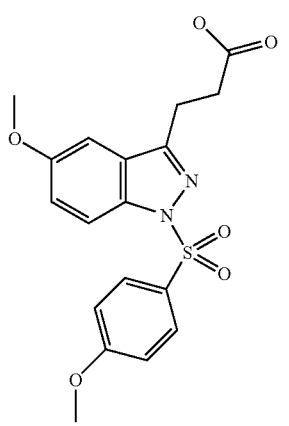

Compound 135 is synthesized from commercially available 5-methoxy-indazole-3-carboxylic acid following synthetic steps shown in Scheme 9.

138

Example 113

Synthesis of 3-[1-(4-Methoxy-benzenesulfonyl)-6-methoxy-1H-indazol-3-yl]-propionic acid 136

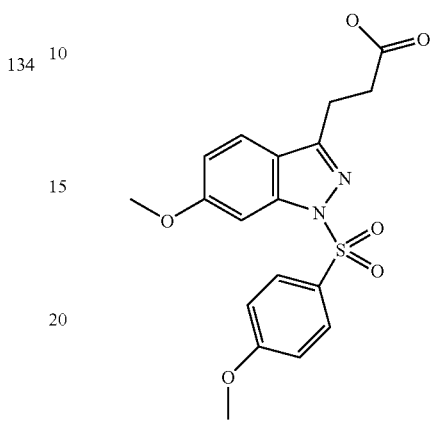

Compound 136 is synthesized from commercially available 6-methoxy-indazole-3-carboxylic acid following synthetic steps shown in Scheme 9.

Example 114

Synthesis of 3-[1-(4-Methoxy-benzenesulfonyl)-5-methoxy-1H-7aza-indazol-3-yl]-propionic acid 137

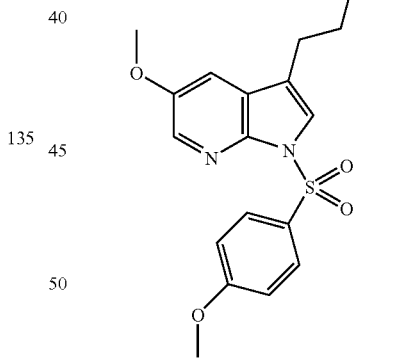

Compound 137 is synthesized from aldehyde 138, prepared from commercially available 7-azainbdole as shown in Scheme 14, following synthetic steps shown in Scheme 12.

Scheme 14

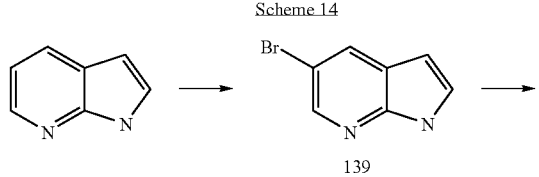

139

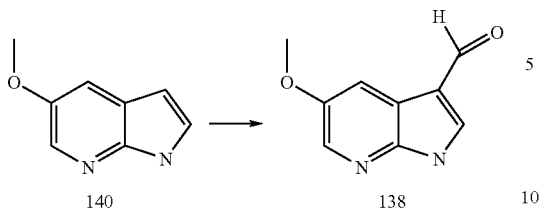

Compound 139, 5-bromo-7-azaindole, was prepared from commercially available 7-azaindole by following the procedure published by Mazeas, Daniel; Guillaumet, Gerald; Marie-Claude Viaud, *Heterocycles*, 1999, v50 (2), 1065-1080. Compound 140 is prepared by heating the bromide 139 with sodium methoxide in dimethyl formamide in presence of cuprous bromide as described by Mazeas, Daniel; Guillaumet, Gerald; Marie-Claude Viaud, *Heterocycles*, 1999, v50 (2), 1065-1080, from which the aldehyde 138 is prepared by Vilsmeier-Haack reaction.

Example 115

Synthesis of Analogs of Compound 1

Analogs of compound 1 can be synthesized, e.g., by using the commercially available compounds shown in Table 3 as described in Example 3 or Example 109.

Synthesis of Carboxylic Acid Bioisosteres

The carboxylic acid functional group of the propionic acid moiety at position 3 can advantageously be replaced with any of a number of carboxylic acid bioisosteres in compounds of Formula I. For example, the following moieties can be used, which are shown with respect to Formula I-1, but which can also be incorporated in other bicyclic rings systems within Formula I.

Thiazolidione (TZD) and Related Analogs:

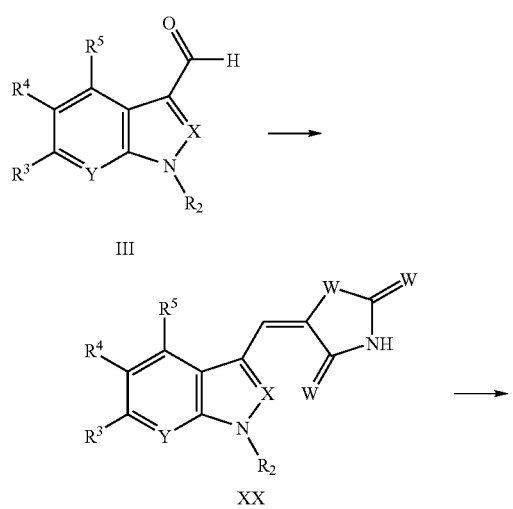

140

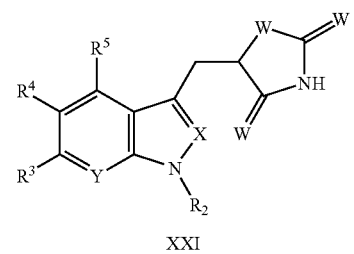

XXI

Step 1

Compound XX can be prepared through a Knoevenagel coupling of thiazolidione or related compounds in presence of an inert solvent, e.g. ethanol, with catalytic amount of piperidine with starting compound III. (L. Sun. et al, *J. Med. Chem.*, 1999, 42, 5120-30.)

Step 2

Compound XXI can be prepared from compound XX through a reduction process using palladium on activated carbon, or a metal reduction reaction (e.g. magnesium). (B. C. Cantello, *J. Med. Chem.*, 1994, 37, 3977-85.)

Hydroxamic Acid:

Scheme 15

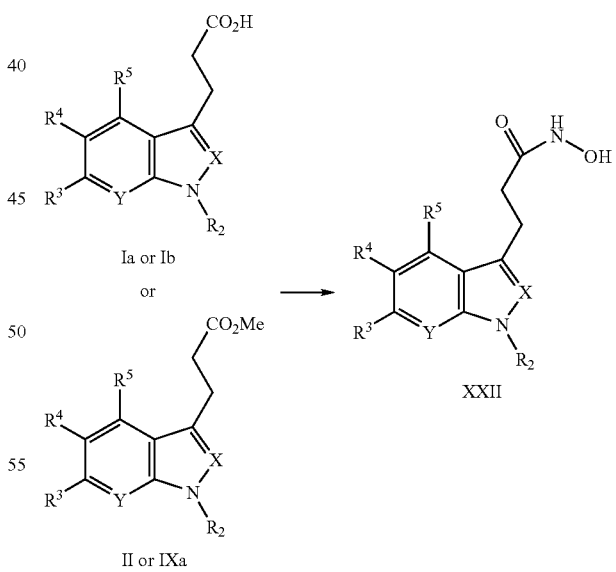

Compound XXII can be prepared through either amide bond formation reaction with Ia or Ib or nucleophilic displacement of the ester II or IXa with n-hydroxyamine. (Hurd et al, *J. Am. Chem. Soc.*, 1954, 76, 2791 and Dinh, T. Q., *Tet. Lett.* 1996, 37, 1161-4).

Tetrazole:

Scheme 16

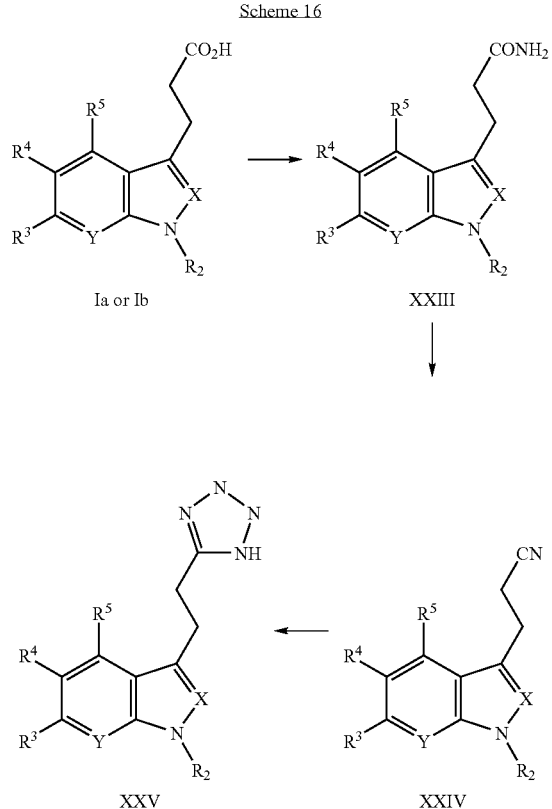

Tetrazole isostere of the carboxylic acid can be prepared through 3 steps from the corresponding acetic or propanoic acid (depending on linker size).

Step 1

The conversion of the carboxylic acid moiety to the corresponding amide XXIII with compound Ia or Ib can be done with ammonia (gas) with ethyl polyphosphate in an inert solvent such as chloroform (Imamoto, T. et al, *Synthesis*, 1983, 142-3).

Step 2

The propionamide XXIII can be converted to the nitrile XXIV by treating the amide with methyl magnesium iodide (Wilson et al, *J. Chem. Soc.*, 1923, 123, 2615) or with formic acid in acetonitrile (Heck, M.-P., J. Org. Chem., 1996, 61, 6486-7).

Step 3

The preparation of the tetrazole isostere involves coupling of the 2-cyano-alkyl group with sodium azide in a cyclization reaction to generate the desired compound XXV. (Juby et al, *J. Med. Chem.*, 1969, 12, 396-401).

Iso-Oxazoles:

Scheme 17

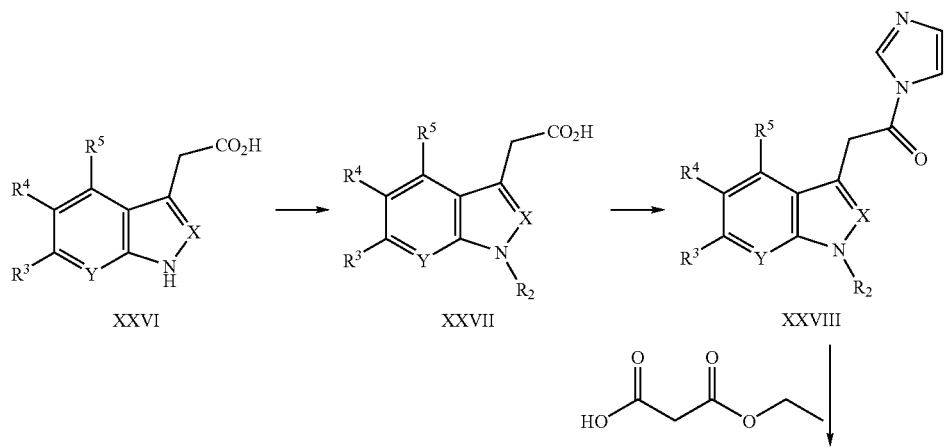

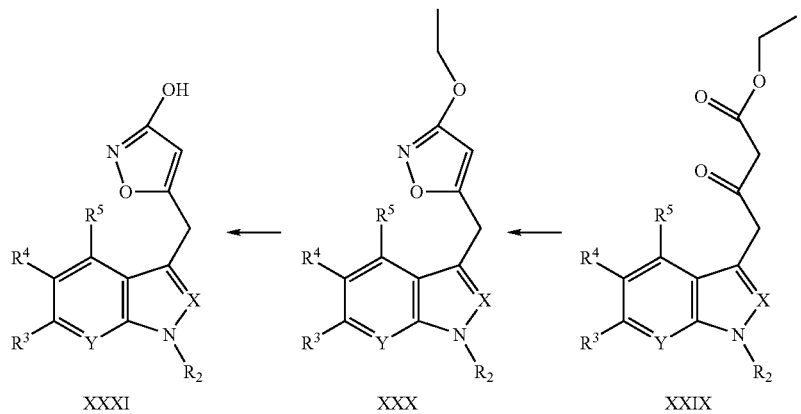

Method 1:

The hydroxyiso-oxazole compound XXVIII can be derived in 5 steps. Using starting material indole-3-acetic acid XXVI, compound XXVII can be prepared through reactions in Example 4. Activation of the acid group with bis-imidazole-carbonyl leads to compound XXVIII (Eils et al, *Synthesis,* 1999, 275-81). The reaction with ethyl malonic acid affords XXIX. Cyclization with hydroxylamine provides the hydroxy protected iso-oxazole XXX. The deprotection of the hydroxy functionality arrives at the desired compound XXXI. (Frolund et al, *J. Med. Chem.,* 2002, 45, 2454-2468)

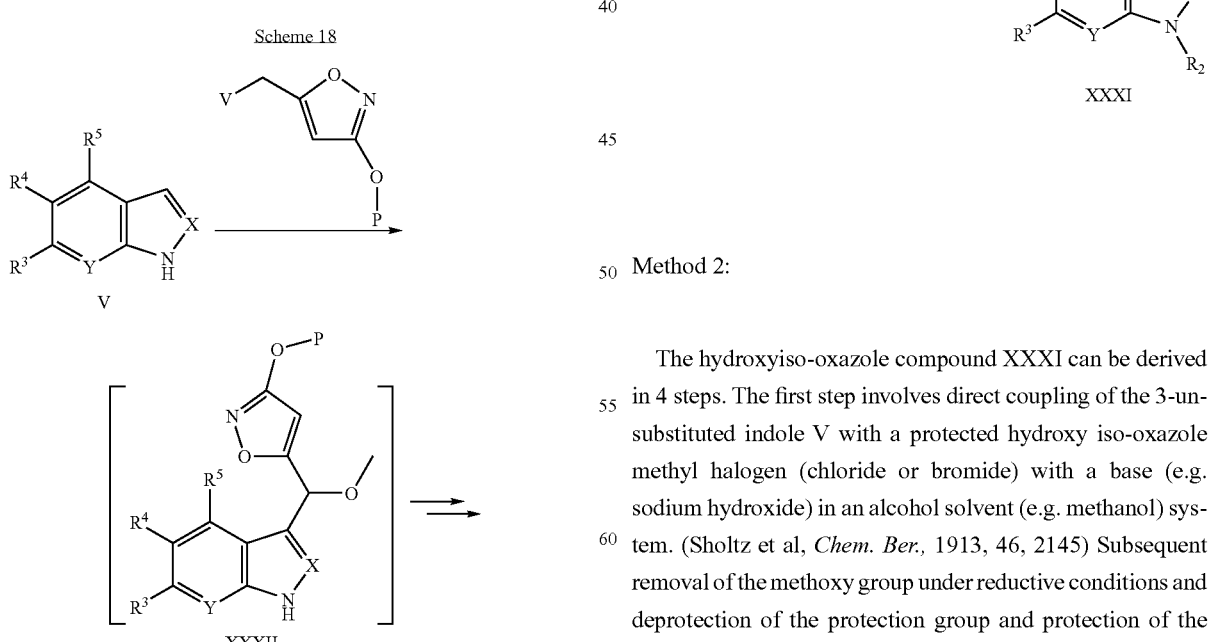

Method 2:

The hydroxyiso-oxazole compound XXXI can be derived in 4 steps. The first step involves direct coupling of the 3-unsubstituted indole V with a protected hydroxy iso-oxazole methyl halogen (chloride or bromide) with a base (e.g. sodium hydroxide) in an alcohol solvent (e.g. methanol) system. (Sholtz et al, *Chem. Ber.,* 1913, 46, 2145) Subsequent removal of the methoxy group under reductive conditions and deprotection of the protection group and protection of the indole nitrogen leads to the desired compound XXXI. (Oster, T. A., et al, *J. Org. Chem.* 1983, 48, 2454-68)

Scheme 19

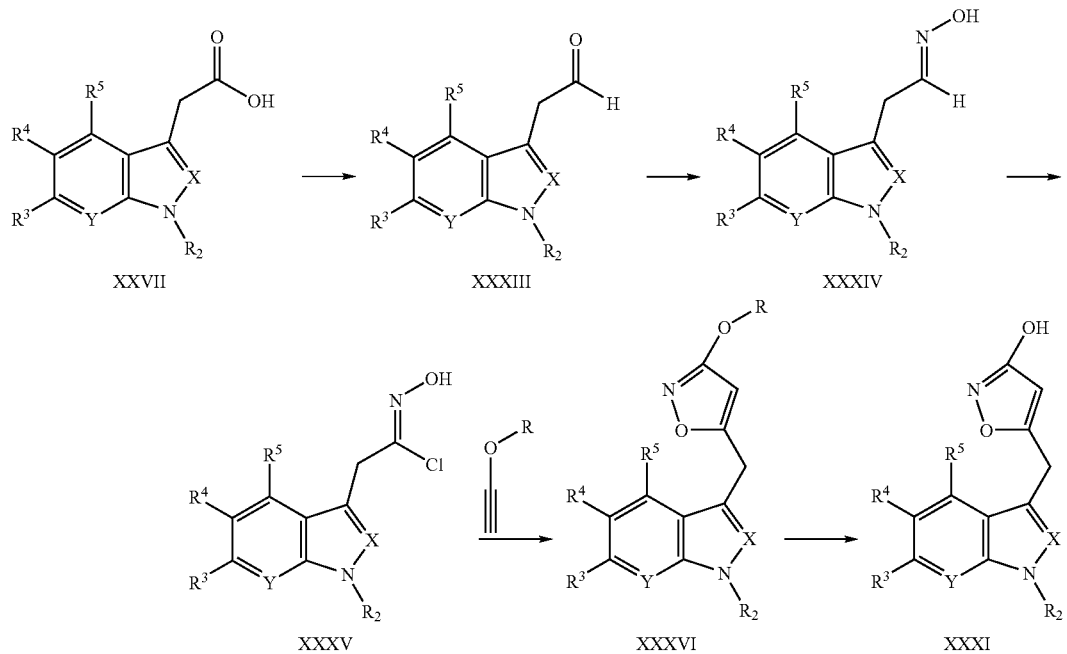

Method 3:

An alternative synthetic approach to compound XXXI, starts with compound XXVII (prepared through reduction of 3-acetic acid) to generate the hydroxy imine XXXIV. Chlorination of XXXIV with chlorination reagents (e.g. NCS) arrive at intermediate XXXV. From the hydroxy iminium chloride, a cyclization with acetylene would afford the protected hydroxy iso-oxazole. The deprotection would provide the desired compound XXXI. (Weidner-Wells, M. A. et al, *Bioorg. & Med. Chem. Lett.*, 2004, 14, 3069-72)

Acyl Cyanamide:

Scheme 20

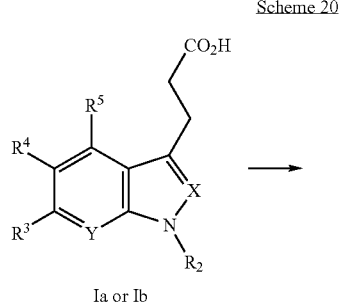

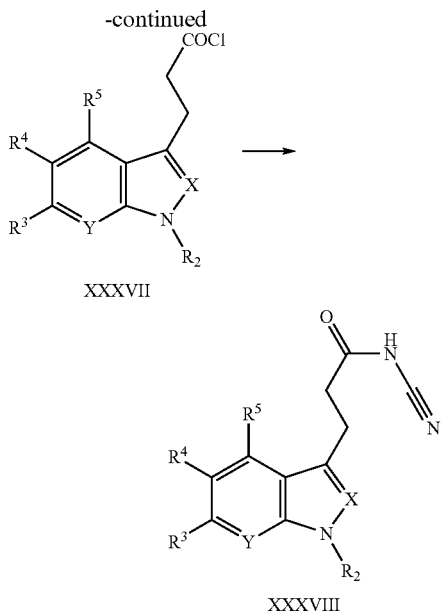

Compound XXXVIII can be prepared through a two step process starting from either Ia or Ib.

Step 1

The carboxylic acid group in Ia or Ib can be converted to acyl halide XXXVII through the use of reagents (e.g. thionyl chloride, phosphorous pentachloride, or phosphorous trichloride) in an inert solvent (e.g. dichloromethane). (Cao, J. et al, *J. Med. Chem.*, 2003, 46, 2589-98 and Kitamura, M. et al, *Synthesis*, 2003, 2415-26)

Step 2

The acyl cyanamide functionality can be introduced via coupling of the cyanamide with compound XXXVII to yield the desired product XXXVIII. (Belletire, J. L. et al, *Syn. Commun.*, 1988, 18, 2063-72)

Sulfonamides:

fonic acid to the corresponding sulfonyl chloride to arrive at intermediate XLII. (Scheme 20, step 1)

Step 6

Sulfonamide isosteres of the carboxylic acid is then generated through coupling of the sulfonyl chloride XLIIIa with amine reagents (e.g. sodium amide or methylamine).

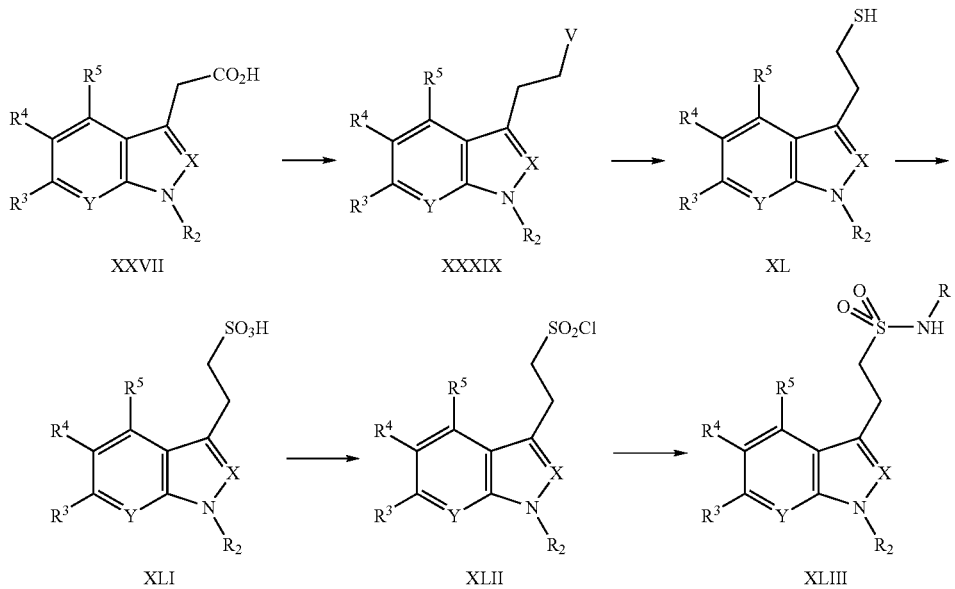

Scheme 21

The sulfonamide bio-isostere for carboxylic acid can be prepared in 6 steps from from indolyl-3-acetic acid or propionic acid (if the linker is to be extended)

Steps 1&2

Compound XXVII can be transformed to the corresponding alcohol XXXIX through treatment with reducing reagent such as lithium aluminum hydride in an inert solvent such as THF. The corresponding alcohol can be converted to mesylate or halogen with the proper reagents such as methane sulfonyl chloride or Phosphorous tribromide respectively.

Step 3

Intermediate XL can be prepared by treating XXXIX with sodium hydrogen sulfide, hexabutyldistannathian, or 1-(2-hydroxyethyl)-4,6-diphenylpyridine-2-thione to get to the ethanethiol or propanethiol. (Gingras et al, *Tet. Lett.* 1990, 31, 1397-1400, Maercker et al, *Justus Liebigs Ann. Chem.*, 1865, 136, 88, or Molina et al, *Tetrahedron Lett.*, 1985, 26 469-472.)

Step 4

The thiol XL can be oxidized to the corresponding sulfonic acid with oxidative reagents such as hydrogen peroxide to afford intermediate XLI.

Step 5

Compound XL can be treated to reagents (e.g. thionyl chloride or phosphorous pentachloride) to convert the sul- Acetyl-Sulfonamides:

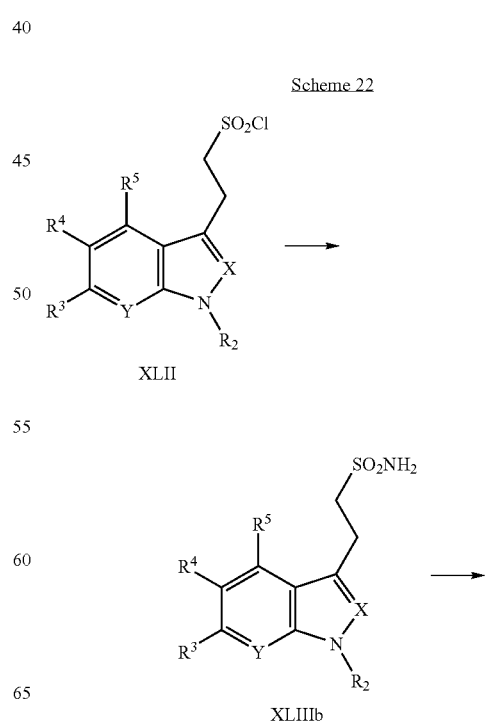

Scheme 22

-continued

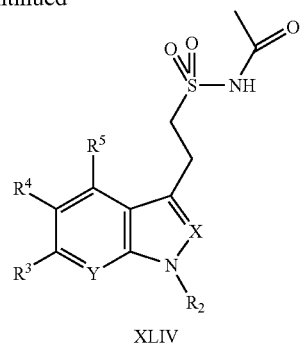

XLIV

Acetyl-sulfonamides XLIV can be prepared through the sulfonyl chloride XLII in two steps.

Step 1

Compound XLII is treated to ammonia or sodium amide to yield XLIIIb.

Step 2

Compound XXXIIIb is then deprotonated and treated to acetic anhydride to arrive at the acetyl-sulfonamide XLIV.

Exemplary general synthesis of compounds of Formula L, where W, Y, and Z are independently N or CH; n=0, 1, or 2.

Scheme 23a-Preparation of sulfonyl chloride XLVIII:

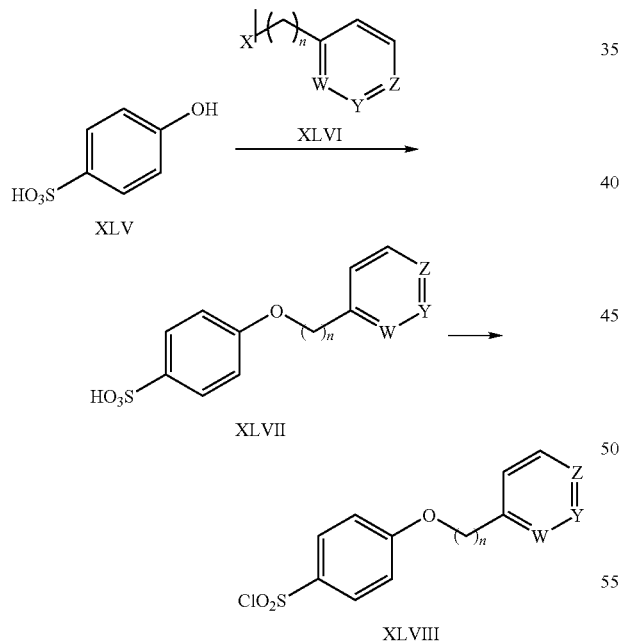

Step 1: Preparation of Intermediate XL VII

Commerically available 4-hydroxy benzenesulfonic acid XLV, can be reacted with aryl halides, e.g., iodobenzene benzyl bromide etc., under Buckwald reaction conditions and $SN_2$ reaction conditions respectively, or with alcohols, e.g. benzyl alcohols under Mitsunobu reaction conditions, or other coupling reactions to afford XLVII.

Step 2: Preparation of Intermediate XL VIII

Compound of formula XLVII can be converted to the corresponding sulfonly chloride with reagents such as $PCl_3$, $PCl_5$, $POCl_3$, or $SOCl_2$.

Scheme 23b-Preparation of Compound of Formula L

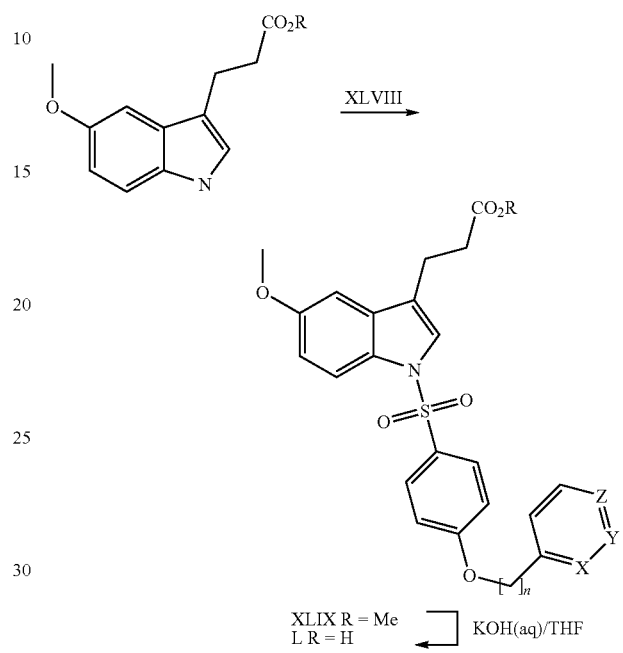

XLIX R = Me
L R = H
KOH(aq)/THF

Compound of formula L can be prepared by reacting the sulfonyl chloride XLVIII with 5-methoxy-indole-3-propionic ester in presence of a base, e.g. aq. Potassium hydroxide, in THF.

Example 116

Synthesis of 3-{5-Methoxy-1-[4-(pyridin-3-yloxy)-benzenesulfonyl]-1H-indol-3-yl}-propionic acid 143

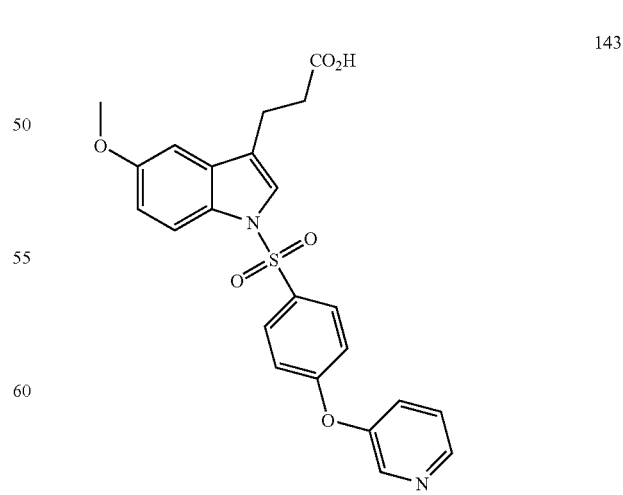

143

Compound 143 can be prepared through methods described in Scheme 23, using 4-hydroxybenzenesulfonic acid and 3-hydroxypyridine to prepare the corresponding sulfonyl chloride. The various coupling of the sulfonyl chloride to 5-methoxy-indole-3-propionic ester or the corresponding acid as described in Scheme 7, 10, or 12.

Example 117

Synthesis of 3-{5-Methoxy-1-[4-(pyridin-4-yloxy)-benzenesulfonyl]-1H-indol-3-yl}-propionic acid 144

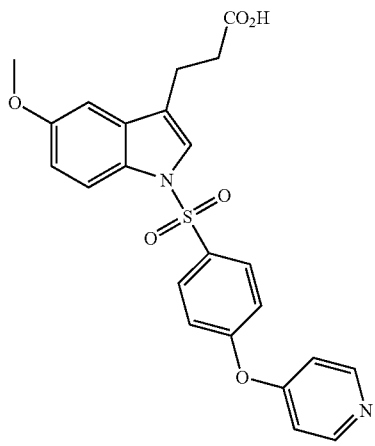

Compound 144 can be prepared through methods described in Scheme 23, using 4-hydroxybenzenesulfonic acid and 4-hydroxypyridine to prepare the corresponding sulfonyl chloride. The various coupling of the sulfonyl chloride to 5-methoxy-indole-3-propionic ester or the corresponding acid as described in Scheme 7, 10, or 12.

Example 118

Synthesis of 3-{5-Methoxy-1-[4-(pyridin-4-yl-methoxy)-benzenesulfonyl]-1H-indol-3-yl}-propionic acid 145

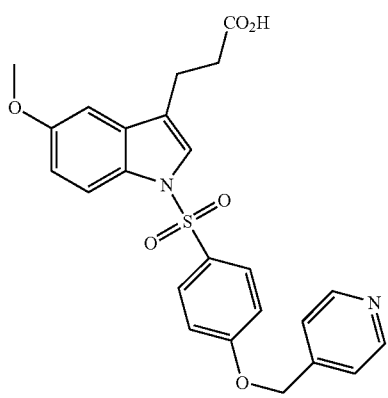

Compound 145 can be prepared through methods described in Scheme 23, using 4-hydroxybenzenesulfonic acid and 4-pyridylcarbinol to prepare the corresponding sulfonyl chloride. The various coupling of the sulfonyl chloride to 5-methoxy-indole-3-propionic ester or the corresponding acid as described in Scheme 7, 10, or 12.

Example 119

Synthesis of 3-[1-(3,5-Dichloro-benzenesulfonyl)-5-methoxy-1H-indol-3-yl]-propionic acid 146

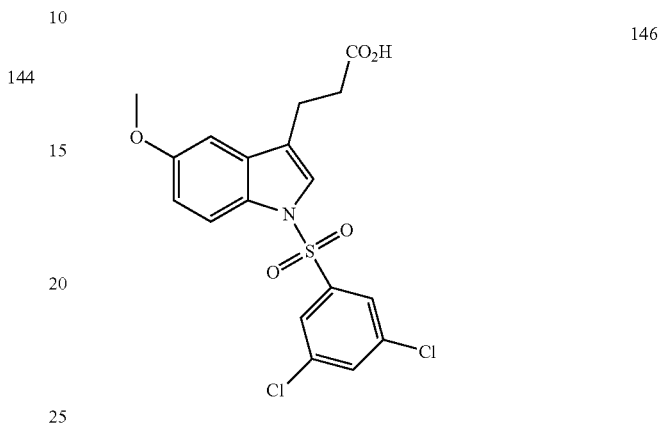

Compound 146 can be prepared by reacting 5-methoxy-indole-3-propionic ester or the corresponding acid through methods with 3,5-dichlorobenzenesulfonyl chloride as described in Scheme 7, 10, or 12.

Example 120

Synthesis of 3-[1-(3,5-Dimethoxy-benzenesulfonyl)-5-methoxy-1H-indol-3-yl]-propionic acid 147

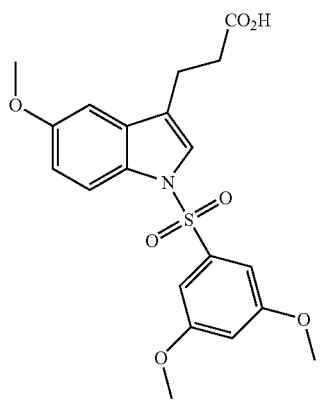

Compound 147 can be prepared by reacting 5-methoxy-indole-3-propionic ester or the corresponding acid through methods with 3,5-dimethoxybenzenesulfonyl chloride as described in Scheme 7, 10, or 12.

General Synthesis of Compounds of Formula LIV and LV

Scheme 24

Step - 1

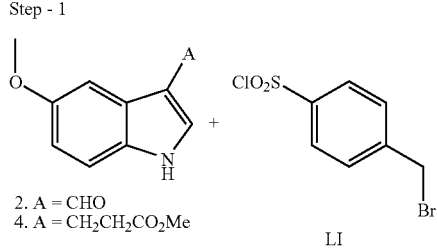

2. A = CHO
4. A = CH₂CH₂CO₂Me

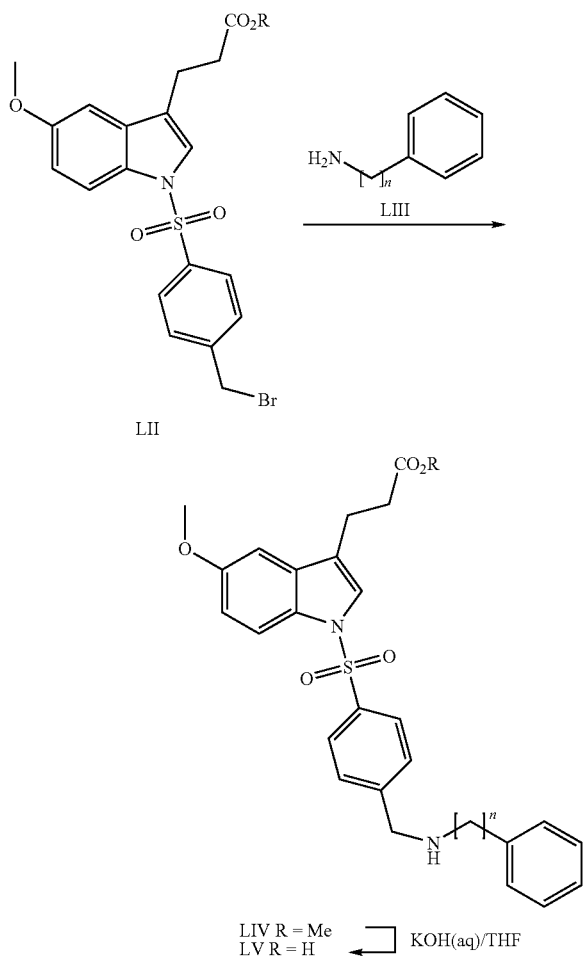

LIV R = Me
LV R = H  ⟵ KOH(aq)/THF

Step 1: Preparation of Intermediate LII

Compound LII can be prepared through coupling of indole (2 or 4) with sulfonyl chloride LI from methodologies described in Scheme 7 or 12.

Step 2: Preparation of Compound LIV or LV

Compound LIV or LV can be prepared through nucleophilic displacement of the bromomethyl group under basic conditions, in an inert solvent such as DMF.

Example 121

Synthesis of 3-{5-Methoxy-1-[4-(quinolin-7-ylaminomethyl)-benzenesulfonyl]-1H-indol-3-yl}-propionic acid 148

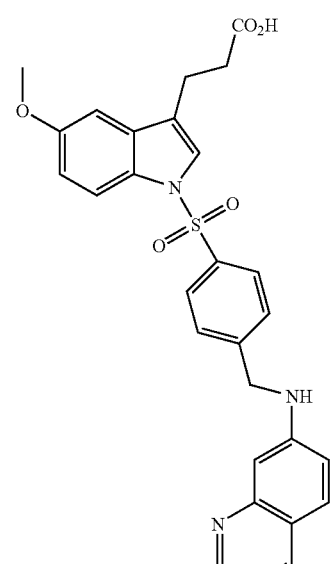

Compound 148 can be prepared via coupling of compound LII with the corresponding Quinol-7-ylamine with the bromomethyl moiety in Scheme 24.

Example 122

Synthesis of 3-{1-[4-(Isoquinolin-3-ylaminomethyl)-benzenesulfonyl]-5-methoxy-1H-indol-3-yl}-propionic acid 149

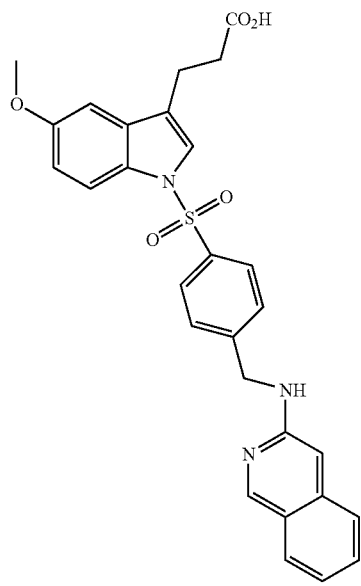

Compound 149 can be prepared via coupling of compound LII with the corresponding isoquinolin-3-yl-amine with the bromomethyl moiety in Scheme 24.

Example 123

Synthesis of 3-{5-Methoxy-1-[4-(quinolin-6-ylaminomethyl)-benzenesulfonyl]-1H-indol-3-yl}-propionic acid 150

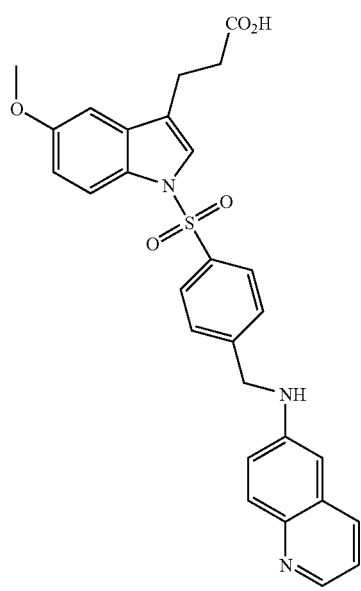

Compound 149 can be prepared via coupling of compound LII with the corresponding quinolin-6-yl amine with the bromomethyl moiety in Scheme 24.

Example 124

Synthesis of 3-[5-Methoxy-1-(4-pyrrolo[2,3-b]pyridin-1-ylmethyl-benzenesulfonyl)-1H-indol-3-yl]-propionic acid 151

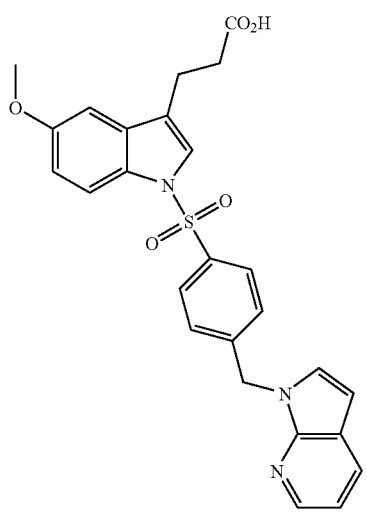

Compound 151 can be prepared via coupling of compound LII with the corresponding 7-azaindole with the bromomethyl moiety in Scheme 24.

Example 125

Synthesis of 3-[5-Methoxy-1-(4-phenoxymethyl-benzenesulfonyl)-1H-indol-3-yl]propionic acid 152

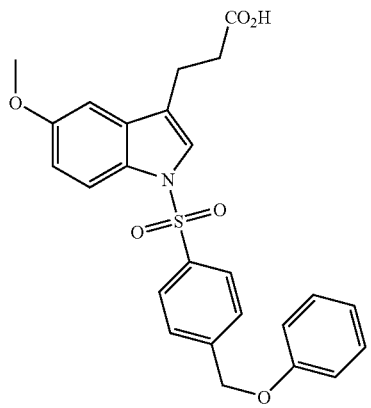

Compound 152 can be prepared via coupling of compound LII with the corresponding phenol with the bromomethyl moiety in Scheme 24.

General Synthesis of Compounds of Formula LIX, LX, or LXI

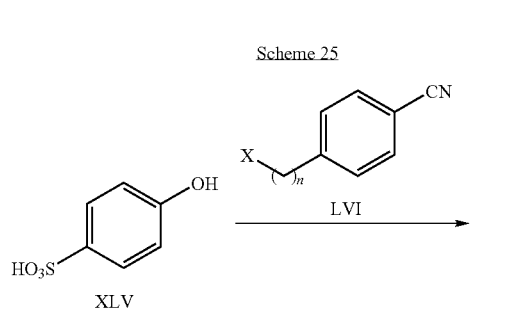

Scheme 25

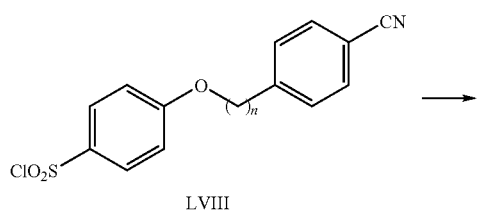

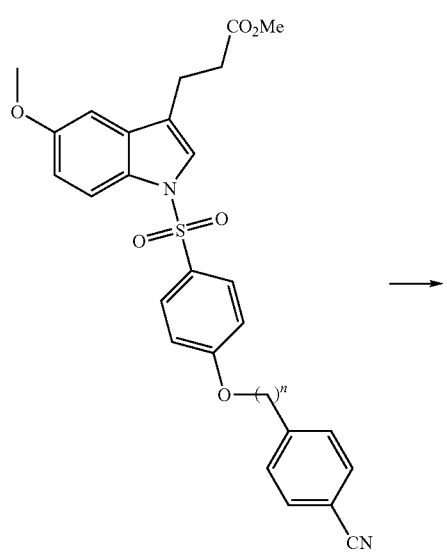

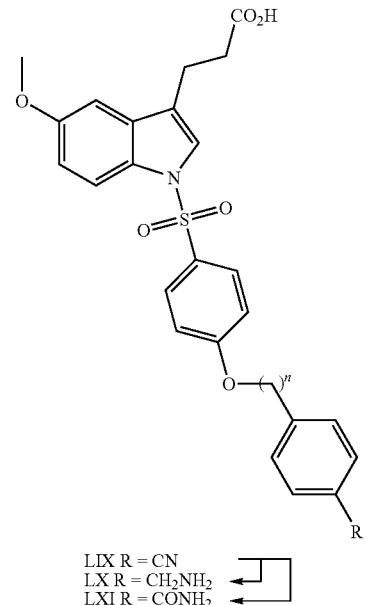

LIX R = CN
LX R = CH$_2$NH$_2$
LXI R = CONH$_2$

Step 1: Preparation of Intermediate LVII

The intermediate LVII can be prepared through either similar methods as described in step 1 of preparation of XLVII, or through nucleophilic displacement of a fluoro group.

Step 2: Preparation of Intermediate LVIII

The sulfonic acid can be converted to the corresponding sulfonyl chloride with PCl$_3$, POCl$_3$, PCl$_5$, or SOCl$_2$.

Step 3: Preparation of Intermediate LIX

The sulfonyl chloride LVIII can be coupled to the indole intermediates 4 to arrive at LIX.

Step 4: Preparation of compound LX and LXI

The nitrile moiety can be further converted to either amide through hydrolysis or amine through reduction.

Example 126

Synthesis of 3-{5-Methoxy-1-[4-(pyridin-3-yl-methoxy)-benzenesulfonyl]-1H-indol-3-yl}-propionic acid 153

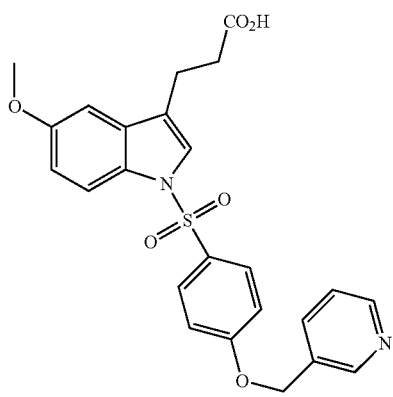

153

Compound 153 can be prepared through methods described in Scheme 23, using 4-hydroxybenzenesulfonic acid and 3-pyridinemethanol to prepare the corresponding sulfonyl chloride. The various coupling of the sulfonyl chloride to the indole-moiety are described in Scheme 7, 10, or 12.

Example 127

Synthesis of 3-{1-[4-(4-Aminomethyl-benzyloxy)-benzenesulfonyl]-5-methoxy-1H-indol-3-yl}-propionic acid 154

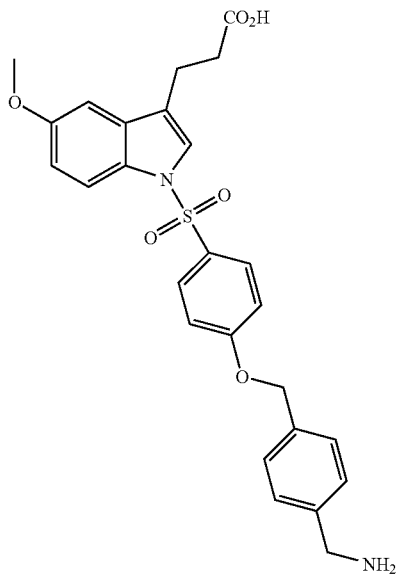

154

Compound 154 can be prepared through reduction of the nitrile group, as described in Scheme 25. The nitrile functionality can be prepared through coupling of the sulfonyl chloride with the 5-methoxyindole-3-propionic acid methyl ester. The sulfonyl chloride can be prepared through coupling of the 4-hydroxy benzenesulfonic acid with 4-cyanobenzyl bromide.

Example 128

Synthesis of 3-{1-[4-(4-Carbamoyl-benzyloxy)-benzenesulfonyl]-5-methoxy-1H-indol-3-yl}-propionic acid 155

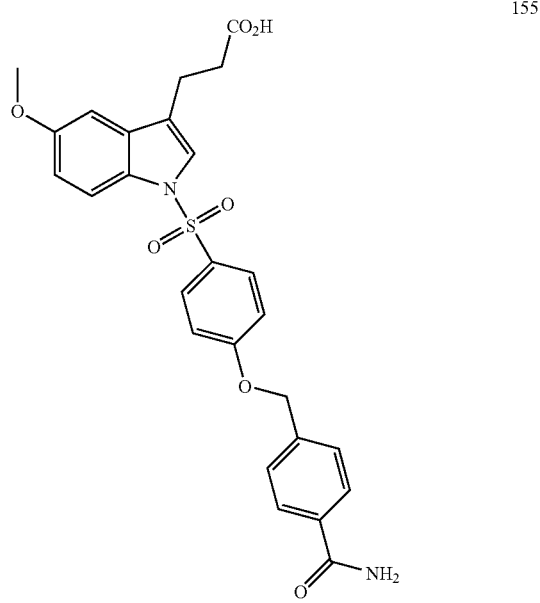

155

Compound 155 can be prepared through hydrolysis of the nitrile group, as described in Scheme 25. The nitrile functionality can be prepared through coupling of the sulfonyl chloride with the 5-methoxyindole-3-propionic acid methyl ester. The sulfonyl chloride can be prepared through coupling of the 4-hydroxy benzenesulfonic acid with 4-cyanobenzyl bromide.

Example 129
Synthesis of Compound 162
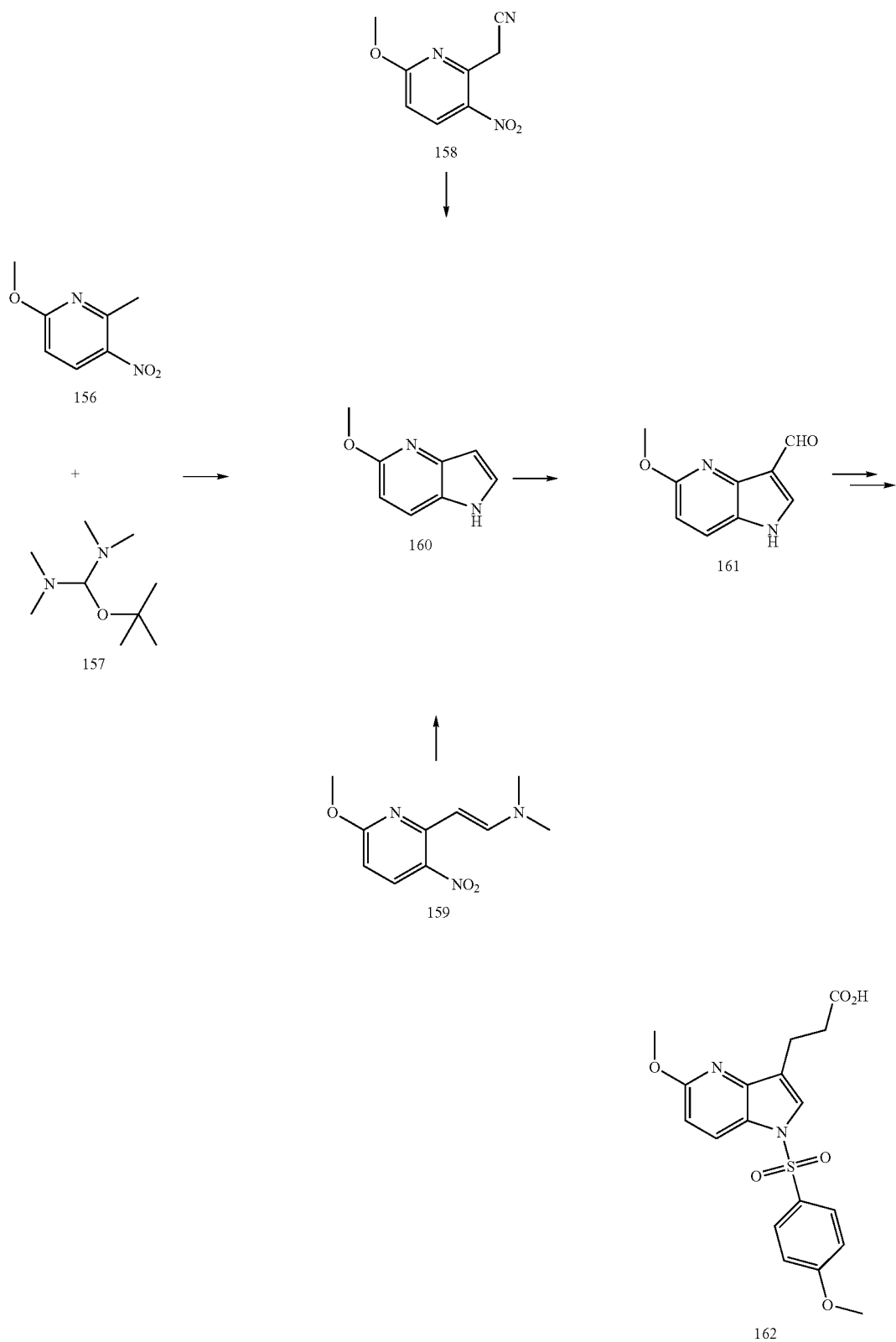

Step 1: Preparation of 5-Methoxy-1H-pyrrolo[3,2-b]pyridine 160

The title compound can be prepared through:
1. Reductive Cyclization with 158 (M. Mieczyslaw et. al, Liebigs Ann. Chem. 1988, 203-208; D. Mazeas. et. al, Heterocycles, 1999, 50, 1065-80.)
2. Reduction through catalytic hydrogenation and cyclization under reflux conditions with C-tert-butoxy-tetra-N-methyl-methanediamine 157 (K-H. Buchheit et al, J. Med. Chem., 1995, 2331-2338).
3. Reductive cyclization with 159 (S. A. Filla et al, J. Med. Chem., 2003, 46, 3060-71)

Step 2: Preparation of 5-Methoxy-1H-pyrrolo[3,2-b]pyridine-3-carbaldehyde 161

The intermediate 161 can be prepared either through Vilsmeier reaction (K-H. Buchheit et al, J. Med. Chem., 1995, 2331-2338) or with 1,3,5,7-tetraaza-adamantane (D. Mazeas et. al, Heterocycles, 1999, 50, 1065-80).

The subsequent conversion to introduce the propionic acid side chain and the sulfonamide can be achieve using methodologies as described in Scheme 7 or 12.

Example 130

Synthesis of Compound 166

Scheme 27

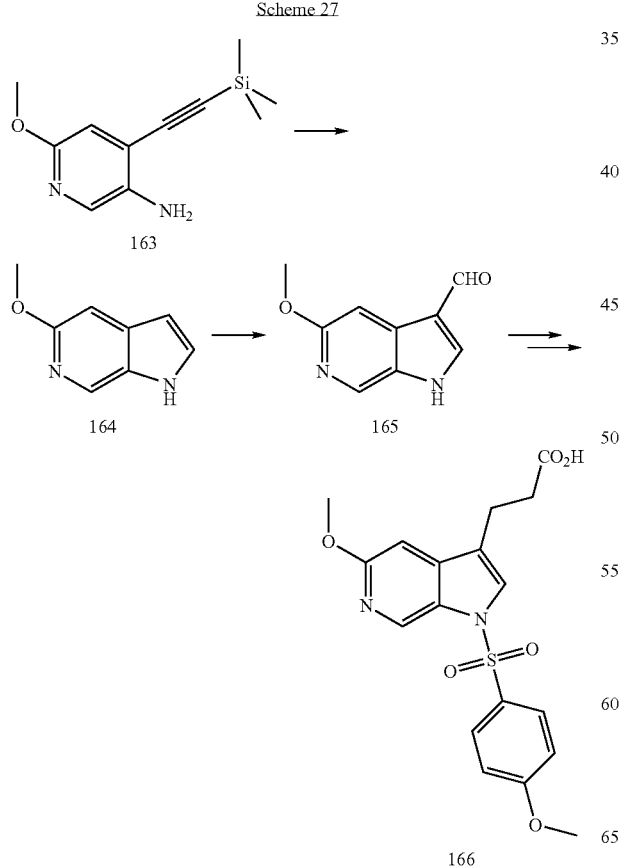

166

Step 1: Preparation of Intermediate 164, 5-Methoxy-1H-pyrrolo[2,3-c]pyridine 5-Methoxy-1H-pyrrolo[2,3-c]pyridine 164 can be prepared through cyclization of 6-methoxy-4-trimethylsilanyl-ethylnyl-pyridin-3-ylamine 163 with cuprous iodide in DMF (D. Mazeas et. al, Heterocycles, 1999, 50, 1065-80).

Step 2: Preparation of Intermediate 165, 5-Methoxy-1H-pyrrolo[2,3-c]pyridine-3-carbaldehyde 5-Methoxy-1H-pyrrolo[2,3-c]pyridine-3-carbaldehyde can be prepared from 165 using with 1,3,5,7-tetraaza-adamantane under refluxing conditions with DMF (D. Mazeas et. al, Heterocycles, 1999, 50, 1065-80).

The subsequent conversion to introduce the propionic acid side chain and the sulfonamide can be achieve using methodologies as described in Scheme 7 or 12.

Example 131

Synthesis of Compound 172

Scheme 28

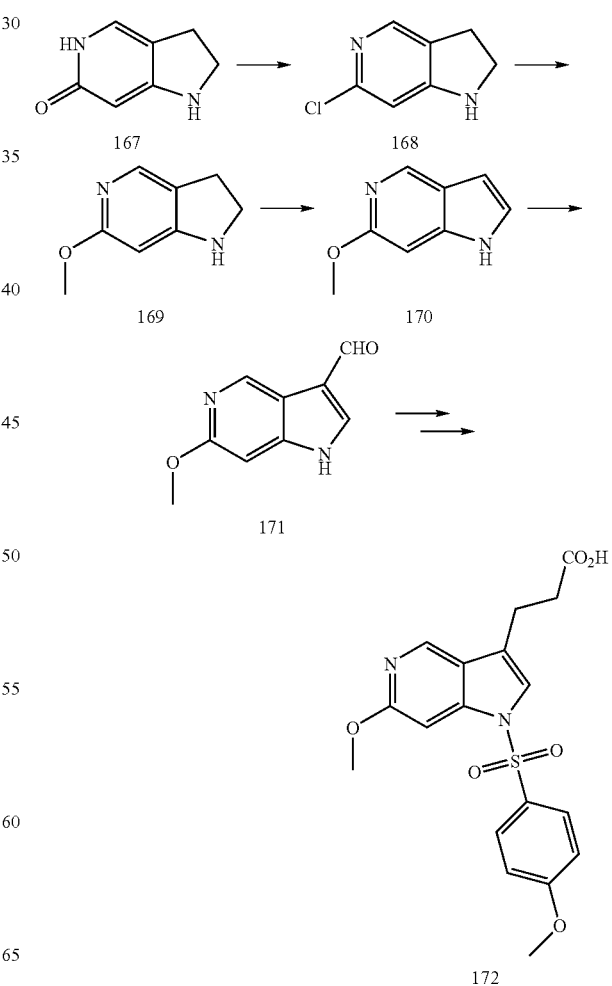

172

Step 1: Preparation of 168, 6-Chloro-2,3-dihydro-1H-pyrrolo[3,2-c]pyridine 1,2,3,5-Tetrahydro-pyrrolo[3,2-c]pyridin-6-one 167 can be converted to the 6-Chloro-2,3-dihydro-1H-pyrrolo[3,2-c]pyridine 168 with Phosphorous oxychloride (N. N. Bychikhina et. al, Chem. Heterocycl. Compds., 1982, 18, 356-360)

Step 2: Preparation of 169, 6-Methoxy-2,3-dihydro-1H-pyrrolo[3,2-c]pyridine

6-Methoxy-2,3-dihydro-1H-pyrrolo[3,2-c]pyridine 169 can be prepared through direct displacement of the chloro group in 168 with sodium methoxide. (V. A. Azimov et. al, Chem. Heterocycl. Compd. 1981, 17, 1648-1653)

Step 3: Preparation of 170, 6-Methoxy-1H-pyrrolo[3,2-c]pyridine

6-Methoxy-2,3-dihydro-1H-pyrrolo[3,2-c]pyridine 169 is oxidized to the corresponding 170 with the use of MnO$_2$. (V. A. Azimov et. al, Chem. Heterocycl. Compd. 1981, 17, 1648-1653)

Step 4: Preparation of 171, 6-Methoxy-1H-pyrrolo[3,2-c]pyridine-3-carbaldehyde 6-Methoxy-1H-pyrrolo[3,2-c]pyridine-3-carbaldehyde is prepared through Vilsmeier conditions with 170. (N. N. Bychikhina et. al, Chem. Heterocycl. Compds., 1982, 18, 356-360)

The subsequent conversion to introduce the propionic acid side chain and the sulfonamide can be achieve using methodologies as described in Scheme 7 or 12.

Example 132

Synthesis of Compound 181

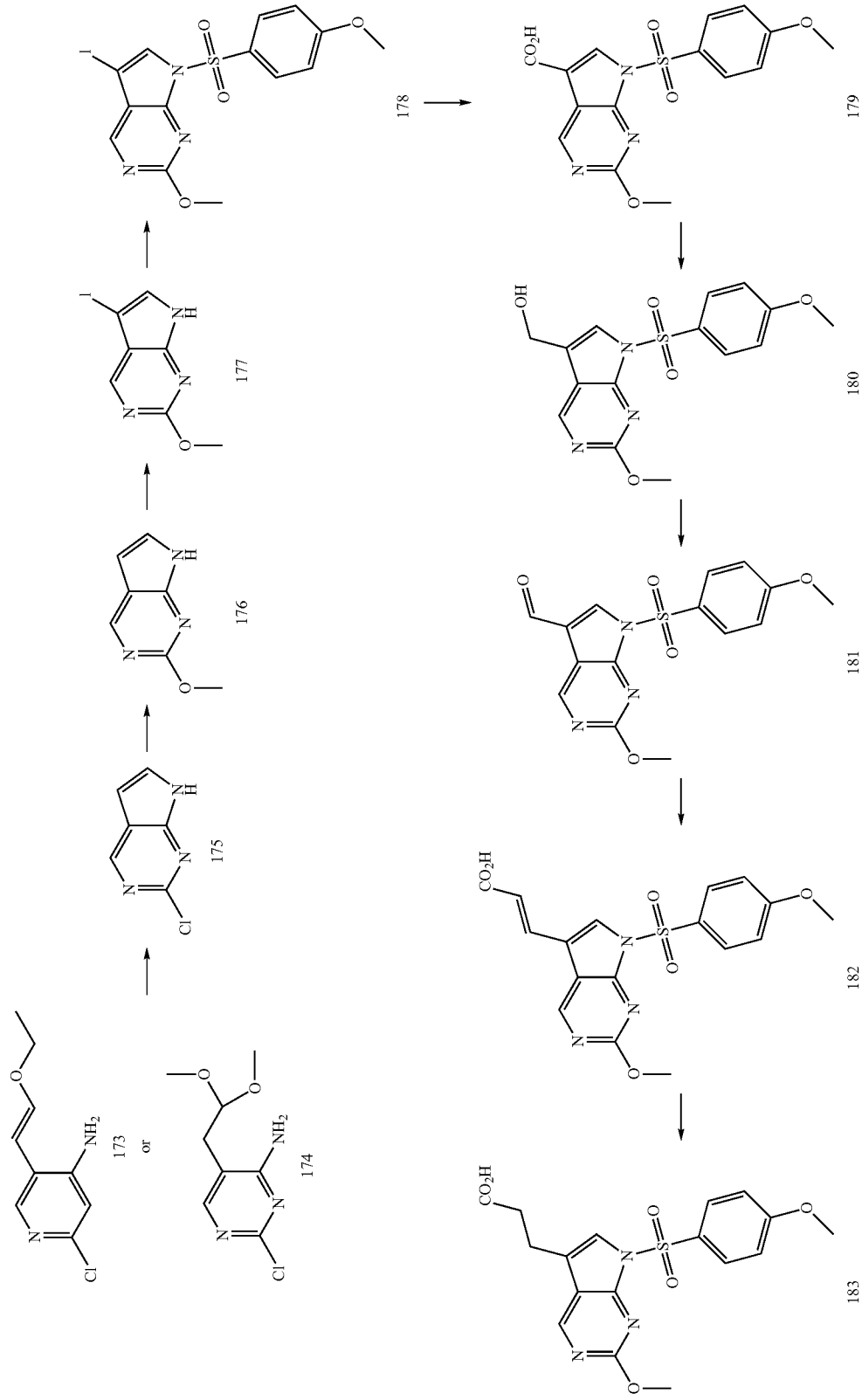

Step 1: Preparation of 175

2-chloro-7H-pyrrolo[2,3-d]pyrimidine 175 can be prepared from either 2-chloro-5-(2-ethoxy-vinyl)-pyrimidin-4-ylamine 173 or 2-chloro-5-(2,2-dimethoxy-ethyl)-pyrimidin-4-ylamine 174 (under reflux conditions in methanol with concentrated hydrochloric acid (M. Cheung et al, Tet. Lett., 2001, 42, 999-1002).

Step 2: Preparation of 176

The 2-chloro group in 2-chloro-7H-pyrrolo[2,3-d]pyrimidine 176 can be converted to the corresponding methoxy moiety 176 through nucleophilic displacement of the chloro group by sodium methoxide (F., Seela et. al, Liebigs Ann. Chem. 1985, 312-320.)

Step 3: Preparation of 177

Intermediate 177 can be prepared from 176 through iodination of 176 with Iodine, with base in N,N-dimethylformamide at ambient temperature. (T., Sakamoto, Takao et. al, J. Chem. Soc. Perkin Trans. 1, 1996; 459-464)

Step 4: Preparation of 178

Protection of the pyrrolopyrimidine 177 with 4-methoxybenzenesulfonyl chloride can be achieve through a bi-phasic coupling using aqueous sodium hydroxide solution or with sodium hydride in DMF.

Step 5: Preparation of 179

The 3-carboxylic acid functionality can be prepared through deprotonation with a grignard reaction, follow by $CO_2$ addition and acidification to yield the desired intermediate from 177. (Y. Kondo, et.al Heterocycles, 1996, 42, 205-8.)

The subsequent conversion to introduce the propionic acid side chain and the sulfonamide can be achieve using methodologies as described in Scheme 9

Example 133

Synthesis of Compound 190

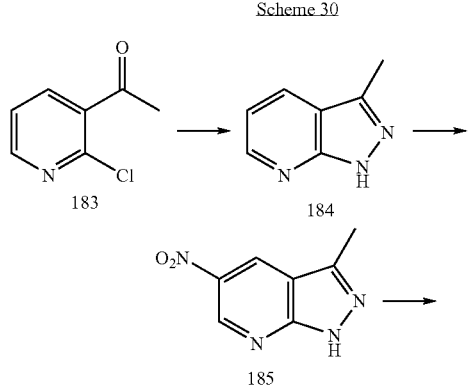

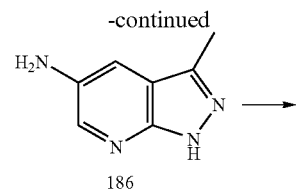

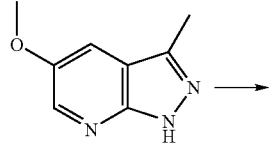

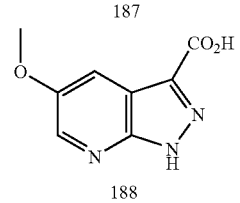

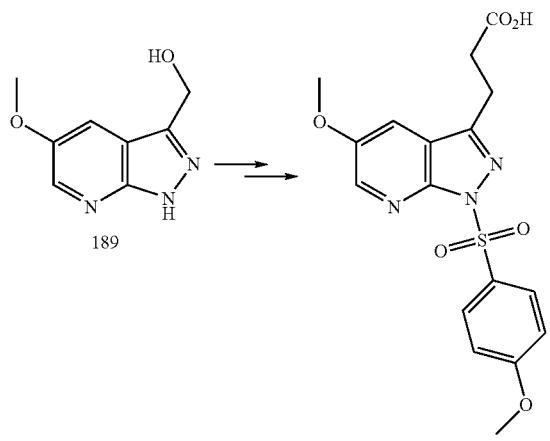

Step 1: Synthesis of Intermediate 184

Intermediate 184 can be prepared from 3-acetyl-2-chloropyridine, through cyclization with methylhyrazine. (B. M. Lynch et. al, Canadian Journal of Chemistry, 1988, 66, 420-8)

Step 2: Synthesis of Intermediate 185

Intermediate 185 is prepared through nitration of the 5-position with nitric acid and sulfuric acid. (B. M. Lynch et.al, Canadian Journal of Chemistry, 1988, 66, 420-8)

Step 3: Synthesis of Intermediate 186

The nitro group is reduced the corresponding amine group through use of reagents such as palladium on activated carbon. (B. M. Lynch et. al, Canadian Journal of Chemistry, 1988, 66, 420-8)

Step 4: Synthesis of Intermediate 187

The amine group is then converted to diazonium salt with sodium nitrate and concentrated hydrochloric acid. The diazonium ion is then quenced with methanol to yield the corresponding methoxy functionality. (B. M. Lynch et. al, Canadian Journal of Chemistry, 1988, 66, 420-8)

Step 5: Synthesis of Intermediate 188

The 3-methyl group is oxidized through $KMnO_4$ oxidation to the carboxylic acid. (B. M. Lynch et. al, Canadian Journal of Chemistry, 1988, 66, 420-8)

The subsequent conversion to introduce the propionic acid side chain and the sulfonamide can be achieve using methodologies as described in Scheme 9 to arrive at the desired compound 190.

Example 134

Crystallization and Crystal Structures of PPARs

PPARα, PPARδ, and PPARγ have each been crystallized and crystal structures determined and reported. Such structures and atomic coordinates are available at Protein Data Bank (PDB) (available on the internet on the Web where the remainder of the address following www is rcsb.org). For PPARα deposited atomic coordinates are available under PDB code 1KKQ, Xu, 2001, Nature 415, p813; for PPARδ under code 1GWX, Xu, 1999, Mol Cell, 3, p397; and for PPARγ under code 1PRG, Notle, et al, 1998, Nature, 395, p137. (Each of the references cited in connection with PPAR structures is hereby incorporated by reference in its entirety.) Additional atomic coordinate deposits are available, where PDB codes of the deposited structures are: 1K7L, 1I7G, and 1KKQ for PPARalpha, 1PRG, 2PRG, 3PRG, 4PRG, $1K_{74}$, 1FM6, 1FM9, 1I7I, and 1KNU for PPARgamma, 1GWX, 2GWX, and 3GWX for PPARdelta.

In addition, high quality crystals of the PPARs can be obtained by crystallization under conditions as described below. The structures can then be readily obtained by using published structures as references. Sequences encoding the individual PPARs can be readily obtained. Sequences encoding the individual PPARs were obtained from the NCBI LocusLink (on the Web where the remainder of the address following www is ncbi.nih.gov/LocusLink). The sequence accession numbers are: NM_005036 (cDNA sequence for PPARa), NP_005027 (protein sequence for PPARa), NM_015869 (cDNA sequence for PPAR9 isoform 2), NP_056953 (protein sequence for PPAR9 isoform 2), NM_006238 (cDNA sequence for $PPAR^d$), and NP_006229 (protein sequence for $PPAR^d$). Using these sequences, the coding sequences can be isolated from a cDNA library using conventional cloning techniques. PPAR proteins can then be expressed and purified by conventional methods.

In the present case, PPAR polypeptides were obtained by PCR from a cDNA library (Invitrogen), and sub-cloned to obtain constructs for expression. Expressing those sequences thus provided PPAR polypeptides for crystallization.

In addition to the conditions published for crystallizing each of the PPARs, the following crystallization conditions have been used for producing co-crystals of each of the PPAR ligand binding domains with compounds of Formula I. The particular ligand binding domain sequence used for PPARalpha: GenBank accession: NP_005027 (protein sequence) and NM_005036 (mRNA sequence), ligand binding domain: amino acid residues 196-468.

For PPARgamma the ligand binding domain used corresponded to amino acid residues 174_475 of GenBank accession: NP_005028 (protein sequence) and NM_005037 (mRNA sequence).

For PPARdelta the ligand binding domain used corresponded to amino acid 165-441 of GenBank accession: NP_006229 (protein sequence) and NM_006238 (mRNA sequence).

Exemplary Crystallization conditions for PPARgamma:
1. with 2× molar excess of SRC-1 and 1 mM compound
   0.2M Ammonium Acetate, 0.1M Bistris, pH 6.5, 13-25% PEG4k, or
   0.2M Ammonium Acetate, 0.1M Hepes, pH 7.5, 13-25% PEG4k
2. with 0.3-1 mM compound
   12-22% PEG 8k, 0.2M NaAcetate, 0.1M Hepes pH 7.5; or
   0.6M-1.0M NaCltrate, 0.1M Hepes pH 7.5; or
   0.9-1.4M Ammonium Sulfate, 0.1M Hepes pH 7.5

Crystallization conditions for PPARalpha:
1. with 2× molar excess of SRC-1 and 1 mM compound
   9-30% PEG 4K, 0.2M Ammonium Acetate, 0.1M Citrate, pH 5.6; or
   17-30% PEG4k, 0.2M Lithium Sulfate, 0.1M Tris/HCl, pH 8.5; or
   22-30% PEG4k, 0.2M NaAcetate, 0.1M Tris/HCl, pH 8.5
2. with co-concentrated compound
   0.6-1.0M Lithium Sulfate, 0.1M Tris/HCl pH 8.5

Crystallization conditions for PPARdelta:
1. with 2× molar excess of SRC-1 and co-concentrated compound
   0.2-1.2M KNaTartrate, 2.5% 1,2 Propanediol, 0.1M Mes pH 5.5-6.5

The X-ray diffraction data from such co-crystals were then collected from synchrotron radiation facilities. The useable diffraction data were of high resolution such as 1.9 A-3.0 A, preferably 2.5 A or higher, more preferably 2.2A or higher, most preferably 2.0 A or higher. The 3-dimensional structures of proteins were determined with the co-crystal diffraction data by molecular replacement method using the published structures as starting search model. The molecular replacement solutions of the protein structures were then refined and used for calculating difference Fourier maps. The difference Fourier maps provide basis for the determination of compound binding geometry. The compound orientation and structure within the protein ligand binding site were determined based on the information obtained from the co-crystal diffraction data. A skilled person in this art will be able to interpret the X-ray diffraction data according to the compound structures which were involved in the co-crystallization experiments. Water molecules that are tightly bound to the proteins are an integral part of the protein structures. They can also be critical mediators of protein ligand interactions. Such water molecules are termed "structural water". The structural water molecules are built into the structure model based on difference Fourier maps through the iterative refinement process. The compound-protein complex structures including structural water molecules were refined against the co-crystal diffraction data using computational crystallography methods in an iterative manner to yield accurate atomic coordinates for further ligand design process.

Example 135

Exemplary Compounds of Formula I

The structures, IUPAC names, and molecular weights for synthesized exemplary compounds of Structure I are shown below in Table 1.

TABLE 1
| Number | Structure | M. Wt | IUPAC name |
|---|---|---|---|
| 28 | 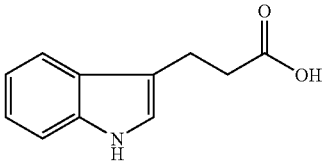 | 189.2 | 3-(1H-Indol-3-yl)-propionic acid |
| 96 | 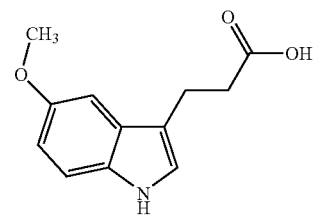 | 219.2 | 3-(5-Methoxy-1H-indol-3-yl)-propionic acid |
| 4 | 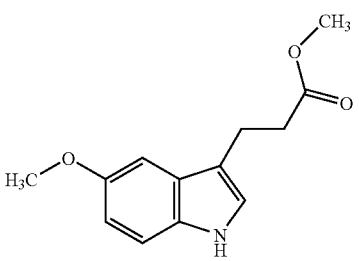 | 233.3 | 3-(5-Methoxy-1H-indol-3-yl)-propionic acid methyl ester |
| 29 | 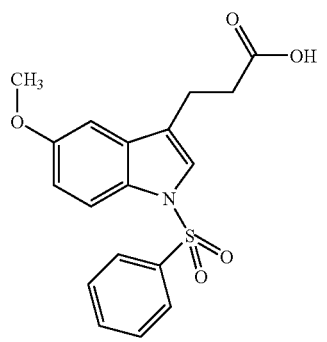 | 359.4 | 3-(1-Benzenesulfonyl-5-methoxy-1H-indol-3-yl)-propionic acid |
| 30 | 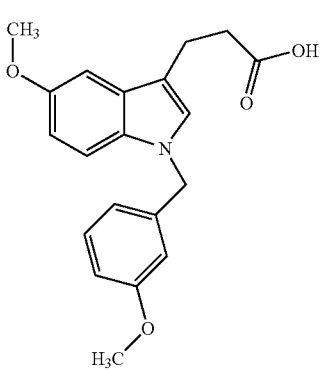 | 339.4 | 3-[5-Methoxy-1-(3-methoxy-benzyl)-1H-indol-3-yl]-propionic acid |

TABLE 1-continued

| Number | Structure | M. Wt | IUPAC name |
|---|---|---|---|
| 31 | 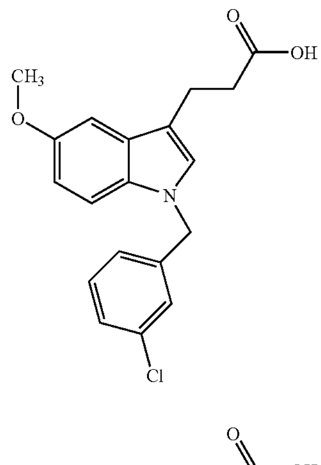 | 343.8 | 3-[1-(3-Chloro-benzyl)-5-methoxy-1H-indol-3-yl]-propionic acid |
| 32 | 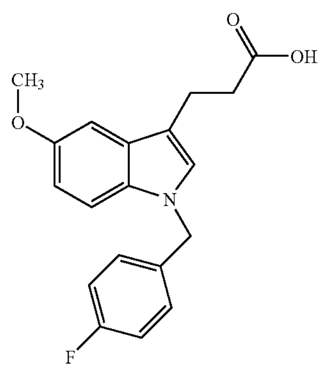 | 327.3 | 3-[1-(4-Fluoro-benzyl)-5-methoxy-1H-indol-3-yl]-propionic acid |
| 33 | 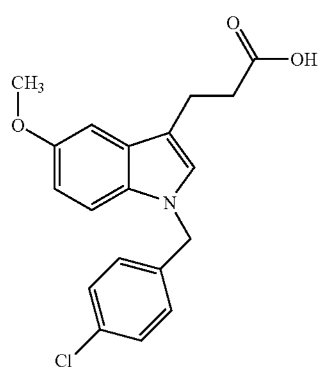 | 343.8 | 3-[1-(4-Chloro-benzyl)-5-methoxy-1H-indol-3-yl]-propionic acid |
| 34 | 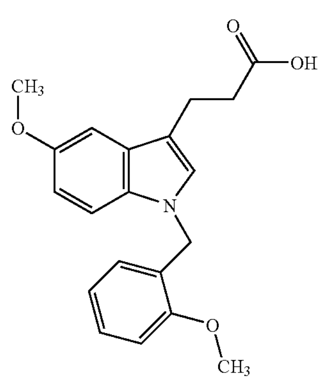 | 339.4 | 3-[5-Methoxy-1-(2-methoxy-benzyl)-1H-indol-3-yl]-propionic acid |

TABLE 1-continued

| Number | Structure | M. Wt | IUPAC name |
|---|---|---|---|
| 35 | 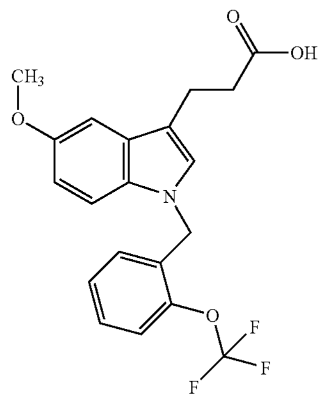 | 393.4 | 3-[5-Methoxy-1-(2-trifluoromethoxy-benzyl)-1H-indol-3-yl]-propionic acid |
| 36 | 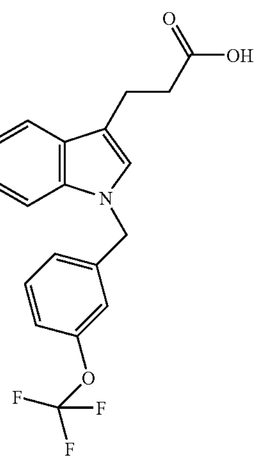 | 393.4 | 3-[5-Methoxy-1-(3-trifluoromethoxy-benzyl)-1H-indol-3-yl]-propionic acid |
| 37 | 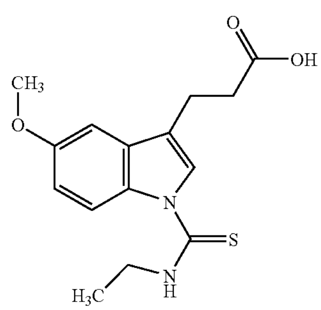 | 306.4 | 3-(1-Ethylthiocarbamoyl-5-methoxy-1H-indol-3-yl)-propionic acid |
| 38 | 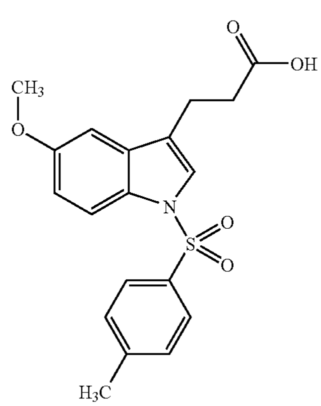 | 373.4 | 3-[5-Methoxy-1-(toluene-4-sulfonyl)-1H-indol-3-yl]-propionic acid |

TABLE 1-continued

| Number | Structure | M. Wt | IUPAC name |
|---|---|---|---|
| 97 | 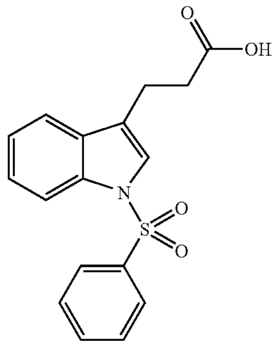 | 329.4 | 3-(1-Benzenesulfonyl-1H-indol-3-yl)-propionic acid |
| 41 | 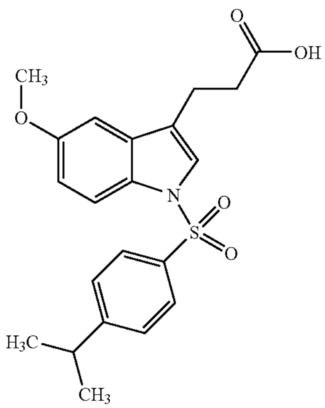 | 401.5 | 3-[1-(4-Isopropyl-benzenesulfonyl)-5-methoxy-1H-indol-3-yl]-propionic acid |
| 40 | 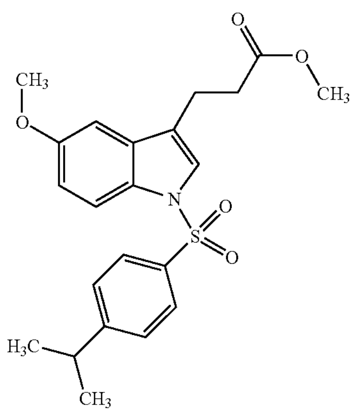 | 415.5 | 3-[1-(4-Isopropyl-benzenesulfonyl)-5-methoxy-1H-indol-3-yl]-propionic acid methyl ester |
| 43 | 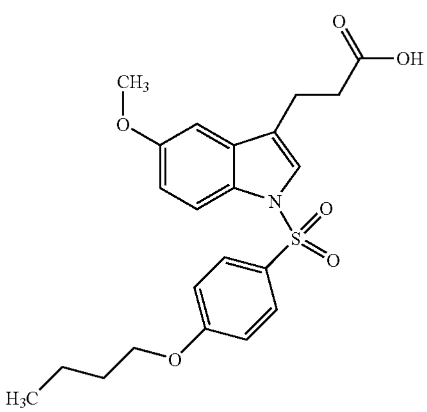 | 431.5 | 3-[1-(4-Butoxy-benzenesulfonyl)-5-methoxy-1H-indol-3-yl]-propionic acid |

TABLE 1-continued

| Number | Structure | M. Wt | IUPAC name |
|---|---|---|---|
| 42 | 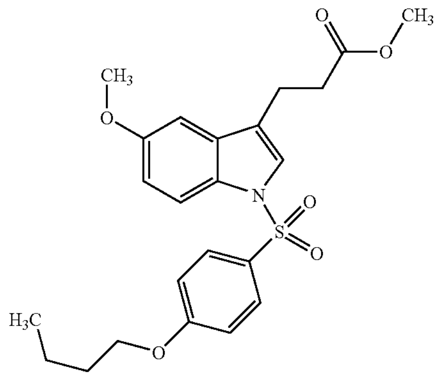 | 445.5 | 3-[1-(4-Butoxy-benzenesulfonyl)-5-methoxy-1H-indol-3-yl]-propionic acid methyl ester |
| 45 | 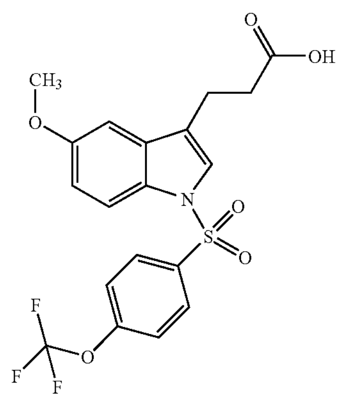 | 443.4 | 3-[5-Methoxy-1-(4-trifluoromethoxy-benzenesulfonyl)-1H-indol-3-yl]-propionic acid |
| 44 | 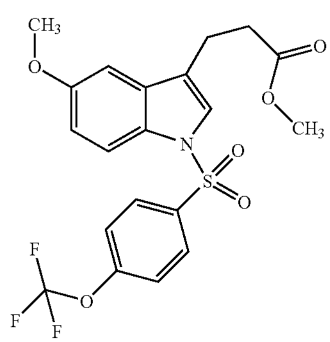 | 457.4 | 3-[5-Methoxy-1-(4-trifluoromethoxy-benzenesulfonyl)-1H-indol-3-yl]-propionic acid methyl ester |
| 47 | 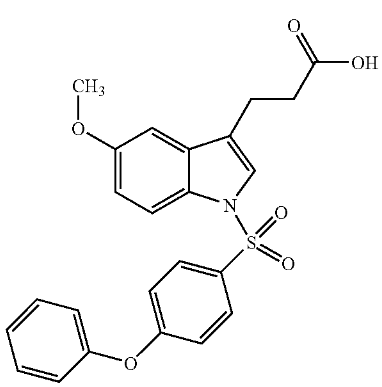 | 451.5 | 3-[5-Methoxy-1-(4-phenoxy-benzenesulfonyl)-1H-indol-3-yl]-propionic acid |

TABLE 1-continued

| Number | Structure | M. Wt | IUPAC name |
|---|---|---|---|
| 46 | 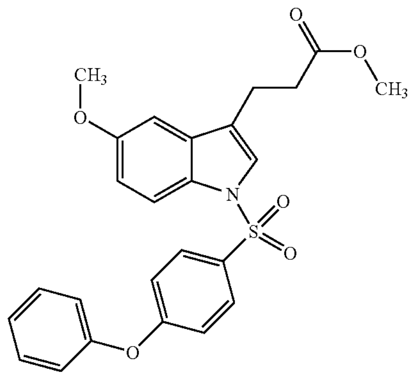 | 465.5 | 3-[5-Methoxy-1-(4-phenoxy-benzenesulfonyl)-1H-indol-3-yl]-propionic acid methyl ester |
| 49 | 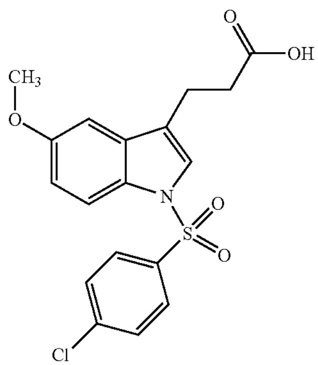 | 393.8 | 3-[1-(4-Chloro-benzenesulfonyl)-5-methoxy-1H-indol-3-yl]-propionic acid |
| 48 | 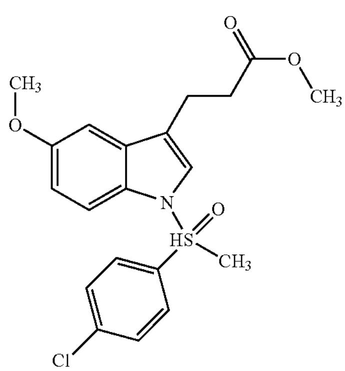 | 407.9 | 3-[1-(4-Chloro-benzenesulfonyl)-5-methoxy-1H-indol-3-yl]-propionic acid methyl ester |
| 50 | 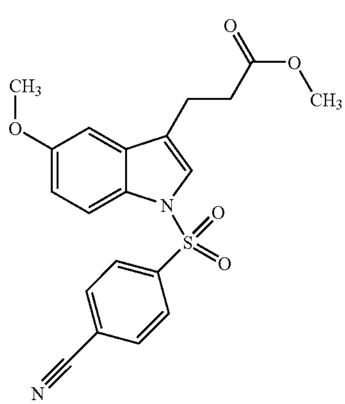 | 398.4 | 3-[1-(4-Cyano-benzenesulfonyl)-5-methoxy-1H-indol-3-yl]-propionic acid methyl ester |

TABLE 1-continued

| Number | Structure | M. Wt | IUPAC name |
|---|---|---|---|
| 52 | 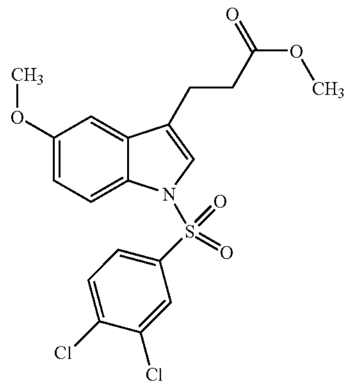 | 442.3 | 3-[1-(3,4-Dichloro-benzenesulfonyl)-5-methoxy-1H-indol-3-yl]-propionic acid methyl ester |
| 5 | 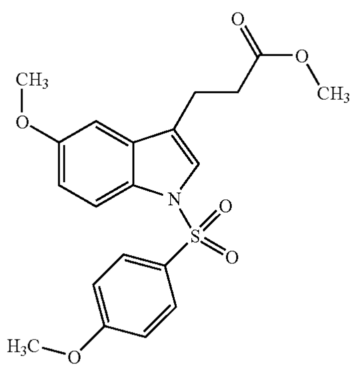 | 403.4 | 3-[5-Methoxy-1-(4-methoxy-benzenesulfonyl)-1H-indol-3-yl]-propionic acid methyl ester |
| 54 | 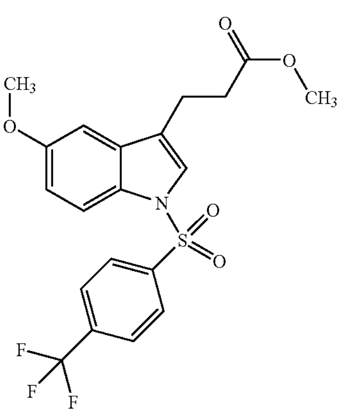 | 441.4 | 3-[5-Methoxy-1-(4-trifluoromethyl-benzenesulfonyl)-1H-indol-3-yl]-propionic acid methyl ester |
| 56 | 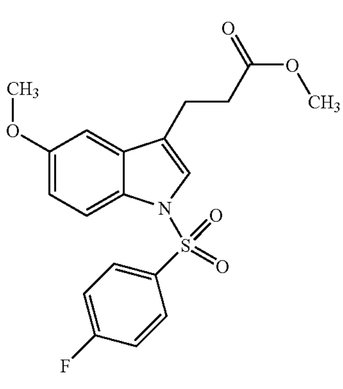 | 391.4 | 3-[1-(4-Fluoro-benzenesulfonyl)-5-methoxy-1H-indol-3-yl]-propionic acid methyl ester |

TABLE 1-continued

| Number | Structure | M. Wt | IUPAC name |
|---|---|---|---|
| 72 | 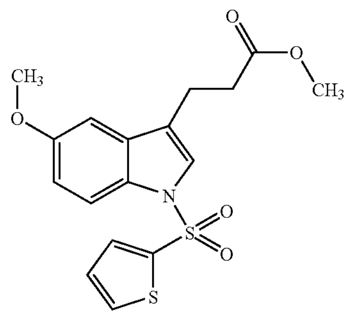 | 379.4 | 3-[5-Methoxy-1-(thiophene-2-sulfonyl)-1H-indol-3-yl]-propionic acid methyl ester |
| 73 | 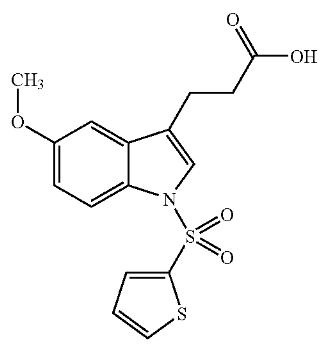 | 365.4 | 3-[5-Methoxy-1-(thiophene-2-sulfonyl)-1H-indol-3-yl]-propionic acid |
| 74 | 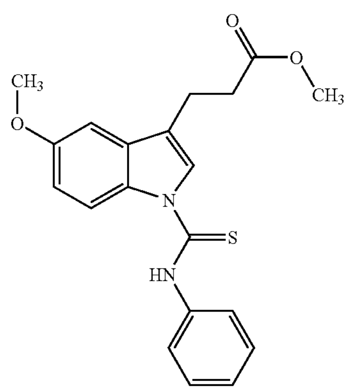 | 368.4 | 3-(5-Methoxy-1-phenylthiocarbamoyl-1H-indol-3-yl)-propionic acid methyl ester |
| 75 | 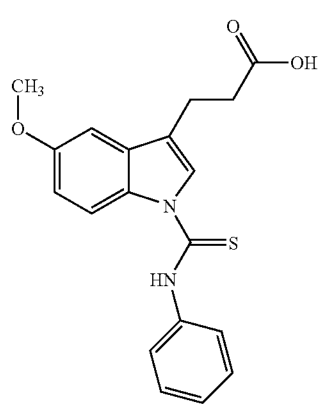 | 354.4 | 3-(5-Methoxy-1-phenylthiocarbamoyl-1H-indol-3-yl)-propionic acid |

TABLE 1-continued

| Number | Structure | M. Wt | IUPAC name |
|---|---|---|---|
| 58 | 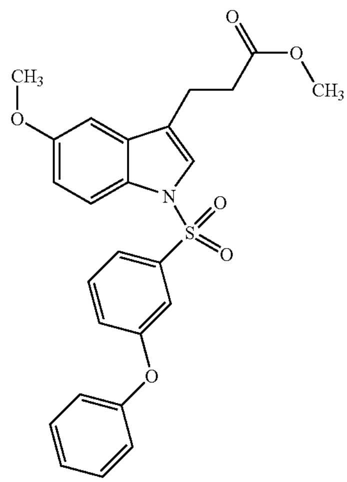 | 465.5 | 3-[5-Methoxy-1-(3-phenoxy-benzenesulfonyl)-1H-indol-3-yl]-propionic acid methyl ester |
| 60 | 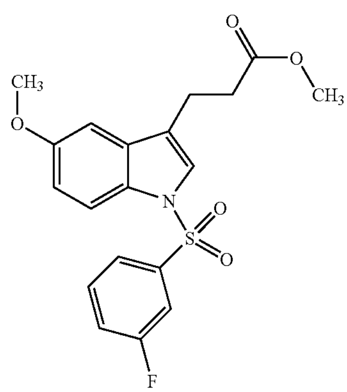 | 391.4 | 3-[1-(3-Fluoro-benzenesulfonyl)-5-methoxy-1H-indol-3-yl]-propionic acid methyl ester |
| 62 | 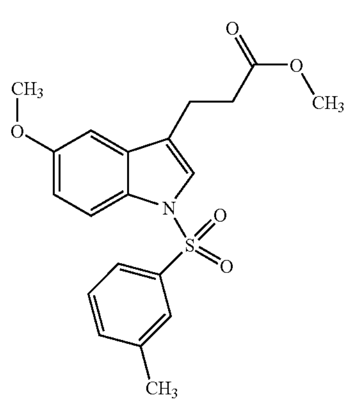 | 387.4 | 3-[5-Methoxy-1-(toluene-3-sulfonyl)-1H-indol-3-yl]-propionic acid methyl ester |

TABLE 1-continued

| Number | Structure | M. Wt | IUPAC name |
|---|---|---|---|
| 64 | 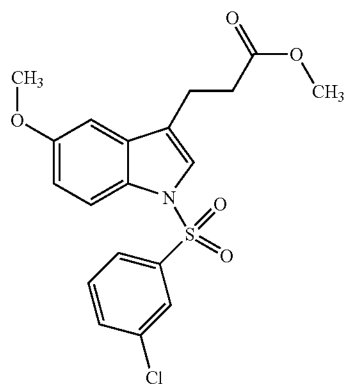 | 407.9 | 3-[1-(3-Chloro-benzenesulfonyl)-5-methoxy-1H-indol-3-yl]-propionic acid methyl ester |
| 66 | 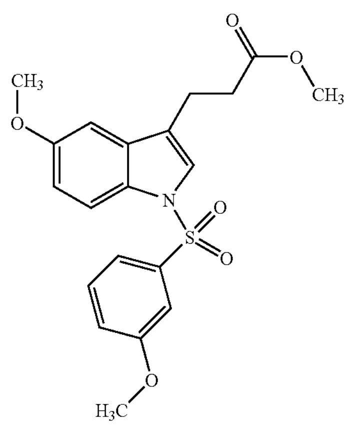 | 403.4 | 3-[5-Methoxy-1-(3-methoxy-benzenesulfonyl)-1H-indol-3-yl]-propionic acid methyl ester |
| 68 | 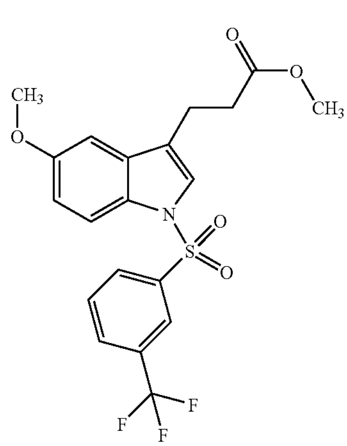 | 441.4 | 3-[5-Methoxy-1-(3-trifluoromethyl-benzenesulfonyl)-1H-indol-3-yl]-propionic acid methyl ester |

TABLE 1-continued

| Number | M. Wt | IUPAC name |
|---|---|---|
| 51 | 384.4 | 3-[1-(4-Cyano-benzenesulfonyl)-5-methoxy-1H-indol-3-yl]-propionic acid |
| 53 | 428.3 | 3-[1-(3,4-Dichloro-benzenesulfonyl)-5-methoxy-1H-indol-3-yl]-propionic acid |
| 1 | 389.4 | 3-[5-Methoxy-1-(4-methoxy-benzenesulfonyl)-1H-indol-3-yl]-propionic acid |
| 55 | 427.4 | 3-[5-Methoxy-1-(4-trifluoromethyl-benzenesulfonyl)-1H-indol-3-yl]-propionic acid |

TABLE 1-continued

| Number | Structure | M. Wt | IUPAC name |
|---|---|---|---|
| 57 | 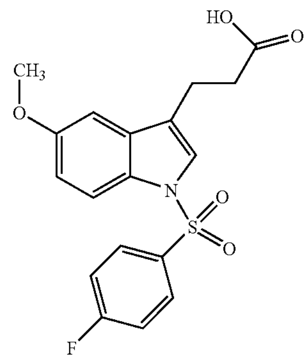 | 377.4 | 3-[1-(4-Fluoro-benzenesulfonyl)-5-methoxy-1H-indol-3-yl]-propionic acid |
| 98 | 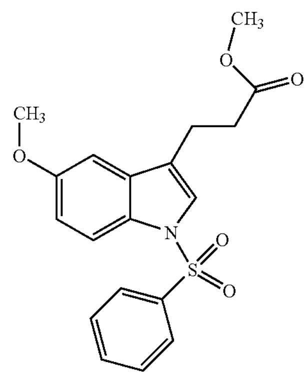 | 373.4 | 3-(1-Benzenesulfonyl-5-methoxy-1H-indol-3-yl)-propionic acid methyl ester |
| 71 | 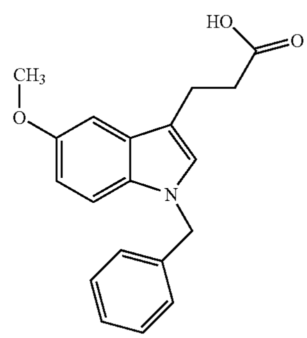 | 309.4 | 3-(1-Benzyl-5-methoxy-1H-indol-3-yl)-propionic acid |
| 70 | 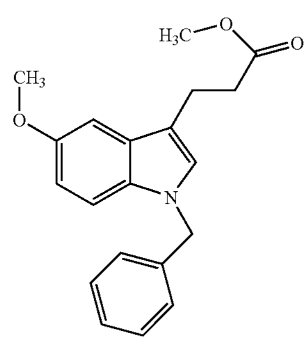 | 323.4 | 3-(1-Benzyl-5-methoxy-1H-indol-3-yl)-propionic acid methyl ester |

TABLE 1-continued

| Number | Structure | M. Wt | IUPAC name |
|---|---|---|---|
| 59 | 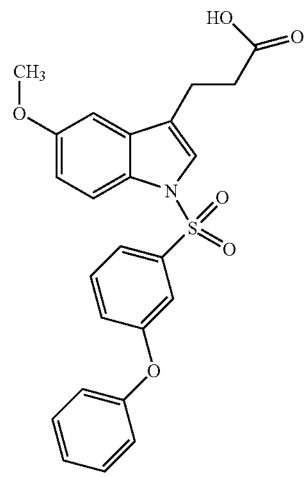 | 451.5 | 3-[5-Methoxy-1-(3-phenoxy-benzenesulfonyl)-1H-indol-3-yl]-propionic acid |
| 61 | 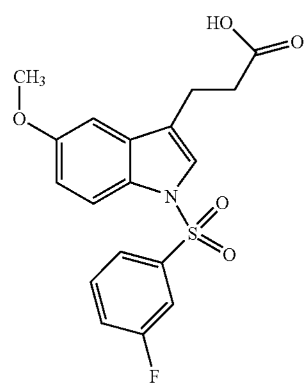 | 377.4 | 3-[1-(3-Fluoro-benzenesulfonyl)-5-methoxy-1H-indol-3-yl]-propionic acid |
| 63 | 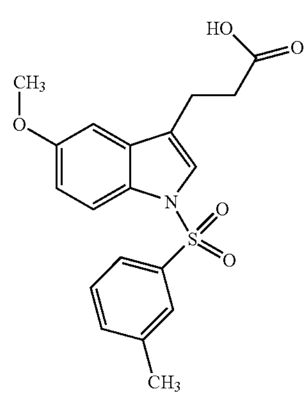 | 373.4 | 3-[5-Methoxy-1-(toluene-3-sulfonyl)-1H-indol-3-yl]-propionic acid |

TABLE 1-continued

| Number | Structure | M. Wt | IUPAC name |
|---|---|---|---|
| 65 | 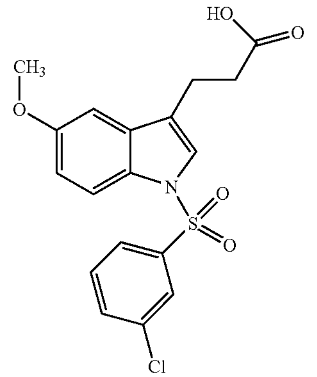 | 393.8 | 3-[1-(3-Chloro-benzenesulfonyl)-5-methoxy-1H-indol-3-yl]-propionic acid |
| 67 | 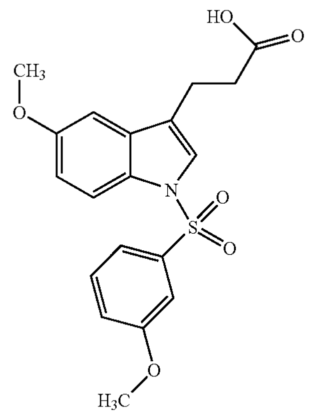 | 389.4 | 3-[5-Methoxy-1-(3-methoxy-benzenesulfonyl)-1H-indol-3-yl]-propionic acid |
| 69 | 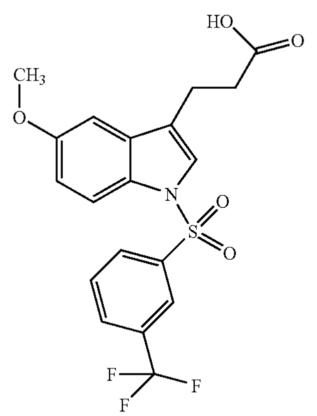 | 427.4 | 3-[5-Methoxy-1-(3-trifluoromethyl-benzenesulfonyl)-1H-indol-3-yl]-propionic acid |
| 90 | 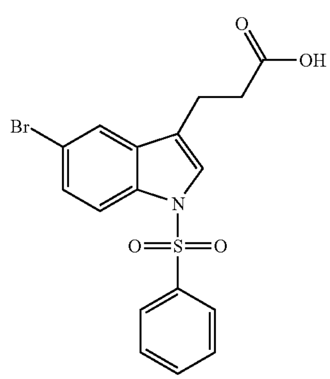 | 408.3 | 3-(1-Benzenesulfonyl-5-bromo-1H-indol-3-yl)-propionic acid |

TABLE 1-continued

| Number | Structure | M. Wt | IUPAC name |
|---|---|---|---|
| 79 | 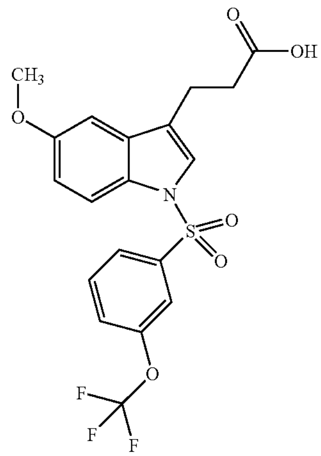 | 443.4 | 3-[5-Methoxy-1-(3-trifluoromethoxy-benzenesulfonyl)-1H-indol-3-yl]-propionic acid |
| 78 | 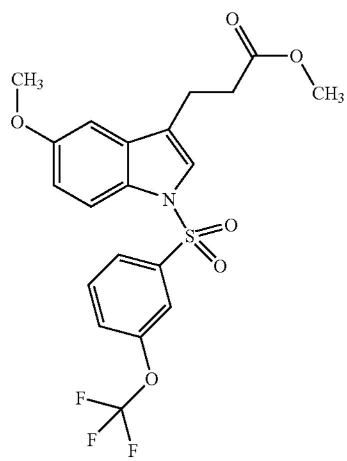 | 457.4 | 3-[5-Methoxy-1-(3-trifluoromethoxy-benzenesulfonyl)-1H-indol-3-yl]-propionic acid methyl ester |
| 77 | 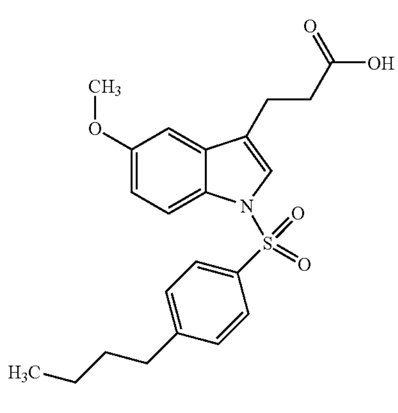 | 415.5 | 3-[1-(4-Butyl-benzenesulfonyl)-5-methoxy-1H-indol-3-yl]-propionic acid |

TABLE 1-continued

| Number | Structure | M. Wt | IUPAC name |
|---|---|---|---|
| 76 | 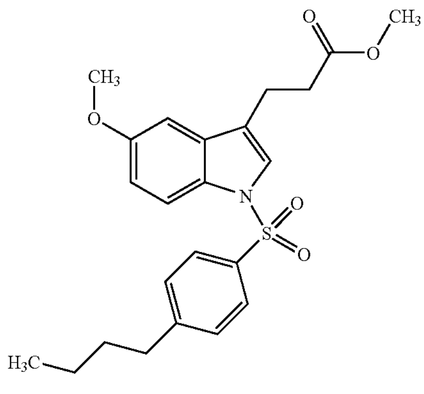 | 429.5 | 3-[1-(4-Butyl-benzenesulfonyl)-5-methoxy-1H-indol-3-yl]-propionic acid methyl ester |
| 91 | 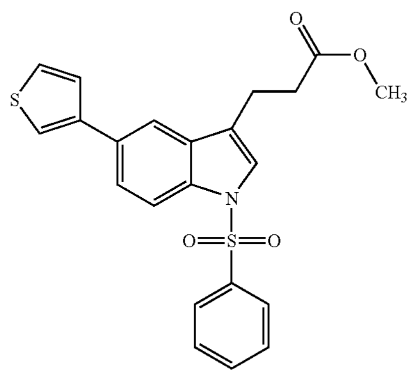 | 425.5 | 3-(1-Benzenesulfonyl-5-thiophen-3-yl-1H-indol-3-yl)-propionic acid methyl ester |
| 93 | 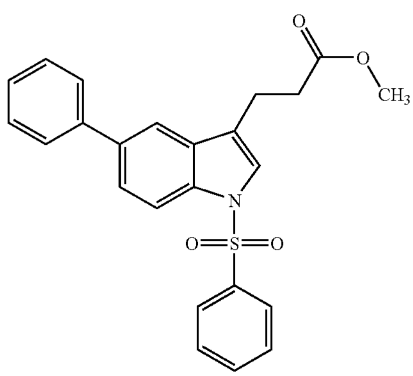 | 419.5 | 3-(1-Benzenesulfonyl-5-phenyl-1H-indol-3-yl)-propionic acid methyl ester |
| 80 | 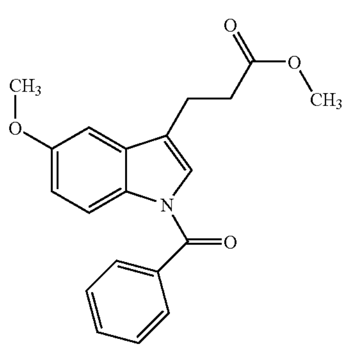 | 337.4 | 3-(1-Benzoyl-5-methoxy-1H-indol-3-yl)-propionic acid methyl ester |

TABLE 1-continued

| Number | Structure | M. Wt | IUPAC name |
|---|---|---|---|
| 81 | 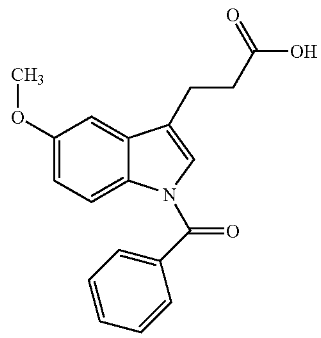 | 323.3 | 3-(1-Benzoyl-5-methoxy-1H-indol-3-yl)-propionic acid |
| 92 | 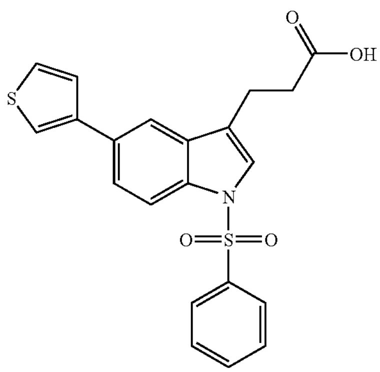 | 411.5 | 3-(1-Benzenesulfonyl-5-thiophen-3-yl-1H-indol-3-yl)-propionic acid |
| 94 | 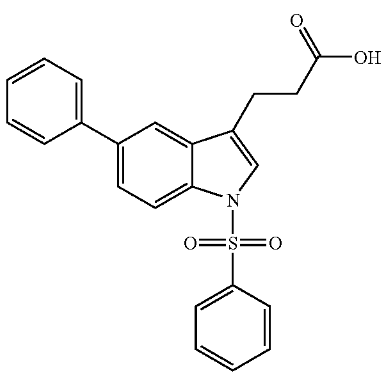 | 405.5 | 3-(1-Benzenesulfonyl-5-phenyl-1H-indol-3-yl)-propionic acid |
| 82 | 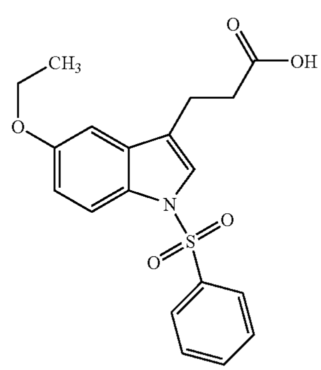 | 373.4 | 3-(1-Benzenesulfonyl-5-ethoxy-1H-indol-3-yl)-propionic acid |

TABLE 1-continued

| Number | Structure | M. Wt | IUPAC name |
| --- | --- | --- | --- |
| 83 | 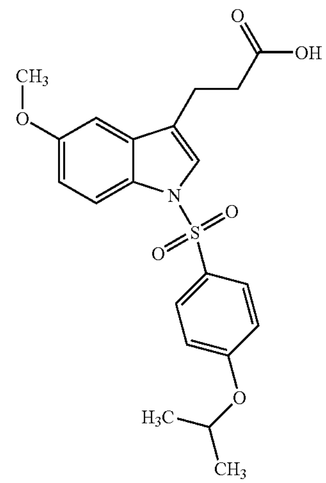 | 417.5 | 3-[1-(4-Isopropoxy-benzenesulfonyl)-5-methoxy-1H-indol-3-yl]-propionic acid |
| 84 | 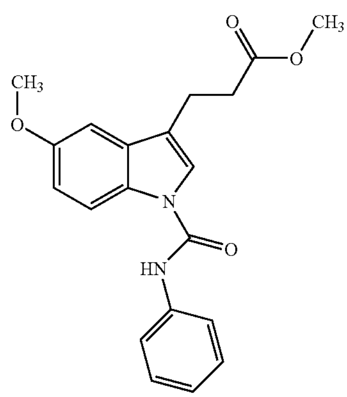 | 352.4 | 3-(5-Methoxy-1-phenylcarbamoyl-1H-indol-3-yl)-propionic acid methyl ester |
| 86 | 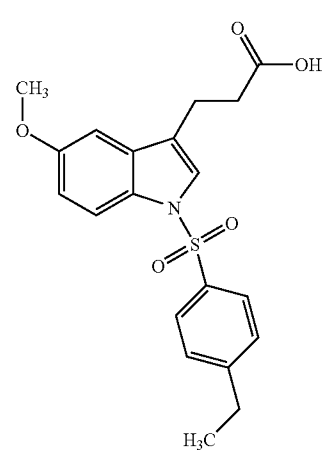 | 387.5 | 3-[1-(4-Ethyl-benzenesulfonyl)-5-methoxy-1H-indol-3-yl]-propionic acid |

TABLE 1-continued

| Number | Structure | M. Wt | IUPAC name |
|---|---|---|---|
| 85 | 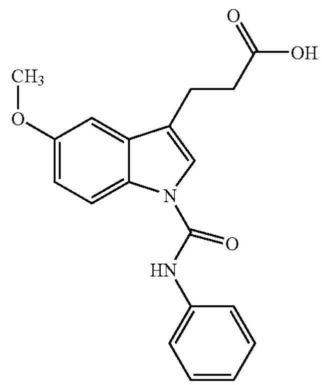 | 338.4 | 3-(5-Methoxy-1-phenylcarbamoyl-1H-indol-3-yl)-propionic acid |
| 6 | 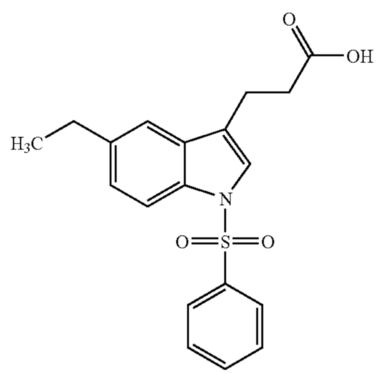 | 357.4 | 3-(1-Benzenesulfonyl-5-ethyl-1H-indol-3-yl)-propionic acid |
| 22 | 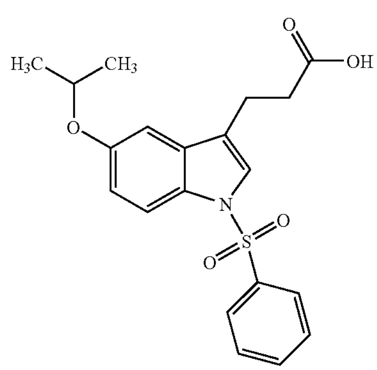 | 387.5 | 3-(1-Benzenesulfonyl-5-isopropoxy-1H-indol-3-yl)-propionic acid |
| 99 | 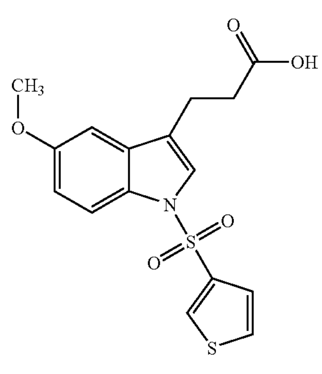 | 365.4 | 3-[5-Methoxy-1-(thiophene-3-sulfonyl)-1H-indol-3-yl]-propionic acid |

TABLE 1-continued

| Number | Structure | M. Wt | IUPAC name |
|---|---|---|---|
| 16 | 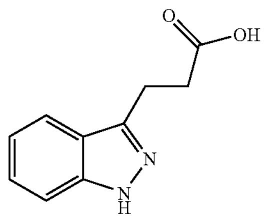 | 190.2 | Indazole-3-propionic acid |
| 39 | 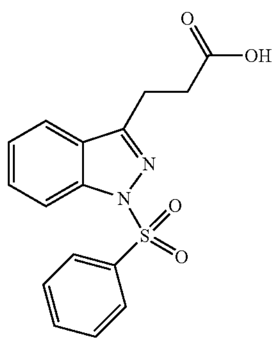 | 330.4 | 3-(1-Benzenesulfonyl-1H-indazol-3-yl)-propionic acid |
| 95 | 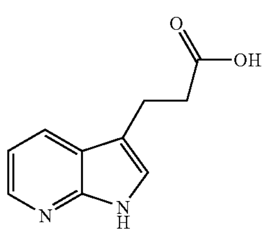 | 190.2 | 3-(1H-Pyrrolo[2,3-b]pyridin-3-yl)-propionic acid |
| 101 | 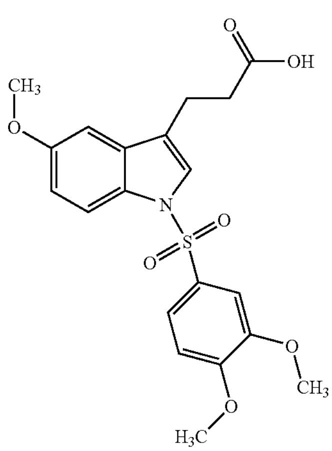 | 419.5 | 3-[1-(3,4-Dimethoxy-benzenesulfonyl)-5-methoxy-1H-indol-3-yl]-propionic acid |

TABLE 1-continued

| Number | Structure | M. Wt | IUPAC name |
|---|---|---|---|
| 102 | 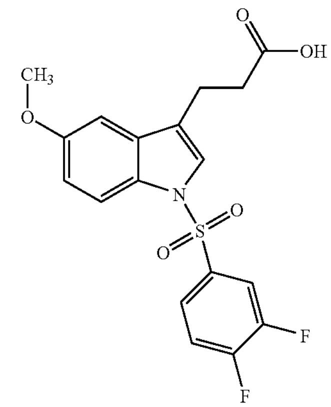 | 396.4 | 3-[1-(3,4-Difluoro-benzenesulfonyl)-5-methoxy-1H-indol-3-yl]-propionic acid |
| 103 | 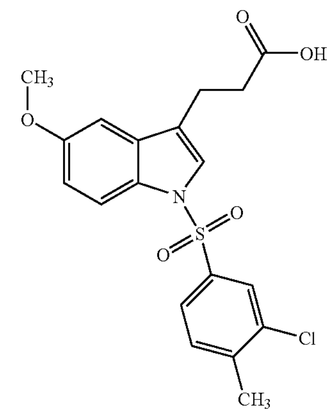 | 407.8 | 3-[1-(3-chloro-4-methyl-benzenesulfonyl)-5-methoxy-1H-indol-3-yl]-propionic acid |
| 104 | 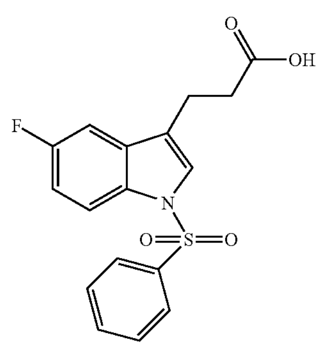 | 347.5 | 3-[1-(benzenesulfonyl)-5-fluoro-1H-indol-3-yl]-propionic acid |
| 105 | 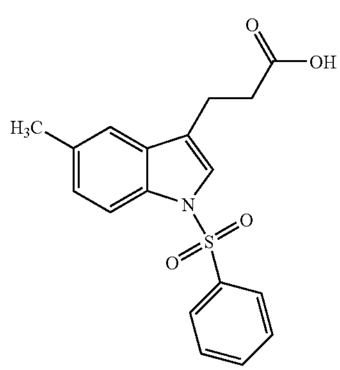 | 323.2 | 3-[1-(benzenesulfonyl)-5-methyl-1H-indol-3-yl]-propionic acid |

TABLE 1-continued

| Number | Structure | M. Wt | IUPAC name |
|---|---|---|---|
| 106 | 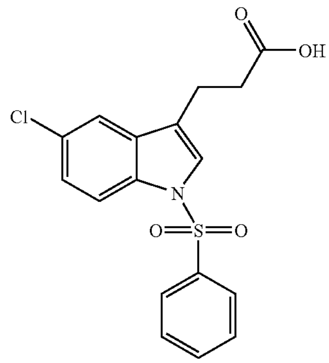 | 363.7 | 3-[1-(benzenesulfonyl)-5-chloro-1H-indol-3-yl]-propionic acid |
| 107 | 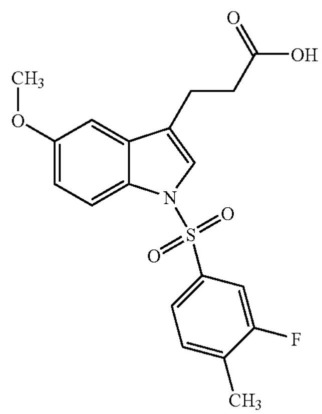 | 391.3 | 3-[1-(3-fluoro-4-methyl-benzenesulfonyl)-5-methoxy-1H-indol-3-yl]-propionic acid |
| 108 | 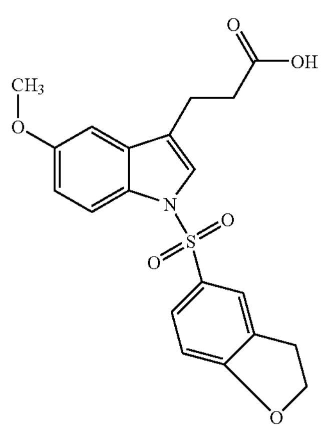 | 401.2 | 3-[1-(2,3-Dihydro-benzofuran-5-sulfonyl)-5-methoxy-1H-indol-3-yl]-propionic acid |

TABLE 1-continued

| Number | Structure | M. Wt | IUPAC name |
|---|---|---|---|
| 109 | 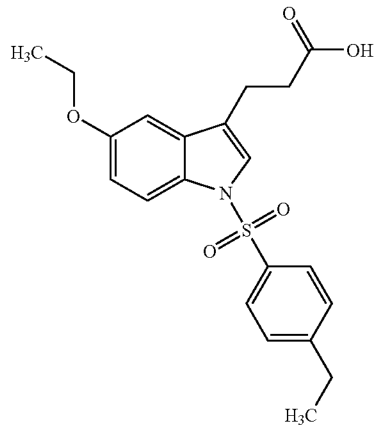 | 401.5 | 3-[1-(4-ethyl-benzenesulfonyl)-5-ethoxy-1 H-indol-3-yl]-propionic acid |
| 110 | 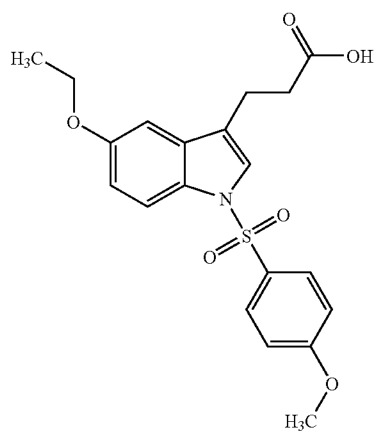 | 403.6 | 3-[1-(4-methoxy-benzenesulfonyl)-5-ethoxy-1H-indol-3-yl]-propionic acid |
| 111 | 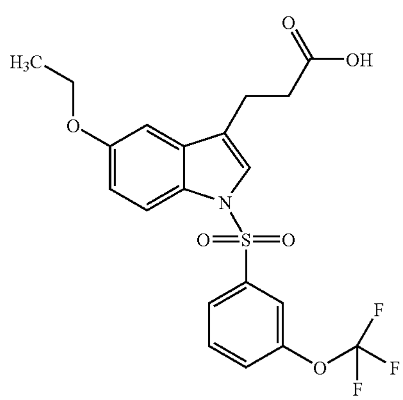 | | 3-[1-(3-trifluoromethoxy-benzenesulfonyl)-5-ethoxy-1H-indol-3-yl]-propionic acid |

TABLE 1-continued

| Number | Structure | M. Wt | IUPAC name |
|---|---|---|---|
| 112 | 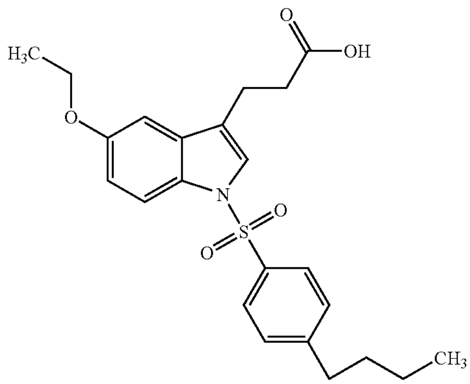 | 429.4 | 3-[1-(4-butyl-benzenesulfonyl)-5-ethoxy-1H-indol-3-yl]-propionic acid |
| 113 | 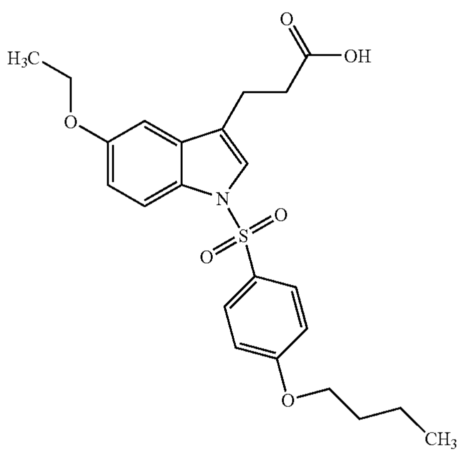 | 445.5 | 3-[1-(4-butoxy-benzenesulfonyl)-5-ethoxy-1H-indol-3-yl]-propionic acid |
| 114 | 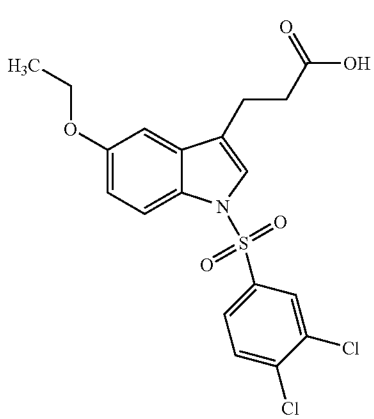 | 442.2 | 3-[1-(3,4-dichloro-benzenesulfonyl)-5-ethoxy-1H-indol-3-yl]-propionic acid |

TABLE 1-continued
| Number | Structure | M. Wt | IUPAC name |
|---|---|---|---|
| 115 | 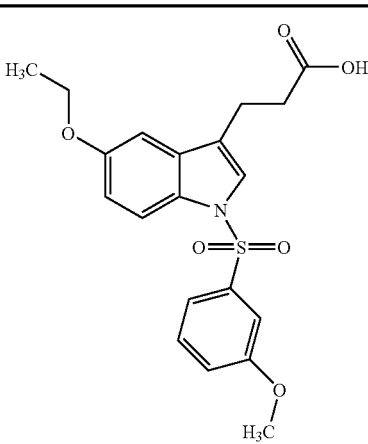 | 403.5 | 3-[1-(3-methoxy-benzenesulfonyl)-5-ethoxy-1H-indol-3-yl]-propionic acid |
| 116 | 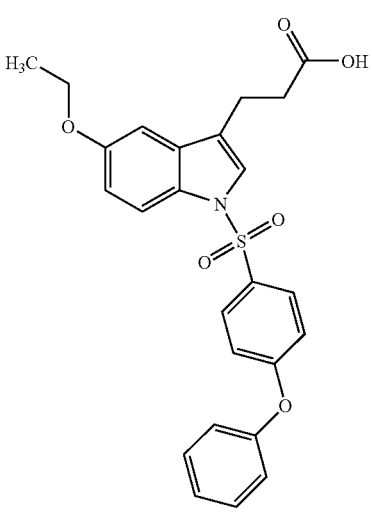 | 465.3 | 3-[1-(4-phenoxy-benzenesulfonyl)-5-ethoxy-1H-indol-3-yl]-propionic acid |
| 143 | 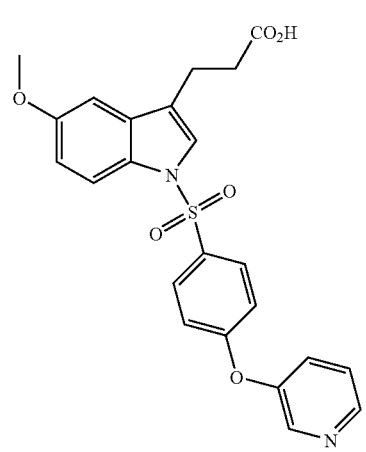 | 452.58 | 3-{5-Methoxy-1-[4-(pyridin-3-yloxy)-benzenesulfonyl]-1H-indol-3-yl}-propionic acid |

TABLE 1-continued

| Number | Structure | M. Wt | IUPAC name |
|---|---|---|---|
| 144 | 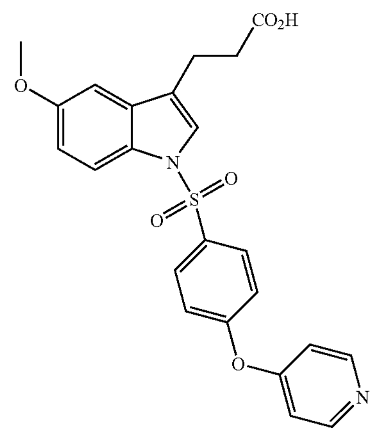 | 452.58 | 3-{5-Methoxy-1-[4-(pyridin-4-yloxy)-benzenesulfonyl]-1H-indol-3-yl}-propionic acid |
| 145 | 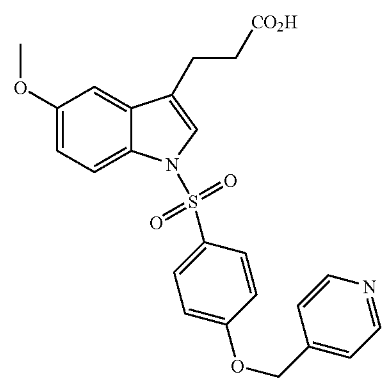 | 466.51 | 3-{5-Methoxy-1-[4-(pyridin-4-ylmethoxy)-benzenesulfonyl]-1H-indol-3-yl}-propionic acid |
| 146 | 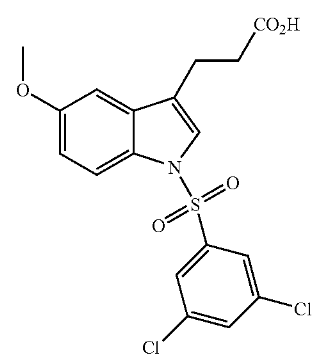 | 428.29 | 3-[1-(3,5-Dichloro-benzenesulfonyl)-5-methoxy-1H-indol-3-yl]-propionic acid |
| 147 | 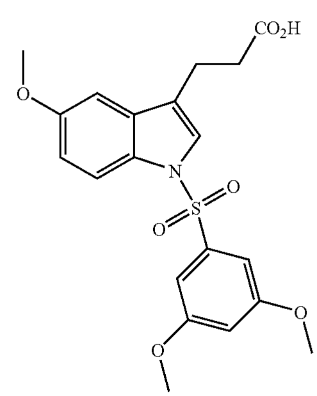 | 419.45 | 3-[1-(3,5-Dimethoxy-benzenesulfonyl)-5-methoxy-1H-indol-3-yl]-propionic acid |

TABLE 1-continued

| Number | Structure | M. Wt | IUPAC name |
|---|---|---|---|
| 148 | 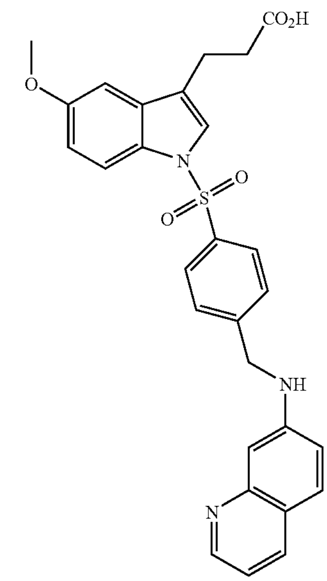 | 515.58 | 3-{5-Methoxy-1-[4-(quinolin-7-ylaminomethyl)-benzenesulfonyl]-1H-indol-3-yl}-propionic acid |
| 149 | 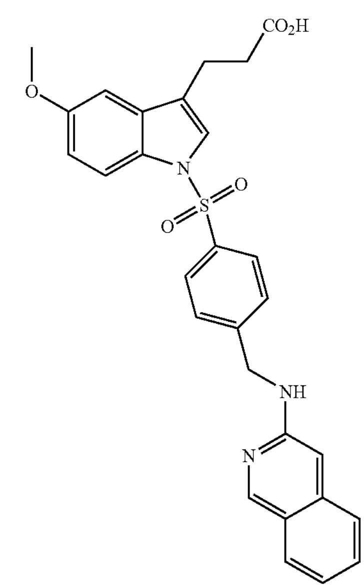 | 515.58 | 3-{1-[4-(Isoquinolin-3-ylaminomethyl)-benzenesulfonyl]-5-methoxy-1H-indol-3-yl}-propionic acid |

TABLE 1-continued

| Number | Structure | M. Wt | IUPAC name |
|---|---|---|---|
| 150 | 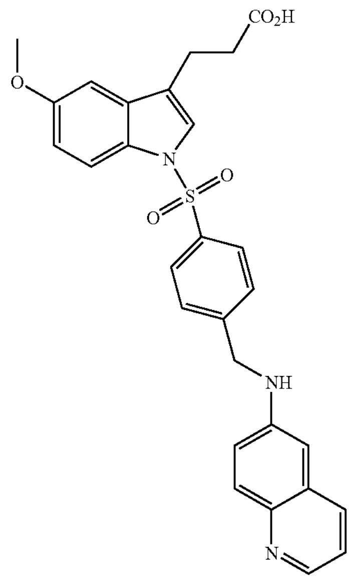 | 515.58 | 3-{5-Methoxy-1-[4-(quinolin-6-ylaminomethyl)-benzenesulfonyl]-1H-indol-3-yl}-propionic acid |
| 151 | 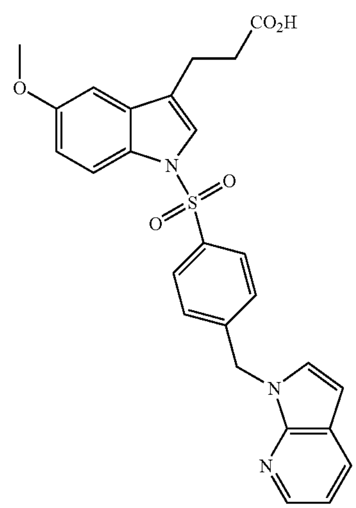 | 489.54 | 3-[5-Methoxy-1-(4-pyrrolo[2,3-b]pyridin-1-ylmethyl-benzenesulfonyl)-1H-indol-3-yl]-propionic acid |
| 152 | 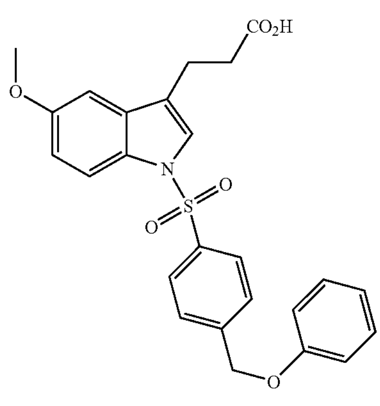 | 465.53 | 3-[5-Methoxy-1-(4-phenoxymethyl-benzenesulfonyl)-1H-indol-3-yl]propionic acid |

TABLE 1-continued

| Number | Structure | M. Wt | IUPAC name |
|---|---|---|---|
| 153 | 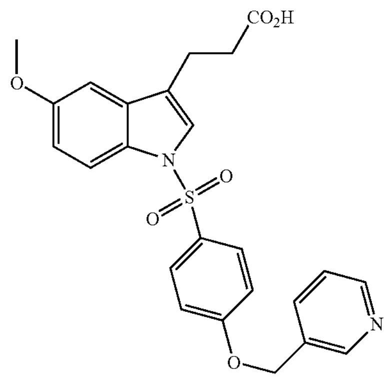 | 466.51 | 3-{5-Methoxy-1-[4-(pyridin-3-ylmethoxy)-benzenesulfonyl]-1H-indol-3-yl}-propionic acid |
| 154 | 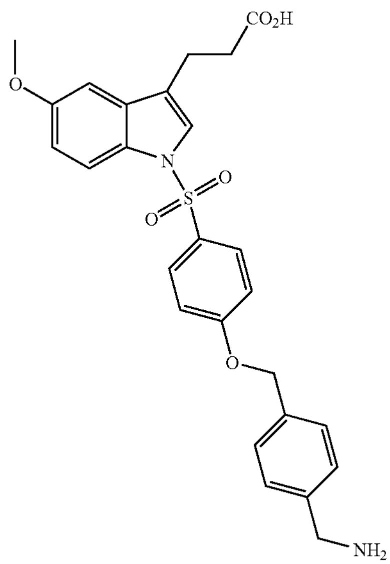 | 494.57 | 3-{1-[4-(4-Aminomethyl-benzyloxy)-benzenesulfonyl]-5-methoxy-1H-indol-3-yl}-propionic acid |
| 155 | 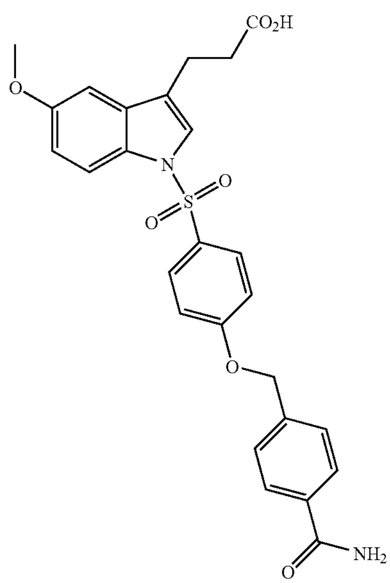 | 508.55 | 3-{1-[4-(4-Carbamoyl-benzyloxy)-benzenesulfonyl]-5-methoxy-1H-indol-3-yl}-propionic acid |

Agonist activities for exemplary compounds from Table 1 were determined, and are shown in Table 2, where "+" indicates activity $\leq 10$ μM, and "−" indicates >10 μM. These activities were determined as described in Example 1.

TABLE 2

| Compound # | PPARα agonist (μM) | PPARδ Agonist (μM) | PPARγ Agonist (μM) |
|---|---|---|---|
| 29 | + | + | + |
| 97 | − | − | − |
| 39 | − | − | − |
| 43 | + | + | + |
| 49 | + | + | + |
| 75 | − | − | − |
| 53 | + | + | + |
| 71 | + | − | − |

TABLE 2-continued

| Compound # | PPARα agonist (μM) | PPARδ Agonist (μM) | PPARγ Agonist (μM) |
|---|---|---|---|
| 79 | + | + | + |
| 77 | + | + | + |
| 81 | + | − | − |
| 92 | + | − | + |
| 82 | + | + | + |
| 85 | − | − | − |
| 6 | − | − | + |

TABLE 3

| MOLSTRUCTURE | molecular weight | MOLNAME |
|---|---|---|
|  | 251.284 | 5-BENZYLOXYINDOLE-3-CARBOXALDEHYDE |
|  | 159.187 | 4-METHYLINDOLE-3-ALDEHYDE |
|  | 159.187 | 6-METHYLINDOLE-3-CARBOXALDEHYDE |
|  | 251.284 | 7-BENZYLOXYINDOLE-3-CARBOXALDEHYDE |
|  | 251.284 | 6-BENZYLOXYINDOLE-3-CARBOXALDEHYDE |
|  | 179.605 | 2-CHLORO-1H-INDOLE-3-CARBALDEHYDE |

TABLE 3-continued

| MOLSTRUCTURE | molecular weight | MOLNAME |
| --- | --- | --- |
| | 251.284 | 4-BENZYLOXYINDOLE-3-CARBOXALDEHYDE |
| | 203.196 | 3-FORMYLINDOLE-5-CARBOXYLIC ACID METHYL ESTER |
| | 203.196 | METHYL 3-FORMYLINDOLE-6-CARBOXYLATE |
| | 204.184 | 3-FORMYL-2-METHYL-5-NITROINDOLE |
| | 189.169 | 3-FORMYL-1H-INDOLE-7-CARBOXYLIC ACID |
| | 231.25 | TIMTEC-BB ST002282 |
| | 190.157 | 7-NITROINDOLE-2-CARBOXALDEHYDE |

TABLE 3-continued

| MOLSTRUCTURE | molecular weight | MOLNAME |
|---|---|---|
| | 190.157 | 5-NITROINDOLE-3-CARBOXALDEHYDE |
| | 170.17 | 5-CYANOINDOLE-3-ALDEHYDE |
| | 249.268 | 6-BENZOYL-1H-1NDOLE-3-CARBOXALDEHYDE |
| | 249.268 | 5-BENZOYL-1H-1NDOLE-3-CARBOXALDEHYDE |
| | 173.214 | 7-ETHYL-1H-INDOLE-3-CARBOXALDEHYDE |
| | 196.636 | 5-AMINO-1H-INDOLE-3-CARBOXALDEHYDE HYDROCHLORIDE |
| | 207.252 | 5-METHYLSULPHINYLINDOLE-3-CARBOXALDEHYDE |
| | 163.15 | 7-FLUOROINDOLE-3-CARBOXALDEHYDE |

TABLE 3-continued
| MOLSTRUCTURE | molecular weight | MOLNAME |
|---|---|---|
| 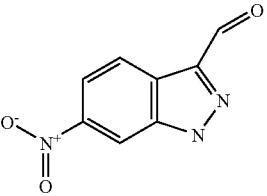 | 191.145 | 6-NITRO-1H-INDAZOLE-3-CARBALDEHYDE |
| 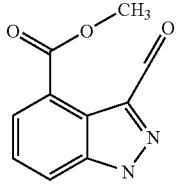 | 204.184 | METHYL-3-AL-4-INDAZOLE CARBOXYLATE |
| 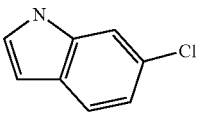 | 151.595 | 6-CHLOROINDOLE |
| 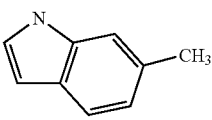 | 131.177 | 6-METHYLINDOLE |
| 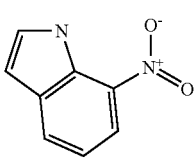 | 162.147 | 7-NITROINDOLE |
| 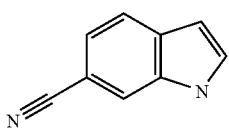 | 142.16 | 6-CYANOINDOLE |
| 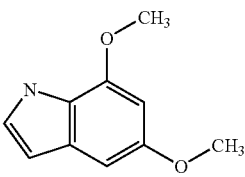 | 177.202 | 5,7-DIMETHOXY INDOLE |
| 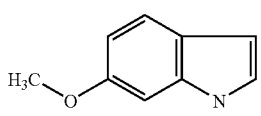 | 147.176 | 6-METHOXYINDOLE |
| 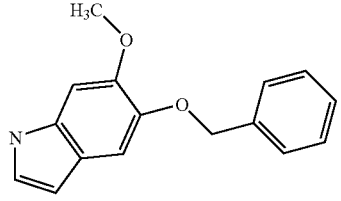 | 253.299 | 5-BENZYLOXY-6-METHOXYINDOLE |

TABLE 3-continued

| MOLSTRUCTURE | molecular weight | MOLNAME |
| --- | --- | --- |
| | 147.176 | 7-METHOXYINDOLE |
| | 162.147 | 6-NITROINDOLE |
| | 145.204 | 7-ETHYLINDOLE |
| | 163.175 | 5-HYDROXY-6-METHOXYINDOLE |
| | 175.186 | METHYL INDOLE-5-CARBOXYLATE |
| | 175.186 | METHYL INDOLE-6-CARBOXYLATE |
| | 175.186 | METHYL INDOLE-7-CARBOXYLATE |
| | 273.334 | N-(4-MORPHOLINOETHYL)INDOLE-6-CARBOXAMIDE |
| | 204.228 | N-METHOXY-N-METHYL-INDOLE-6-CARBOXAMIDE |

TABLE 3-continued
| MOLSTRUCTURE | molecular weight | MOLNAME |
|---|---|---|
| 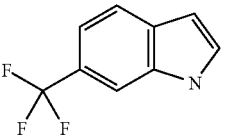 | | |
| 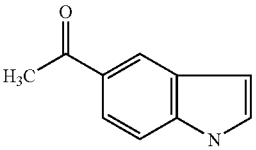 | 159.187 | 5-ACETYLINDOLE |
| 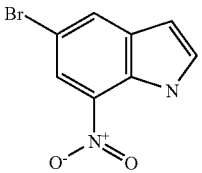 | 241.044 | 5-BROMO-7-NITROINDOLE |
|  | 196.046 | 7-BROMOINDOLE |
| 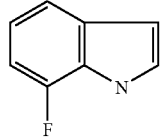 | 135.14 | 7-FLUOROINDOLE |
| 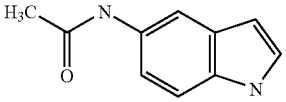 | 174.202 | 5-ACETAMIDOINDOLE |
| 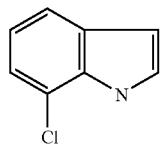 | 151.595 | 7-CHLOROINDOLE |
| 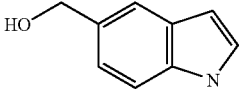 | 147.176 | INDOLE-5-METHANOL |
| 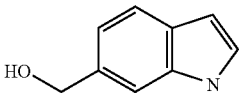 | 147.176 | INDOLE-6-METHANOL |
| 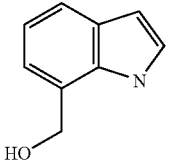 | 147.176 | INDOLE-7-METHANOL |

TABLE 3-continued

| MOLSTRUCTURE | molecular weight | MOLNAME |
|---|---|---|
| | 179.242 | 5-METHYLSULPHINYLINDOLE |
| | 179.242 | 6-METHYLSULPHINYLINDOLE |
| | 185.147 | 5-(TRIFLUOROMETHYL)INDOLE |
| | 191.257 | N-(1H-INDOL-6-YL)THIOUREA |
| | 226.072 | 7-BROMO-5-METHOXYINDOLE |
| | 195.241 | 6-(METHYLSULFONYL)-1H-INDOLE |
| | 163.135 | 5-NITROINDAZOLE |
| | 163.135 | 6-NITROINDAZOLE |
| | 163.135 | 7-NITROINDAZOLE |
| | 183.213 | ACB-BLOCKS PYR-0331 |

TABLE 3-continued

| MOLSTRUCTURE | molecular weight | MOLNAME |
| --- | --- | --- |
| | 183.213 | ACB-BLOCKS PYR-0332 |
| | 206.272 | N-(6-METHYL-1H-INDAZOL-5-YL)THIOUREA |
| | 192.245 | N-(1H-INDAZOL-7-YL)THIOUREA |
| | 192.245 | N-(1H-INDAZOL-6-YL)THIOUREA |
| | 197.035 | 6-BROMOINDAZOLE |
| | 190.201 | ETHYL 1H-INDAZOLE-5-CARBOXYLATE |
| | 211.061 | CBI-BB ZER0/005553 |
| | 148.164 | 5-HYDROXYMETHYL-1H-INDAZOLE |

Additional exemplary compounds of Formula I are described in Table 4. Table 4 describes exemplary compounds by specifying substituents for each of the bicyclic cores shown in the Summary herein, except that substituents on a nitrogen (N) in the 6-membered ring are excluded, and the 6-membered ring includes at least one alkoxy or thioether substituent at the 5- or 6-position. Thus, for example, for a bicyclic core that includes a N at the 5-position, only those substitutent combinations that do not have a substituent at the 5-position and have an alkoxy or thioether at the 6-position apply to that bicylic core. Where no substituent is specified for a ring position, it is to be understood that there is no substituent if the ring atom at that position is a N, and as H if the ring atom at that position is a carbon (C). All compounds include a —CH$_2$CH$_2$— linker at the 3-position; the specification of the 3-substituent in Table 4 is thus the moiety attached to that linker.

The numbering of the ring atoms as referenced herein, including in Table 4, is shown in the following structure. This structure includes the indolyl ring structure, but as used

TABLE 4

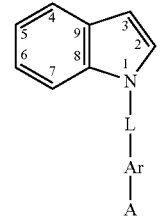

| L¹ | Ar | A | 3 | 5 | 6 |
|---|---|---|---|---|---|
| SO₂ | phenyl |  | COOH | methoxy |  |
| SO₂ | phenyl | CF₃ | COOH | methoxy |  |
| SO₂ | phenyl | CH₂CF₃ | COOH | methoxy |  |
| SO₂ | phenyl | Halo substituted alkyl | COOH | methoxy |  |
| SO₂ | phenyl | OCH₃ | COOH | methoxy |  |
| SO₂ | phenyl | OCH₂CH₃ | COOH | methoxy |  |
| SO₂ | phenyl | OCH₂CH₂CH₃ | COOH | methoxy |  |
| SO₂ | phenyl | OCH₂CH₂CH₂CH₃ | COOH | methoxy |  |
| SO₂ | phenyl | OCH₂CH₂CH₂CH₂CH₃ | COOH | methoxy |  |
| SO₂ | phenyl | C5-C8 alkoxy | COOH | methoxy |  |
| SO₂ | phenyl | Halo substituted alkoxy | COOH | methoxy |  |
| SO₂ | phenyl | CH₃ | COOH | methoxy |  |
| SO₂ | phenyl | CH₂CH₃ | COOH | methoxy |  |
| SO₂ | phenyl | CH₂CH₂CH₃ | COOH | methoxy |  |
| SO₂ | phenyl | CH₂CH₂CH₂CH₃ | COOH | methoxy |  |
| SO₂ | phenyl | C5-C8 alkyl | COOH | methoxy |  |
| SO₂ | phenyl | F | COOH | methoxy |  |
| SO₂ | phenyl | F, F | COOH | methoxy |  |
| SO₂ | phenyl | F, Cl | COOH | methoxy |  |
| SO₂ | phenyl | Cl | COOH | methoxy |  |
| SO₂ | phenyl | Cl, Cl | COOH | methoxy |  |
| SO₂ | phenyl | -(1 to 4 linearly linked atom linker)-optionally subst. aryl | COOH | methoxy |  |
| SO₂ | phenyl | -(1 to 4 linearly linked atom linker)-optionally subst. heteroaryl | COOH | methoxy |  |
| SO₂ | pyridinyl |  | COOH | methoxy |  |
| SO₂ | Pyridinyl | CF₃ | COOH | methoxy |  |
| SO₂ | Pyridinyl | CH₂CF₃ | COOH | methoxy |  |
| SO₂ | Pyridinyl | Halo substituted alkyl | COOH | methoxy |  |
| SO₂ | Pyridinyl | OCH₃ | COOH | methoxy |  |
| SO₂ | Pyridinyl | OCH₂CH₃ | COOH | methoxy |  |
| SO₂ | Pyridinyl | OCH₂CH₂CH₃ | COOH | methoxy |  |
| SO₂ | Pyridinyl | OCH₂CH₂CH₂CH₃ | COOH | methoxy |  |
| SO₂ | Pyridinyl | OCH₂CH₂CH₂CH₂CH₃ | COOH | methoxy |  |
| SO₂ | Pyridinyl | C5-C8 alkoxy | COOH | methoxy |  |
| SO₂ | Pyridinyl | Halo substituted alkoxy | COOH | methoxy |  |
| SO₂ | Pyridinyl | CH₃ | COOH | methoxy |  |
| SO₂ | Pyridinyl | CH₂CH₃ | COOH | methoxy |  |
| SO₂ | Pyridinyl | CH₂CH₂CH₃ | COOH | methoxy |  |
| SO₂ | Pyridinyl | CH₂CH₂CH₂CH₃ | COOH | methoxy |  |
| SO₂ | Pyridinyl | C5-C8 alkyl | COOH | methoxy |  |
| SO₂ | Pyridinyl | F | COOH | methoxy |  |
| SO₂ | Pyridinyl | F, F | COOH | methoxy |  |
| SO₂ | Pyridinyl | F, Cl | COOH | methoxy |  |
| SO₂ | Pyridinyl | Cl | COOH | methoxy |  |
| SO₂ | Pyridinyl | Cl, Cl | COOH | methoxy |  |
| SO₂ | Pyridinyl | -(1 to 4 linearly linked atom linker)-optionally subst. aryl | COOH | methoxy |  |
| SO₂ | Pyridinyl | -(1 to 4 linearly linked atom linker)-optionally subst. heteroaryl | COOH | methoxy |  |
| CO | Phenyl |  | COOH | methoxy |  |
| CO | Phenyl | CF₃ | COOH | methoxy |  |
| CO | Phenyl | CH₂CF₃ | COOH | methoxy |  |
| CO | Phenyl | Halo substituted alkyl | COOH | methoxy |  |
| CO | Phenyl | OCH₃ | COOH | methoxy |  |

TABLE 4-continued

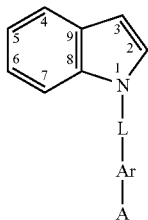

| L¹ | Ar | A | 3 | 5 | 6 |
|---|---|---|---|---|---|
| CO | Phenyl | OCH₂CH₃ | COOH | methoxy | |
| CO | Phenyl | OCH₂CH₂CH₃ | COOH | methoxy | |
| CO | Phenyl | OCH₂CH₂CH₂CH₃ | COOH | methoxy | |
| CO | Phenyl | OCH₂CH₂CH₂CH₂CH₃ | COOH | methoxy | |
| CO | Phenyl | C5-C8 alkoxy | COOH | methoxy | |
| CO | Phenyl | Halo substituted alkoxy | COOH | methoxy | |
| CO | Phenyl | CH₃ | COOH | methoxy | |
| CO | Phenyl | CH₂CH₃ | COOH | methoxy | |
| CO | Phenyl | CH₂CH₂CH₃ | COOH | methoxy | |
| CO | Phenyl | CH₂CH₂CH₂CH₃ | COOH | methoxy | |
| CO | Phenyl | C5-C8 alkyl | COOH | methoxy | |
| CO | Phenyl | F | COOH | methoxy | |
| CO | Phenyl | F, F | COOH | methoxy | |
| CO | Phenyl | F, Cl | COOH | methoxy | |
| CO | Phenyl | Cl | COOH | methoxy | |
| CO | Phenyl | Cl, Cl | COOH | methoxy | |
| CO | Phenyl | -(1 to 4 linearly linked atom linker)-optionally subst. aryl | COOH | methoxy | |
| CO | Phenyl | -(1 to 4 linearly linked atom linker)-optionally subst. heteroaryl | COOH | methoxy | |
| CO | pyridinyl | | COOH | methoxy | |
| CO | Pyridinyl | CF₃ | COOH | methoxy | |
| CO | Pyridinyl | CH₂CF₃ | COOH | methoxy | |
| CO | Pyridinyl | Halo substituted alkyl | COOH | methoxy | |
| CO | Pyridinyl | OCH₃ | COOH | methoxy | |
| CO | Pyridinyl | OCH₂CH₃ | COOH | methoxy | |
| CO | Pyridinyl | OCH₂CH₂CH₃ | COOH | methoxy | |
| CO | Pyridinyl | OCH₂CH₂CH₂CH₃ | COOH | methoxy | |
| CO | Pyridinyl | OCH₂CH₂CH₂CH₂CH₃ | COOH | methoxy | |
| CO | Pyridinyl | C5-G8 alkoxy | COOH | methoxy | |
| CO | Pyridinyl | Halo substituted alkoxy | COOH | methoxy | |
| CO | Pyridinyl | CH₃ | COOH | methoxy | |
| CO | Pyridinyl | CH₂CH₃ | COOH | methoxy | |
| CO | Pyridinyl | CH₂CH₂CH₃ | COOH | methoxy | |
| CO | Pyridinyl | CH₂CH₂CH₂CH₃ | COOH | methoxy | |
| CO | Pyridinyl | C5-G8 alkyl | COOH | methoxy | |
| CO | Pyridinyl | F | COOH | methoxy | |
| CO | Pyridinyl | F, F | COOH | methoxy | |
| CO | Pyridinyl | F, Cl | COOH | methoxy | |
| CO | Pyridinyl | Cl | COOH | methoxy | |
| CO | Pyridinyl | Cl, Cl | COOH | methoxy | |
| CO | Pyridinyl | -(1 to 4 linearly linked atom linker)-optionally subst. aryl | COOH | methoxy | |
| CO | Pyridinyl | -(1 to 4 linearly linked atom linker)-optionally subst. heteroaryl | COOH | methoxy | |
| SO₂ | phenyl | | COOH | ethoxy | |
| SO₂ | phenyl | CF₃ | COOH | ethoxy | |
| SO₂ | phenyl | CH₂CF₃ | COOH | ethoxy | |
| SO₂ | phenyl | Halo substituted alkyl | COOH | ethoxy | |
| SO₂ | phenyl | OCH₃ | COOH | ethoxy | |
| SO₂ | phenyl | OCH₂CH₃ | COOH | ethoxy | |
| SO₂ | phenyl | OCH₂CH₂CH₃ | COOH | ethoxy | |
| SO₂ | phenyl | OCH₂CH₂CH₂CH₃ | COOH | ethoxy | |
| SO₂ | phenyl | OCH₂CH₂CH₂CH₂CH₃ | COOH | ethoxy | |
| SO₂ | phenyl | C5-C8 alkoxy | COOH | ethoxy | |
| SO₂ | phenyl | Halo substituted alkoxy | COOH | ethoxy | |
| SO₂ | phenyl | CH₃ | COOH | ethoxy | |
| SO₂ | phenyl | CH₂CH₃ | COOH | ethoxy | |
| SO₂ | phenyl | CH₂CH₂CH₃ | COOH | ethoxy | |

TABLE 4-continued

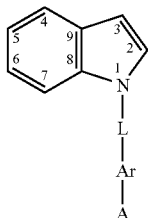

| $L^1$ | Ar | A | 3 | 5 | 6 |
|---|---|---|---|---|---|
| $SO_2$ | phenyl | $CH_2CH_2CH_2CH_3$ | COOH | ethoxy | |
| $SO_2$ | phenyl | C5-C8 alkyl | COOH | ethoxy | |
| $SO_2$ | phenyl | F | COOH | ethoxy | |
| $SO_2$ | phenyl | F, F | COOH | ethoxy | |
| $SO_2$ | phenyl | F, Cl | COOH | ethoxy | |
| $SO_2$ | phenyl | Cl | COOH | ethoxy | |
| $SO_2$ | phenyl | Cl, Cl | COOH | ethoxy | |
| $SO_2$ | phenyl | -(1 to 4 linearly linked atom linker)-optionally subst. aryl | COOH | ethoxy | |
| $SO_2$ | phenyl | -(1 to 4 linearly linked atom linker)-optionally subst. heteroaryl | COOH | ethoxy | |
| $SO_2$ | pyridinyl | | COOH | ethoxy | |
| $SO_2$ | Pyridinyl | $CF_3$ | COOH | ethoxy | |
| $SO_2$ | Pyridinyl | $CH_2CF_3$ | COOH | ethoxy | |
| $SO_2$ | Pyridinyl | Halo substituted alkyl | COOH | ethoxy | |
| $SO_2$ | Pyridinyl | $OCH_3$ | COOH | ethoxy | |
| $SO_2$ | Pyridinyl | $OCH_2CH_3$ | COOH | ethoxy | |
| $SO_2$ | Pyridinyl | $OCH_2CH_2CH_3$ | COOH | ethoxy | |
| $SO_2$ | Pyridinyl | $OCH_2CH_2CH_2CH_3$ | COOH | ethoxy | |
| $SO_2$ | Pyridinyl | $OCH_2CH_2CH_2CH_2CH_3$ | COOH | ethoxy | |
| $SO_2$ | Pyridinyl | C5-C8 alkoxy | COOH | ethoxy | |
| $SO_2$ | Pyridinyl | Halo substituted alkoxy | COOH | ethoxy | |
| $SO_2$ | Pyridinyl | $CH_3$ | COOH | ethoxy | |
| $SO_2$ | Pyridinyl | $CH_2CH_3$ | COOH | ethoxy | |
| $SO_2$ | Pyridinyl | $CH_2CH_2CH_3$ | COOH | ethoxy | |
| $SO_2$ | Pyridinyl | $CH_2CH_2CH_2CH_3$ | COOH | ethoxy | |
| $SO_2$ | Pyridinyl | C5-C8 alkyl | COOH | ethoxy | |
| $SO_2$ | Pyridinyl | F | COOH | ethoxy | |
| $SO_2$ | Pyridinyl | F, F | COOH | ethoxy | |
| $SO_2$ | Pyridinyl | F, Cl | COOH | ethoxy | |
| $SO_2$ | Pyridinyl | Cl | COOH | ethoxy | |
| $SO_2$ | Pyridinyl | Cl, Cl | COOH | ethoxy | |
| $SO_2$ | Pyridinyl | -(1 to 4 linearly linked atom linker)-optionally subst. aryl | COOH | ethoxy | |
| $SO_2$ | Pyridinyl | -(1 to 4 linearly linked atom linker)-optionally subst. heteroaryl | COOH | ethoxy | |
| CO | Phenyl | | COOH | ethoxy | |
| CO | Phenyl | $CF_3$ | COOH | ethoxy | |
| CO | Phenyl | $CH_2CF_3$ | COOH | ethoxy | |
| CO | Phenyl | Halo substituted alkyl | COOH | ethoxy | |
| CO | Phenyl | $OCH_3$ | COOH | ethoxy | |
| CO | Phenyl | $OCH_2CH_3$ | COOH | ethoxy | |
| CO | Phenyl | $OCH_2CH_2CH_3$ | COOH | ethoxy | |
| CO | Phenyl | $OCH_2CH_2CH_2CH_3$ | COOH | ethoxy | |
| CO | Phenyl | $OCH_2CH_2CH_2CH_2CH_3$ | COOH | ethoxy | |
| CO | Phenyl | C5-C8 alkoxy | COOH | ethoxy | |
| CO | Phenyl | Halo substituted alkoxy | COOH | ethoxy | |
| CO | Phenyl | $CH_3$ | COOH | ethoxy | |
| CO | Phenyl | $CH_2CH_3$ | COOH | ethoxy | |
| CO | Phenyl | $CH_2CH_2CH_3$ | COOH | ethoxy | |
| CO | Phenyl | $CH_2CH_2CH_2CH_3$ | COOH | ethoxy | |
| CO | Phenyl | C5-C8 alkyl | COOH | ethoxy | |
| CO | Phenyl | F | COOH | ethoxy | |
| CO | Phenyl | F, F | COOH | ethoxy | |
| CO | Phenyl | F, Cl | COOH | ethoxy | |
| CO | Phenyl | Cl | COOH | ethoxy | |
| CO | Phenyl | Cl, Cl | COOH | ethoxy | |

TABLE 4-continued

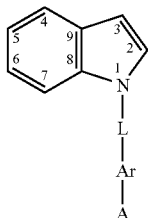

| L¹ | Ar | A | 3 | 5 | 6 |
|---|---|---|---|---|---|
| CO | Phenyl | -(1 to 4 linearly linked atom linker)-optionally subst. aryl | COOH | ethoxy | |
| CO | Phenyl | -(1 to 4 linearly linked atom linker)-optionally subst. heteroaryl | COOH | ethoxy | |
| CO | pyridinyl | | COOH | ethoxy | |
| CO | Pyridinyl | $CF_3$ | COOH | ethoxy | |
| CO | Pyridinyl | $CH_2CF_3$ | COOH | ethoxy | |
| CO | Pyridinyl | Halo substituted alkyl | COOH | ethoxy | |
| CO | Pyridinyl | $OCH_3$ | COOH | ethoxy | |
| CO | Pyridinyl | $OCH_2CH_3$ | COOH | ethoxy | |
| CO | Pyridinyl | $OCH_2CH_2CH_3$ | COOH | ethoxy | |
| CO | Pyridinyl | $OCH_2CH_2CH_2CH_3$ | COOH | ethoxy | |
| CO | Pyridinyl | $OCH_2CH_2CH_2CH_2CH_3$ | COOH | ethoxy | |
| CO | Pyridinyl | C5-G8 alkoxy | COOH | ethoxy | |
| CO | Pyridinyl | Halo substituted alkoxy | COOH | ethoxy | |
| CO | Pyridinyl | $CH_3$ | COOH | ethoxy | |
| CO | Pyridinyl | $CH_2CH_3$ | COOH | ethoxy | |
| CO | Pyridinyl | $CH_2CH_2CH_3$ | COOH | ethoxy | |
| CO | Pyridinyl | $CH_2CH_2CH_2CH_3$ | COOH | ethoxy | |
| CO | Pyridinyl | C5-G8 alkyl | COOH | ethoxy | |
| CO | Pyridinyl | F | COOH | ethoxy | |
| CO | Pyridinyl | F, F | COOH | ethoxy | |
| CO | Pyridinyl | F, Cl | COOH | ethoxy | |
| CO | Pyridinyl | Cl | COOH | ethoxy | |
| CO | Pyridinyl | Cl, Cl | COOH | ethoxy | |
| CO | Pyridinyl | -(1 to 4 linearly linked atom linker)-optionally subst. aryl | COOH | ethoxy | |
| CO | Pyridinyl | -(1 to 4 linearly linked atom linker)-optionally subst. heteroaryl | COOH | ethoxy | |
| $SO_2$ | phenyl | | COOH | propoxy | |
| $SO_2$ | phenyl | $CF_3$ | COOH | propoxy | |
| $SO_2$ | phenyl | $CH_2CF_3$ | COOH | propoxy | |
| $SO_2$ | phenyl | Halo substituted alkyl | COOH | propoxy | |
| $SO_2$ | phenyl | $OCH_3$ | COOH | propoxy | |
| $SO_2$ | phenyl | $OCH_2CH_3$ | COOH | propoxy | |
| $SO_2$ | phenyl | $OCH_2CH_2CH_3$ | COOH | propoxy | |
| $SO_2$ | phenyl | $OCH_2CH_2CH_2CH_3$ | COOH | propoxy | |
| $SO_2$ | phenyl | $OCH_2CH_2CH_2CH_2CH_3$ | COOH | propoxy | |
| $SO_2$ | phenyl | C5-C8 alkoxy | COOH | propoxy | |
| $SO_2$ | phenyl | Halo substituted alkoxy | COOH | propoxy | |
| $SO_2$ | phenyl | $CH_3$ | COOH | propoxy | |
| $SO_2$ | phenyl | $CH_2CH_3$ | COOH | propoxy | |
| $SO_2$ | phenyl | $CH_2CH_2CH_3$ | COOH | propoxy | |
| $SO_2$ | phenyl | $CH_2CH_2CH_2CH_3$ | COOH | propoxy | |
| $SO_2$ | phenyl | C5-C8 alkyl | COOH | propoxy | |
| $SO_2$ | phenyl | F | COOH | propoxy | |
| $SO_2$ | phenyl | F, F | COOH | propoxy | |
| $SO_2$ | phenyl | F, Cl | COOH | propoxy | |
| $SO_2$ | phenyl | Cl | COOH | propoxy | |
| $SO_2$ | phenyl | Cl, Cl | COOH | propoxy | |
| $SO_2$ | phenyl | -(1 to 4 linearly linked atom linker)-optionally subst. aryl | COOH | propoxy | |
| $SO_2$ | phenyl | -(1 to 4 linearly linked atom linker)-optionally subst. heteroaryl | COOH | propoxy | |
| $SO_2$ | pyridinyl | | COOH | propoxy | |
| $SO_2$ | Pyridinyl | $CF_3$ | COOH | propoxy | |
| $SO_2$ | Pyridinyl | $CH_2CF_3$ | COOH | propoxy | |

TABLE 4-continued

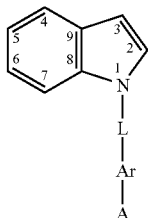

| $L^1$ | Ar | A | 3 | 5 | 6 |
|---|---|---|---|---|---|
| $SO_2$ | Pyridinyl | Halo substituted alkyl | COOH | propoxy | |
| $SO_2$ | Pyridinyl | $OCH_3$ | COOH | propoxy | |
| $SO_2$ | Pyridinyl | $OCH_2CH_3$ | COOH | propoxy | |
| $SO_2$ | Pyridinyl | $OCH_2CH_2CH_3$ | COOH | propoxy | |
| $SO_2$ | Pyridinyl | $OCH_2CH_2CH_2CH_3$ | COOH | propoxy | |
| $SO_2$ | Pyridinyl | $OCH_2CH_2CH_2CH_2CH_3$ | COOH | propoxy | |
| $SO_2$ | Pyridinyl | C5-C8 alkoxy | COOH | propoxy | |
| $SO_2$ | Pyridinyl | Halo substituted alkoxy | COOH | propoxy | |
| $SO_2$ | Pyridinyl | $CH_3$ | COOH | propoxy | |
| $SO_2$ | Pyridinyl | $CH_2CH_3$ | COOH | propoxy | |
| $SO_2$ | Pyridinyl | $CH_2CH_2CH_3$ | COOH | propoxy | |
| $SO_2$ | Pyridinyl | $CH_2CH_2CH_2CH_3$ | COOH | propoxy | |
| $SO_2$ | Pyridinyl | C5-C8 alkyl | COOH | propoxy | |
| $SO_2$ | Pyridinyl | F | COOH | propoxy | |
| $SO_2$ | Pyridinyl | F, F | COOH | propoxy | |
| $SO_2$ | Pyridinyl | F, Cl | COOH | propoxy | |
| $SO_2$ | Pyridinyl | Cl | COOH | propoxy | |
| $SO_2$ | Pyridinyl | Cl, Cl | COOH | propoxy | |
| $SO_2$ | Pyridinyl | -(1 to 4 linearly linked atom linker)-optionally subst. aryl | COOH | propoxy | |
| $SO_2$ | Pyridinyl | -(1 to 4 linearly linked atom linker)-optionally subst. heteroaryl | COOH | propoxy | |
| CO | Phenyl | | COOH | propoxy | |
| CO | Phenyl | $CF_3$ | COOH | propoxy | |
| CO | Phenyl | $CH_2CF_3$ | COOH | propoxy | |
| CO | Phenyl | Halo substituted alkyl | COOH | propoxy | |
| CO | Phenyl | $OCH_3$ | COOH | propoxy | |
| CO | Phenyl | $OCH_2CH_3$ | COOH | propoxy | |
| CO | Phenyl | $OCH_2CH_2CH_3$ | COOH | propoxy | |
| CO | Phenyl | $OCH_2CH_2CH_2CH_3$ | COOH | propoxy | |
| CO | Phenyl | $OCH_2CH_2CH_2CH_2CH_3$ | COOH | propoxy | |
| CO | Phenyl | C5-C8 alkoxy | COOH | propoxy | |
| CO | Phenyl | Halo substituted alkoxy | COOH | propoxy | |
| CO | Phenyl | $CH_3$ | COOH | propoxy | |
| CO | Phenyl | $CH_2CH_3$ | COOH | propoxy | |
| CO | Phenyl | $CH_2CH_2CH_3$ | COOH | propoxy | |
| CO | Phenyl | $CH_2CH_2CH_2CH_3$ | COOH | propoxy | |
| CO | Phenyl | C5-C8 alkyl | COOH | propoxy | |
| CO | Phenyl | F | COOH | propoxy | |
| CO | Phenyl | F, F | COOH | propoxy | |
| CO | Phenyl | F, Cl | COOH | propoxy | |
| CO | Phenyl | Cl | COOH | propoxy | |
| CO | Phenyl | Cl, Cl | COOH | propoxy | |
| CO | Phenyl | -(1 to 4 linearly linked atom linker)-optionally subst. aryl | COOH | propoxy | |
| CO | Phenyl | -(1 to 4 linearly linked atom linker)-optionally subst. heteroaryl | COOH | propoxy | |
| CO | pyridinyl | | COOH | propoxy | |
| CO | Pyridinyl | $CF_3$ | COOH | propoxy | |
| CO | Pyridinyl | $CH_2CF_3$ | COOH | propoxy | |
| CO | Pyridinyl | Halo substituted alkyl | COOH | propoxy | |
| CO | Pyridinyl | $OCH_3$ | COOH | propoxy | |
| CO | Pyridinyl | $OCH_2CH_3$ | COOH | propoxy | |
| CO | Pyridinyl | $OCH_2CH_2CH_3$ | COOH | propoxy | |
| CO | Pyridinyl | $OCH_2CH_2CH_2CH_3$ | COOH | propoxy | |
| CO | Pyridinyl | $OCH_2CH_2CH_2CH_2CH_3$ | COOH | propoxy | |
| CO | Pyridinyl | C5-G8 alkoxy | COOH | propoxy | |
| CO | Pyridinyl | Halo substituted alkoxy | COOH | propoxy | |
| CO | Pyridinyl | $CH_3$ | COOH | propoxy | |

TABLE 4-continued

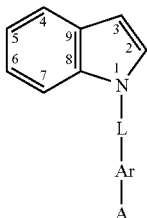

| L¹ | Ar | A | 3 | 5 | 6 |
|---|---|---|---|---|---|
| CO | Pyridinyl | CH₂CH₃ | COOH | propoxy | |
| CO | Pyridinyl | CH₂CH₂CH₃ | COOH | propoxy | |
| CO | Pyridinyl | CH₂CH₂CH₂CH₃ | COOH | propoxy | |
| CO | Pyridinyl | C5-G8 alkyl | COOH | propoxy | |
| CO | Pyridinyl | F | COOH | propoxy | |
| CO | Pyridinyl | F, F | COOH | propoxy | |
| CO | Pyridinyl | F, Cl | COOH | propoxy | |
| CO | Pyridinyl | Cl | COOH | propoxy | |
| CO | Pyridinyl | Cl, Cl | COOH | propoxy | |
| CO | Pyridinyl | -(1 to 4 linearly linked atom linker)-optionally subst. aryl | COOH | propoxy | |
| CO | Pyridinyl | -(1 to 4 linearly linked atom linker)-optionally subst. heteroaryl | COOH | propoxy | |
| SO₂ | phenyl | | COOH | —SCH₃ | |
| SO₂ | phenyl | CF₃ | COOH | —SCH₃ | |
| SO₂ | phenyl | CH₂CF₃ | COOH | —SCH₃ | |
| SO₂ | phenyl | Halo substituted alkyl | COOH | —SCH₃ | |
| SO₂ | phenyl | OCH₃ | COOH | —SCH₃ | |
| SO₂ | phenyl | OCH₂CH₃ | COOH | —SCH₃ | |
| SO₂ | phenyl | OCH₂CH₂CH₃ | COOH | —SCH₃ | |
| SO₂ | phenyl | OCH₂CH₂CH₂CH₃ | COOH | —SCH₃ | |
| SO₂ | phenyl | OCH₂CH₂CH₂CH₂CH₃ | COOH | —SCH₃ | |
| SO₂ | phenyl | C5-C8 alkoxy | COOH | —SCH₃ | |
| SO₂ | phenyl | Halo substituted alkoxy | COOH | —SCH₃ | |
| SO₂ | phenyl | CH₃ | COOH | —SCH₃ | |
| SO₂ | phenyl | CH₂CH₃ | COOH | —SCH₃ | |
| SO₂ | phenyl | CH₂CH₂CH₃ | COOH | —SCH₃ | |
| SO₂ | phenyl | CH₂CH₂CH₂CH₃ | COOH | —SCH₃ | |
| SO₂ | phenyl | C5-C8 alkyl | COOH | —SCH₃ | |
| SO₂ | phenyl | F | COOH | —SCH₃ | |
| SO₂ | phenyl | F, F | COOH | —SCH₃ | |
| SO₂ | phenyl | F, Cl | COOH | —SCH₃ | |
| SO₂ | phenyl | Cl | COOH | —SCH₃ | |
| SO₂ | phenyl | Cl, Cl | COOH | —SCH₃ | |
| SO₂ | phenyl | -(1 to 4 linearly linked atom linker)-optionally subst. aryl | COOH | —SCH₃ | |
| SO₂ | phenyl | -(1 to 4 linearly linked atom linker)-optionally subst. heteroaryl | COOH | —SCH₃ | |
| SO₂ | pyridinyl | | COOH | —SCH₃ | |
| SO₂ | Pyridinyl | CF₃ | COOH | —SCH₃ | |
| SO₂ | Pyridinyl | CH₂CF₃ | COOH | —SCH₃ | |
| SO₂ | Pyridinyl | Halo substituted alkyl | COOH | —SCH₃ | |
| SO₂ | Pyridinyl | OCH₃ | COOH | —SCH₃ | |
| SO₂ | Pyridinyl | OCH₂CH₃ | COOH | —SCH₃ | |
| SO₂ | Pyridinyl | OCH₂CH₂CH₃ | COOH | —SCH₃ | |
| SO₂ | Pyridinyl | OCH₂CH₂CH₂CH₃ | COOH | —SCH₃ | |
| SO₂ | Pyridinyl | OCH₂CH₂CH₂CH₂CH₃ | COOH | —SCH₃ | |
| SO₂ | Pyridinyl | C5-C8 alkoxy | COOH | —SCH₃ | |
| SO₂ | Pyridinyl | Halo substituted alkoxy | COOH | —SCH₃ | |
| SO₂ | Pyridinyl | CH₃ | COOH | —SCH₃ | |
| SO₂ | Pyridinyl | CH₂CH₃ | COOH | —SCH₃ | |
| SO₂ | Pyridinyl | CH₂CH₂CH₃ | COOH | —SCH₃ | |
| SO₂ | Pyridinyl | CH₂CH₂CH₂CH₃ | COOH | —SCH₃ | |
| SO₂ | Pyridinyl | C5-C8 alkyl | COOH | —SCH₃ | |
| SO₂ | Pyridinyl | F | COOH | —SCH₃ | |
| SO₂ | Pyridinyl | F, F | COOH | —SCH₃ | |
| SO₂ | Pyridinyl | F, Cl | COOH | —SCH₃ | |
| SO₂ | Pyridinyl | Cl | COOH | —SCH₃ | |
| SO₂ | Pyridinyl | Cl, Cl | COOH | —SCH₃ | |

TABLE 4-continued

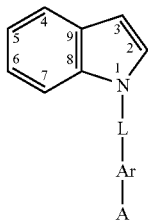

| L¹ | Ar | A | 3 | 5 | 6 |
|---|---|---|---|---|---|
| SO₂ | Pyridinyl | -(1 to 4 linearly linked atom linker)-optionally subst. aryl | COOH | —SCH₃ | |
| SO₂ | Pyridinyl | -(1 to 4 linearly linked atom linker)-optionally subst. heteroaryl | COOH | —SCH₃ | |
| CO | Phenyl | | COOH | —SCH₃ | |
| CO | Phenyl | CF₃ | COOH | —SCH₃ | |
| CO | Phenyl | CH₂CF₃ | COOH | —SCH₃ | |
| CO | Phenyl | Halo substituted alkyl | COOH | —SCH₃ | |
| CO | Phenyl | OCH₃ | COOH | —SCH₃ | |
| CO | Phenyl | OCH₂CH₃ | COOH | —SCH₃ | |
| CO | Phenyl | OCH₂CH₂CH₃ | COOH | —SCH₃ | |
| CO | Phenyl | OCH₂CH₂CH₂CH₃ | COOH | —SCH₃ | |
| CO | Phenyl | OCH₂CH₂CH₂CH₂CH₃ | COOH | —SCH₃ | |
| CO | Phenyl | C5-C8 alkoxy | COOH | —SCH₃ | |
| CO | Phenyl | Halo substituted alkoxy | COOH | —SCH₃ | |
| CO | Phenyl | CH₃ | COOH | —SCH₃ | |
| CO | Phenyl | CH₂CH₃ | COOH | —SCH₃ | |
| CO | Phenyl | CH₂CH₂CH₃ | COOH | —SCH₃ | |
| CO | Phenyl | CH₂CH₂CH₂CH₃ | COOH | —SCH₃ | |
| CO | Phenyl | C5-C8 alkyl | COOH | —SCH₃ | |
| CO | Phenyl | F | COOH | —SCH₃ | |
| CO | Phenyl | F, F | COOH | —SCH₃ | |
| CO | Phenyl | F, Cl | COOH | —SCH₃ | |
| CO | Phenyl | Cl | COOH | —SCH₃ | |
| CO | Phenyl | Cl, Cl | COOH | —SCH₃ | |
| CO | Phenyl | -(1 to 4 linearly linked atom linker)-optionally subst. aryl | COOH | —SCH₃ | |
| CO | Phenyl | -(1 to 4 linearly linked atom linker)-optionally subst. heteroaryl | COOH | —SCH₃ | |
| CO | pyridinyl | | COOH | —SCH₃ | |
| CO | Pyridinyl | CF₃ | COOH | —SCH₃ | |
| CO | Pyridinyl | CH₂CF₃ | COOH | —SCH₃ | |
| CO | Pyridinyl | Halo substituted alkyl | COOH | —SCH₃ | |
| CO | Pyridinyl | OCH₃ | COOH | —SCH₃ | |
| CO | Pyridinyl | OCH₂CH₃ | COOH | —SCH₃ | |
| CO | Pyridinyl | OCH₂CH₂CH₃ | COOH | —SCH₃ | |
| CO | Pyridinyl | OCH₂CH₂CH₂CH₃ | COOH | —SCH₃ | |
| CO | Pyridinyl | OCH₂CH₂CH₂CH₂CH₃ | COOH | —SCH₃ | |
| CO | Pyridinyl | C5-G8 alkoxy | COOH | —SCH₃ | |
| CO | Pyridinyl | Halo substituted alkoxy | COOH | —SCH₃ | |
| CO | Pyridinyl | CH₃ | COOH | —SCH₃ | |
| CO | Pyridinyl | CH₂CH₃ | COOH | —SCH₃ | |
| CO | Pyridinyl | CH₂CH₂CH₃ | COOH | —SCH₃ | |
| CO | Pyridinyl | CH₂CH₂CH₂CH₃ | COOH | —SCH₃ | |
| CO | Pyridinyl | C5-G8 alkyl | COOH | —SCH₃ | |
| CO | Pyridinyl | F | COOH | —SCH₃ | |
| CO | Pyridinyl | F, F | COOH | —SCH₃ | |
| CO | Pyridinyl | F, Cl | COOH | —SCH₃ | |
| CO | Pyridinyl | Cl | COOH | —SCH₃ | |
| CO | Pyridinyl | Cl, Cl | COOH | —SCH₃ | |
| CO | Pyridinyl | -(1 to 4 linearly linked atom linker)-optionally subst. aryl | COOH | —SCH₃ | |
| CO | Pyridinyl | -(1 to 4 linearly linked atom linker)-optionally subst. heteroaryl | COOH | —SCH₃ | |
| SO₂ | phenyl | | COOH | —SCH₂CH₃ | |
| SO₂ | phenyl | CF₃ | COOH | —SCH₂CH₃ | |
| SO₂ | phenyl | CH₂CF₃ | COOH | —SCH₂CH₃ | |

TABLE 4-continued

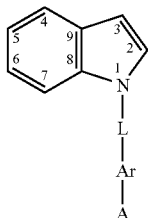

| $L^1$ | Ar | A | 3 | 5 | 6 |
|---|---|---|---|---|---|
| SO$_2$ | phenyl | Halo substituted alkyl | COOH | —SCH$_2$CH$_3$ | |
| SO$_2$ | phenyl | OCH$_3$ | COOH | —SCH$_2$CH$_3$ | |
| SO$_2$ | phenyl | OCH$_2$CH$_3$ | COOH | —SCH$_2$CH$_3$ | |
| SO$_2$ | phenyl | OCH$_2$CH$_2$CH$_3$ | COOH | —SCH$_2$CH$_3$ | |
| SO$_2$ | phenyl | OCH$_2$CH$_2$CH$_2$CH$_3$ | COOH | —SCH$_2$CH$_3$ | |
| SO$_2$ | phenyl | OCH$_2$CH$_2$CH$_2$CH$_2$CH$_3$ | COOH | —SCH$_2$CH$_3$ | |
| SO$_2$ | phenyl | C5-C8 alkoxy | COOH | —SCH$_2$CH$_3$ | |
| SO$_2$ | phenyl | Halo substituted alkoxy | COOH | —SCH$_2$CH$_3$ | |
| SO$_2$ | phenyl | CH$_3$ | COOH | —SCH$_2$CH$_3$ | |
| SO$_2$ | phenyl | CH$_2$CH$_3$ | COOH | —SCH$_2$CH$_3$ | |
| SO$_2$ | phenyl | CH$_2$CH$_2$CH$_3$ | COOH | —SCH$_2$CH$_3$ | |
| SO$_2$ | phenyl | CH$_2$CH$_2$CH$_2$CH$_3$ | COOH | —SCH$_2$CH$_3$ | |
| SO$_2$ | phenyl | C5-C8 alkyl | COOH | —SCH$_2$CH$_3$ | |
| SO$_2$ | phenyl | F | COOH | —SCH$_2$CH$_3$ | |
| SO$_2$ | phenyl | F, F | COOH | —SCH$_2$CH$_3$ | |
| SO$_2$ | phenyl | F, Cl | COOH | —SCH$_2$CH$_3$ | |
| SO$_2$ | phenyl | Cl | COOH | —SCH$_2$CH$_3$ | |
| SO$_2$ | phenyl | Cl, Cl | COOH | —SCH$_2$CH$_3$ | |
| SO$_2$ | phenyl | -(1 to 4 linearly linked atom linker)-optionally subst. aryl | COOH | —SCH$_2$CH$_3$ | |
| SO$_2$ | phenyl | -(1 to 4 linearly linked atom linker)-optionally subst. heteroaryl | COOH | —SCH$_2$CH$_3$ | |
| SO$_2$ | pyridinyl | | COOH | —SCH$_2$CH$_3$ | |
| SO$_2$ | Pyridinyl | CF$_3$ | COOH | —SCH$_2$CH$_3$ | |
| SO$_2$ | Pyridinyl | CH$_2$CF$_3$ | COOH | —SCH$_2$CH$_3$ | |
| SO$_2$ | Pyridinyl | Halo substituted alkyl | COOH | —SCH$_2$CH$_3$ | |
| SO$_2$ | Pyridinyl | OCH$_3$ | COOH | —SCH$_2$CH$_3$ | |
| SO$_2$ | Pyridinyl | OCH$_2$CH$_3$ | COOH | —SCH$_2$CH$_3$ | |
| SO$_2$ | Pyridinyl | OCH$_2$CH$_2$CH$_3$ | COOH | —SCH$_2$CH$_3$ | |
| SO$_2$ | Pyridinyl | OCH$_2$CH$_2$CH$_2$CH$_3$ | COOH | —SCH$_2$CH$_3$ | |
| SO$_2$ | Pyridinyl | OCH$_2$CH$_2$CH$_2$CH$_2$CH$_3$ | COOH | —SCH$_2$CH$_3$ | |
| SO$_2$ | Pyridinyl | C5-C8 alkoxy | COOH | —SCH$_2$CH$_3$ | |
| SO$_2$ | Pyridinyl | Halo substituted alkoxy | COOH | —SCH$_2$CH$_3$ | |
| SO$_2$ | Pyridinyl | CH$_3$ | COOH | —SCH$_2$CH$_3$ | |
| SO$_2$ | Pyridinyl | CH$_2$CH$_3$ | COOH | —SCH$_2$CH$_3$ | |
| SO$_2$ | Pyridinyl | CH$_2$CH$_2$CH$_3$ | COOH | —SCH$_2$CH$_3$ | |
| SO$_2$ | Pyridinyl | CH$_2$CH$_2$CH$_2$CH$_3$ | COOH | —SCH$_2$CH$_3$ | |
| SO$_2$ | Pyridinyl | C5-C8 alkyl | COOH | —SCH$_2$CH$_3$ | |
| SO$_2$ | Pyridinyl | F | COOH | —SCH$_2$CH$_3$ | |
| SO$_2$ | Pyridinyl | F, F | COOH | —SCH$_2$CH$_3$ | |
| SO$_2$ | Pyridinyl | F, Cl | COOH | —SCH$_2$CH$_3$ | |
| SO$_2$ | Pyridinyl | Cl | COOH | —SCH$_2$CH$_3$ | |
| SO$_2$ | Pyridinyl | Cl, Cl | COOH | —SCH$_2$CH$_3$ | |
| SO$_2$ | Pyridinyl | -(1 to 4 linearly linked atom linker)-optionally subst. aryl | COOH | —SCH$_2$CH$_3$ | |
| SO$_2$ | Pyridinyl | -(1 to 4 linearly linked atom linker)-optionally subst. heteroaryl | COOH | —SCH$_2$CH$_3$ | |
| CO | Phenyl | | COOH | —SCH$_2$CH$_3$ | |
| CO | Phenyl | CF$_3$ | COOH | —SCH$_2$CH$_3$ | |
| CO | Phenyl | CH$_2$CF$_3$ | COOH | —SCH$_2$CH$_3$ | |
| CO | Phenyl | Halo substituted alkyl | COOH | —SCH$_2$CH$_3$ | |
| CO | Phenyl | OCH$_3$ | COOH | —SCH$_2$CH$_3$ | |
| CO | Phenyl | OCH$_2$CH$_3$ | COOH | —SCH$_2$CH$_3$ | |
| CO | Phenyl | OCH$_2$CH$_2$CH$_3$ | COOH | —SCH$_2$CH$_3$ | |
| CO | Phenyl | OCH$_2$CH$_2$CH$_2$CH$_3$ | COOH | —SCH$_2$CH$_3$ | |
| CO | Phenyl | OCH$_2$CH$_2$CH$_2$CH$_2$CH$_3$ | COOH | —SCH$_2$CH$_3$ | |
| CO | Phenyl | C5-C8 alkoxy | COOH | —SCH$_2$CH$_3$ | |
| CO | Phenyl | Halo substituted alkoxy | COOH | —SCH$_2$CH$_3$ | |
| CO | Phenyl | CH$_3$ | COOH | —SCH$_2$CH$_3$ | |

TABLE 4-continued

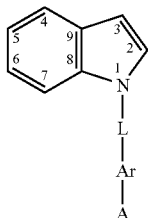

| L¹ | Ar | A | 3 | 5 | 6 |
|---|---|---|---|---|---|
| CO | Phenyl | CH₂CH₃ | COOH | —SCH₂CH₃ | |
| CO | Phenyl | CH₂CH₂CH₃ | COOH | —SCH₂CH₃ | |
| CO | Phenyl | CH₂CH₂CH₂CH₃ | COOH | —SCH₂CH₃ | |
| CO | Phenyl | C5-C8 alkyl | COOH | —SCH₂CH₃ | |
| CO | Phenyl | F | COOH | —SCH₂CH₃ | |
| CO | Phenyl | F, F | COOH | —SCH₂CH₃ | |
| CO | Phenyl | F, Cl | COOH | —SCH₂CH₃ | |
| CO | Phenyl | Cl | COOH | —SCH₂CH₃ | |
| CO | Phenyl | Cl, Cl | COOH | —SCH₂CH₃ | |
| CO | Phenyl | -(1 to 4 linearly linked atom linker)-optionally subst. aryl | COOH | —SCH₂CH₃ | |
| CO | Phenyl | -(1 to 4 linearly linked atom linker)-optionally subst. heteroaryl | COOH | —SCH₂CH₃ | |
| CO | pyridinyl | | COOH | —SCH₂CH₃ | |
| CO | Pyridinyl | CF₃ | COOH | —SCH₂CH₃ | |
| CO | Pyridinyl | CH₂CF₃ | COOH | —SCH₂CH₃ | |
| CO | Pyridinyl | Halo substituted alkyl | COOH | —SCH₂CH₃ | |
| CO | Pyridinyl | OCH₃ | COOH | —SCH₂CH₃ | |
| CO | Pyridinyl | OCH₂CH₃ | COOH | —SCH₂CH₃ | |
| CO | Pyridinyl | OCH₂CH₂CH₃ | COOH | —SCH₂CH₃ | |
| CO | Pyridinyl | OCH₂CH₂CH₂CH₃ | COOH | —SCH₂CH₃ | |
| CO | Pyridinyl | OCH₂CH₂CH₂CH₂CH₃ | COOH | —SCH₂CH₃ | |
| CO | Pyridinyl | C5-G8 alkoxy | COOH | —SCH₂CH₃ | |
| CO | Pyridinyl | Halo substituted alkoxy | COOH | —SCH₂CH₃ | |
| CO | Pyridinyl | CH₃ | COOH | —SCH₂CH₃ | |
| CO | Pyridinyl | CH₂CH₃ | COOH | —SCH₂CH₃ | |
| CO | Pyridinyl | CH₂CH₂CH₃ | COOH | —SCH₂CH₃ | |
| CO | Pyridinyl | CH₂CH₂CH₂CH₃ | COOH | —SCH₂CH₃ | |
| CO | Pyridinyl | C5-G8 alkyl | COOH | —SCH₂CH₃ | |
| CO | Pyridinyl | F | COOH | —SCH₂CH₃ | |
| CO | Pyridinyl | F, F | COOH | —SCH₂CH₃ | |
| CO | Pyridinyl | F, Cl | COOH | —SCH₂CH₃ | |
| CO | Pyridinyl | Cl | COOH | —SCH₂CH₃ | |
| CO | Pyridinyl | Cl, Cl | COOH | —SCH₂CH₃ | |
| CO | Pyridinyl | -(1 to 4 linearly linked atom linker)-optionally subst. aryl | COOH | —SCH₂CH₃ | |
| CO | Pyridinyl | -(1 to 4 linearly linked atom linker)-optionally subst. heteroaryl | COOH | —SCH₂CH₃ | |
| SO₂ | phenyl | | tetrazole | methoxy | |
| SO₂ | phenyl | CF₃ | Tetrazole | methoxy | |
| SO₂ | phenyl | CH₂CF₃ | Tetrazole | methoxy | |
| SO₂ | phenyl | Halo substituted alkyl | Tetrazole | methoxy | |
| SO₂ | phenyl | OCH₃ | Tetrazole | methoxy | |
| SO₂ | phenyl | OCH₂CH₃ | tetrazole | methoxy | |
| SO₂ | phenyl | OCH₂CH₂CH₃ | tetrazole | methoxy | |
| SO₂ | phenyl | OCH₂CH₂CH₂CH₃ | Tetrazole | methoxy | |
| SO₂ | phenyl | OCH₂CH₂CH₂CH₂CH₃ | Tetrazole | methoxy | |
| SO₂ | phenyl | C5-C8 alkoxy | Tetrazole | methoxy | |
| SO₂ | phenyl | Halo substituted alkoxy | Tetrazole | methoxy | |
| SO₂ | phenyl | CH₃ | tetrazole | methoxy | |
| SO₂ | phenyl | CH₂CH₃ | tetrazole | methoxy | |
| SO₂ | phenyl | CH₂CH₂CH₃ | Tetrazole | methoxy | |
| SO₂ | phenyl | CH₂CH₂CH₂CH₃ | Tetrazole | methoxy | |
| SO₂ | phenyl | C5-C8 alkyl | Tetrazole | methoxy | |
| SO₂ | phenyl | F | Tetrazole | methoxy | |
| SO₂ | phenyl | F, F | tetrazole | methoxy | |
| SO₂ | phenyl | F, Cl | tetrazole | methoxy | |
| SO₂ | phenyl | Cl | Tetrazole | methoxy | |
| SO₂ | phenyl | Cl, Cl | Tetrazole | methoxy | |

TABLE 4-continued

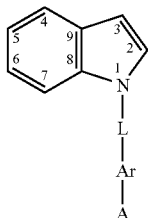

| L¹ | Ar | A | 3 | 5 | 6 |
|---|---|---|---|---|---|
| SO₂ | phenyl | -(1 to 4 linearly linked atom linker)-optionally subst. aryl | Tetrazole | methoxy | |
| SO₂ | phenyl | -(1 to 4 linearly linked atom linker)-optionally subst. heteroaryl | Tetrazole | methoxy | |
| SO₂ | pyridinyl | | tetrazole | methoxy | |
| SO₂ | Pyridinyl | CF₃ | tetrazole | methoxy | |
| SO₂ | Pyridinyl | CH₂CF₃ | Tetrazole | methoxy | |
| SO₂ | Pyridinyl | Halo substituted alkyl | Tetrazole | methoxy | |
| SO₂ | Pyridinyl | OCH₃ | Tetrazole | methoxy | |
| SO₂ | Pyridinyl | OCH₂CH₃ | Tetrazole | methoxy | |
| SO₂ | Pyridinyl | OCH₂CH₂CH₃ | tetrazole | methoxy | |
| SO₂ | Pyridinyl | OCH₂CH₂CH₂CH₃ | tetrazole | methoxy | |
| SO₂ | Pyridinyl | OCH₂CH₂CH₂CH₂CH₃ | Tetrazole | methoxy | |
| SO₂ | Pyridinyl | C5-C8 alkoxy | Tetrazole | methoxy | |
| SO₂ | Pyridinyl | Halo substituted alkoxy | Tetrazole | methoxy | |
| SO₂ | Pyridinyl | CH₃ | Tetrazole | methoxy | |
| SO₂ | Pyridinyl | CH₂CH₃ | tetrazole | methoxy | |
| SO₂ | Pyridinyl | CH₂CH₂CH₃ | tetrazole | methoxy | |
| SO₂ | Pyridinyl | CH₂CH₂CH₂CH₃ | Tetrazole | methoxy | |
| SO₂ | Pyridinyl | C5-C8 alkyl | Tetrazole | methoxy | |
| SO₂ | Pyridinyl | F | Tetrazole | methoxy | |
| SO₂ | Pyridinyl | F, F | Tetrazole | methoxy | |
| SO₂ | Pyridinyl | F, Cl | tetrazole | methoxy | |
| SO₂ | Pyridinyl | Cl | tetrazole | methoxy | |
| SO₂ | Pyridinyl | Cl, Cl | Tetrazole | methoxy | |
| SO₂ | Pyridinyl | -(1 to 4 linearly linked atom linker)-optionally subst. aryl | Tetrazole | methoxy | |
| SO₂ | Pyridinyl | -(1 to 4 linearly linked atom linker)-optionally subst. heteroaryl | Tetrazole | methoxy | |
| CO | Phenyl | | Tetrazole | methoxy | |
| CO | Phenyl | CF₃ | tetrazole | methoxy | |
| CO | Phenyl | CH₂CF₃ | tetrazole | methoxy | |
| CO | Phenyl | Halo substituted alkyl | Tetrazole | methoxy | |
| CO | Phenyl | OCH₃ | Tetrazole | methoxy | |
| CO | Phenyl | OCH₂CH₃ | Tetrazole | methoxy | |
| CO | Phenyl | OCH₂CH₂CH₃ | Tetrazole | methoxy | |
| CO | Phenyl | OCH₂CH₂CH₂CH₃ | tetrazole | methoxy | |
| CO | Phenyl | OCH₂CH₂CH₂CH₂CH₃ | tetrazole | methoxy | |
| CO | Phenyl | C5-C8 alkoxy | Tetrazole | methoxy | |
| CO | Phenyl | Halo substituted alkoxy | Tetrazole | methoxy | |
| CO | Phenyl | CH₃ | Tetrazole | methoxy | |
| CO | Phenyl | CH₂CH₃ | Tetrazole | methoxy | |
| CO | Phenyl | CH₂CH₂CH₃ | tetrazole | methoxy | |
| CO | Phenyl | CH₂CH₂CH₂CH₃ | tetrazole | methoxy | |
| CO | Phenyl | C5-C8 alkyl | Tetrazole | methoxy | |
| CO | Phenyl | F | Tetrazole | methoxy | |
| CO | Phenyl | F, F | Tetrazole | methoxy | |
| CO | Phenyl | F, Cl | Tetrazole | methoxy | |
| CO | Phenyl | Cl | tetrazole | methoxy | |
| CO | Phenyl | Cl, Cl | tetrazole | methoxy | |
| CO | Phenyl | -(1 to 4 linearly linked atom linker)-optionally subst. aryl | Tetrazole | methoxy | |
| CO | Phenyl | -(1 to 4 linearly linked atom linker)-optionally subst. heteroaryl | Tetrazole | methoxy | |
| CO | pyridinyl | | Tetrazole | methoxy | |
| CO | Pyridinyl | CF₃ | Tetrazole | methoxy | |
| CO | Pyridinyl | CH₂CF₃ | tetrazole | methoxy | |

TABLE 4-continued

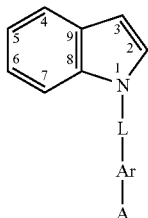

| $L^1$ | Ar | A | 3 | 5 | 6 |
|---|---|---|---|---|---|
| CO | Pyridinyl | Halo substituted alkyl | tetrazole | methoxy | |
| CO | Pyridinyl | $OCH_3$ | Tetrazole | methoxy | |
| CO | Pyridinyl | $OCH_2CH_3$ | Tetrazole | methoxy | |
| CO | Pyridinyl | $OCH_2CH_2CH_3$ | Tetrazole | methoxy | |
| CO | Pyridinyl | $OCH_2CH_2CH_2CH_3$ | Tetrazole | methoxy | |
| CO | Pyridinyl | $OCH_2CH_2CH_2CH_2CH_3$ | tetrazole | methoxy | |
| CO | Pyridinyl | C5-G8 alkoxy | tetrazole | methoxy | |
| CO | Pyridinyl | Halo substituted alkoxy | Tetrazole | methoxy | |
| CO | Pyridinyl | $CH_3$ | Tetrazole | methoxy | |
| CO | Pyridinyl | $CH_2CH_3$ | Tetrazole | methoxy | |
| CO | Pyridinyl | $CH_2CH_2CH_3$ | Tetrazole | methoxy | |
| CO | Pyridinyl | $CH_2CH_2CH_2CH_3$ | tetrazole | methoxy | |
| CO | Pyridinyl | C5-G8 alkyl | tetrazole | methoxy | |
| CO | Pyridinyl | F | Tetrazole | methoxy | |
| CO | Pyridinyl | F, F | Tetrazole | methoxy | |
| CO | Pyridinyl | F, Cl | Tetrazole | methoxy | |
| CO | Pyridinyl | Cl | Tetrazole | methoxy | |
| CO | Pyridinyl | Cl, Cl | tetrazole | methoxy | |
| CO | Pyridinyl | -(1 to 4 linearly linked atom linker)-optionally subst. aryl | tetrazole | methoxy | |
| CO | Pyridinyl | -(1 to 4 linearly linked atom linker)-optionally subst. heteroaryl | Tetrazole | methoxy | |
| $SO_2$ | phenyl | | Tetrazole | ethoxy | |
| $SO_2$ | phenyl | $CF_3$ | Tetrazole | ethoxy | |
| $SO_2$ | phenyl | $CH_2CF_3$ | Tetrazole | ethoxy | |
| $SO_2$ | phenyl | Halo substituted alkyl | tetrazole | ethoxy | |
| $SO_2$ | phenyl | $OCH_3$ | tetrazole | ethoxy | |
| $SO_2$ | phenyl | $OCH_2CH_3$ | Tetrazole | ethoxy | |
| $SO_2$ | phenyl | $OCH_2CH_2CH_3$ | Tetrazole | ethoxy | |
| $SO_2$ | phenyl | $OCH_2CH_2CH_2CH_3$ | Tetrazole | ethoxy | |
| $SO_2$ | phenyl | $OCH_2CH_2CH_2CH_2CH_3$ | Tetrazole | ethoxy | |
| $SO_2$ | phenyl | C5-C8 alkoxy | tetrazole | ethoxy | |
| $SO_2$ | phenyl | Halo substituted alkoxy | tetrazole | ethoxy | |
| $SO_2$ | phenyl | $CH_3$ | Tetrazole | ethoxy | |
| $SO_2$ | phenyl | $CH_2CH_3$ | Tetrazole | ethoxy | |
| $SO_2$ | phenyl | $CH_2CH_2CH_3$ | Tetrazole | ethoxy | |
| $SO_2$ | phenyl | $CH_2CH_2CH_2CH_3$ | Tetrazole | ethoxy | |
| $SO_2$ | phenyl | C5-C8 alkyl | tetrazole | ethoxy | |
| $SO_2$ | phenyl | F | tetrazole | ethoxy | |
| $SO_2$ | phenyl | F, F | Tetrazole | ethoxy | |
| $SO_2$ | phenyl | F, Cl | Tetrazole | ethoxy | |
| $SO_2$ | phenyl | Cl | Tetrazole | ethoxy | |
| $SO_2$ | phenyl | Cl, Cl | Tetrazole | ethoxy | |
| $SO_2$ | phenyl | -(1 to 4 linearly linked atom linker)-optionally subst. aryl | tetrazole | ethoxy | |
| $SO_2$ | phenyl | -(1 to 4 linearly linked atom linker)-optionally subst. heteroaryl | tetrazole | ethoxy | |
| $SO_2$ | pyridinyl | | Tetrazole | ethoxy | |
| $SO_2$ | Pyridinyl | $CF_3$ | Tetrazole | ethoxy | |
| $SO_2$ | Pyridinyl | $CH_2CF_3$ | Tetrazole | ethoxy | |
| $SO_2$ | Pyridinyl | Halo substituted alkyl | Tetrazole | ethoxy | |
| $SO_2$ | Pyridinyl | $OCH_3$ | tetrazole | ethoxy | |
| $SO_2$ | Pyridinyl | $OCH_2CH_3$ | tetrazole | ethoxy | |
| $SO_2$ | Pyridinyl | $OCH_2CH_2CH_3$ | Tetrazole | ethoxy | |
| $SO_2$ | Pyridinyl | $OCH_2CH_2CH_2CH_3$ | Tetrazole | ethoxy | |
| $SO_2$ | Pyridinyl | $OCH_2CH_2CH_2CH_2CH_3$ | Tetrazole | ethoxy | |
| $SO_2$ | Pyridinyl | C5-C8 alkoxy | Tetrazole | ethoxy | |
| $SO_2$ | Pyridinyl | Halo substituted alkoxy | tetrazole | ethoxy | |
| $SO_2$ | Pyridinyl | $CH_3$ | tetrazole | ethoxy | |

TABLE 4-continued

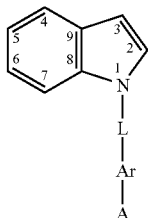

| $L^1$ | Ar | A | 3 | 5 | 6 |
|---|---|---|---|---|---|
| SO$_2$ | Pyridinyl | CH$_2$CH$_3$ | Tetrazole | ethoxy | |
| SO$_2$ | Pyridinyl | CH$_2$CH$_2$CH$_3$ | Tetrazole | ethoxy | |
| SO$_2$ | Pyridinyl | CH$_2$CH$_2$CH$_2$CH$_3$ | Tetrazole | ethoxy | |
| SO$_2$ | Pyridinyl | C5-C8 alkyl | Tetrazole | ethoxy | |
| SO$_2$ | Pyridinyl | F | tetrazole | ethoxy | |
| SO$_2$ | Pyridinyl | F, F | tetrazole | ethoxy | |
| SO$_2$ | Pyridinyl | F, Cl | Tetrazole | ethoxy | |
| SO$_2$ | Pyridinyl | Cl | Tetrazole | ethoxy | |
| SO$_2$ | Pyridinyl | Cl, Cl | Tetrazole | ethoxy | |
| SO$_2$ | Pyridinyl | -(1 to 4 linearly linked atom linker)-optionally subst. aryl | Tetrazole | ethoxy | |
| SO$_2$ | Pyridinyl | -(1 to 4 linearly linked atom linker)-optionally subst. heteroaryl | tetrazole | ethoxy | |
| CO | Phenyl | | tetrazole | ethoxy | |
| CO | Phenyl | CF$_3$ | Tetrazole | ethoxy | |
| CO | Phenyl | CH$_2$CF$_3$ | Tetrazole | ethoxy | |
| CO | Phenyl | Halo substituted alkyl | Tetrazole | ethoxy | |
| CO | Phenyl | OCH$_3$ | Tetrazole | ethoxy | |
| CO | Phenyl | OCH$_2$CH$_3$ | tetrazole | ethoxy | |
| CO | Phenyl | OCH$_2$CH$_2$CH$_3$ | tetrazole | ethoxy | |
| CO | Phenyl | OCH$_2$CH$_2$CH$_2$CH$_3$ | Tetrazole | ethoxy | |
| CO | Phenyl | OCH$_2$CH$_2$CH$_2$CH$_2$CH$_3$ | Tetrazole | ethoxy | |
| CO | Phenyl | C5-C8 alkoxy | Tetrazole | ethoxy | |
| CO | Phenyl | Halo substituted alkoxy | Tetrazole | ethoxy | |
| CO | Phenyl | CH$_3$ | tetrazole | ethoxy | |
| CO | Phenyl | CH$_2$CH$_3$ | tetrazole | ethoxy | |
| CO | Phenyl | CH$_2$CH$_2$CH$_3$ | Tetrazole | ethoxy | |
| CO | Phenyl | CH$_2$CH$_2$CH$_2$CH$_3$ | Tetrazole | ethoxy | |
| CO | Phenyl | C5-C8 alkyl | Tetrazole | ethoxy | |
| CO | Phenyl | F | Tetrazole | ethoxy | |
| CO | Phenyl | F, F | tetrazole | ethoxy | |
| CO | Phenyl | F, Cl | tetrazole | ethoxy | |
| CO | Phenyl | Cl | Tetrazole | ethoxy | |
| CO | Phenyl | Cl, Cl | Tetrazole | ethoxy | |
| CO | Phenyl | -(1 to 4 linearly linked atom linker)-optionally subst. aryl | Tetrazole | ethoxy | |
| CO | Phenyl | -(1 to 4 linearly linked atom linker)-optionally subst. heteroaryl | Tetrazole | ethoxy | |
| CO | pyridinyl | | tetrazole | ethoxy | |
| CO | Pyridinyl | CF$_3$ | tetrazole | ethoxy | |
| CO | Pyridinyl | CH$_2$CF$_3$ | Tetrazole | ethoxy | |
| CO | Pyridinyl | Halo substituted alkyl | Tetrazole | ethoxy | |
| CO | Pyridinyl | OCH$_3$ | Tetrazole | ethoxy | |
| CO | Pyridinyl | OCH$_2$CH$_3$ | Tetrazole | ethoxy | |
| CO | Pyridinyl | OCH$_2$CH$_2$CH$_3$ | tetrazole | ethoxy | |
| CO | Pyridinyl | OCH$_2$CH$_2$CH$_2$CH$_3$ | tetrazole | ethoxy | |
| CO | Pyridinyl | OCH$_2$CH$_2$CH$_2$CH$_2$CH$_3$ | Tetrazole | ethoxy | |
| CO | Pyridinyl | C5-G8 alkoxy | Tetrazole | ethoxy | |
| CO | Pyridinyl | Halo substituted alkoxy | Tetrazole | ethoxy | |
| CO | Pyridinyl | CH$_3$ | Tetrazole | ethoxy | |
| CO | Pyridinyl | CH$_2$CH$_3$ | tetrazole | ethoxy | |
| CO | Pyridinyl | CH$_2$CH$_2$CH$_3$ | tetrazole | ethoxy | |
| CO | Pyridinyl | CH$_2$CH$_2$CH$_2$CH$_3$ | Tetrazole | ethoxy | |
| CO | Pyridinyl | C5-G8 alkyl | Tetrazole | ethoxy | |
| CO | Pyridinyl | F | Tetrazole | ethoxy | |
| CO | Pyridinyl | F, F | Tetrazole | ethoxy | |
| CO | Pyridinyl | F, Cl | tetrazole | ethoxy | |
| CO | Pyridinyl | Cl | tetrazole | ethoxy | |
| CO | Pyridinyl | Cl, Cl | Tetrazole | ethoxy | |

TABLE 4-continued

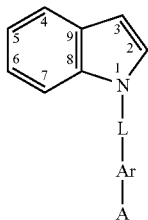

| L¹ | Ar | A | 3 | 5 | 6 |
|---|---|---|---|---|---|
| CO | Pyridinyl | -(1 to 4 linearly linked atom linker)-optionally subst. aryl | Tetrazole | ethoxy | |
| CO | Pyridinyl | -(1 to 4 linearly linked atom linker)-optionally subst. heteroaryl | Tetrazole | ethoxy | |
| SO₂ | phenyl | | tetrazole | propoxy | |
| SO₂ | phenyl | CF₃ | Tetrazole | propoxy | |
| SO₂ | phenyl | CH₂CF₃ | Tetrazole | propoxy | |
| SO₂ | phenyl | Halo substituted alkyl | Tetrazole | propoxy | |
| SO₂ | phenyl | OCH₃ | Tetrazole | propoxy | |
| SO₂ | phenyl | OCH₂CH₃ | tetrazole | propoxy | |
| SO₂ | phenyl | OCH₂CH₂CH₃ | tetrazole | propoxy | |
| SO₂ | phenyl | OCH₂CH₂CH₂CH₃ | Tetrazole | propoxy | |
| SO₂ | phenyl | OCH₂CH₂CH₂CH₂CH₃ | Tetrazole | propoxy | |
| SO₂ | phenyl | C5-C8 alkoxy | Tetrazole | propoxy | |
| SO₂ | phenyl | Halo substituted alkoxy | Tetrazole | propoxy | |
| SO₂ | phenyl | CH₃ | tetrazole | propoxy | |
| SO₂ | phenyl | CH₂CH₃ | tetrazole | propoxy | |
| SO₂ | phenyl | CH₂CH₂CH₃ | Tetrazole | propoxy | |
| SO₂ | phenyl | CH₂CH₂CH₂CH₃ | Tetrazole | propoxy | |
| SO₂ | phenyl | C5-C8 alkyl | Tetrazole | propoxy | |
| SO₂ | phenyl | F | Tetrazole | propoxy | |
| SO₂ | phenyl | F, F | tetrazole | propoxy | |
| SO₂ | phenyl | F, Cl | tetrazole | propoxy | |
| SO₂ | phenyl | Cl | Tetrazole | propoxy | |
| SO₂ | phenyl | Cl, Cl | Tetrazole | propoxy | |
| SO₂ | phenyl | -(1 to 4 linearly linked atom linker)-optionally subst. aryl | Tetrazole | propoxy | |
| SO₂ | phenyl | -(1 to 4 linearly linked atom linker)-optionally subst. heteroaryl | Tetrazole | propoxy | |
| SO₂ | pyridinyl | | tetrazole | propoxy | |
| SO₂ | Pyridinyl | CF₃ | tetrazole | propoxy | |
| SO₂ | Pyridinyl | CH₂CF₃ | Tetrazole | propoxy | |
| SO₂ | Pyridinyl | Halo substituted alkyl | Tetrazole | propoxy | |
| SO₂ | Pyridinyl | OCH₃ | Tetrazole | propoxy | |
| SO₂ | Pyridinyl | OCH₂CH₃ | Tetrazole | propoxy | |
| SO₂ | Pyridinyl | OCH₂CH₂CH₃ | tetrazole | propoxy | |
| SO₂ | Pyridinyl | OCH₂CH₂CH₂CH₃ | tetrazole | propoxy | |
| SO₂ | Pyridinyl | OCH₂CH₂CH₂CH₂CH₃ | Tetrazole | propoxy | |
| SO₂ | Pyridinyl | C5-C8 alkoxy | Tetrazole | propoxy | |
| SO₂ | Pyridinyl | Halo substituted alkoxy | Tetrazole | propoxy | |
| SO₂ | Pyridinyl | CH₃ | Tetrazole | propoxy | |
| SO₂ | Pyridinyl | CH₂CH₃ | tetrazole | propoxy | |
| SO₂ | Pyridinyl | CH₂CH₂CH₃ | tetrazole | propoxy | |
| SO₂ | Pyridinyl | CH₂CH₂CH₂CH₃ | Tetrazole | propoxy | |
| SO₂ | Pyridinyl | C5-C8 alkyl | Tetrazole | propoxy | |
| SO₂ | Pyridinyl | F | Tetrazole | propoxy | |
| SO₂ | Pyridinyl | F, F | Tetrazole | propoxy | |
| SO₂ | Pyridinyl | F, Cl | tetrazole | propoxy | |
| SO₂ | Pyridinyl | Cl | tetrazole | propoxy | |
| SO₂ | Pyridinyl | Cl, Cl | Tetrazole | propoxy | |
| SO₂ | Pyridinyl | -(1 to 4 linearly linked atom linker)-optionally subst. aryl | Tetrazole | propoxy | |
| SO₂ | Pyridinyl | -(1 to 4 linearly linked atom linker)-optionally subst. heteroaryl | Tetrazole | propoxy | |
| CO | Phenyl | | Tetrazole | propoxy | |
| CO | Phenyl | CF₃ | tetrazole | propoxy | |
| CO | Phenyl | CH₂CF₃ | tetrazole | propoxy | |

TABLE 4-continued

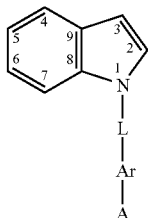

| $L^1$ | Ar | A | 3 | 5 | 6 |
|---|---|---|---|---|---|
| CO | Phenyl | Halo substituted alkyl | Tetrazole | propoxy | |
| CO | Phenyl | $OCH_3$ | Tetrazole | propoxy | |
| CO | Phenyl | $OCH_2CH_3$ | Tetrazole | propoxy | |
| CO | Phenyl | $OCH_2CH_2CH_3$ | Tetrazole | propoxy | |
| CO | Phenyl | $OCH_2CH_2CH_2CH_3$ | tetrazole | propoxy | |
| CO | Phenyl | $OCH_2CH_2CH_2CH_2CH_3$ | tetrazole | propoxy | |
| CO | Phenyl | C5-C8 alkoxy | Tetrazole | propoxy | |
| CO | Phenyl | Halo substituted alkoxy | Tetrazole | propoxy | |
| CO | Phenyl | $CH_3$ | Tetrazole | propoxy | |
| CO | Phenyl | $CH_2CH_3$ | Tetrazole | propoxy | |
| CO | Phenyl | $CH_2CH_2CH_3$ | tetrazole | propoxy | |
| CO | Phenyl | $CH_2CH_2CH_2CH_3$ | tetrazole | propoxy | |
| CO | Phenyl | C5-C8 alkyl | Tetrazole | propoxy | |
| CO | Phenyl | F | Tetrazole | propoxy | |
| CO | Phenyl | F, F | Tetrazole | propoxy | |
| CO | Phenyl | F, Cl | Tetrazole | propoxy | |
| CO | Phenyl | Cl | tetrazole | propoxy | |
| CO | Phenyl | Cl, Cl | tetrazole | propoxy | |
| CO | Phenyl | -(1 to 4 linearly linked atom linker)-optionally subst. aryl | Tetrazole | propoxy | |
| CO | Phenyl | -(1 to 4 linearly linked atom linker)-optionally subst. heteroaryl | Tetrazole | propoxy | |
| CO | pyridinyl | | Tetrazole | propoxy | |
| CO | Pyridinyl | $CF_3$ | Tetrazole | propoxy | |
| CO | Pyridinyl | $CH_2CF_3$ | tetrazole | propoxy | |
| CO | Pyridinyl | Halo substituted alkyl | tetrazole | propoxy | |
| CO | Pyridinyl | $OCH_3$ | Tetrazole | propoxy | |
| CO | Pyridinyl | $OCH_2CH_3$ | Tetrazole | propoxy | |
| CO | Pyridinyl | $OCH_2CH_2CH_3$ | Tetrazole | propoxy | |
| CO | Pyridinyl | $OCH_2CH_2CH_2CH_3$ | Tetrazole | propoxy | |
| CO | Pyridinyl | $OCH_2CH_2CH_2CH_2CH_3$ | tetrazole | propoxy | |
| CO | Pyridinyl | C5-G8 alkoxy | tetrazole | propoxy | |
| CO | Pyridinyl | Halo substituted alkoxy | Tetrazole | propoxy | |
| CO | Pyridinyl | $CH_3$ | Tetrazole | propoxy | |
| CO | Pyridinyl | $CH_2CH_3$ | Tetrazole | propoxy | |
| CO | Pyridinyl | $CH_2CH_2CH_3$ | Tetrazole | propoxy | |
| CO | Pyridinyl | $CH_2CH_2CH_2CH_3$ | tetrazole | propoxy | |
| CO | Pyridinyl | C5-G8 alkyl | tetrazole | propoxy | |
| CO | Pyridinyl | F | Tetrazole | propoxy | |
| CO | Pyridinyl | F, F | Tetrazole | propoxy | |
| CO | Pyridinyl | F, Cl | Tetrazole | propoxy | |
| CO | Pyridinyl | Cl | Tetrazole | propoxy | |
| CO | Pyridinyl | Cl, Cl | tetrazole | propoxy | |
| CO | Pyridinyl | -(1 to 4 linearly linked atom linker)-optionally subst. aryl | tetrazole | propoxy | |
| CO | Pyridinyl | -(1 to 4 linearly linked atom linker)-optionally subst. heteroaryl | Tetrazole | propoxy | |
| $SO_2$ | phenyl | | Tetrazole | —$SCH_3$ | |
| $SO_2$ | phenyl | $CF_3$ | Tetrazole | —$SCH_3$ | |
| $SO_2$ | phenyl | $CH_2CF_3$ | Tetrazole | —$SCH_3$ | |
| $SO_2$ | phenyl | Halo substituted alkyl | tetrazole | —$SCH_3$ | |
| $SO_2$ | phenyl | $OCH_3$ | tetrazole | —$SCH_3$ | |
| $SO_2$ | phenyl | $OCH_2CH_3$ | Tetrazole | —$SCH_3$ | |
| $SO_2$ | phenyl | $OCH_2CH_2CH_3$ | Tetrazole | —$SCH_3$ | |
| $SO_2$ | phenyl | $OCH_2CH_2CH_2CH_3$ | Tetrazole | —$SCH_3$ | |
| $SO_2$ | phenyl | $OCH_2CH_2CH_2CH_2CH_3$ | Tetrazole | —$SCH_3$ | |
| $SO_2$ | phenyl | C5-C8 alkoxy | tetrazole | —$SCH_3$ | |
| $SO_2$ | phenyl | Halo substituted alkoxy | tetrazole | —$SCH_3$ | |
| $SO_2$ | phenyl | $CH_3$ | Tetrazole | —$SCH_3$ | |

TABLE 4-continued

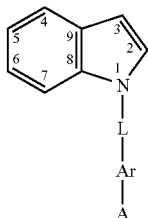

| $L^1$ | Ar | A | 3 | 5 | 6 |
|---|---|---|---|---|---|
| $SO_2$ | phenyl | $CH_2CH_3$ | Tetrazole | —$SCH_3$ | |
| $SO_2$ | phenyl | $CH_2CH_2CH_3$ | Tetrazole | —$SCH_3$ | |
| $SO_2$ | phenyl | $CH_2CH_2CH_2CH_3$ | Tetrazole | —$SCH_3$ | |
| $SO_2$ | phenyl | C5-C8 alkyl | tetrazole | —$SCH_3$ | |
| $SO_2$ | phenyl | F | tetrazole | —$SCH_3$ | |
| $SO_2$ | phenyl | F, F | Tetrazole | —$SCH_3$ | |
| $SO_2$ | phenyl | F, Cl | Tetrazole | —$SCH_3$ | |
| $SO_2$ | phenyl | Cl | Tetrazole | —$SCH_3$ | |
| $SO_2$ | phenyl | Cl, Cl | Tetrazole | —$SCH_3$ | |
| $SO_2$ | phenyl | -(1 to 4 linearly linked atom linker)-optionally subst. aryl | tetrazole | —$SCH_3$ | |
| $SO_2$ | phenyl | -(1 to 4 linearly linked atom linker)-optionally subst. heteroaryl | tetrazole | —$SCH_3$ | |
| $SO_2$ | pyridinyl | | Tetrazole | —$SCH_3$ | |
| $SO_2$ | Pyridinyl | $CF_3$ | Tetrazole | —$SCH_3$ | |
| $SO_2$ | Pyridinyl | $CH_2CF_3$ | Tetrazole | —$SCH_3$ | |
| $SO_2$ | Pyridinyl | Halo substituted alkyl | Tetrazole | —$SCH_3$ | |
| $SO_2$ | Pyridinyl | $OCH_3$ | tetrazole | —$SCH_3$ | |
| $SO_2$ | Pyridinyl | $OCH_2CH_3$ | tetrazole | —$SCH_3$ | |
| $SO_2$ | Pyridinyl | $OCH_2CH_2CH_3$ | Tetrazole | —$SCH_3$ | |
| $SO_2$ | Pyridinyl | $OCH_2CH_2CH_2CH_3$ | Tetrazole | —$SCH_3$ | |
| $SO_2$ | Pyridinyl | $OCH_2CH_2CH_2CH_2CH_3$ | Tetrazole | —$SCH_3$ | |
| $SO_2$ | Pyridinyl | C5-C8 alkoxy | Tetrazole | —$SCH_3$ | |
| $SO_2$ | Pyridinyl | Halo substituted alkoxy | tetrazole | —$SCH_3$ | |
| $SO_2$ | Pyridinyl | $CH_3$ | tetrazole | —$SCH_3$ | |
| $SO_2$ | Pyridinyl | $CH_2CH_3$ | Tetrazole | —$SCH_3$ | |
| $SO_2$ | Pyridinyl | $CH_2CH_2CH_3$ | Tetrazole | —$SCH_3$ | |
| $SO_2$ | Pyridinyl | $CH_2CH_2CH_2CH_3$ | Tetrazole | —$SCH_3$ | |
| $SO_2$ | Pyridinyl | C5-C8 alkyl | Tetrazole | —$SCH_3$ | |
| $SO_2$ | Pyridinyl | F | tetrazole | —$SCH_3$ | |
| $SO_2$ | Pyridinyl | F, F | tetrazole | —$SCH_3$ | |
| $SO_2$ | Pyridinyl | F, Cl | Tetrazole | —$SCH_3$ | |
| $SO_2$ | Pyridinyl | Cl | Tetrazole | —$SCH_3$ | |
| $SO_2$ | Pyridinyl | Cl, Cl | Tetrazole | —$SCH_3$ | |
| $SO_2$ | Pyridinyl | -(1 to 4 linearly linked atom linker)-optionally subst. aryl | Tetrazole | —$SCH_3$ | |
| $SO_2$ | Pyridinyl | -(1 to 4 linearly linked atom linker)-optionally subst. heteroaryl | tetrazole | —$SCH_3$ | |
| CO | Phenyl | | tetrazole | —$SCH_3$ | |
| CO | Phenyl | $CF_3$ | Tetrazole | —$SCH_3$ | |
| CO | Phenyl | $CH_2CF_3$ | Tetrazole | —$SCH_3$ | |
| CO | Phenyl | Halo substituted alkyl | Tetrazole | —$SCH_3$ | |
| CO | Phenyl | $OCH_3$ | Tetrazole | —$SCH_3$ | |
| CO | Phenyl | $OCH_2CH_3$ | tetrazole | —$SCH_3$ | |
| CO | Phenyl | $OCH_2CH_2CH_3$ | tetrazole | —$SCH_3$ | |
| CO | Phenyl | $OCH_2CH_2CH_2CH_3$ | Tetrazole | —$SCH_3$ | |
| CO | Phenyl | $OCH_2CH_2CH_2CH_2CH_3$ | Tetrazole | —$SCH_3$ | |
| CO | Phenyl | C5-C8 alkoxy | Tetrazole | —$SCH_3$ | |
| CO | Phenyl | Halo substituted alkoxy | Tetrazole | —$SCH_3$ | |
| CO | Phenyl | $CH_3$ | tetrazole | —$SCH_3$ | |
| CO | Phenyl | $CH_2CH_3$ | tetrazole | —$SCH_3$ | |
| CO | Phenyl | $CH_2CH_2CH_3$ | Tetrazole | —$SCH_3$ | |
| CO | Phenyl | $CH_2CH_2CH_2CH_3$ | Tetrazole | —$SCH_3$ | |
| CO | Phenyl | C5-C8 alkyl | Tetrazole | —$SCH_3$ | |
| CO | Phenyl | F | Tetrazole | —$SCH_3$ | |
| CO | Phenyl | F, F | tetrazole | —$SCH_3$ | |
| CO | Phenyl | F, Cl | tetrazole | —$SCH_3$ | |
| CO | Phenyl | Cl | Tetrazole | —$SCH_3$ | |
| CO | Phenyl | Cl, Cl | Tetrazole | —$SCH_3$ | |

TABLE 4-continued

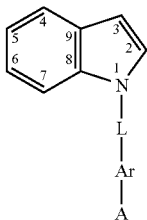

| L¹ | Ar | A | 3 | 5 | 6 |
|---|---|---|---|---|---|
| CO | Phenyl | -(1 to 4 linearly linked atom linker)-optionally subst. aryl | Tetrazole | —SCH₃ | |
| CO | Phenyl | -(1 to 4 linearly linked atom linker)-optionally subst. heteroaryl | Tetrazole | —SCH₃ | |
| CO | pyridinyl | | tetrazole | —SCH₃ | |
| CO | Pyridinyl | CF₃ | tetrazole | —SCH₃ | |
| CO | Pyridinyl | CH₂CF₃ | Tetrazole | —SCH₃ | |
| CO | Pyridinyl | Halo substituted alkyl | Tetrazole | —SCH₃ | |
| CO | Pyridinyl | OCH₃ | Tetrazole | —SCH₃ | |
| CO | Pyridinyl | OCH₂CH₃ | Tetrazole | —SCH₃ | |
| CO | Pyridinyl | OCH₂CH₂CH₃ | tetrazole | —SCH₃ | |
| CO | Pyridinyl | OCH₂CH₂CH₂CH₃ | tetrazole | —SCH₃ | |
| CO | Pyridinyl | OCH₂CH₂CH₂CH₂CH₃ | Tetrazole | —SCH₃ | |
| CO | Pyridinyl | C5-G8 alkoxy | Tetrazole | —SCH₃ | |
| CO | Pyridinyl | Halo substituted alkoxy | Tetrazole | —SCH₃ | |
| CO | Pyridinyl | CH₃ | Tetrazole | —SCH₃ | |
| CO | Pyridinyl | CH₂CH₃ | tetrazole | —SCH₃ | |
| CO | Pyridinyl | CH₂CH₂CH₃ | tetrazole | —SCH₃ | |
| CO | Pyridinyl | CH₂CH₂CH₂CH₃ | Tetrazole | —SCH₃ | |
| CO | Pyridinyl | C5-G8 alkyl | Tetrazole | —SCH₃ | |
| CO | Pyridinyl | F | Tetrazole | —SCH₃ | |
| CO | Pyridinyl | F, F | Tetrazole | —SCH₃ | |
| CO | Pyridinyl | F, Cl | tetrazole | —SCH₃ | |
| CO | Pyridinyl | Cl | tetrazole | —SCH₃ | |
| CO | Pyridinyl | Cl, Cl | Tetrazole | —SCH₃ | |
| CO | Pyridinyl | -(1 to 4 linearly linked atom linker)-optionally subst. aryl | Tetrazole | —SCH₃ | |
| CO | Pyridinyl | -(1 to 4 linearly linked atom linker)-optionally subst. heteroaryl | Tetrazole | —SCH₃ | |
| SO₂ | phenyl | | Tetrazole | —SCH₂CH₃ | |
| SO₂ | phenyl | CF₃ | tetrazole | —SCH₂CH₃ | |
| SO₂ | phenyl | CH₂CF₃ | tetrazole | —SCH₂CH₃ | |
| SO₂ | phenyl | Halo substituted alkyl | Tetrazole | —SCH₂CH₃ | |
| SO₂ | phenyl | OCH₃ | Tetrazole | —SCH₂CH₃ | |
| SO₂ | phenyl | OCH₂CH₃ | Tetrazole | —SCH₂CH₃ | |
| SO₂ | phenyl | OCH₂CH₂CH₃ | Tetrazole | —SCH₂CH₃ | |
| SO₂ | phenyl | OCH₂CH₂CH₂CH₃ | tetrazole | —SCH₂CH₃ | |
| SO₂ | phenyl | OCH₂CH₂CH₂CH₂CH₃ | tetrazole | —SCH₂CH₃ | |
| SO₂ | phenyl | C5-C8 alkoxy | Tetrazole | —SCH₂CH₃ | |
| SO₂ | phenyl | Halo substituted alkoxy | Tetrazole | —SCH₂CH₃ | |
| SO₂ | phenyl | CH₃ | Tetrazole | —SCH₂CH₃ | |
| SO₂ | phenyl | CH₂CH₃ | Tetrazole | —SCH₂CH₃ | |
| SO₂ | phenyl | CH₂CH₂CH₃ | tetrazole | —SCH₂CH₃ | |
| SO₂ | phenyl | CH₂CH₂CH₂CH₃ | tetrazole | —SCH₂CH₃ | |
| SO₂ | phenyl | C5-C8 alkyl | Tetrazole | —SCH₂CH₃ | |
| SO₂ | phenyl | F | Tetrazole | —SCH₂CH₃ | |
| SO₂ | phenyl | F, F | Tetrazole | —SCH₂CH₃ | |
| SO₂ | phenyl | F, Cl | Tetrazole | —SCH₂CH₃ | |
| SO₂ | phenyl | Cl | tetrazole | —SCH₂CH₃ | |
| SO₂ | phenyl | Cl, Cl | tetrazole | —SCH₂CH₃ | |
| SO₂ | phenyl | -(1 to 4 linearly linked atom linker)-optionally subst. aryl | Tetrazole | —SCH₂CH₃ | |
| SO₂ | phenyl | -(1 to 4 linearly linked atom linker)-optionally subst. heteroaryl | Tetrazole | —SCH₂CH₃ | |
| SO₂ | pyridinyl | | Tetrazole | —SCH₂CH₃ | |
| SO₂ | Pyridinyl | CF₃ | Tetrazole | —SCH₂CH₃ | |
| SO₂ | Pyridinyl | CH₂CF₃ | tetrazole | —SCH₂CH₃ | |

TABLE 4-continued

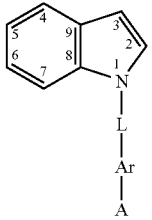

| L$^1$ | Ar | A | 3 | 5 | 6 |
|---|---|---|---|---|---|
| SO$_2$ | Pyridinyl | Halo substituted alkyl | tetrazole | —SCH$_2$CH$_3$ | |
| SO$_2$ | Pyridinyl | OCH$_3$ | Tetrazole | —SCH$_2$CH$_3$ | |
| SO$_2$ | Pyridinyl | OCH$_2$CH$_3$ | Tetrazole | —SCH$_2$CH$_3$ | |
| SO$_2$ | Pyridinyl | OCH$_2$CH$_2$CH$_3$ | Tetrazole | —SCH$_2$CH$_3$ | |
| SO$_2$ | Pyridinyl | OCH$_2$CH$_2$CH$_2$CH$_3$ | Tetrazole | —SCH$_2$CH$_3$ | |
| SO$_2$ | Pyridinyl | OCH$_2$CH$_2$CH$_2$CH$_2$CH$_3$ | tetrazole | —SCH$_2$CH$_3$ | |
| SO$_2$ | Pyridinyl | C5-C8 alkoxy | tetrazole | —SCH$_2$CH$_3$ | |
| SO$_2$ | Pyridinyl | Halo substituted alkoxy | Tetrazole | —SCH$_2$CH$_3$ | |
| SO$_2$ | Pyridinyl | CH$_3$ | Tetrazole | —SCH$_2$CH$_3$ | |
| SO$_2$ | Pyridinyl | CH$_2$CH$_3$ | Tetrazole | —SCH$_2$CH$_3$ | |
| SO$_2$ | Pyridinyl | CH$_2$CH$_2$CH$_3$ | Tetrazole | —SCH$_2$CH$_3$ | |
| SO$_2$ | Pyridinyl | CH$_2$CH$_2$CH$_2$CH$_3$ | tetrazole | —SCH$_2$CH$_3$ | |
| SO$_2$ | Pyridinyl | C5-C8 alkyl | tetrazole | —SCH$_2$CH$_3$ | |
| SO$_2$ | Pyridinyl | F | Tetrazole | —SCH$_2$CH$_3$ | |
| SO$_2$ | Pyridinyl | F, F | Tetrazole | —SCH$_2$CH$_3$ | |
| SO$_2$ | Pyridinyl | F, Cl | Tetrazole | —SCH$_2$CH$_3$ | |
| SO$_2$ | Pyridinyl | Cl | Tetrazole | —SCH$_2$CH$_3$ | |
| SO$_2$ | Pyridinyl | Cl, Cl | tetrazole | —SCH$_2$CH$_3$ | |
| SO$_2$ | Pyridinyl | -(1 to 4 linearly linked atom linker)-optionally subst. aryl | tetrazole | —SCH$_2$CH$_3$ | |
| SO$_2$ | Pyridinyl | -(1 to 4 linearly linked atom linker)-optionally subst. heteroaryl | Tetrazole | —SCH$_2$CH$_3$ | |
| CO | Phenyl | | Tetrazole | —SCH$_2$CH$_3$ | |
| CO | Phenyl | CF$_3$ | Tetrazole | —SCH$_2$CH$_3$ | |
| CO | Phenyl | CH$_2$CF$_3$ | Tetrazole | —SCH$_2$CH$_3$ | |
| CO | Phenyl | Halo substituted alkyl | tetrazole | —SCH$_2$CH$_3$ | |
| CO | Phenyl | OCH$_3$ | tetrazole | —SCH$_2$CH$_3$ | |
| CO | Phenyl | OCH$_2$CH$_3$ | Tetrazole | —SCH$_2$CH$_3$ | |
| CO | Phenyl | OCH$_2$CH$_2$CH$_3$ | Tetrazole | —SCH$_2$CH$_3$ | |
| CO | Phenyl | OCH$_2$CH$_2$CH$_2$CH$_3$ | Tetrazole | —SCH$_2$CH$_3$ | |
| CO | Phenyl | OCH$_2$CH$_2$CH$_2$CH$_2$CH$_3$ | Tetrazole | —SCH$_2$CH$_3$ | |
| CO | Phenyl | C5-C8 alkoxy | tetrazole | —SCH$_2$CH$_3$ | |
| CO | Phenyl | Halo substituted alkoxy | tetrazole | —SCH$_2$CH$_3$ | |
| CO | Phenyl | CH$_3$ | Tetrazole | —SCH$_2$CH$_3$ | |
| CO | Phenyl | CH$_2$CH$_3$ | Tetrazole | —SCH$_2$CH$_3$ | |
| CO | Phenyl | CH$_2$CH$_2$CH$_3$ | Tetrazole | —SCH$_2$CH$_3$ | |
| CO | Phenyl | CH$_2$CH$_2$CH$_2$CH$_3$ | Tetrazole | —SCH$_2$CH$_3$ | |
| CO | Phenyl | C5-C8 alkyl | tetrazole | —SCH$_2$CH$_3$ | |
| CO | Phenyl | F | tetrazole | —SCH$_2$CH$_3$ | |
| CO | Phenyl | F, F | Tetrazole | —SCH$_2$CH$_3$ | |
| CO | Phenyl | F, Cl | Tetrazole | —SCH$_2$CH$_3$ | |
| CO | Phenyl | Cl | Tetrazole | —SCH$_2$CH$_3$ | |
| CO | Phenyl | Cl, Cl | Tetrazole | —SCH$_2$CH$_3$ | |
| CO | Phenyl | -(1 to 4 linearly linked atom linker)-optionally subst. aryl | tetrazole | —SCH$_2$CH$_3$ | |
| CO | Phenyl | -(1 to 4 linearly linked atom linker)-optionally subst. heteroaryl | tetrazole | —SCH$_2$CH$_3$ | |
| CO | pyridinyl | | Tetrazole | —SCH$_2$CH$_3$ | |
| CO | Pyridinyl | CF$_3$ | Tetrazole | —SCH$_2$CH$_3$ | |
| CO | Pyridinyl | CH$_2$CF$_3$ | Tetrazole | —SCH$_2$CH$_3$ | |
| CO | Pyridinyl | Halo substituted alkyl | Tetrazole | —SCH$_2$CH$_3$ | |
| CO | Pyridinyl | OCH$_3$ | tetrazole | —SCH$_2$CH$_3$ | |
| CO | Pyridinyl | OCH$_2$CH$_3$ | tetrazole | —SCH$_2$CH$_3$ | |
| CO | Pyridinyl | OCH$_2$CH$_2$CH$_3$ | Tetrazole | —SCH$_2$CH$_3$ | |
| CO | Pyridinyl | OCH$_2$CH$_2$CH$_2$CH$_3$ | Tetrazole | —SCH$_2$CH$_3$ | |
| CO | Pyridinyl | OCH$_2$CH$_2$CH$_2$CH$_2$CH$_3$ | Tetrazole | —SCH$_2$CH$_3$ | |
| CO | Pyridinyl | C5-G8 alkoxy | Tetrazole | —SCH$_2$CH$_3$ | |
| CO | Pyridinyl | Halo substituted alkoxy | tetrazole | —SCH$_2$CH$_3$ | |
| CO | Pyridinyl | CH$_3$ | tetrazole | —SCH$_2$CH$_3$ | |

TABLE 4-continued

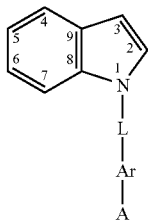

| L¹ | Ar | A | 3 | 5 | 6 |
|---|---|---|---|---|---|
| CO | Pyridinyl | CH₂CH₃ | Tetrazole | —SCH₂CH₃ | |
| CO | Pyridinyl | CH₂CH₂CH₃ | Tetrazole | —SCH₂CH₃ | |
| CO | Pyridinyl | CH₂CH₂CH₂CH₃ | Tetrazole | —SCH₂CH₃ | |
| CO | Pyridinyl | C5-G8 alkyl | Tetrazole | —SCH₂CH₃ | |
| CO | Pyridinyl | F | tetrazole | —SCH₂CH₃ | |
| CO | Pyridinyl | F, F | tetrazole | —SCH₂CH₃ | |
| CO | Pyridinyl | F, Cl | Tetrazole | —SCH₂CH₃ | |
| CO | Pyridinyl | Cl | Tetrazole | —SCH₂CH₃ | |
| CO | Pyridinyl | Cl, Cl | Tetrazole | —SCH₂CH₃ | |
| CO | Pyridinyl | -(1 to 4 linearly linked atom linker)-optionally subst. aryl | Tetrazole | —SCH₂CH₃ | |
| CO | Pyridinyl | -(1 to 4 linearly linked atom linker)-optionally subst. heteroaryl | tetrazole | —SCH₂CH₃ | |
| SO₂ | phenyl | | 3-hydroxy isoxazole | methoxy | |
| SO₂ | phenyl | CF₃ | 3-hydroxy isoxazole | methoxy | |
| SO₂ | phenyl | CH₂CF₃ | 3-hydroxy isoxazole | methoxy | |
| SO₂ | phenyl | Halo substituted alkyl | 3-hydroxy isoxazole | methoxy | |
| SO₂ | phenyl | OCH₃ | 3-hydroxy isoxazole | methoxy | |
| SO₂ | phenyl | OCH₂CH₃ | 3-hydroxy isoxazole | methoxy | |
| SO₂ | phenyl | OCH₂CH₂CH₃ | 3-hydroxy isoxazole | methoxy | |
| SO₂ | phenyl | OCH₂CH₂CH₂CH₃ | 3-hydroxy isoxazole | methoxy | |
| SO₂ | phenyl | OCH₂CH₂CH₂CH₂CH₃ | 3-hydroxy isoxazole | methoxy | |
| SO₂ | phenyl | C5-C8 alkoxy | 3-hydroxy isoxazole | methoxy | |
| SO₂ | phenyl | Halo substituted alkoxy | 3-hydroxy isoxazole | methoxy | |
| SO₂ | phenyl | CH₃ | 3-hydroxy isoxazole | methoxy | |
| SO₂ | phenyl | CH₂CH₃ | 3-hydroxy isoxazole | methoxy | |
| SO₂ | phenyl | CH₂CH₂CH₃ | 3-hydroxy isoxazole | methoxy | |
| SO₂ | phenyl | CH₂CH₂CH₂CH₃ | 3-hydroxy isoxazole | methoxy | |
| SO₂ | phenyl | C5-C8 alkyl | 3-hydroxy isoxazole | methoxy | |
| SO₂ | phenyl | F | 3-hydroxy isoxazole | methoxy | |
| SO₂ | phenyl | F, F | 3-hydroxy isoxazole | methoxy | |
| SO₂ | phenyl | F, Cl | 3-hydroxy isoxazole | methoxy | |
| SO₂ | phenyl | Cl | 3-hydroxy isoxazole | methoxy | |
| SO₂ | phenyl | Cl, Cl | 3-hydroxy isoxazole | methoxy | |
| SO₂ | phenyl | -(1 to 4 linearly linked atom linker)-optionally subst. aryl | 3-hydroxy isoxazole | methoxy | |
| SO₂ | phenyl | -(1 to 4 linearly linked atom linker)-optionally subst. heteroaryl | 3-hydroxy isoxazole | methoxy | |
| SO₂ | pyridinyl | | 3-hydroxy isoxazole | methoxy | |
| SO₂ | Pyridinyl | CF₃ | 3-hydroxy isoxazole | methoxy | |
| SO₂ | Pyridinyl | CH₂CF₃ | 3-hydroxy isoxazole | methoxy | |
| SO₂ | Pyridinyl | Halo substituted alkyl | 3-hydroxy isoxazole | methoxy | |
| SO₂ | Pyridinyl | OCH₃ | 3-hydroxy isoxazole | methoxy | |
| SO₂ | Pyridinyl | OCH₂CH₃ | 3-hydroxy isoxazole | methoxy | |
| SO₂ | Pyridinyl | OCH₂CH₂CH₃ | 3-hydroxy isoxazole | methoxy | |
| SO₂ | Pyridinyl | OCH₂CH₂CH₂CH₃ | 3-hydroxy isoxazole | methoxy | |
| SO₂ | Pyridinyl | OCH₂CH₂CH₂CH₂CH₃ | 3-hydroxy isoxazole | methoxy | |
| SO₂ | Pyridinyl | C5-C8 alkoxy | 3-hydroxy isoxazole | methoxy | |
| SO₂ | Pyridinyl | Halo substituted alkoxy | 3-hydroxy isoxazole | methoxy | |
| SO₂ | Pyridinyl | CH₃ | 3-hydroxy isoxazole | methoxy | |
| SO₂ | Pyridinyl | CH₂CH₃ | 3-hydroxy isoxazole | methoxy | |
| SO₂ | Pyridinyl | CH₂CH₂CH₃ | 3-hydroxy isoxazole | methoxy | |
| SO₂ | Pyridinyl | CH₂CH₂CH₂CH₃ | 3-hydroxy isoxazole | methoxy | |
| SO₂ | Pyridinyl | C5-C8 alkyl | 3-hydroxy isoxazole | methoxy | |
| SO₂ | Pyridinyl | F | 3-hydroxy isoxazole | methoxy | |
| SO₂ | Pyridinyl | F, F | 3-hydroxy isoxazole | methoxy | |
| SO₂ | Pyridinyl | F, Cl | 3-hydroxy isoxazole | methoxy | |
| SO₂ | Pyridinyl | Cl | 3-hydroxy isoxazole | methoxy | |
| SO₂ | Pyridinyl | Cl, Cl | 3-hydroxy isoxazole | methoxy | |

TABLE 4-continued

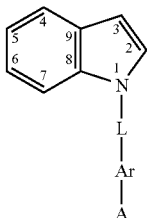

| L¹ | Ar | A | 3 | 5 | 6 |
|---|---|---|---|---|---|
| SO₂ | Pyridinyl | -(1 to 4 linearly linked atom linker)-optionally subst. aryl | 3-hydroxy isoxazole | methoxy | |
| SO₂ | Pyridinyl | -(1 to 4 linearly linked atom linker)-optionally subst. heteroaryl | 3-hydroxy isoxazole | methoxy | |
| CO | Phenyl | | 3-hydroxy isoxazole | methoxy | |
| CO | Phenyl | CF₃ | 3-hydroxy isoxazole | methoxy | |
| CO | Phenyl | CH₂CF₃ | 3-hydroxy isoxazole | methoxy | |
| CO | Phenyl | Halo substituted alkyl | 3-hydroxy isoxazole | methoxy | |
| CO | Phenyl | OCH₃ | 3-hydroxy isoxazole | methoxy | |
| CO | Phenyl | OCH₂CH₃ | 3-hydroxy isoxazole | methoxy | |
| CO | Phenyl | OCH₂CH₂CH₃ | 3-hydroxy isoxazole | methoxy | |
| CO | Phenyl | OCH₂CH₂CH₂CH₃ | 3-hydroxy isoxazole | methoxy | |
| CO | Phenyl | OCH₂CH₂CH₂CH₂CH₃ | 3-hydroxy isoxazole | methoxy | |
| CO | Phenyl | C5-C8 alkoxy | 3-hydroxy isoxazole | methoxy | |
| CO | Phenyl | Halo substituted alkoxy | 3-hydroxy isoxazole | methoxy | |
| CO | Phenyl | CH₃ | 3-hydroxy isoxazole | methoxy | |
| CO | Phenyl | CH₂CH₃ | 3-hydroxy isoxazole | methoxy | |
| CO | Phenyl | CH₂CH₂CH₃ | 3-hydroxy isoxazole | methoxy | |
| CO | Phenyl | CH₂CH₂CH₂CH₃ | 3-hydroxy isoxazole | methoxy | |
| CO | Phenyl | C5-C8 alkyl | 3-hydroxy isoxazole | methoxy | |
| CO | Phenyl | F | 3-hydroxy isoxazole | methoxy | |
| CO | Phenyl | F, F | 3-hydroxy isoxazole | methoxy | |
| CO | Phenyl | F, Cl | 3-hydroxy isoxazole | methoxy | |
| CO | Phenyl | Cl | 3-hydroxy isoxazole | methoxy | |
| CO | Phenyl | Cl, Cl | 3-hydroxy isoxazole | methoxy | |
| CO | Phenyl | -(1 to 4 linearly linked atom linker)-optionally subst. aryl | 3-hydroxy isoxazole | methoxy | |
| CO | Phenyl | -(1 to 4 linearly linked atom linker)-optionally subst. heteroaryl | 3-hydroxy isoxazole | methoxy | |
| CO | pyridinyl | | 3-hydroxy isoxazole | methoxy | |
| CO | Pyridinyl | CF₃ | 3-hydroxy isoxazole | methoxy | |
| CO | Pyridinyl | CH₂CF₃ | 3-hydroxy isoxazole | methoxy | |
| CO | Pyridinyl | Halo substituted alkyl | 3-hydroxy isoxazole | methoxy | |
| CO | Pyridinyl | OCH₃ | 3-hydroxy isoxazole | methoxy | |
| CO | Pyridinyl | OCH₂CH₃ | 3-hydroxy isoxazole | methoxy | |
| CO | Pyridinyl | OCH₂CH₂CH₃ | 3-hydroxy isoxazole | methoxy | |
| CO | Pyridinyl | OCH₂CH₂CH₂CH₃ | 3-hydroxy isoxazole | methoxy | |
| CO | Pyridinyl | OCH₂CH₂CH₂CH₂CH₃ | 3-hydroxy isoxazole | methoxy | |
| CO | Pyridinyl | C5-G8 alkoxy | 3-hydroxy isoxazole | methoxy | |
| CO | Pyridinyl | Halo substituted alkoxy | 3-hydroxy isoxazole | methoxy | |
| CO | Pyridinyl | CH₃ | 3-hydroxy isoxazole | methoxy | |
| CO | Pyridinyl | CH₂CH₃ | 3-hydroxy isoxazole | methoxy | |
| CO | Pyridinyl | CH₂CH₂CH₃ | 3-hydroxy isoxazole | methoxy | |
| CO | Pyridinyl | CH₂CH₂CH₂CH₃ | 3-hydroxy isoxazole | methoxy | |
| CO | Pyridinyl | C5-G8 alkyl | 3-hydroxy isoxazole | methoxy | |
| CO | Pyridinyl | F | 3-hydroxy isoxazole | methoxy | |
| CO | Pyridinyl | F, F | 3-hydroxy isoxazole | methoxy | |
| CO | Pyridinyl | F, Cl | 3-hydroxy isoxazole | methoxy | |
| CO | Pyridinyl | Cl | 3-hydroxy isoxazole | methoxy | |
| CO | Pyridinyl | Cl, Cl | 3-hydroxy isoxazole | methoxy | |
| CO | Pyridinyl | -(1 to 4 linearly linked atom linker)-optionally subst. aryl | 3-hydroxy isoxazole | methoxy | |
| CO | Pyridinyl | -(1 to 4 linearly linked atom linker)-optionally subst. heteroaryl | 3-hydroxy isoxazole | methoxy | |
| SO₂ | phenyl | | 3-hydroxy isoxazole | ethoxy | |
| SO₂ | phenyl | CF₃ | 3-hydroxy isoxazole | ethoxy | |
| SO₂ | phenyl | CH₂CF₃ | 3-hydroxy isoxazole | ethoxy | |

TABLE 4-continued

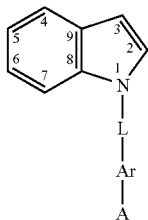

| $L^1$ | Ar | A | 3 | 5 | 6 |
|---|---|---|---|---|---|
| $SO_2$ | phenyl | Halo substituted alkyl | 3-hydroxy isoxazole | ethoxy | |
| $SO_2$ | phenyl | $OCH_3$ | 3-hydroxy isoxazole | ethoxy | |
| $SO_2$ | phenyl | $OCH_2CH_3$ | 3-hydroxy isoxazole | ethoxy | |
| $SO_2$ | phenyl | $OCH_2CH_2CH_3$ | 3-hydroxy isoxazole | ethoxy | |
| $SO_2$ | phenyl | $OCH_2CH_2CH_2CH_3$ | 3-hydroxy isoxazole | ethoxy | |
| $SO_2$ | phenyl | $OCH_2CH_2CH_2CH_2CH_3$ | 3-hydroxy isoxazole | ethoxy | |
| $SO_2$ | phenyl | C5-C8 alkoxy | 3-hydroxy isoxazole | ethoxy | |
| $SO_2$ | phenyl | Halo substituted alkoxy | 3-hydroxy isoxazole | ethoxy | |
| $SO_2$ | phenyl | $CH_3$ | 3-hydroxy isoxazole | ethoxy | |
| $SO_2$ | phenyl | $CH_2CH_3$ | 3-hydroxy isoxazole | ethoxy | |
| $SO_2$ | phenyl | $CH_2CH_2CH_3$ | 3-hydroxy isoxazole | ethoxy | |
| $SO_2$ | phenyl | $CH_2CH_2CH_2CH_3$ | 3-hydroxy isoxazole | ethoxy | |
| $SO_2$ | phenyl | C5-C8 alkyl | 3-hydroxy isoxazole | ethoxy | |
| $SO_2$ | phenyl | F | 3-hydroxy isoxazole | ethoxy | |
| $SO_2$ | phenyl | F, F | 3-hydroxy isoxazole | ethoxy | |
| $SO_2$ | phenyl | F, Cl | 3-hydroxy isoxazole | ethoxy | |
| $SO_2$ | phenyl | Cl | 3-hydroxy isoxazole | ethoxy | |
| $SO_2$ | phenyl | Cl, Cl | 3-hydroxy isoxazole | ethoxy | |
| $SO_2$ | phenyl | -(1 to 4 linearly linked atom linker)-optionally subst. aryl | 3-hydroxy isoxazole | ethoxy | |
| $SO_2$ | phenyl | -(1 to 4 linearly linked atom linker)-optionally subst. heteroaryl | 3-hydroxy isoxazole | ethoxy | |
| $SO_2$ | pyridinyl | | 3-hydroxy isoxazole | ethoxy | |
| $SO_2$ | Pyridinyl | $CF_3$ | 3-hydroxy isoxazole | ethoxy | |
| $SO_2$ | Pyridinyl | $CH_2CF_3$ | 3-hydroxy isoxazole | ethoxy | |
| $SO_2$ | Pyridinyl | Halo substituted alkyl | 3-hydroxy isoxazole | ethoxy | |
| $SO_2$ | Pyridinyl | $OCH_3$ | 3-hydroxy isoxazole | ethoxy | |
| $SO_2$ | Pyridinyl | $OCH_2CH_3$ | 3-hydroxy isoxazole | ethoxy | |
| $SO_2$ | Pyridinyl | $OCH_2CH_2CH_3$ | 3-hydroxy isoxazole | ethoxy | |
| $SO_2$ | Pyridinyl | $OCH_2CH_2CH_2CH_3$ | 3-hydroxy isoxazole | ethoxy | |
| $SO_2$ | Pyridinyl | $OCH_2CH_2CH_2CH_2CH_3$ | 3-hydroxy isoxazole | ethoxy | |
| $SO_2$ | Pyridinyl | C5-C8 alkoxy | 3-hydroxy isoxazole | ethoxy | |
| $SO_2$ | Pyridinyl | Halo substituted alkoxy | 3-hydroxy isoxazole | ethoxy | |
| $SO_2$ | Pyridinyl | $CH_3$ | 3-hydroxy isoxazole | ethoxy | |
| $SO_2$ | Pyridinyl | $CH_2CH_3$ | 3-hydroxy isoxazole | ethoxy | |
| $SO_2$ | Pyridinyl | $CH_2CH_2CH_3$ | 3-hydroxy isoxazole | ethoxy | |
| $SO_2$ | Pyridinyl | $CH_2CH_2CH_2CH_3$ | 3-hydroxy isoxazole | ethoxy | |
| $SO_2$ | Pyridinyl | C5-C8 alkyl | 3-hydroxy isoxazole | ethoxy | |
| $SO_2$ | Pyridinyl | F | 3-hydroxy isoxazole | ethoxy | |
| $SO_2$ | Pyridinyl | F, F | 3-hydroxy isoxazole | ethoxy | |
| $SO_2$ | Pyridinyl | F, Cl | 3-hydroxy isoxazole | ethoxy | |
| $SO_2$ | Pyridinyl | Cl | 3-hydroxy isoxazole | ethoxy | |
| $SO_2$ | Pyridinyl | Cl, Cl | 3-hydroxy isoxazole | ethoxy | |
| $SO_2$ | Pyridinyl | -(1 to 4 linearly linked atom linker)-optionally subst. aryl | 3-hydroxy isoxazole | ethoxy | |
| $SO_2$ | Pyridinyl | -(1 to 4 linearly linked atom linker)-optionally subst. heteroaryl | 3-hydroxy isoxazole | ethoxy | |
| CO | Phenyl | | 3-hydroxy isoxazole | ethoxy | |
| CO | Phenyl | $CF_3$ | 3-hydroxy isoxazole | ethoxy | |
| CO | Phenyl | $CH_2CF_3$ | 3-hydroxy isoxazole | ethoxy | |
| CO | Phenyl | Halo substituted alkyl | 3-hydroxy isoxazole | ethoxy | |
| CO | Phenyl | $OCH_3$ | 3-hydroxy isoxazole | ethoxy | |
| CO | Phenyl | $OCH_2CH_3$ | 3-hydroxy isoxazole | ethoxy | |
| CO | Phenyl | $OCH_2CH_2CH_3$ | 3-hydroxy isoxazole | ethoxy | |
| CO | Phenyl | $OCH_2CH_2CH_2CH_3$ | 3-hydroxy isoxazole | ethoxy | |
| CO | Phenyl | $OCH_2CH_2CH_2CH_2CH_3$ | 3-hydroxy isoxazole | ethoxy | |
| CO | Phenyl | C5-C8 alkoxy | 3-hydroxy isoxazole | ethoxy | |
| CO | Phenyl | Halo substituted alkoxy | 3-hydroxy isoxazole | ethoxy | |
| CO | Phenyl | $CH_3$ | 3-hydroxy isoxazole | ethoxy | |

TABLE 4-continued

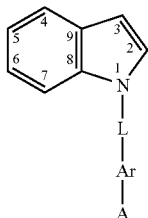

| L¹ | Ar | A | 3 | 5 | 6 |
|---|---|---|---|---|---|
| CO | Phenyl | $CH_2CH_3$ | 3-hydroxy isoxazole | ethoxy | |
| CO | Phenyl | $CH_2CH_2CH_3$ | 3-hydroxy isoxazole | ethoxy | |
| CO | Phenyl | $CH_2CH_2CH_2CH_3$ | 3-hydroxy isoxazole | ethoxy | |
| CO | Phenyl | C5-C8 alkyl | 3-hydroxy isoxazole | ethoxy | |
| CO | Phenyl | F | 3-hydroxy isoxazole | ethoxy | |
| CO | Phenyl | F, F | 3-hydroxy isoxazole | ethoxy | |
| CO | Phenyl | F, Cl | 3-hydroxy isoxazole | ethoxy | |
| CO | Phenyl | Cl | 3-hydroxy isoxazole | ethoxy | |
| CO | Phenyl | Cl, Cl | 3-hydroxy isoxazole | ethoxy | |
| CO | Phenyl | -(1 to 4 linearly linked atom linker)-optionally subst. aryl | 3-hydroxy isoxazole | ethoxy | |
| CO | Phenyl | -(1 to 4 linearly linked atom linker)-optionally subst. heteroaryl | 3-hydroxy isoxazole | ethoxy | |
| CO | pyridinyl | | 3-hydroxy isoxazole | ethoxy | |
| CO | Pyridinyl | $CF_3$ | 3-hydroxy isoxazole | ethoxy | |
| CO | Pyridinyl | $CH_2CF_3$ | 3-hydroxy isoxazole | ethoxy | |
| CO | Pyridinyl | Halo substituted alkyl | 3-hydroxy isoxazole | ethoxy | |
| CO | Pyridinyl | $OCH_3$ | 3-hydroxy isoxazole | ethoxy | |
| CO | Pyridinyl | $OCH_2CH_3$ | 3-hydroxy isoxazole | ethoxy | |
| CO | Pyridinyl | $OCH_2CH_2CH_3$ | 3-hydroxy isoxazole | ethoxy | |
| CO | Pyridinyl | $OCH_2CH_2CH_2CH_3$ | 3-hydroxy isoxazole | ethoxy | |
| CO | Pyridinyl | $OCH_2CH_2CH_2CH_2CH_3$ | 3-hydroxy isoxazole | ethoxy | |
| CO | Pyridinyl | C5-G8 alkoxy | 3-hydroxy isoxazole | ethoxy | |
| CO | Pyridinyl | Halo substituted alkoxy | 3-hydroxy isoxazole | ethoxy | |
| CO | Pyridinyl | $CH_3$ | 3-hydroxy isoxazole | ethoxy | |
| CO | Pyridinyl | $CH_2CH_3$ | 3-hydroxy isoxazole | ethoxy | |
| CO | Pyridinyl | $CH_2CH_2CH_3$ | 3-hydroxy isoxazole | ethoxy | |
| CO | Pyridinyl | $CH_2CH_2CH_2CH_3$ | 3-hydroxy isoxazole | ethoxy | |
| CO | Pyridinyl | C5-G8 alkyl | 3-hydroxy isoxazole | ethoxy | |
| CO | Pyridinyl | F | 3-hydroxy isoxazole | ethoxy | |
| CO | Pyridinyl | F, F | 3-hydroxy isoxazole | ethoxy | |
| CO | Pyridinyl | F, Cl | 3-hydroxy isoxazole | ethoxy | |
| CO | Pyridinyl | Cl | 3-hydroxy isoxazole | ethoxy | |
| CO | Pyridinyl | Cl, Cl | 3-hydroxy isoxazole | ethoxy | |
| CO | Pyridinyl | -(1 to 4 linearly linked atom linker)-optionally subst. aryl | 3-hydroxy isoxazole | ethoxy | |
| CO | Pyridinyl | -(1 to 4 linearly linked atom linker)-optionally subst. heteroaryl | 3-hydroxy isoxazole | ethoxy | |
| $SO_2$ | phenyl | | 3-hydroxy isoxazole | propoxy | |
| $SO_2$ | phenyl | $CF_3$ | 3-hydroxy isoxazole | propoxy | |
| $SO_2$ | phenyl | $CH_2CF_3$ | 3-hydroxy isoxazole | propoxy | |
| $SO_2$ | phenyl | Halo substituted alkyl | 3-hydroxy isoxazole | propoxy | |
| $SO_2$ | phenyl | $OCH_3$ | 3-hydroxy isoxazole | propoxy | |
| $SO_2$ | phenyl | $OCH_2CH_3$ | 3-hydroxy isoxazole | propoxy | |
| $SO_2$ | phenyl | $OCH_2CH_2CH_3$ | 3-hydroxy isoxazole | propoxy | |
| $SO_2$ | phenyl | $OCH_2CH_2CH_2CH_3$ | 3-hydroxy isoxazole | propoxy | |
| $SO_2$ | phenyl | $OCH_2CH_2CH_2CH_2CH_3$ | 3-hydroxy isoxazole | propoxy | |
| $SO_2$ | phenyl | C5-C8 alkoxy | 3-hydroxy isoxazole | propoxy | |
| $SO_2$ | phenyl | Halo substituted alkoxy | 3-hydroxy isoxazole | propoxy | |
| $SO_2$ | phenyl | $CH_3$ | 3-hydroxy isoxazole | propoxy | |
| $SO_2$ | phenyl | $CH_2CH_3$ | 3-hydroxy isoxazole | propoxy | |
| $SO_2$ | phenyl | $CH_2CH_2CH_3$ | 3-hydroxy isoxazole | propoxy | |
| $SO_2$ | phenyl | $CH_2CH_2CH_2CH_3$ | 3-hydroxy isoxazole | propoxy | |
| $SO_2$ | phenyl | C5-C8 alkyl | 3-hydroxy isoxazole | propoxy | |
| $SO_2$ | phenyl | F | 3-hydroxy isoxazole | propoxy | |
| $SO_2$ | phenyl | F, F | 3-hydroxy isoxazole | propoxy | |
| $SO_2$ | phenyl | F, Cl | 3-hydroxy isoxazole | propoxy | |
| $SO_2$ | phenyl | Cl | 3-hydroxy isoxazole | propoxy | |
| $SO_2$ | phenyl | Cl, Cl | 3-hydroxy isoxazole | propoxy | |

TABLE 4-continued

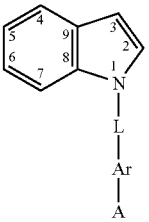

| L¹ | Ar | A | 3 | 5 | 6 |
|---|---|---|---|---|---|
| SO₂ | phenyl | -(1 to 4 linearly linked atom linker)-optionally subst. aryl | 3-hydroxy isoxazole | propoxy | |
| SO₂ | phenyl | -(1 to 4 linearly linked atom linker)-optionally subst. heteroaryl | 3-hydroxy isoxazole | propoxy | |
| SO₂ | pyridinyl | | 3-hydroxy isoxazole | propoxy | |
| SO₂ | Pyridinyl | CF₃ | 3-hydroxy isoxazole | propoxy | |
| SO₂ | Pyridinyl | CH₂CF₃ | 3-hydroxy isoxazole | propoxy | |
| SO₂ | Pyridinyl | Halo substituted alkyl | 3-hydroxy isoxazole | propoxy | |
| SO₂ | Pyridinyl | OCH₃ | 3-hydroxy isoxazole | propoxy | |
| SO₂ | Pyridinyl | OCH₂CH₃ | 3-hydroxy isoxazole | propoxy | |
| SO₂ | Pyridinyl | OCH₂CH₂CH₃ | 3-hydroxy isoxazole | propoxy | |
| SO₂ | Pyridinyl | OCH₂CH₂CH₂CH₃ | 3-hydroxy isoxazole | propoxy | |
| SO₂ | Pyridinyl | OCH₂CH₂CH₂CH₂CH₃ | 3-hydroxy isoxazole | propoxy | |
| SO₂ | Pyridinyl | C5-C8 alkoxy | 3-hydroxy isoxazole | propoxy | |
| SO₂ | Pyridinyl | Halo substituted alkoxy | 3-hydroxy isoxazole | propoxy | |
| SO₂ | Pyridinyl | CH₃ | 3-hydroxy isoxazole | propoxy | |
| SO₂ | Pyridinyl | CH₂CH₃ | 3-hydroxy isoxazole | propoxy | |
| SO₂ | Pyridinyl | CH₂CH₂CH₃ | 3-hydroxy isoxazole | propoxy | |
| SO₂ | Pyridinyl | CH₂CH₂CH₂CH₃ | 3-hydroxy isoxazole | propoxy | |
| SO₂ | Pyridinyl | C5-C8 alkyl | 3-hydroxy isoxazole | propoxy | |
| SO₂ | Pyridinyl | F | 3-hydroxy isoxazole | propoxy | |
| SO₂ | Pyridinyl | F, F | 3-hydroxy isoxazole | propoxy | |
| SO₂ | Pyridinyl | F, Cl | 3-hydroxy isoxazole | propoxy | |
| SO₂ | Pyridinyl | Cl | 3-hydroxy isoxazole | propoxy | |
| SO₂ | Pyridinyl | Cl, Cl | 3-hydroxy isoxazole | propoxy | |
| SO₂ | Pyridinyl | -(1 to 4 linearly linked atom linker)-optionally subst. aryl | 3-hydroxy isoxazole | propoxy | |
| SO₂ | Pyridinyl | -(1 to 4 linearly linked atom linker)-optionally subst. heteroaryl | 3-hydroxy isoxazole | propoxy | |
| CO | Phenyl | | 3-hydroxy isoxazole | propoxy | |
| CO | Phenyl | CF₃ | 3-hydroxy isoxazole | propoxy | |
| CO | Phenyl | CH₂CF₃ | 3-hydroxy isoxazole | propoxy | |
| CO | Phenyl | Halo substituted alkyl | 3-hydroxy isoxazole | propoxy | |
| CO | Phenyl | OCH₃ | 3-hydroxy isoxazole | propoxy | |
| CO | Phenyl | OCH₂CH₃ | 3-hydroxy isoxazole | propoxy | |
| CO | Phenyl | OCH₂CH₂CH₃ | 3-hydroxy isoxazole | propoxy | |
| CO | Phenyl | OCH₂CH₂CH₂CH₃ | 3-hydroxy isoxazole | propoxy | |
| CO | Phenyl | OCH₂CH₂CH₂CH₂CH₃ | 3-hydroxy isoxazole | propoxy | |
| CO | Phenyl | C5-C8 alkoxy | 3-hydroxy isoxazole | propoxy | |
| CO | Phenyl | Halo substituted alkoxy | 3-hydroxy isoxazole | propoxy | |
| CO | Phenyl | CH₃ | 3-hydroxy isoxazole | propoxy | |
| CO | Phenyl | CH₂CH₃ | 3-hydroxy isoxazole | propoxy | |
| CO | Phenyl | CH₂CH₂CH₃ | 3-hydroxy isoxazole | propoxy | |
| CO | Phenyl | CH₂CH₂CH₂CH₃ | 3-hydroxy isoxazole | propoxy | |
| CO | Phenyl | C5-C8 alkyl | 3-hydroxy isoxazole | propoxy | |
| CO | Phenyl | F | 3-hydroxy isoxazole | propoxy | |
| CO | Phenyl | F, F | 3-hydroxy isoxazole | propoxy | |
| CO | Phenyl | F, Cl | 3-hydroxy isoxazole | propoxy | |
| CO | Phenyl | Cl | 3-hydroxy isoxazole | propoxy | |
| CO | Phenyl | Cl, Cl | 3-hydroxy isoxazole | propoxy | |
| CO | Phenyl | -(1 to 4 linearly linked atom linker)-optionally subst. aryl | 3-hydroxy isoxazole | propoxy | |
| CO | Phenyl | -(1 to 4 linearly linked atom linker)-optionally subst. heteroaryl | 3-hydroxy isoxazole | propoxy | |
| CO | pyridinyl | | 3-hydroxy isoxazole | propoxy | |
| CO | Pyridinyl | CF₃ | 3-hydroxy isoxazole | propoxy | |
| CO | Pyridinyl | CH₂CF₃ | 3-hydroxy isoxazole | propoxy | |

TABLE 4-continued

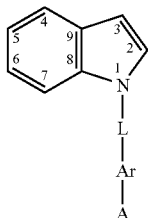

| L¹ | Ar | A | 3 | 5 | 6 |
|---|---|---|---|---|---|
| CO | Pyridinyl | Halo substituted alkyl | 3-hydroxy isoxazole | propoxy | |
| CO | Pyridinyl | OCH₃ | 3-hydroxy isoxazole | propoxy | |
| CO | Pyridinyl | OCH₂CH₃ | 3-hydroxy isoxazole | propoxy | |
| CO | Pyridinyl | OCH₂CH₂CH₃ | 3-hydroxy isoxazole | propoxy | |
| CO | Pyridinyl | OCH₂CH₂CH₂CH₃ | 3-hydroxy isoxazole | propoxy | |
| CO | Pyridinyl | OCH₂CH₂CH₂CH₂CH₃ | 3-hydroxy isoxazole | propoxy | |
| CO | Pyridinyl | C5-G8 alkoxy | 3-hydroxy isoxazole | propoxy | |
| CO | Pyridinyl | Halo substituted alkoxy | 3-hydroxy isoxazole | propoxy | |
| CO | Pyridinyl | CH₃ | 3-hydroxy isoxazole | propoxy | |
| CO | Pyridinyl | CH₂CH₃ | 3-hydroxy isoxazole | propoxy | |
| CO | Pyridinyl | CH₂CH₂CH₃ | 3-hydroxy isoxazole | propoxy | |
| CO | Pyridinyl | CH₂CH₂CH₂CH₃ | 3-hydroxy isoxazole | propoxy | |
| CO | Pyridinyl | C5-G8 alkyl | 3-hydroxy isoxazole | propoxy | |
| CO | Pyridinyl | F | 3-hydroxy isoxazole | propoxy | |
| CO | Pyridinyl | F, F | 3-hydroxy isoxazole | propoxy | |
| CO | Pyridinyl | F, Cl | 3-hydroxy isoxazole | propoxy | |
| CO | Pyridinyl | Cl | 3-hydroxy isoxazole | propoxy | |
| CO | Pyridinyl | Cl, Cl | 3-hydroxy isoxazole | propoxy | |
| CO | Pyridinyl | -(1 to 4 linearly linked atom linker)-optionally subst. aryl | 3-hydroxy isoxazole | propoxy | |
| CO | Pyridinyl | -(1 to 4 linearly linked atom linker)-optionally subst. heteroaryl | 3-hydroxy isoxazole | propoxy | |
| SO₂ | phenyl | | 3-hydroxy isoxazole | —SCH₃ | |
| SO₂ | phenyl | CF₃ | 3-hydroxy isoxazole | —SCH₃ | |
| SO₂ | phenyl | CH₂CF₃ | 3-hydroxy isoxazole | —SCH₃ | |
| SO₂ | phenyl | Halo substituted alkyl | 3-hydroxy isoxazole | —SCH₃ | |
| SO₂ | phenyl | OCH₃ | 3-hydroxy isoxazole | —SCH₃ | |
| SO₂ | phenyl | OCH₂CH₃ | 3-hydroxy isoxazole | —SCH₃ | |
| SO₂ | phenyl | OCH₂CH₂CH₃ | 3-hydroxy isoxazole | —SCH₃ | |
| SO₂ | phenyl | OCH₂CH₂CH₂CH₃ | 3-hydroxy isoxazole | —SCH₃ | |
| SO₂ | phenyl | OCH₂CH₂CH₂CH₂CH₃ | 3-hydroxy isoxazole | —SCH₃ | |
| SO₂ | phenyl | C5-C8 alkoxy | 3-hydroxy isoxazole | —SCH₃ | |
| SO₂ | phenyl | Halo substituted alkoxy | 3-hydroxy isoxazole | —SCH₃ | |
| SO₂ | phenyl | CH₃ | 3-hydroxy isoxazole | —SCH₃ | |
| SO₂ | phenyl | CH₂CH₃ | 3-hydroxy isoxazole | —SCH₃ | |
| SO₂ | phenyl | CH₂CH₂CH₃ | 3-hydroxy isoxazole | —SCH₃ | |
| SO₂ | phenyl | CH₂CH₂CH₂CH₃ | 3-hydroxy isoxazole | —SCH₃ | |
| SO₂ | phenyl | C5-C8 alkyl | 3-hydroxy isoxazole | —SCH₃ | |
| SO₂ | phenyl | F | 3-hydroxy isoxazole | —SCH₃ | |
| SO₂ | phenyl | F, F | 3-hydroxy isoxazole | —SCH₃ | |
| SO₂ | phenyl | F, Cl | 3-hydroxy isoxazole | —SCH₃ | |
| SO₂ | phenyl | Cl | 3-hydroxy isoxazole | —SCH₃ | |
| SO₂ | phenyl | Cl, Cl | 3-hydroxy isoxazole | —SCH₃ | |
| SO₂ | phenyl | -(1 to 4 linearly linked atom linker)-optionally subst. aryl | 3-hydroxy isoxazole | —SCH₃ | |
| SO₂ | phenyl | -(1 to 4 linearly linked atom linker)-optionally subst. heteroaryl | 3-hydroxy isoxazole | —SCH₃ | |
| SO₂ | pyridinyl | | 3-hydroxy isoxazole | —SCH₃ | |
| SO₂ | Pyridinyl | CF₃ | 3-hydroxy isoxazole | —SCH₃ | |
| SO₂ | Pyridinyl | CH₂CF₃ | 3-hydroxy isoxazole | —SCH₃ | |
| SO₂ | Pyridinyl | Halo substituted alkyl | 3-hydroxy isoxazole | —SCH₃ | |
| SO₂ | Pyridinyl | OCH₃ | 3-hydroxy isoxazole | —SCH₃ | |
| SO₂ | Pyridinyl | OCH₂CH₃ | 3-hydroxy isoxazole | —SCH₃ | |
| SO₂ | Pyridinyl | OCH₂CH₂CH₃ | 3-hydroxy isoxazole | —SCH₃ | |
| SO₂ | Pyridinyl | OCH₂CH₂CH₂CH₃ | 3-hydroxy isoxazole | —SCH₃ | |
| SO₂ | Pyridinyl | OCH₂CH₂CH₂CH₂CH₃ | 3-hydroxy isoxazole | —SCH₃ | |
| SO₂ | Pyridinyl | C5-C8 alkoxy | 3-hydroxy isoxazole | —SCH₃ | |
| SO₂ | Pyridinyl | Halo substituted alkoxy | 3-hydroxy isoxazole | —SCH₃ | |
| SO₂ | Pyridinyl | CH₃ | 3-hydroxy isoxazole | —SCH₃ | |

TABLE 4-continued

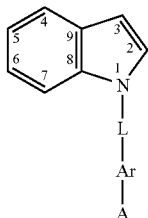

| $L^1$ | Ar | A | 3 | 5 | 6 |
|---|---|---|---|---|---|
| SO$_2$ | Pyridinyl | CH$_2$CH$_3$ | 3-hydroxy isoxazole | —SCH$_3$ | |
| SO$_2$ | Pyridinyl | CH$_2$CH$_2$CH$_3$ | 3-hydroxy isoxazole | —SCH$_3$ | |
| SO$_2$ | Pyridinyl | CH$_2$CH$_2$CH$_2$CH$_3$ | 3-hydroxy isoxazole | —SCH$_3$ | |
| SO$_2$ | Pyridinyl | C5-C8 alkyl | 3-hydroxy isoxazole | —SCH$_3$ | |
| SO$_2$ | Pyridinyl | F | 3-hydroxy isoxazole | —SCH$_3$ | |
| SO$_2$ | Pyridinyl | F, F | 3-hydroxy isoxazole | —SCH$_3$ | |
| SO$_2$ | Pyridinyl | F, Cl | 3-hydroxy isoxazole | —SCH$_3$ | |
| SO$_2$ | Pyridinyl | Cl | 3-hydroxy isoxazole | —SCH$_3$ | |
| SO$_2$ | Pyridinyl | Cl, Cl | 3-hydroxy isoxazole | —SCH$_3$ | |
| SO$_2$ | Pyridinyl | -(1 to 4 linearly linked atom linker)-optionally subst. aryl | 3-hydroxy isoxazole | —SCH$_3$ | |
| SO$_2$ | Pyridinyl | -(1 to 4 linearly linked atom linker)-optionally subst. heteroaryl | 3-hydroxy isoxazole | —SCH$_3$ | |
| CO | Phenyl | | 3-hydroxy isoxazole | —SCH$_3$ | |
| CO | Phenyl | CF$_3$ | 3-hydroxy isoxazole | —SCH$_3$ | |
| CO | Phenyl | CH$_2$CF$_3$ | 3-hydroxy isoxazole | —SCH$_3$ | |
| CO | Phenyl | Halo substituted alkyl | 3-hydroxy isoxazole | —SCH$_3$ | |
| CO | Phenyl | OCH$_3$ | 3-hydroxy isoxazole | —SCH$_3$ | |
| CO | Phenyl | OCH$_2$CH$_3$ | 3-hydroxy isoxazole | —SCH$_3$ | |
| CO | Phenyl | OCH$_2$CH$_2$CH$_3$ | 3-hydroxy isoxazole | —SCH$_3$ | |
| CO | Phenyl | OCH$_2$CH$_2$CH$_2$CH$_3$ | 3-hydroxy isoxazole | —SCH$_3$ | |
| CO | Phenyl | OCH$_2$CH$_2$CH$_2$CH$_2$CH$_3$ | 3-hydroxy isoxazole | —SCH$_3$ | |
| CO | Phenyl | C5-C8 alkoxy | 3-hydroxy isoxazole | —SCH$_3$ | |
| CO | Phenyl | Halo substituted alkoxy | 3-hydroxy isoxazole | —SCH$_3$ | |
| CO | Phenyl | CH$_3$ | 3-hydroxy isoxazole | —SCH$_3$ | |
| CO | Phenyl | CH$_2$CH$_3$ | 3-hydroxy isoxazole | —SCH$_3$ | |
| CO | Phenyl | CH$_2$CH$_2$CH$_3$ | 3-hydroxy isoxazole | —SCH$_3$ | |
| CO | Phenyl | CH$_2$CH$_2$CH$_2$CH$_3$ | 3-hydroxy isoxazole | —SCH$_3$ | |
| CO | Phenyl | C5-C8 alkyl | 3-hydroxy isoxazole | —SCH$_3$ | |
| CO | Phenyl | F | 3-hydroxy isoxazole | —SCH$_3$ | |
| CO | Phenyl | F, F | 3-hydroxy isoxazole | —SCH$_3$ | |
| CO | Phenyl | F, Cl | 3-hydroxy isoxazole | —SCH$_3$ | |
| CO | Phenyl | Cl | 3-hydroxy isoxazole | —SCH$_3$ | |
| CO | Phenyl | Cl, Cl | 3-hydroxy isoxazole | —SCH$_3$ | |
| CO | Phenyl | -(1 to 4 linearly linked atom linker)-optionally subst. aryl | 3-hydroxy isoxazole | —SCH$_3$ | |
| CO | Phenyl | -(1 to 4 linearly linked atom linker)-optionally subst. heteroaryl | 3-hydroxy isoxazole | —SCH$_3$ | |
| CO | pyridinyl | | 3-hydroxy isoxazole | —SCH$_3$ | |
| CO | Pyridinyl | CF$_3$ | 3-hydroxy isoxazole | —SCH$_3$ | |
| CO | Pyridinyl | CH$_2$CF$_3$ | 3-hydroxy isoxazole | —SCH$_3$ | |
| CO | Pyridinyl | Halo substituted alkyl | 3-hydroxy isoxazole | —SCH$_3$ | |
| CO | Pyridinyl | OCH$_3$ | 3-hydroxy isoxazole | —SCH$_3$ | |
| CO | Pyridinyl | OCH$_2$CH$_3$ | 3-hydroxy isoxazole | —SCH$_3$ | |
| CO | Pyridinyl | OCH$_2$CH$_2$CH$_3$ | 3-hydroxy isoxazole | —SCH$_3$ | |
| CO | Pyridinyl | OCH$_2$CH$_2$CH$_2$CH$_3$ | 3-hydroxy isoxazole | —SCH$_3$ | |
| CO | Pyridinyl | OCH$_2$CH$_2$CH$_2$CH$_2$CH$_3$ | 3-hydroxy isoxazole | —SCH$_3$ | |
| CO | Pyridinyl | C5-G8 alkoxy | 3-hydroxy isoxazole | —SCH$_3$ | |
| CO | Pyridinyl | Halo substituted alkoxy | 3-hydroxy isoxazole | —SCH$_3$ | |
| CO | Pyridinyl | CH$_3$ | 3-hydroxy isoxazole | —SCH$_3$ | |
| CO | Pyridinyl | CH$_2$CH$_3$ | 3-hydroxy isoxazole | —SCH$_3$ | |
| CO | Pyridinyl | CH$_2$CH$_2$CH$_3$ | 3-hydroxy isoxazole | —SCH$_3$ | |
| CO | Pyridinyl | CH$_2$CH$_2$CH$_2$CH$_3$ | 3-hydroxy isoxazole | —SCH$_3$ | |
| CO | Pyridinyl | C5-G8 alkyl | 3-hydroxy isoxazole | —SCH$_3$ | |
| CO | Pyridinyl | F | 3-hydroxy isoxazole | —SCH$_3$ | |
| CO | Pyridinyl | F, F | 3-hydroxy isoxazole | —SCH$_3$ | |
| CO | Pyridinyl | F, Cl | 3-hydroxy isoxazole | —SCH$_3$ | |
| CO | Pyridinyl | Cl | 3-hydroxy isoxazole | —SCH$_3$ | |
| CO | Pyridinyl | Cl, Cl | 3-hydroxy isoxazole | —SCH$_3$ | |

TABLE 4-continued

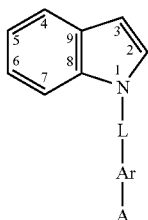

| $L^1$ | Ar | A | 3 | 5 | 6 |
|---|---|---|---|---|---|
| CO | Pyridinyl | -(1 to 4 linearly linked atom linker)-optionally subst. aryl | 3-hydroxy isoxazole | —SCH$_3$ | |
| CO | Pyridinyl | -(1 to 4 linearly linked atom linker)-optionally subst. heteroaryl | 3-hydroxy isoxazole | —SCH$_3$ | |
| SO$_2$ | phenyl | | 3-hydroxy isoxazole | —SCH$_2$CH$_3$ | |
| SO$_2$ | phenyl | CF$_3$ | 3-hydroxy isoxazole | —SCH$_2$CH$_3$ | |
| SO$_2$ | phenyl | CH$_2$CF$_3$ | 3-hydroxy isoxazole | —SCH$_2$CH$_3$ | |
| SO$_2$ | phenyl | Halo substituted alkyl | 3-hydroxy isoxazole | —SCH$_2$CH$_3$ | |
| SO$_2$ | phenyl | OCH$_3$ | 3-hydroxy isoxazole | —SCH$_2$CH$_3$ | |
| SO$_2$ | phenyl | OCH$_2$CH$_3$ | 3-hydroxy isoxazole | —SCH$_2$CH$_3$ | |
| SO$_2$ | phenyl | OCH$_2$CH$_2$CH$_3$ | 3-hydroxy isoxazole | —SCH$_2$CH$_3$ | |
| SO$_2$ | phenyl | OCH$_2$CH$_2$CH$_2$CH$_3$ | 3-hydroxy isoxazole | —SCH$_2$CH$_3$ | |
| SO$_2$ | phenyl | OCH$_2$CH$_2$CH$_2$CH$_2$CH$_3$ | 3-hydroxy isoxazole | —SCH$_2$CH$_3$ | |
| SO$_2$ | phenyl | C5-C8 alkoxy | 3-hydroxy isoxazole | —SCH$_2$CH$_3$ | |
| SO$_2$ | phenyl | Halo substituted alkoxy | 3-hydroxy isoxazole | —SCH$_2$CH$_3$ | |
| SO$_2$ | phenyl | CH$_3$ | 3-hydroxy isoxazole | —SCH$_2$CH$_3$ | |
| SO$_2$ | phenyl | CH$_2$CH$_3$ | 3-hydroxy isoxazole | —SCH$_2$CH$_3$ | |
| SO$_2$ | phenyl | CH$_2$CH$_2$CH$_3$ | 3-hydroxy isoxazole | —SCH$_2$CH$_3$ | |
| SO$_2$ | phenyl | CH$_2$CH$_2$CH$_2$CH$_3$ | 3-hydroxy isoxazole | —SCH$_2$CH$_3$ | |
| SO$_2$ | phenyl | C5-C8 alkyl | 3-hydroxy isoxazole | —SCH$_2$CH$_3$ | |
| SO$_2$ | phenyl | F | 3-hydroxy isoxazole | —SCH$_2$CH$_3$ | |
| SO$_2$ | phenyl | F, F | 3-hydroxy isoxazole | —SCH$_2$CH$_3$ | |
| SO$_2$ | phenyl | F, Cl | 3-hydroxy isoxazole | —SCH$_2$CH$_3$ | |
| SO$_2$ | phenyl | Cl | 3-hydroxy isoxazole | —SCH$_2$CH$_3$ | |
| SO$_2$ | phenyl | Cl, Cl | 3-hydroxy isoxazole | —SCH$_2$CH$_3$ | |
| SO$_2$ | phenyl | -(1 to 4 linearly linked atom linker)-optionally subst. aryl | 3-hydroxy isoxazole | —SCH$_2$CH$_3$ | |
| SO$_2$ | phenyl | -(1 to 4 linearly linked atom linker)-optionally subst. heteroaryl | 3-hydroxy isoxazole | —SCH$_2$CH$_3$ | |
| SO$_2$ | pyridinyl | | 3-hydroxy isoxazole | —SCH$_2$CH$_3$ | |
| SO$_2$ | Pyridinyl | CF$_3$ | 3-hydroxy isoxazole | —SCH$_2$CH$_3$ | |
| SO$_2$ | Pyridinyl | CH$_2$CF$_3$ | 3-hydroxy isoxazole | —SCH$_2$CH$_3$ | |
| SO$_2$ | Pyridinyl | Halo substituted alkyl | 3-hydroxy isoxazole | —SCH$_2$CH$_3$ | |
| SO$_2$ | Pyridinyl | OCH$_3$ | 3-hydroxy isoxazole | —SCH$_2$CH$_3$ | |
| SO$_2$ | Pyridinyl | OCH$_2$CH$_3$ | 3-hydroxy isoxazole | —SCH$_2$CH$_3$ | |
| SO$_2$ | Pyridinyl | OCH$_2$CH$_2$CH$_3$ | 3-hydroxy isoxazole | —SCH$_2$CH$_3$ | |
| SO$_2$ | Pyridinyl | OCH$_2$CH$_2$CH$_2$CH$_3$ | 3-hydroxy isoxazole | —SCH$_2$CH$_3$ | |
| SO$_2$ | Pyridinyl | OCH$_2$CH$_2$CH$_2$CH$_2$CH$_3$ | 3-hydroxy isoxazole | —SCH$_2$CH$_3$ | |
| SO$_2$ | Pyridinyl | C5-C8 alkoxy | 3-hydroxy isoxazole | —SCH$_2$CH$_3$ | |
| SO$_2$ | Pyridinyl | Halo substituted alkoxy | 3-hydroxy isoxazole | —SCH$_2$CH$_3$ | |
| SO$_2$ | Pyridinyl | CH$_3$ | 3-hydroxy isoxazole | —SCH$_2$CH$_3$ | |
| SO$_2$ | Pyridinyl | CH$_2$CH$_3$ | 3-hydroxy isoxazole | —SCH$_2$CH$_3$ | |
| SO$_2$ | Pyridinyl | CH$_2$CH$_2$CH$_3$ | 3-hydroxy isoxazole | —SCH$_2$CH$_3$ | |
| SO$_2$ | Pyridinyl | CH$_2$CH$_2$CH$_2$CH$_3$ | 3-hydroxy isoxazole | —SCH$_2$CH$_3$ | |
| SO$_2$ | Pyridinyl | C5-C8 alkyl | 3-hydroxy isoxazole | —SCH$_2$CH$_3$ | |
| SO$_2$ | Pyridinyl | F | 3-hydroxy isoxazole | —SCH$_2$CH$_3$ | |
| SO$_2$ | Pyridinyl | F, F | 3-hydroxy isoxazole | —SCH$_2$CH$_3$ | |
| SO$_2$ | Pyridinyl | F, Cl | 3-hydroxy isoxazole | —SCH$_2$CH$_3$ | |
| SO$_2$ | Pyridinyl | Cl | 3-hydroxy isoxazole | —SCH$_2$CH$_3$ | |
| SO$_2$ | Pyridinyl | Cl, Cl | 3-hydroxy isoxazole | —SCH$_2$CH$_3$ | |
| SO$_2$ | Pyridinyl | -(1 to 4 linearly linked atom linker)-optionally subst. aryl | 3-hydroxy isoxazole | —SCH$_2$CH$_3$ | |
| SO$_2$ | Pyridinyl | -(1 to 4 linearly linked atom linker)-optionally subst. heteroaryl | 3-hydroxy isoxazole | —SCH$_2$CH$_3$ | |
| CO | Phenyl | | 3-hydroxy isoxazole | —SCH$_2$CH$_3$ | |
| CO | Phenyl | CF$_3$ | 3-hydroxy isoxazole | —SCH$_2$CH$_3$ | |
| CO | Phenyl | CH$_2$CF$_3$ | 3-hydroxy isoxazole | —SCH$_2$CH$_3$ | |

TABLE 4-continued

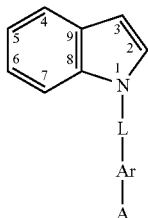

| L¹ | Ar | A | 3 | 5 | 6 |
|---|---|---|---|---|---|
| CO | Phenyl | Halo substituted alkyl | 3-hydroxy isoxazole | —SCH₂CH₃ | |
| CO | Phenyl | OCH₃ | 3-hydroxy isoxazole | —SCH₂CH₃ | |
| CO | Phenyl | OCH₂CH₃ | 3-hydroxy isoxazole | —SCH₂CH₃ | |
| CO | Phenyl | OCH₂CH₂CH₃ | 3-hydroxy isoxazole | —SCH₂CH₃ | |
| CO | Phenyl | OCH₂CH₂CH₂CH₃ | 3-hydroxy isoxazole | —SCH₂CH₃ | |
| CO | Phenyl | OCH₂CH₂CH₂CH₂CH₃ | 3-hydroxy isoxazole | —SCH₂CH₃ | |
| CO | Phenyl | C5-C8 alkoxy | 3-hydroxy isoxazole | —SCH₂CH₃ | |
| CO | Phenyl | Halo substituted alkoxy | 3-hydroxy isoxazole | —SCH₂CH₃ | |
| CO | Phenyl | CH₃ | 3-hydroxy isoxazole | —SCH₂CH₃ | |
| CO | Phenyl | CH₂CH₃ | 3-hydroxy isoxazole | —SCH₂CH₃ | |
| CO | Phenyl | CH₂CH₂CH₃ | 3-hydroxy isoxazole | —SCH₂CH₃ | |
| CO | Phenyl | CH₂CH₂CH₂CH₃ | 3-hydroxy isoxazole | —SCH₂CH₃ | |
| CO | Phenyl | C5-C8 alkyl | 3-hydroxy isoxazole | —SCH₂CH₃ | |
| CO | Phenyl | F | 3-hydroxy isoxazole | —SCH₂CH₃ | |
| CO | Phenyl | F, F | 3-hydroxy isoxazole | —SCH₂CH₃ | |
| CO | Phenyl | F, Cl | 3-hydroxy isoxazole | —SCH₂CH₃ | |
| CO | Phenyl | Cl | 3-hydroxy isoxazole | —SCH₂CH₃ | |
| CO | Phenyl | Cl, Cl | 3-hydroxy isoxazole | —SCH₂CH₃ | |
| CO | Phenyl | -(1 to 4 linearly linked atom linker)-optionally subst. aryl | 3-hydroxy isoxazole | —SCH₂CH₃ | |
| CO | Phenyl | -(1 to 4 linearly linked atom linker)-optionally subst. heteroaryl | 3-hydroxy isoxazole | —SCH₂CH₃ | |
| CO | pyridinyl | | 3-hydroxy isoxazole | —SCH₂CH₃ | |
| CO | Pyridinyl | CF₃ | 3-hydroxy isoxazole | —SCH₂CH₃ | |
| CO | Pyridinyl | CH₂CF₃ | 3-hydroxy isoxazole | —SCH₂CH₃ | |
| CO | Pyridinyl | Halo substituted alkyl | 3-hydroxy isoxazole | —SCH₂CH₃ | |
| CO | Pyridinyl | OCH₃ | 3-hydroxy isoxazole | —SCH₂CH₃ | |
| CO | Pyridinyl | OCH₂CH₃ | 3-hydroxy isoxazole | —SCH₂CH₃ | |
| CO | Pyridinyl | OCH₂CH₂CH₃ | 3-hydroxy isoxazole | —SCH₂CH₃ | |
| CO | Pyridinyl | OCH₂CH₂CH₂CH₃ | 3-hydroxy isoxazole | —SCH₂CH₃ | |
| CO | Pyridinyl | OCH₂CH₂CH₂CH₂CH₃ | 3-hydroxy isoxazole | —SCH₂CH₃ | |
| CO | Pyridinyl | C5-G8 alkoxy | 3-hydroxy isoxazole | —SCH₂CH₃ | |
| CO | Pyridinyl | Halo substituted alkoxy | 3-hydroxy isoxazole | —SCH₂CH₃ | |
| CO | Pyridinyl | CH₃ | 3-hydroxy isoxazole | —SCH₂CH₃ | |
| CO | Pyridinyl | CH₂CH₃ | 3-hydroxy isoxazole | —SCH₂CH₃ | |
| CO | Pyridinyl | CH₂CH₂CH₃ | 3-hydroxy isoxazole | —SCH₂CH₃ | |
| CO | Pyridinyl | CH₂CH₂CH₂CH₃ | 3-hydroxy isoxazole | —SCH₂CH₃ | |
| CO | Pyridinyl | C5-G8 alkyl | 3-hydroxy isoxazole | —SCH₂CH₃ | |
| CO | Pyridinyl | F | 3-hydroxy isoxazole | —SCH₂CH₃ | |
| CO | Pyridinyl | F, F | 3-hydroxy isoxazole | —SCH₂CH₃ | |
| CO | Pyridinyl | F, Cl | 3-hydroxy isoxazole | —SCH₂CH₃ | |
| CO | Pyridinyl | Cl | 3-hydroxy isoxazole | —SCH₂CH₃ | |
| CO | Pyridinyl | Cl, Cl | 3-hydroxy isoxazole | —SCH₂CH₃ | |
| CO | Pyridinyl | -(1 to 4 linearly linked atom linker)-optionally subst. aryl | 3-hydroxy isoxazole | —SCH₂CH₃ | |
| CO | Pyridinyl | -(1 to 4 linearly linked atom linker)-optionally subst. heteroaryl | 3-hydroxy isoxazole | —SCH₂CH₃ | |
| SO₂ | phenyl | | COOH | | methoxy |
| SO₂ | phenyl | CF₃ | COOH | | methoxy |
| SO₂ | phenyl | CH₂CF₃ | COOH | | methoxy |
| SO₂ | phenyl | Halo substituted alkyl | COOH | | methoxy |
| SO₂ | phenyl | OCH₃ | COOH | | methoxy |
| SO₂ | phenyl | OCH₂CH₃ | COOH | | methoxy |
| SO₂ | phenyl | OCH₂CH₂CH₃ | COOH | | methoxy |
| SO₂ | phenyl | OCH₂CH₂CH₂CH₃ | COOH | | methoxy |
| SO₂ | phenyl | OCH₂CH₂CH₂CH₂CH₃ | COOH | | methoxy |
| SO₂ | phenyl | C5-C8 alkoxy | COOH | | methoxy |
| SO₂ | phenyl | Halo substituted alkoxy | COOH | | methoxy |
| SO₂ | phenyl | CH₃ | COOH | | methoxy |

TABLE 4-continued

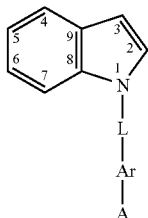

| L¹ | Ar | A | 3 | 5 | 6 |
|---|---|---|---|---|---|
| SO₂ | phenyl | CH₂CH₃ | COOH | | methoxy |
| SO₂ | phenyl | CH₂CH₂CH₃ | COOH | | methoxy |
| SO₂ | phenyl | CH₂CH₂CH₂CH₃ | COOH | | methoxy |
| SO₂ | phenyl | C5-C8 alkyl | COOH | | methoxy |
| SO₂ | phenyl | F | COOH | | methoxy |
| SO₂ | phenyl | F, F | COOH | | methoxy |
| SO₂ | phenyl | F, Cl | COOH | | methoxy |
| SO₂ | phenyl | Cl | COOH | | methoxy |
| SO₂ | phenyl | Cl, Cl | COOH | | methoxy |
| SO₂ | phenyl | -(1 to 4 linearly linked atom linker)-optionally subst. aryl | COOH | | methoxy |
| SO₂ | phenyl | -(1 to 4 linearly linked atom linker)-optionally subst. heteroaryl | COOH | | methoxy |
| SO₂ | pyridinyl | | COOH | | methoxy |
| SO₂ | Pyridinyl | CF₃ | COOH | | methoxy |
| SO₂ | Pyridinyl | CH₂CF₃ | COOH | | methoxy |
| SO₂ | Pyridinyl | Halo substituted alkyl | COOH | | methoxy |
| SO₂ | Pyridinyl | OCH₃ | COOH | | methoxy |
| SO₂ | Pyridinyl | OCH₂CH₃ | COOH | | methoxy |
| SO₂ | Pyridinyl | OCH₂CH₂CH₃ | COOH | | methoxy |
| SO₂ | Pyridinyl | OCH₂CH₂CH₂CH₃ | COOH | | methoxy |
| SO₂ | Pyridinyl | OCH₂CH₂CH₂CH₂CH₃ | COOH | | methoxy |
| SO₂ | Pyridinyl | C5-C8 alkoxy | COOH | | methoxy |
| SO₂ | Pyridinyl | Halo substituted alkoxy | COOH | | methoxy |
| SO₂ | Pyridinyl | CH₃ | COOH | | methoxy |
| SO₂ | Pyridinyl | CH₂CH₃ | COOH | | methoxy |
| SO₂ | Pyridinyl | CH₂CH₂CH₃ | COOH | | methoxy |
| SO₂ | Pyridinyl | CH₂CH₂CH₂CH₃ | COOH | | methoxy |
| SO₂ | Pyridinyl | C5-C8 alkyl | COOH | | methoxy |
| SO₂ | Pyridinyl | F | COOH | | methoxy |
| SO₂ | Pyridinyl | F, F | COOH | | methoxy |
| SO₂ | Pyridinyl | F, Cl | COOH | | methoxy |
| SO₂ | Pyridinyl | Cl | COOH | | methoxy |
| SO₂ | Pyridinyl | Cl, Cl | COOH | | methoxy |
| SO₂ | Pyridinyl | -(1 to 4 linearly linked atom linker)-optionally subst. aryl | COOH | | methoxy |
| SO₂ | Pyridinyl | -(1 to 4 linearly linked atom linker)-optionally subst. heteroaryl | COOH | | methoxy |
| CO | Phenyl | | COOH | | methoxy |
| CO | Phenyl | CF₃ | COOH | | methoxy |
| CO | Phenyl | CH₂CF₃ | COOH | | methoxy |
| CO | Phenyl | Halo substituted alkyl | COOH | | methoxy |
| CO | Phenyl | OCH₃ | COOH | | methoxy |
| CO | Phenyl | OCH₂CH₃ | COOH | | methoxy |
| CO | Phenyl | OCH₂CH₂CH₃ | COOH | | methoxy |
| CO | Phenyl | OCH₂CH₂CH₂CH₃ | COOH | | methoxy |
| CO | Phenyl | OCH₂CH₂CH₂CH₂CH₃ | COOH | | methoxy |
| CO | Phenyl | C5-C8 alkoxy | COOH | | methoxy |
| CO | Phenyl | Halo substituted alkoxy | COOH | | methoxy |
| CO | Phenyl | CH₃ | COOH | | methoxy |
| CO | Phenyl | CH₂CH₃ | COOH | | methoxy |
| CO | Phenyl | CH₂CH₂CH₃ | COOH | | methoxy |
| CO | Phenyl | CH₂CH₂CH₂CH₃ | COOH | | methoxy |
| CO | Phenyl | C5-C8 alkyl | COOH | | methoxy |
| CO | Phenyl | F | COOH | | methoxy |
| CO | Phenyl | F, F | COOH | | methoxy |
| CO | Phenyl | F, Cl | COOH | | methoxy |
| CO | Phenyl | Cl | COOH | | methoxy |
| CO | Phenyl | Cl, Cl | COOH | | methoxy |

TABLE 4-continued

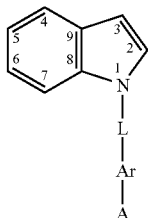

| L¹ | Ar | A | 3 | 5 | 6 |
|---|---|---|---|---|---|
| CO | Phenyl | -(1 to 4 linearly linked atom linker)-optionally subst. aryl | COOH | | methoxy |
| CO | Phenyl | -(1 to 4 linearly linked atom linker)-optionally subst. heteroaryl | COOH | | methoxy |
| CO | pyridinyl | | COOH | | methoxy |
| CO | Pyridinyl | CF₃ | COOH | | methoxy |
| CO | Pyridinyl | CH₂CF₃ | COOH | | methoxy |
| CO | Pyridinyl | Halo substituted alkyl | COOH | | methoxy |
| CO | Pyridinyl | OCH₃ | COOH | | methoxy |
| CO | Pyridinyl | OCH₂CH₃ | COOH | | methoxy |
| CO | Pyridinyl | OCH₂CH₂CH₃ | COOH | | methoxy |
| CO | Pyridinyl | OCH₂CH₂CH₂CH₃ | COOH | | methoxy |
| CO | Pyridinyl | OCH₂CH₂CH₂CH₂CH₃ | COOH | | methoxy |
| CO | Pyridinyl | C5-G8 alkoxy | COOH | | methoxy |
| CO | Pyridinyl | Halo substituted alkoxy | COOH | | methoxy |
| CO | Pyridinyl | CH₃ | COOH | | methoxy |
| CO | Pyridinyl | CH₂CH₃ | COOH | | methoxy |
| CO | Pyridinyl | CH₂CH₂CH₃ | COOH | | methoxy |
| CO | Pyridinyl | CH₂CH₂CH₂CH₃ | COOH | | methoxy |
| CO | Pyridinyl | C5-G8 alkyl | COOH | | methoxy |
| CO | Pyridinyl | F | COOH | | methoxy |
| CO | Pyridinyl | F, F | COOH | | methoxy |
| CO | Pyridinyl | F, Cl | COOH | | methoxy |
| CO | Pyridinyl | Cl | COOH | | methoxy |
| CO | Pyridinyl | Cl, Cl | COOH | | methoxy |
| CO | Pyridinyl | -(1 to 4 linearly linked atom linker)-optionally subst. aryl | COOH | | methoxy |
| CO | Pyridinyl | -(1 to 4 linearly linked atom linker)-optionally subst. heteroaryl | COOH | | methoxy |
| SO₂ | phenyl | | COOH | | ethoxy |
| SO₂ | phenyl | CF₃ | COOH | | ethoxy |
| SO₂ | phenyl | CH₂CF₃ | COOH | | ethoxy |
| SO₂ | phenyl | Halo substituted alkyl | COOH | | ethoxy |
| SO₂ | phenyl | OCH₃ | COOH | | ethoxy |
| SO₂ | phenyl | OCH₂CH₃ | COOH | | ethoxy |
| SO₂ | phenyl | OCH₂CH₂CH₃ | COOH | | ethoxy |
| SO₂ | phenyl | OCH₂CH₂CH₂CH₃ | COOH | | ethoxy |
| SO₂ | phenyl | OCH₂CH₂CH₂CH₂CH₃ | COOH | | ethoxy |
| SO₂ | phenyl | C5-C8 alkoxy | COOH | | ethoxy |
| SO₂ | phenyl | Halo substituted alkoxy | COOH | | ethoxy |
| SO₂ | phenyl | CH₃ | COOH | | ethoxy |
| SO₂ | phenyl | CH₂CH₃ | COOH | | ethoxy |
| SO₂ | phenyl | CH₂CH₂CH₃ | COOH | | ethoxy |
| SO₂ | phenyl | CH₂CH₂CH₂CH₃ | COOH | | ethoxy |
| SO₂ | phenyl | C5-C8 alkyl | COOH | | ethoxy |
| SO₂ | phenyl | F | COOH | | ethoxy |
| SO₂ | phenyl | F, F | COOH | | ethoxy |
| SO₂ | phenyl | F, Cl | COOH | | ethoxy |
| SO₂ | phenyl | Cl | COOH | | ethoxy |
| SO₂ | phenyl | Cl, Cl | COOH | | ethoxy |
| SO₂ | phenyl | -(1 to 4 linearly linked atom linker)-optionally subst. aryl | COOH | | ethoxy |
| SO₂ | phenyl | -(1 to 4 linearly linked atom linker)-optionally subst. heteroaryl | COOH | | ethoxy |
| SO₂ | pyridinyl | | COOH | | ethoxy |
| SO₂ | Pyridinyl | CF₃ | COOH | | ethoxy |
| SO₂ | Pyridinyl | CH₂CF₃ | COOH | | ethoxy |

TABLE 4-continued

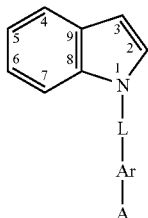

| L¹ | Ar | A | 3 | 5 | 6 |
|---|---|---|---|---|---|
| SO₂ | Pyridinyl | Halo substituted alkyl | COOH | | ethoxy |
| SO₂ | Pyridinyl | OCH₃ | COOH | | ethoxy |
| SO₂ | Pyridinyl | OCH₂CH₃ | COOH | | ethoxy |
| SO₂ | Pyridinyl | OCH₂CH₂CH₃ | COOH | | ethoxy |
| SO₂ | Pyridinyl | OCH₂CH₂CH₂CH₃ | COOH | | ethoxy |
| SO₂ | Pyridinyl | OCH₂CH₂CH₂CH₂CH₃ | COOH | | ethoxy |
| SO₂ | Pyridinyl | C5-C8 alkoxy | COOH | | ethoxy |
| SO₂ | Pyridinyl | Halo substituted alkoxy | COOH | | ethoxy |
| SO₂ | Pyridinyl | CH₃ | COOH | | ethoxy |
| SO₂ | Pyridinyl | CH₂CH₃ | COOH | | ethoxy |
| SO₂ | Pyridinyl | CH₂CH₂CH₃ | COOH | | ethoxy |
| SO₂ | Pyridinyl | CH₂CH₂CH₂CH₃ | COOH | | ethoxy |
| SO₂ | Pyridinyl | C5-C8 alkyl | COOH | | ethoxy |
| SO₂ | Pyridinyl | F | COOH | | ethoxy |
| SO₂ | Pyridinyl | F, F | COOH | | ethoxy |
| SO₂ | Pyridinyl | F, Cl | COOH | | ethoxy |
| SO₂ | Pyridinyl | Cl | COOH | | ethoxy |
| SO₂ | Pyridinyl | Cl, Cl | COOH | | ethoxy |
| SO₂ | Pyridinyl | -(1 to 4 linearly linked atom linker)-optionally subst. aryl | COOH | | ethoxy |
| SO₂ | Pyridinyl | -(1 to 4 linearly linked atom linker)-optionally subst. heteroaryl | COOH | | ethoxy |
| CO | Phenyl | | COOH | | ethoxy |
| CO | Phenyl | CF₃ | COOH | | ethoxy |
| CO | Phenyl | CH₂CF₃ | COOH | | ethoxy |
| CO | Phenyl | Halo substituted alkyl | COOH | | ethoxy |
| CO | Phenyl | OCH₃ | COOH | | ethoxy |
| CO | Phenyl | OCH₂CH₃ | COOH | | ethoxy |
| CO | Phenyl | OCH₂CH₂CH₃ | COOH | | ethoxy |
| CO | Phenyl | OCH₂CH₂CH₂CH₃ | COOH | | ethoxy |
| CO | Phenyl | OCH₂CH₂CH₂CH₂CH₃ | COOH | | ethoxy |
| CO | Phenyl | C5-C8 alkoxy | COOH | | ethoxy |
| CO | Phenyl | Halo substituted alkoxy | COOH | | ethoxy |
| CO | Phenyl | CH₃ | COOH | | ethoxy |
| CO | Phenyl | CH₂CH₃ | COOH | | ethoxy |
| CO | Phenyl | CH₂CH₂CH₃ | COOH | | ethoxy |
| CO | Phenyl | CH₂CH₂CH₂CH₃ | COOH | | ethoxy |
| CO | Phenyl | C5-C8 alkyl | COOH | | ethoxy |
| CO | Phenyl | F | COOH | | ethoxy |
| CO | Phenyl | F, F | COOH | | ethoxy |
| CO | Phenyl | F, Cl | COOH | | ethoxy |
| CO | Phenyl | Cl | COOH | | ethoxy |
| CO | Phenyl | Cl, Cl | COOH | | ethoxy |
| CO | Phenyl | -(1 to 4 linearly linked atom linker)-optionally subst. aryl | COOH | | ethoxy |
| CO | Phenyl | -(1 to 4 linearly linked atom linker)-optionally subst. heteroaryl | COOH | | ethoxy |
| CO | pyridinyl | | COOH | | ethoxy |
| CO | Pyridinyl | CF₃ | COOH | | ethoxy |
| CO | Pyridinyl | CH₂CF₃ | COOH | | ethoxy |
| CO | Pyridinyl | Halo substituted alkyl | COOH | | ethoxy |
| CO | Pyridinyl | OCH₃ | COOH | | ethoxy |
| CO | Pyridinyl | OCH₂CH₃ | COOH | | ethoxy |
| CO | Pyridinyl | OCH₂CH₂CH₃ | COOH | | ethoxy |
| CO | Pyridinyl | OCH₂CH₂CH₂CH₃ | COOH | | ethoxy |
| CO | Pyridinyl | OCH₂CH₂CH₂CH₂CH₃ | COOH | | ethoxy |
| CO | Pyridinyl | C5-G8 alkoxy | COOH | | ethoxy |
| CO | Pyridinyl | Halo substituted alkoxy | COOH | | ethoxy |
| CO | Pyridinyl | CH₃ | COOH | | ethoxy |

TABLE 4-continued

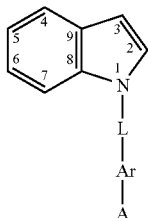

| L¹ | Ar | A | 3 | 5 | 6 |
|---|---|---|---|---|---|
| CO | Pyridinyl | $CH_2CH_3$ | COOH | | ethoxy |
| CO | Pyridinyl | $CH_2CH_2CH_3$ | COOH | | ethoxy |
| CO | Pyridinyl | $CH_2CH_2CH_2CH_3$ | COOH | | ethoxy |
| CO | Pyridinyl | C5-G8 alkyl | COOH | | ethoxy |
| CO | Pyridinyl | F | COOH | | ethoxy |
| CO | Pyridinyl | F, F | COOH | | ethoxy |
| CO | Pyridinyl | F, Cl | COOH | | ethoxy |
| CO | Pyridinyl | Cl | COOH | | ethoxy |
| CO | Pyridinyl | Cl, Cl | COOH | | ethoxy |
| CO | Pyridinyl | -(1 to 4 linearly linked atom linker)-optionally subst. aryl | COOH | | ethoxy |
| CO | Pyridinyl | -(1 to 4 linearly linked atom linker)-optionally subst. heteroaryl | COOH | | ethoxy |
| $SO_2$ | phenyl | | COOH | | propoxy |
| $SO_2$ | phenyl | $CF_3$ | COOH | | propoxy |
| $SO_2$ | phenyl | $CH_2CF_3$ | COOH | | propoxy |
| $SO_2$ | phenyl | Halo substituted alkyl | COOH | | propoxy |
| $SO_2$ | phenyl | $OCH_3$ | COOH | | propoxy |
| $SO_2$ | phenyl | $OCH_2CH_3$ | COOH | | propoxy |
| $SO_2$ | phenyl | $OCH_2CH_2CH_3$ | COOH | | propoxy |
| $SO_2$ | phenyl | $OCH_2CH_2CH_2CH_3$ | COOH | | propoxy |
| $SO_2$ | phenyl | $OCH_2CH_2CH_2CH_2CH_3$ | COOH | | propoxy |
| $SO_2$ | phenyl | C5-C8 alkoxy | COOH | | propoxy |
| $SO_2$ | phenyl | Halo substituted alkoxy | COOH | | propoxy |
| $SO_2$ | phenyl | $CH_3$ | COOH | | propoxy |
| $SO_2$ | phenyl | $CH_2CH_3$ | COOH | | propoxy |
| $SO_2$ | phenyl | $CH_2CH_2CH_3$ | COOH | | propoxy |
| $SO_2$ | phenyl | $CH_2CH_2CH_2CH_3$ | COOH | | propoxy |
| $SO_2$ | phenyl | C5-C8 alkyl | COOH | | propoxy |
| $SO_2$ | phenyl | F | COOH | | propoxy |
| $SO_2$ | phenyl | F, F | COOH | | propoxy |
| $SO_2$ | phenyl | F, Cl | COOH | | propoxy |
| $SO_2$ | phenyl | Cl | COOH | | propoxy |
| $SO_2$ | phenyl | Cl, Cl | COOH | | propoxy |
| $SO_2$ | phenyl | -(1 to 4 linearly linked atom linker)-optionally subst. aryl | COOH | | propoxy |
| $SO_2$ | phenyl | -(1 to 4 linearly linked atom linker)-optionally subst. heteroaryl | COOH | | propoxy |
| $SO_2$ | pyridinyl | | COOH | | propoxy |
| $SO_2$ | Pyridinyl | $CF_3$ | COOH | | propoxy |
| $SO_2$ | Pyridinyl | $CH_2CF_3$ | COOH | | propoxy |
| $SO_2$ | Pyridinyl | Halo substituted alkyl | COOH | | propoxy |
| $SO_2$ | Pyridinyl | $OCH_3$ | COOH | | propoxy |
| $SO_2$ | Pyridinyl | $OCH_2CH_3$ | COOH | | propoxy |
| $SO_2$ | Pyridinyl | $OCH_2CH_2CH_3$ | COOH | | propoxy |
| $SO_2$ | Pyridinyl | $OCH_2CH_2CH_2CH_3$ | COOH | | propoxy |
| $SO_2$ | Pyridinyl | $OCH_2CH_2CH_2CH_2CH_3$ | COOH | | propoxy |
| $SO_2$ | Pyridinyl | C5-C8 alkoxy | COOH | | propoxy |
| $SO_2$ | Pyridinyl | Halo substituted alkoxy | COOH | | propoxy |
| $SO_2$ | Pyridinyl | $CH_3$ | COOH | | propoxy |
| $SO_2$ | Pyridinyl | $CH_2CH_3$ | COOH | | propoxy |
| $SO_2$ | Pyridinyl | $CH_2CH_2CH_3$ | COOH | | propoxy |
| $SO_2$ | Pyridinyl | $CH_2CH_2CH_2CH_3$ | COOH | | propoxy |
| $SO_2$ | Pyridinyl | C5-C8 alkyl | COOH | | propoxy |
| $SO_2$ | Pyridinyl | F | COOH | | propoxy |
| $SO_2$ | Pyridinyl | F, F | COOH | | propoxy |
| $SO_2$ | Pyridinyl | F, Cl | COOH | | propoxy |
| $SO_2$ | Pyridinyl | Cl | COOH | | propoxy |
| $SO_2$ | Pyridinyl | Cl, Cl | COOH | | propoxy |

TABLE 4-continued

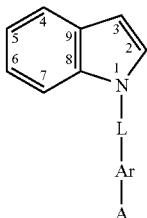

| L¹ | Ar | A | 3 | 5 | 6 |
|---|---|---|---|---|---|
| SO₂ | Pyridinyl | -(1 to 4 linearly linked atom linker)-optionally subst. aryl | COOH | | propoxy |
| SO₂ | Pyridinyl | -(1 to 4 linearly linked atom linker)-optionally subst. heteroaryl | COOH | | propoxy |
| CO | Phenyl | | COOH | | propoxy |
| CO | Phenyl | CF₃ | COOH | | propoxy |
| CO | Phenyl | CH₂CF₃ | COOH | | propoxy |
| CO | Phenyl | Halo substituted alkyl | COOH | | propoxy |
| CO | Phenyl | OCH₃ | COOH | | propoxy |
| CO | Phenyl | OCH₂CH₃ | COOH | | propoxy |
| CO | Phenyl | OCH₂CH₂CH₃ | COOH | | propoxy |
| CO | Phenyl | OCH₂CH₂CH₂CH₃ | COOH | | propoxy |
| CO | Phenyl | OCH₂CH₂CH₂CH₂CH₃ | COOH | | propoxy |
| CO | Phenyl | C5-C8 alkoxy | COOH | | propoxy |
| CO | Phenyl | Halo substituted alkoxy | COOH | | propoxy |
| CO | Phenyl | CH₃ | COOH | | propoxy |
| CO | Phenyl | CH₂CH₃ | COOH | | propoxy |
| CO | Phenyl | CH₂CH₂CH₃ | COOH | | propoxy |
| CO | Phenyl | CH₂CH₂CH₂CH₃ | COOH | | propoxy |
| CO | Phenyl | C5-C8 alkyl | COOH | | propoxy |
| CO | Phenyl | F | COOH | | propoxy |
| CO | Phenyl | F, F | COOH | | propoxy |
| CO | Phenyl | F, Cl | COOH | | propoxy |
| CO | Phenyl | Cl | COOH | | propoxy |
| CO | Phenyl | Cl, Cl | COOH | | propoxy |
| CO | Phenyl | -(1 to 4 linearly linked atom linker)-optionally subst. aryl | COOH | | propoxy |
| CO | Phenyl | -(1 to 4 linearly linked atom linker)-optionally subst. heteroaryl | COOH | | propoxy |
| CO | pyridinyl | | COOH | | propoxy |
| CO | Pyridinyl | CF₃ | COOH | | propoxy |
| CO | Pyridinyl | CH₂CF₃ | COOH | | propoxy |
| CO | Pyridinyl | Halo substituted alkyl | COOH | | propoxy |
| CO | Pyridinyl | OCH₃ | COOH | | propoxy |
| CO | Pyridinyl | OCH₂CH₃ | COOH | | propoxy |
| CO | Pyridinyl | OCH₂CH₂CH₃ | COOH | | propoxy |
| CO | Pyridinyl | OCH₂CH₂CH₂CH₃ | COOH | | propoxy |
| CO | Pyridinyl | OCH₂CH₂CH₂CH₂CH₃ | COOH | | propoxy |
| CO | Pyridinyl | C5-G8 alkoxy | COOH | | propoxy |
| CO | Pyridinyl | Halo substituted alkoxy | COOH | | propoxy |
| CO | Pyridinyl | CH₃ | COOH | | propoxy |
| CO | Pyridinyl | CH₂CH₃ | COOH | | propoxy |
| CO | Pyridinyl | CH₂CH₂CH₃ | COOH | | propoxy |
| CO | Pyridinyl | CH₂CH₂CH₂CH₃ | COOH | | propoxy |
| CO | Pyridinyl | C5-G8 alkyl | COOH | | propoxy |
| CO | Pyridinyl | F | COOH | | propoxy |
| CO | Pyridinyl | F, F | COOH | | propoxy |
| CO | Pyridinyl | F, Cl | COOH | | propoxy |
| CO | Pyridinyl | Cl | COOH | | propoxy |
| CO | Pyridinyl | Cl, Cl | COOH | | propoxy |
| CO | Pyridinyl | -(1 to 4 linearly linked atom linker)-optionally subst. aryl | COOH | | propoxy |
| CO | Pyridinyl | -(1 to 4 linearly linked atom linker)-optionally subst. heteroaryl | COOH | | propoxy |
| SO₂ | phenyl | | COOH | | —SCH₃ |
| SO₂ | phenyl | CF₃ | COOH | | —SCH₃ |
| SO₂ | phenyl | CH₂CF₃ | COOH | | —SCH₃ |

TABLE 4-continued

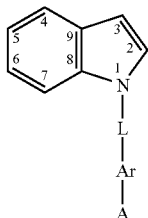

| L¹ | Ar | A | 3 | 5 | 6 |
|---|---|---|---|---|---|
| $SO_2$ | phenyl | Halo substituted alkyl | COOH | | —$SCH_3$ |
| $SO_2$ | phenyl | $OCH_3$ | COOH | | —$SCH_3$ |
| $SO_2$ | phenyl | $OCH_2CH_3$ | COOH | | —$SCH_3$ |
| $SO_2$ | phenyl | $OCH_2CH_2CH_3$ | COOH | | —$SCH_3$ |
| $SO_2$ | phenyl | $OCH_2CH_2CH_2CH_3$ | COOH | | —$SCH_3$ |
| $SO_2$ | phenyl | $OCH_2CH_2CH_2CH_2CH_3$ | COOH | | —$SCH_3$ |
| $SO_2$ | phenyl | C5-C8 alkoxy | COOH | | —$SCH_3$ |
| $SO_2$ | phenyl | Halo substituted alkoxy | COOH | | —$SCH_3$ |
| $SO_2$ | phenyl | $CH_3$ | COOH | | —$SCH_3$ |
| $SO_2$ | phenyl | $CH_2CH_3$ | COOH | | —$SCH_3$ |
| $SO_2$ | phenyl | $CH_2CH_2CH_3$ | COOH | | —$SCH_3$ |
| $SO_2$ | phenyl | $CH_2CH_2CH_2CH_3$ | COOH | | —$SCH_3$ |
| $SO_2$ | phenyl | C5-C8 alkyl | COOH | | —$SCH_3$ |
| $SO_2$ | phenyl | F | COOH | | —$SCH_3$ |
| $SO_2$ | phenyl | F, F | COOH | | —$SCH_3$ |
| $SO_2$ | phenyl | F, Cl | COOH | | —$SCH_3$ |
| $SO_2$ | phenyl | Cl | COOH | | —$SCH_3$ |
| $SO_2$ | phenyl | Cl, Cl | COOH | | —$SCH_3$ |
| $SO_2$ | phenyl | -(1 to 4 linearly linked atom linker)-optionally subst. aryl | COOH | | —$SCH_3$ |
| $SO_2$ | phenyl | -(1 to 4 linearly linked atom linker)-optionally subst. heteroaryl | COOH | | —$SCH_3$ |
| $SO_2$ | pyridinyl | | COOH | | —$SCH_3$ |
| $SO_2$ | Pyridinyl | $CF_3$ | COOH | | —$SCH_3$ |
| $SO_2$ | Pyridinyl | $CH_2CF_3$ | COOH | | —$SCH_3$ |
| $SO_2$ | Pyridinyl | Halo substituted alkyl | COOH | | —$SCH_3$ |
| $SO_2$ | Pyridinyl | $OCH_3$ | COOH | | —$SCH_3$ |
| $SO_2$ | Pyridinyl | $OCH_2CH_3$ | COOH | | —$SCH_3$ |
| $SO_2$ | Pyridinyl | $OCH_2CH_2CH_3$ | COOH | | —$SCH_3$ |
| $SO_2$ | Pyridinyl | $OCH_2CH_2CH_2CH_3$ | COOH | | —$SCH_3$ |
| $SO_2$ | Pyridinyl | $OCH_2CH_2CH_2CH_2CH_3$ | COOH | | —$SCH_3$ |
| $SO_2$ | Pyridinyl | C5-C8 alkoxy | COOH | | —$SCH_3$ |
| $SO_2$ | Pyridinyl | Halo substituted alkoxy | COOH | | —$SCH_3$ |
| $SO_2$ | Pyridinyl | $CH_3$ | COOH | | —$SCH_3$ |
| $SO_2$ | Pyridinyl | $CH_2CH_3$ | COOH | | —$SCH_3$ |
| $SO_2$ | Pyridinyl | $CH_2CH_2CH_3$ | COOH | | —$SCH_3$ |
| $SO_2$ | Pyridinyl | $CH_2CH_2CH_2CH_3$ | COOH | | —$SCH_3$ |
| $SO_2$ | Pyridinyl | C5-C8 alkyl | COOH | | —$SCH_3$ |
| $SO_2$ | Pyridinyl | F | COOH | | —$SCH_3$ |
| $SO_2$ | Pyridinyl | F, F | COOH | | —$SCH_3$ |
| $SO_2$ | Pyridinyl | F, Cl | COOH | | —$SCH_3$ |
| $SO_2$ | Pyridinyl | Cl | COOH | | —$SCH_3$ |
| $SO_2$ | Pyridinyl | Cl, Cl | COOH | | —$SCH_3$ |
| $SO_2$ | Pyridinyl | -(1 to 4 linearly linked atom linker)-optionally subst. aryl | COOH | | —$SCH_3$ |
| $SO_2$ | Pyridinyl | -(1 to 4 linearly linked atom linker)-optionally subst. heteroaryl | COOH | | —$SCH_3$ |
| CO | Phenyl | | COOH | | —$SCH_3$ |
| CO | Phenyl | $CF_3$ | COOH | | —$SCH_3$ |
| CO | Phenyl | $CH_2CF_3$ | COOH | | —$SCH_3$ |
| CO | Phenyl | Halo substituted alkyl | COOH | | —$SCH_3$ |
| CO | Phenyl | $OCH_3$ | COOH | | —$SCH_3$ |
| CO | Phenyl | $OCH_2CH_3$ | COOH | | —$SCH_3$ |
| CO | Phenyl | $OCH_2CH_2CH_3$ | COOH | | —$SCH_3$ |
| CO | Phenyl | $OCH_2CH_2CH_2CH_3$ | COOH | | —$SCH_3$ |
| CO | Phenyl | $OCH_2CH_2CH_2CH_2CH_3$ | COOH | | —$SCH_3$ |
| CO | Phenyl | C5-C8 alkoxy | COOH | | —$SCH_3$ |
| CO | Phenyl | Halo substituted alkoxy | COOH | | —$SCH_3$ |
| CO | Phenyl | $CH_3$ | COOH | | —$SCH_3$ |

TABLE 4-continued

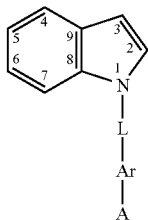

| L¹ | Ar | A | 3 | 5 | 6 |
|---|---|---|---|---|---|
| CO | Phenyl | CH₂CH₃ | COOH | | —SCH₃ |
| CO | Phenyl | CH₂CH₂CH₃ | COOH | | —SCH₃ |
| CO | Phenyl | CH₂CH₂CH₂CH₃ | COOH | | —SCH₃ |
| CO | Phenyl | C5-C8 alkyl | COOH | | —SCH₃ |
| CO | Phenyl | F | COOH | | —SCH₃ |
| CO | Phenyl | F, F | COOH | | —SCH₃ |
| CO | Phenyl | F, Cl | COOH | | —SCH₃ |
| CO | Phenyl | Cl | COOH | | —SCH₃ |
| CO | Phenyl | Cl, Cl | COOH | | —SCH₃ |
| CO | Phenyl | -(1 to 4 linearly linked atom linker)-optionally subst. aryl | COOH | | —SCH₃ |
| CO | Phenyl | -(1 to 4 linearly linked atom linker)-optionally subst. heteroaryl | COOH | | —SCH₃ |
| CO | pyridinyl | | COOH | | —SCH₃ |
| CO | Pyridinyl | CF₃ | COOH | | —SCH₃ |
| CO | Pyridinyl | CH₂CF₃ | COOH | | —SCH₃ |
| CO | Pyridinyl | Halo substituted alkyl | COOH | | —SCH₃ |
| CO | Pyridinyl | OCH₃ | COOH | | —SCH₃ |
| CO | Pyridinyl | OCH₂CH₃ | COOH | | —SCH₃ |
| CO | Pyridinyl | OCH₂CH₂CH₃ | COOH | | —SCH₃ |
| CO | Pyridinyl | OCH₂CH₂CH₂CH₃ | COOH | | —SCH₃ |
| CO | Pyridinyl | OCH₂CH₂CH₂CH₂CH₃ | COOH | | —SCH₃ |
| CO | Pyridinyl | C5-G8 alkoxy | COOH | | —SCH₃ |
| CO | Pyridinyl | Halo substituted alkoxy | COOH | | —SCH₃ |
| CO | Pyridinyl | CH₃ | COOH | | —SCH₃ |
| CO | Pyridinyl | CH₂CH₃ | COOH | | —SCH₃ |
| CO | Pyridinyl | CH₂CH₂CH₃ | COOH | | —SCH₃ |
| CO | Pyridinyl | CH₂CH₂CH₂CH₃ | COOH | | —SCH₃ |
| CO | Pyridinyl | C5-G8 alkyl | COOH | | —SCH₃ |
| CO | Pyridinyl | F | COOH | | —SCH₃ |
| CO | Pyridinyl | F, F | COOH | | —SCH₃ |
| CO | Pyridinyl | F, Cl | COOH | | —SCH₃ |
| CO | Pyridinyl | Cl | COOH | | —SCH₃ |
| CO | Pyridinyl | Cl, Cl | COOH | | —SCH₃ |
| CO | Pyridinyl | -(1 to 4 linearly linked atom linker)-optionally subst. aryl | COOH | | —SCH₃ |
| CO | Pyridinyl | -(1 to 4 linearly linked atom linker)-optionally subst. heteroaryl | COOH | | —SCH₃ |
| SO₂ | phenyl | | COOH | | —SCH₂CH₃ |
| SO₂ | phenyl | CF₃ | COOH | | —SCH₂CH₃ |
| SO₂ | phenyl | CH₂CF₃ | COOH | | —SCH₂CH₃ |
| SO₂ | phenyl | Halo substituted alkyl | COOH | | —SCH₂CH₃ |
| SO₂ | phenyl | OCH₃ | COOH | | —SCH₂CH₃ |
| SO₂ | phenyl | OCH₂CH₃ | COOH | | —SCH₂CH₃ |
| SO₂ | phenyl | OCH₂CH₂CH₃ | COOH | | —SCH₂CH₃ |
| SO₂ | phenyl | OCH₂CH₂CH₂CH₃ | COOH | | —SCH₂CH₃ |
| SO₂ | phenyl | OCH₂CH₂CH₂CH₂CH₃ | COOH | | —SCH₂CH₃ |
| SO₂ | phenyl | C5-C8 alkoxy | COOH | | —SCH₂CH₃ |
| SO₂ | phenyl | Halo substituted alkoxy | COOH | | —SCH₂CH₃ |
| SO₂ | phenyl | CH₃ | COOH | | —SCH₂CH₃ |
| SO₂ | phenyl | CH₂CH₃ | COOH | | —SCH₂CH₃ |
| SO₂ | phenyl | CH₂CH₂CH₃ | COOH | | —SCH₂CH₃ |
| SO₂ | phenyl | CH₂CH₂CH₂CH₃ | COOH | | —SCH₂CH₃ |
| SO₂ | phenyl | C5-C8 alkyl | COOH | | —SCH₂CH₃ |
| SO₂ | phenyl | F | COOH | | —SCH₂CH₃ |
| SO₂ | phenyl | F, F | COOH | | —SCH₂CH₃ |
| SO₂ | phenyl | F, Cl | COOH | | —SCH₂CH₃ |
| SO₂ | phenyl | Cl | COOH | | —SCH₂CH₃ |
| SO₂ | phenyl | Cl, Cl | COOH | | —SCH₂CH₃ |

TABLE 4-continued

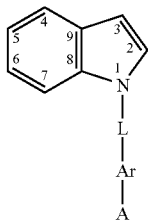

| L¹ | Ar | A | 3 | 5 | 6 |
|---|---|---|---|---|---|
| SO₂ | phenyl | -(1 to 4 linearly linked atom linker)-optionally subst. aryl | COOH | | —SCH₂CH₃ |
| SO₂ | phenyl | -(1 to 4 linearly linked atom linker)-optionally subst. heteroaryl | COOH | | —SCH₂CH₃ |
| SO₂ | pyridinyl | | COOH | | —SCH₂CH₃ |
| SO₂ | Pyridinyl | CF₃ | COOH | | —SCH₂CH₃ |
| SO₂ | Pyridinyl | CH₂CF₃ | COOH | | —SCH₂CH₃ |
| SO₂ | Pyridinyl | Halo substituted alkyl | COOH | | —SCH₂CH₃ |
| SO₂ | Pyridinyl | OCH₃ | COOH | | —SCH₂CH₃ |
| SO₂ | Pyridinyl | OCH₂CH₃ | COOH | | —SCH₂CH₃ |
| SO₂ | Pyridinyl | OCH₂CH₂CH₃ | COOH | | —SCH₂CH₃ |
| SO₂ | Pyridinyl | OCH₂CH₂CH₂CH₃ | COOH | | —SCH₂CH₃ |
| SO₂ | Pyridinyl | OCH₂CH₂CH₂CH₂CH₃ | COOH | | —SCH₂CH₃ |
| SO₂ | Pyridinyl | C5-C8 alkoxy | COOH | | —SCH₂CH₃ |
| SO₂ | Pyridinyl | Halo substituted alkoxy | COOH | | —SCH₂CH₃ |
| SO₂ | Pyridinyl | CH₃ | COOH | | —SCH₂CH₃ |
| SO₂ | Pyridinyl | CH₂CH₃ | COOH | | —SCH₂CH₃ |
| SO₂ | Pyridinyl | CH₂CH₂CH₃ | COOH | | —SCH₂CH₃ |
| SO₂ | Pyridinyl | CH₂CH₂CH₂CH₃ | COOH | | —SCH₂CH₃ |
| SO₂ | Pyridinyl | C5-C8 alkyl | COOH | | —SCH₂CH₃ |
| SO₂ | Pyridinyl | F | COOH | | —SCH₂CH₃ |
| SO₂ | Pyridinyl | F, F | COOH | | —SCH₂CH₃ |
| SO₂ | Pyridinyl | F, Cl | COOH | | —SCH₂CH₃ |
| SO₂ | Pyridinyl | Cl | COOH | | —SCH₂CH₃ |
| SO₂ | Pyridinyl | Cl, Cl | COOH | | —SCH₂CH₃ |
| SO₂ | Pyridinyl | -(1 to 4 linearly linked atom linker)-optionally subst. aryl | COOH | | —SCH₂CH₃ |
| SO₂ | Pyridinyl | -(1 to 4 linearly linked atom linker)-optionally subst. heteroaryl | COOH | | —SCH₂CH₃ |
| CO | Phenyl | | COOH | | —SCH₂CH₃ |
| CO | Phenyl | CF₃ | COOH | | —SCH₂CH₃ |
| CO | Phenyl | CH₂CF₃ | COOH | | —SCH₂CH₃ |
| CO | Phenyl | Halo substituted alkyl | COOH | | —SCH₂CH₃ |
| CO | Phenyl | OCH₃ | COOH | | —SCH₂CH₃ |
| CO | Phenyl | OCH₂CH₃ | COOH | | —SCH₂CH₃ |
| CO | Phenyl | OCH₂CH₂CH₃ | COOH | | —SCH₂CH₃ |
| CO | Phenyl | OCH₂CH₂CH₂CH₃ | COOH | | —SCH₂CH₃ |
| CO | Phenyl | OCH₂CH₂CH₂CH₂CH₃ | COOH | | —SCH₂CH₃ |
| CO | Phenyl | C5-C8 alkoxy | COOH | | —SCH₂CH₃ |
| CO | Phenyl | Halo substituted alkoxy | COOH | | —SCH₂CH₃ |
| CO | Phenyl | CH₃ | COOH | | —SCH₂CH₃ |
| CO | Phenyl | CH₂CH₃ | COOH | | —SCH₂CH₃ |
| CO | Phenyl | CH₂CH₂CH₃ | COOH | | —SCH₂CH₃ |
| CO | Phenyl | CH₂CH₂CH₂CH₃ | COOH | | —SCH₂CH₃ |
| CO | Phenyl | C5-C8 alkyl | COOH | | —SCH₂CH₃ |
| CO | Phenyl | F | COOH | | —SCH₂CH₃ |
| CO | Phenyl | F, F | COOH | | —SCH₂CH₃ |
| CO | Phenyl | F, Cl | COOH | | —SCH₂CH₃ |
| CO | Phenyl | Cl | COOH | | —SCH₂CH₃ |
| CO | Phenyl | Cl, Cl | COOH | | —SCH₂CH₃ |
| CO | Phenyl | -(1 to 4 linearly linked atom linker)-optionally subst. aryl | COOH | | —SCH₂CH₃ |
| CO | Phenyl | -(1 to 4 linearly linked atom linker)-optionally subst. heteroaryl | COOH | | —SCH₂CH₃ |
| CO | pyridinyl | | COOH | | —SCH₂CH₃ |
| CO | Pyridinyl | CF₃ | COOH | | —SCH₂CH₃ |
| CO | Pyridinyl | CH₂CF₃ | COOH | | —SCH₂CH₃ |

TABLE 4-continued

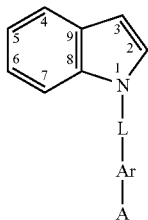

| L¹ | Ar | A | 3 | 5 | 6 |
|---|---|---|---|---|---|
| CO | Pyridinyl | Halo substituted alkyl | COOH | | —SCH$_2$CH$_3$ |
| CO | Pyridinyl | OCH$_3$ | COOH | | —SCH$_2$CH$_3$ |
| CO | Pyridinyl | OCH$_2$CH$_3$ | COOH | | —SCH$_2$CH$_3$ |
| CO | Pyridinyl | OCH$_2$CH$_2$CH$_3$ | COOH | | —SCH$_2$CH$_3$ |
| CO | Pyridinyl | OCH$_2$CH$_2$CH$_2$CH$_3$ | COOH | | —SCH$_2$CH$_3$ |
| CO | Pyridinyl | OCH$_2$CH$_2$CH$_2$CH$_2$CH$_3$ | COOH | | —SCH$_2$CH$_3$ |
| CO | Pyridinyl | C5-G8 alkoxy | COOH | | —SCH$_2$CH$_3$ |
| CO | Pyridinyl | Halo substituted alkoxy | COOH | | —SCH$_2$CH$_3$ |
| CO | Pyridinyl | CH$_3$ | COOH | | —SCH$_2$CH$_3$ |
| CO | Pyridinyl | CH$_2$CH$_3$ | COOH | | —SCH$_2$CH$_3$ |
| CO | Pyridinyl | CH$_2$CH$_2$CH$_3$ | COOH | | —SCH$_2$CH$_3$ |
| CO | Pyridinyl | CH$_2$CH$_2$CH$_2$CH$_3$ | COOH | | —SCH$_2$CH$_3$ |
| CO | Pyridinyl | C5-G8 alkyl | COOH | | —SCH$_2$CH$_3$ |
| CO | Pyridinyl | F | COOH | | —SCH$_2$CH$_3$ |
| CO | Pyridinyl | F, F | COOH | | —SCH$_2$CH$_3$ |
| CO | Pyridinyl | F, Cl | COOH | | —SCH$_2$CH$_3$ |
| CO | Pyridinyl | Cl | COOH | | —SCH$_2$CH$_3$ |
| CO | Pyridinyl | Cl, Cl | COOH | | —SCH$_2$CH$_3$ |
| CO | Pyridinyl | -(1 to 4 linearly linked atom linker)-optionally subst. aryl | COOH | | —SCH$_2$CH$_3$ |
| CO | Pyridinyl | -(1 to 4 linearly linked atom linker)-optionally subst. heteroaryl | COOH | | —SCH$_2$CH$_3$ |
| SO$_2$ | phenyl | | tetrazole | | methoxy |
| SO$_2$ | phenyl | CF$_3$ | Tetrazole | | methoxy |
| SO$_2$ | phenyl | CH$_2$CF$_3$ | Tetrazole | | methoxy |
| SO$_2$ | phenyl | Halo substituted alkyl | Tetrazole | | methoxy |
| SO$_2$ | phenyl | OCH$_3$ | Tetrazole | | methoxy |
| SO$_2$ | phenyl | OCH$_2$CH$_3$ | tetrazole | | methoxy |
| SO$_2$ | phenyl | OCH$_2$CH$_2$CH$_3$ | tetrazole | | methoxy |
| SO$_2$ | phenyl | OCH$_2$CH$_2$CH$_2$CH$_3$ | Tetrazole | | methoxy |
| SO$_2$ | phenyl | OCH$_2$CH$_2$CH$_2$CH$_2$CH$_3$ | Tetrazole | | methoxy |
| SO$_2$ | phenyl | C5-C8 alkoxy | Tetrazole | | methoxy |
| SO$_2$ | phenyl | Halo substituted alkoxy | Tetrazole | | methoxy |
| SO$_2$ | phenyl | CH$_3$ | tetrazole | | methoxy |
| SO$_2$ | phenyl | CH$_2$CH$_3$ | tetrazole | | methoxy |
| SO$_2$ | phenyl | CH$_2$CH$_2$CH$_3$ | Tetrazole | | methoxy |
| SO$_2$ | phenyl | CH$_2$CH$_2$CH$_2$CH$_3$ | Tetrazole | | methoxy |
| SO$_2$ | phenyl | C5-C8 alkyl | Tetrazole | | methoxy |
| SO$_2$ | phenyl | F | Tetrazole | | methoxy |
| SO$_2$ | phenyl | F, F | tetrazole | | methoxy |
| SO$_2$ | phenyl | F, Cl | tetrazole | | methoxy |
| SO$_2$ | phenyl | Cl | Tetrazole | | methoxy |
| SO$_2$ | phenyl | Cl, Cl | Tetrazole | | methoxy |
| SO$_2$ | phenyl | -(1 to 4 linearly linked atom linker)-optionally subst. aryl | Tetrazole | | methoxy |
| SO$_2$ | phenyl | -(1 to 4 linearly linked atom linker)-optionally subst. heteroaryl | Tetrazole | | methoxy |
| SO$_2$ | pyridinyl | | tetrazole | | methoxy |
| SO$_2$ | Pyridinyl | CF$_3$ | tetrazole | | methoxy |
| SO$_2$ | Pyridinyl | CH$_2$CF$_3$ | Tetrazole | | methoxy |
| SO$_2$ | Pyridinyl | Halo substituted alkyl | Tetrazole | | methoxy |
| SO$_2$ | Pyridinyl | OCH$_3$ | Tetrazole | | methoxy |
| SO$_2$ | Pyridinyl | OCH$_2$CH$_3$ | Tetrazole | | methoxy |
| SO$_2$ | Pyridinyl | OCH$_2$CH$_2$CH$_3$ | tetrazole | | methoxy |
| SO$_2$ | Pyridinyl | OCH$_2$CH$_2$CH$_2$CH$_3$ | tetrazole | | methoxy |
| SO$_2$ | Pyridinyl | OCH$_2$CH$_2$CH$_2$CH$_2$CH$_3$ | Tetrazole | | methoxy |
| SO$_2$ | Pyridinyl | C5-C8 alkoxy | Tetrazole | | methoxy |
| SO$_2$ | Pyridinyl | Halo substituted alkoxy | Tetrazole | | methoxy |
| SO$_2$ | Pyridinyl | CH$_3$ | Tetrazole | | methoxy |

TABLE 4-continued

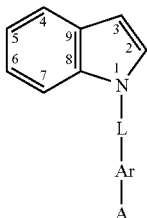

| L¹ | Ar | A | 3 | 5 | 6 |
|---|---|---|---|---|---|
| SO₂ | Pyridinyl | CH₂CH₃ | tetrazole | | methoxy |
| SO₂ | Pyridinyl | CH₂CH₂CH₃ | tetrazole | | methoxy |
| SO₂ | Pyridinyl | CH₂CH₂CH₂CH₃ | Tetrazole | | methoxy |
| SO₂ | Pyridinyl | C5-C8 alkyl | Tetrazole | | methoxy |
| SO₂ | Pyridinyl | F | Tetrazole | | methoxy |
| SO₂ | Pyridinyl | F, F | Tetrazole | | methoxy |
| SO₂ | Pyridinyl | F, Cl | tetrazole | | methoxy |
| SO₂ | Pyridinyl | Cl | tetrazole | | methoxy |
| SO₂ | Pyridinyl | Cl, Cl | Tetrazole | | methoxy |
| SO₂ | Pyridinyl | -(1 to 4 linearly linked atom linker)-optionally subst. aryl | Tetrazole | | methoxy |
| SO₂ | Pyridinyl | -(1 to 4 linearly linked atom linker)-optionally subst. heteroaryl | Tetrazole | | methoxy |
| CO | Phenyl | | Tetrazole | | methoxy |
| CO | Phenyl | CF₃ | tetrazole | | methoxy |
| CO | Phenyl | CH₂CF₃ | tetrazole | | methoxy |
| CO | Phenyl | Halo substituted alkyl | Tetrazole | | methoxy |
| CO | Phenyl | OCH₃ | Tetrazole | | methoxy |
| CO | Phenyl | OCH₂CH₃ | Tetrazole | | methoxy |
| CO | Phenyl | OCH₂CH₂CH₃ | Tetrazole | | methoxy |
| CO | Phenyl | OCH₂CH₂CH₂CH₃ | tetrazole | | methoxy |
| CO | Phenyl | OCH₂CH₂CH₂CH₂CH₃ | tetrazole | | methoxy |
| CO | Phenyl | C5-C8 alkoxy | Tetrazole | | methoxy |
| CO | Phenyl | Halo substituted alkoxy | Tetrazole | | methoxy |
| CO | Phenyl | CH₃ | Tetrazole | | methoxy |
| CO | Phenyl | CH₂CH₃ | Tetrazole | | methoxy |
| CO | Phenyl | CH₂CH₂CH₃ | tetrazole | | methoxy |
| CO | Phenyl | CH₂CH₂CH₂CH₃ | tetrazole | | methoxy |
| CO | Phenyl | C5-C8 alkyl | Tetrazole | | methoxy |
| CO | Phenyl | F | Tetrazole | | methoxy |
| CO | Phenyl | F, F | Tetrazole | | methoxy |
| CO | Phenyl | F, Cl | Tetrazole | | methoxy |
| CO | Phenyl | Cl | tetrazole | | methoxy |
| CO | Phenyl | Cl, Cl | tetrazole | | methoxy |
| CO | Phenyl | -(1 to 4 linearly linked atom linker)-optionally subst. aryl | Tetrazole | | methoxy |
| CO | Phenyl | -(1 to 4 linearly linked atom linker)-optionally subst. heteroaryl | Tetrazole | | methoxy |
| CO | pyridinyl | | Tetrazole | | methoxy |
| CO | Pyridinyl | CF₃ | Tetrazole | | methoxy |
| CO | Pyridinyl | CH₂CF₃ | tetrazole | | methoxy |
| CO | Pyridinyl | Halo substituted alkyl | tetrazole | | methoxy |
| CO | Pyridinyl | OCH₃ | Tetrazole | | methoxy |
| CO | Pyridinyl | OCH₂CH₃ | Tetrazole | | methoxy |
| CO | Pyridinyl | OCH₂CH₂CH₃ | Tetrazole | | methoxy |
| CO | Pyridinyl | OCH₂CH₂CH₂CH₃ | Tetrazole | | methoxy |
| CO | Pyridinyl | OCH₂CH₂CH₂CH₂CH₃ | tetrazole | | methoxy |
| CO | Pyridinyl | C5-G8 alkoxy | tetrazole | | methoxy |
| CO | Pyridinyl | Halo substituted alkoxy | Tetrazole | | methoxy |
| CO | Pyridinyl | CH₃ | Tetrazole | | methoxy |
| CO | Pyridinyl | CH₂CH₃ | Tetrazole | | methoxy |
| CO | Pyridinyl | CH₂CH₂CH₃ | Tetrazole | | methoxy |
| CO | Pyridinyl | CH₂CH₂CH₂CH₃ | tetrazole | | methoxy |
| CO | Pyridinyl | C5-G8 alkyl | tetrazole | | methoxy |
| CO | Pyridinyl | F | Tetrazole | | methoxy |
| CO | Pyridinyl | F, F | Tetrazole | | methoxy |
| CO | Pyridinyl | F, Cl | Tetrazole | | methoxy |
| CO | Pyridinyl | Cl | Tetrazole | | methoxy |
| CO | Pyridinyl | Cl, Cl | tetrazole | | methoxy |

TABLE 4-continued

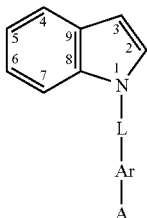

| L¹ | Ar | A | 3 | 5 | 6 |
|---|---|---|---|---|---|
| CO | Pyridinyl | -(1 to 4 linearly linked atom linker)-optionally subst. aryl | tetrazole | | methoxy |
| CO | Pyridinyl | -(1 to 4 linearly linked atom linker)-optionally subst. heteroaryl | Tetrazole | | methoxy |
| SO₂ | phenyl | | Tetrazole | | ethoxy |
| SO₂ | phenyl | CF₃ | Tetrazole | | ethoxy |
| SO₂ | phenyl | CH₂CF₃ | Tetrazole | | ethoxy |
| SO₂ | phenyl | Halo substituted alkyl | tetrazole | | ethoxy |
| SO₂ | phenyl | OCH₃ | tetrazole | | ethoxy |
| SO₂ | phenyl | OCH₂CH₃ | Tetrazole | | ethoxy |
| SO₂ | phenyl | OCH₂CH₂CH₃ | Tetrazole | | ethoxy |
| SO₂ | phenyl | OCH₂CH₂CH₂CH₃ | Tetrazole | | ethoxy |
| SO₂ | phenyl | OCH₂CH₂CH₂CH₂CH₃ | Tetrazole | | ethoxy |
| SO₂ | phenyl | C5-C8 alkoxy | tetrazole | | ethoxy |
| SO₂ | phenyl | Halo substituted alkoxy | tetrazole | | ethoxy |
| SO₂ | phenyl | CH₃ | Tetrazole | | ethoxy |
| SO₂ | phenyl | CH₂CH₃ | Tetrazole | | ethoxy |
| SO₂ | phenyl | CH₂CH₂CH₃ | Tetrazole | | ethoxy |
| SO₂ | phenyl | CH₂CH₂CH₂CH₃ | Tetrazole | | ethoxy |
| SO₂ | phenyl | C5-C8 alkyl | tetrazole | | ethoxy |
| SO₂ | phenyl | F | tetrazole | | ethoxy |
| SO₂ | phenyl | F, F | Tetrazole | | ethoxy |
| SO₂ | phenyl | F, Cl | Tetrazole | | ethoxy |
| SO₂ | phenyl | Cl | Tetrazole | | ethoxy |
| SO₂ | phenyl | Cl, Cl | Tetrazole | | ethoxy |
| SO₂ | phenyl | -(1 to 4 linearly linked atom linker)-optionally subst. aryl | tetrazole | | ethoxy |
| SO₂ | phenyl | -(1 to 4 linearly linked atom linker)-optionally subst. heteroaryl | tetrazole | | ethoxy |
| SO₂ | pyridinyl | | Tetrazole | | ethoxy |
| SO₂ | Pyridinyl | CF₃ | Tetrazole | | ethoxy |
| SO₂ | Pyridinyl | CH₂CF₃ | Tetrazole | | ethoxy |
| SO₂ | Pyridinyl | Halo substituted alkyl | Tetrazole | | ethoxy |
| SO₂ | Pyridinyl | OCH₃ | tetrazole | | ethoxy |
| SO₂ | Pyridinyl | OCH₂CH₃ | tetrazole | | ethoxy |
| SO₂ | Pyridinyl | OCH₂CH₂CH₃ | Tetrazole | | ethoxy |
| SO₂ | Pyridinyl | OCH₂CH₂CH₂CH₃ | Tetrazole | | ethoxy |
| SO₂ | Pyridinyl | OCH₂CH₂CH₂CH₂CH₃ | Tetrazole | | ethoxy |
| SO₂ | Pyridinyl | C5-C8 alkoxy | Tetrazole | | ethoxy |
| SO₂ | Pyridinyl | Halo substituted alkoxy | tetrazole | | ethoxy |
| SO₂ | Pyridinyl | CH₃ | tetrazole | | ethoxy |
| SO₂ | Pyridinyl | CH₂CH₃ | Tetrazole | | ethoxy |
| SO₂ | Pyridinyl | CH₂CH₂CH₃ | Tetrazole | | ethoxy |
| SO₂ | Pyridinyl | CH₂CH₂CH₂CH₃ | Tetrazole | | ethoxy |
| SO₂ | Pyridinyl | C5-C8 alkyl | Tetrazole | | ethoxy |
| SO₂ | Pyridinyl | F | tetrazole | | ethoxy |
| SO₂ | Pyridinyl | F, F | tetrazole | | ethoxy |
| SO₂ | Pyridinyl | F, Cl | Tetrazole | | ethoxy |
| SO₂ | Pyridinyl | Cl | Tetrazole | | ethoxy |
| SO₂ | Pyridinyl | Cl, Cl | Tetrazole | | ethoxy |
| SO₂ | Pyridinyl | -(1 to 4 linearly linked atom linker)-optionally subst. aryl | Tetrazole | | ethoxy |
| SO₂ | Pyridinyl | -(1 to 4 linearly linked atom linker)-optionally subst. heteroaryl | tetrazole | | ethoxy |
| CO | Phenyl | | tetrazole | | ethoxy |
| CO | Phenyl | CF₃ | Tetrazole | | ethoxy |
| CO | Phenyl | CH₂CF₃ | Tetrazole | | ethoxy |

TABLE 4-continued

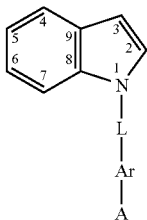

| L¹ | Ar | A | 3 | 5 | 6 |
|---|---|---|---|---|---|
| CO | Phenyl | Halo substituted alkyl | Tetrazole | | ethoxy |
| CO | Phenyl | OCH₃ | Tetrazole | | ethoxy |
| CO | Phenyl | OCH₂CH₃ | tetrazole | | ethoxy |
| CO | Phenyl | OCH₂CH₂CH₃ | tetrazole | | ethoxy |
| CO | Phenyl | OCH₂CH₂CH₂CH₃ | Tetrazole | | ethoxy |
| CO | Phenyl | OCH₂CH₂CH₂CH₂CH₃ | Tetrazole | | ethoxy |
| CO | Phenyl | C5-C8 alkoxy | Tetrazole | | ethoxy |
| CO | Phenyl | Halo substituted alkoxy | Tetrazole | | ethoxy |
| CO | Phenyl | CH₃ | tetrazole | | ethoxy |
| CO | Phenyl | CH₂CH₃ | tetrazole | | ethoxy |
| CO | Phenyl | CH₂CH₂CH₃ | Tetrazole | | ethoxy |
| CO | Phenyl | CH₂CH₂CH₂CH₃ | Tetrazole | | ethoxy |
| CO | Phenyl | C5-C8 alkyl | Tetrazole | | ethoxy |
| CO | Phenyl | F | Tetrazole | | ethoxy |
| CO | Phenyl | F, F | tetrazole | | ethoxy |
| CO | Phenyl | F, Cl | tetrazole | | ethoxy |
| CO | Phenyl | Cl | Tetrazole | | ethoxy |
| CO | Phenyl | Cl, Cl | Tetrazole | | ethoxy |
| CO | Phenyl | -(1 to 4 linearly linked atom linker)-optionally subst. aryl | Tetrazole | | ethoxy |
| CO | Phenyl | -(1 to 4 linearly linked atom linker)-optionally subst. heteroaryl | Tetrazole | | ethoxy |
| CO | pyridinyl | | tetrazole | | ethoxy |
| CO | Pyridinyl | CF₃ | tetrazole | | ethoxy |
| CO | Pyridinyl | CH₂CF₃ | Tetrazole | | ethoxy |
| CO | Pyridinyl | Halo substituted alkyl | Tetrazole | | ethoxy |
| CO | Pyridinyl | OCH₃ | Tetrazole | | ethoxy |
| CO | Pyridinyl | OCH₂CH₃ | Tetrazole | | ethoxy |
| CO | Pyridinyl | OCH₂CH₂CH₃ | tetrazole | | ethoxy |
| CO | Pyridinyl | OCH₂CH₂CH₂CH₃ | tetrazole | | ethoxy |
| CO | Pyridinyl | OCH₂CH₂CH₂CH₂CH₃ | Tetrazole | | ethoxy |
| CO | Pyridinyl | C5-G8 alkoxy | Tetrazole | | ethoxy |
| CO | Pyridinyl | Halo substituted alkoxy | Tetrazole | | ethoxy |
| CO | Pyridinyl | CH₃ | Tetrazole | | ethoxy |
| CO | Pyridinyl | CH₂CH₃ | tetrazole | | ethoxy |
| CO | Pyridinyl | CH₂CH₂CH₃ | tetrazole | | ethoxy |
| CO | Pyridinyl | CH₂CH₂CH₂CH₃ | Tetrazole | | ethoxy |
| CO | Pyridinyl | C5-G8 alkyl | Tetrazole | | ethoxy |
| CO | Pyridinyl | F | Tetrazole | | ethoxy |
| CO | Pyridinyl | F, F | Tetrazole | | ethoxy |
| CO | Pyridinyl | F, Cl | tetrazole | | ethoxy |
| CO | Pyridinyl | Cl | tetrazole | | ethoxy |
| CO | Pyridinyl | Cl, Cl | Tetrazole | | ethoxy |
| CO | Pyridinyl | -(1 to 4 linearly linked atom linker)-optionally subst. aryl | Tetrazole | | ethoxy |
| CO | Pyridinyl | -(1 to 4 linearly linked atom linker)-optionally subst. heteroaryl | Tetrazole | | ethoxy |
| SO₂ | phenyl | | tetrazole | | propoxy |
| SO₂ | phenyl | CF₃ | Tetrazole | | propoxy |
| SO₂ | phenyl | CH₂CF₃ | Tetrazole | | propoxy |
| SO₂ | phenyl | Halo substituted alkyl | Tetrazole | | propoxy |
| SO₂ | phenyl | OCH₃ | Tetrazole | | propoxy |
| SO₂ | phenyl | OCH₂CH₃ | tetrazole | | propoxy |
| SO₂ | phenyl | OCH₂CH₂CH₃ | tetrazole | | propoxy |
| SO₂ | phenyl | OCH₂CH₂CH₂CH₃ | Tetrazole | | propoxy |
| SO₂ | phenyl | OCH₂CH₂CH₂CH₂CH₃ | Tetrazole | | propoxy |
| SO₂ | phenyl | C5-C8 alkoxy | Tetrazole | | propoxy |
| SO₂ | phenyl | Halo substituted alkoxy | Tetrazole | | propoxy |
| SO₂ | phenyl | CH₃ | tetrazole | | propoxy |

TABLE 4-continued

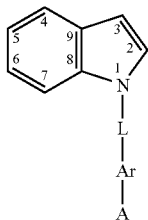

| $L^1$ | Ar | A | 3 | 5 | 6 |
|---|---|---|---|---|---|
| $SO_2$ | phenyl | $CH_2CH_3$ | tetrazole | | propoxy |
| $SO_2$ | phenyl | $CH_2CH_2CH_3$ | Tetrazole | | propoxy |
| $SO_2$ | phenyl | $CH_2CH_2CH_2CH_3$ | Tetrazole | | propoxy |
| $SO_2$ | phenyl | C5-C8 alkyl | Tetrazole | | propoxy |
| $SO_2$ | phenyl | F | Tetrazole | | propoxy |
| $SO_2$ | phenyl | F, F | tetrazole | | propoxy |
| $SO_2$ | phenyl | F, Cl | tetrazole | | propoxy |
| $SO_2$ | phenyl | Cl | Tetrazole | | propoxy |
| $SO_2$ | phenyl | Cl, Cl | Tetrazole | | propoxy |
| $SO_2$ | phenyl | -(1 to 4 linearly linked atom linker)-optionally subst. aryl | Tetrazole | | propoxy |
| $SO_2$ | phenyl | -(1 to 4 linearly linked atom linker)-optionally subst. heteroaryl | Tetrazole | | propoxy |
| $SO_2$ | pyridinyl | | tetrazole | | propoxy |
| $SO_2$ | Pyridinyl | $CF_3$ | tetrazole | | propoxy |
| $SO_2$ | Pyridinyl | $CH_2CF_3$ | Tetrazole | | propoxy |
| $SO_2$ | Pyridinyl | Halo substituted alkyl | Tetrazole | | propoxy |
| $SO_2$ | Pyridinyl | $OCH_3$ | Tetrazole | | propoxy |
| $SO_2$ | Pyridinyl | $OCH_2CH_3$ | Tetrazole | | propoxy |
| $SO_2$ | Pyridinyl | $OCH_2CH_2CH_3$ | tetrazole | | propoxy |
| $SO_2$ | Pyridinyl | $OCH_2CH_2CH_2CH_3$ | tetrazole | | propoxy |
| $SO_2$ | Pyridinyl | $OCH_2CH_2CH_2CH_2CH_3$ | Tetrazole | | propoxy |
| $SO_2$ | Pyridinyl | C5-C8 alkoxy | Tetrazole | | propoxy |
| $SO_2$ | Pyridinyl | Halo substituted alkoxy | Tetrazole | | propoxy |
| $SO_2$ | Pyridinyl | $CH_3$ | Tetrazole | | propoxy |
| $SO_2$ | Pyridinyl | $CH_2CH_3$ | tetrazole | | propoxy |
| $SO_2$ | Pyridinyl | $CH_2CH_2CH_3$ | tetrazole | | propoxy |
| $SO_2$ | Pyridinyl | $CH_2CH_2CH_2CH_3$ | Tetrazole | | propoxy |
| $SO_2$ | Pyridinyl | C5-C8 alkyl | Tetrazole | | propoxy |
| $SO_2$ | Pyridinyl | F | Tetrazole | | propoxy |
| $SO_2$ | Pyridinyl | F, F | Tetrazole | | propoxy |
| $SO_2$ | Pyridinyl | F, Cl | tetrazole | | propoxy |
| $SO_2$ | Pyridinyl | Cl | tetrazole | | propoxy |
| $SO_2$ | Pyridinyl | Cl, Cl | Tetrazole | | propoxy |
| $SO_2$ | Pyridinyl | -(1 to 4 linearly linked atom linker)-optionally subst. aryl | Tetrazole | | propoxy |
| $SO_2$ | Pyridinyl | -(1 to 4 linearly linked atom linker)-optionally subst. heteroaryl | Tetrazole | | propoxy |
| CO | Phenyl | | Tetrazole | | propoxy |
| CO | Phenyl | $CF_3$ | tetrazole | | propoxy |
| CO | Phenyl | $CH_2CF_3$ | tetrazole | | propoxy |
| CO | Phenyl | Halo substituted alkyl | Tetrazole | | propoxy |
| CO | Phenyl | $OCH_3$ | Tetrazole | | propoxy |
| CO | Phenyl | $OCH_2CH_3$ | Tetrazole | | propoxy |
| CO | Phenyl | $OCH_2CH_2CH_3$ | Tetrazole | | propoxy |
| CO | Phenyl | $OCH_2CH_2CH_2CH_3$ | tetrazole | | propoxy |
| CO | Phenyl | $OCH_2CH_2CH_2CH_2CH_3$ | tetrazole | | propoxy |
| CO | Phenyl | C5-C8 alkoxy | Tetrazole | | propoxy |
| CO | Phenyl | Halo substituted alkoxy | Tetrazole | | propoxy |
| CO | Phenyl | $CH_3$ | Tetrazole | | propoxy |
| CO | Phenyl | $CH_2CH_3$ | Tetrazole | | propoxy |
| CO | Phenyl | $CH_2CH_2CH_3$ | tetrazole | | propoxy |
| CO | Phenyl | $CH_2CH_2CH_2CH_3$ | tetrazole | | propoxy |
| CO | Phenyl | C5-C8 alkyl | Tetrazole | | propoxy |
| CO | Phenyl | F | Tetrazole | | propoxy |
| CO | Phenyl | F, F | Tetrazole | | propoxy |
| CO | Phenyl | F, Cl | Tetrazole | | propoxy |
| CO | Phenyl | Cl | tetrazole | | propoxy |
| CO | Phenyl | Cl, Cl | tetrazole | | propoxy |

TABLE 4-continued

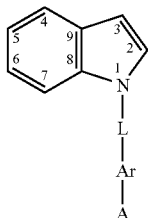

| L¹ | Ar | A | 3 | 5 | 6 |
|---|---|---|---|---|---|
| CO | Phenyl | -(1 to 4 linearly linked atom linker)-optionally subst. aryl | Tetrazole | | propoxy |
| CO | Phenyl | -(1 to 4 linearly linked atom linker)-optionally subst. heteroaryl | Tetrazole | | propoxy |
| CO | pyridinyl | | Tetrazole | | propoxy |
| CO | Pyridinyl | $CF_3$ | Tetrazole | | propoxy |
| CO | Pyridinyl | $CH_2CF_3$ | tetrazole | | propoxy |
| CO | Pyridinyl | Halo substituted alkyl | tetrazole | | propoxy |
| CO | Pyridinyl | $OCH_3$ | Tetrazole | | propoxy |
| CO | Pyridinyl | $OCH_2CH_3$ | Tetrazole | | propoxy |
| CO | Pyridinyl | $OCH_2CH_2CH_3$ | Tetrazole | | propoxy |
| CO | Pyridinyl | $OCH_2CH_2CH_2CH_3$ | Tetrazole | | propoxy |
| CO | Pyridinyl | $OCH_2CH_2CH_2CH_2CH_3$ | tetrazole | | propoxy |
| CO | Pyridinyl | C5-G8 alkoxy | tetrazole | | propoxy |
| CO | Pyridinyl | Halo substituted alkoxy | Tetrazole | | propoxy |
| CO | Pyridinyl | $CH_3$ | Tetrazole | | propoxy |
| CO | Pyridinyl | $CH_2CH_3$ | Tetrazole | | propoxy |
| CO | Pyridinyl | $CH_2CH_2CH_3$ | Tetrazole | | propoxy |
| CO | Pyridinyl | $CH_2CH_2CH_2CH_3$ | tetrazole | | propoxy |
| CO | Pyridinyl | C5-G8 alkyl | tetrazole | | propoxy |
| CO | Pyridinyl | F | Tetrazole | | propoxy |
| CO | Pyridinyl | F, F | Tetrazole | | propoxy |
| CO | Pyridinyl | F, Cl | Tetrazole | | propoxy |
| CO | Pyridinyl | Cl | Tetrazole | | propoxy |
| CO | Pyridinyl | Cl, Cl | tetrazole | | propoxy |
| CO | Pyridinyl | -(1 to 4 linearly linked atom linker)-optionally subst. aryl | tetrazole | | propoxy |
| CO | Pyridinyl | -(1 to 4 linearly linked atom linker)-optionally subst. heteroaryl | Tetrazole | | propoxy |
| $SO_2$ | phenyl | | Tetrazole | | —$SCH_3$ |
| $SO_2$ | phenyl | $CF_3$ | Tetrazole | | —$SCH_3$ |
| $SO_2$ | phenyl | $CH_2CF_3$ | Tetrazole | | —$SCH_3$ |
| $SO_2$ | phenyl | Halo substituted alkyl | tetrazole | | —$SCH_3$ |
| $SO_2$ | phenyl | $OCH_3$ | tetrazole | | —$SCH_3$ |
| $SO_2$ | phenyl | $OCH_2CH_3$ | Tetrazole | | —$SCH_3$ |
| $SO_2$ | phenyl | $OCH_2CH_2CH_3$ | Tetrazole | | —$SCH_3$ |
| $SO_2$ | phenyl | $OCH_2CH_2CH_2CH_3$ | Tetrazole | | —$SCH_3$ |
| $SO_2$ | phenyl | $OCH_2CH_2CH_2CH_2CH_3$ | Tetrazole | | —$SCH_3$ |
| $SO_2$ | phenyl | C5-C8 alkoxy | tetrazole | | —$SCH_3$ |
| $SO_2$ | phenyl | Halo substituted alkoxy | tetrazole | | —$SCH_3$ |
| $SO_2$ | phenyl | $CH_3$ | Tetrazole | | —$SCH_3$ |
| $SO_2$ | phenyl | $CH_2CH_3$ | Tetrazole | | —$SCH_3$ |
| $SO_2$ | phenyl | $CH_2CH_2CH_3$ | Tetrazole | | —$SCH_3$ |
| $SO_2$ | phenyl | $CH_2CH_2CH_2CH_3$ | Tetrazole | | —$SCH_3$ |
| $SO_2$ | phenyl | C5-C8 alkyl | tetrazole | | —$SCH_3$ |
| $SO_2$ | phenyl | F | tetrazole | | —$SCH_3$ |
| $SO_2$ | phenyl | F, F | Tetrazole | | —$SCH_3$ |
| $SO_2$ | phenyl | F, Cl | Tetrazole | | —$SCH_3$ |
| $SO_2$ | phenyl | Cl | Tetrazole | | —$SCH_3$ |
| $SO_2$ | phenyl | Cl, Cl | Tetrazole | | —$SCH_3$ |
| $SO_2$ | phenyl | -(1 to 4 linearly linked atom linker)-optionally subst. aryl | tetrazole | | —$SCH_3$ |
| $SO_2$ | phenyl | -(1 to 4 linearly linked atom linker)-optionally subst. heteroaryl | tetrazole | | —$SCH_3$ |
| $SO_2$ | pyridinyl | | Tetrazole | | —$SCH_3$ |
| $SO_2$ | Pyridinyl | $CF_3$ | Tetrazole | | —$SCH_3$ |
| $SO_2$ | Pyridinyl | $CH_2CF_3$ | Tetrazole | | —$SCH_3$ |

TABLE 4-continued

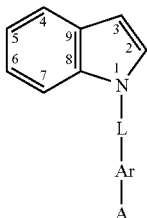

| $L^1$ | Ar | A | 3 | 5 | 6 |
|---|---|---|---|---|---|
| $SO_2$ | Pyridinyl | Halo substituted alkyl | Tetrazole | | —$SCH_3$ |
| $SO_2$ | Pyridinyl | $OCH_3$ | tetrazole | | —$SCH_3$ |
| $SO_2$ | Pyridinyl | $OCH_2CH_3$ | tetrazole | | —$SCH_3$ |
| $SO_2$ | Pyridinyl | $OCH_2CH_2CH_3$ | Tetrazole | | —$SCH_3$ |
| $SO_2$ | Pyridinyl | $OCH_2CH_2CH_2CH_3$ | Tetrazole | | —$SCH_3$ |
| $SO_2$ | Pyridinyl | $OCH_2CH_2CH_2CH_2CH_3$ | Tetrazole | | —$SCH_3$ |
| $SO_2$ | Pyridinyl | C5-C8 alkoxy | Tetrazole | | —$SCH_3$ |
| $SO_2$ | Pyridinyl | Halo substituted alkoxy | tetrazole | | —$SCH_3$ |
| $SO_2$ | Pyridinyl | $CH_3$ | tetrazole | | —$SCH_3$ |
| $SO_2$ | Pyridinyl | $CH_2CH_3$ | Tetrazole | | —$SCH_3$ |
| $SO_2$ | Pyridinyl | $CH_2CH_2CH_3$ | Tetrazole | | —$SCH_3$ |
| $SO_2$ | Pyridinyl | $CH_2CH_2CH_2CH_3$ | Tetrazole | | —$SCH_3$ |
| $SO_2$ | Pyridinyl | C5-C8 alkyl | Tetrazole | | —$SCH_3$ |
| $SO_2$ | Pyridinyl | F | tetrazole | | —$SCH_3$ |
| $SO_2$ | Pyridinyl | F, F | tetrazole | | —$SCH_3$ |
| $SO_2$ | Pyridinyl | F, Cl | Tetrazole | | —$SCH_3$ |
| $SO_2$ | Pyridinyl | Cl | Tetrazole | | —$SCH_3$ |
| $SO_2$ | Pyridinyl | Cl, Cl | Tetrazole | | —$SCH_3$ |
| $SO_2$ | Pyridinyl | -(1 to 4 linearly linked atom linker)-optionally subst. aryl | Tetrazole | | —$SCH_3$ |
| $SO_2$ | Pyridinyl | -(1 to 4 linearly linked atom linker)-optionally subst. heteroaryl | tetrazole | | —$SCH_3$ |
| CO | Phenyl | | tetrazole | | —$SCH_3$ |
| CO | Phenyl | $CF_3$ | Tetrazole | | —$SCH_3$ |
| CO | Phenyl | $CH_2CF_3$ | Tetrazole | | —$SCH_3$ |
| CO | Phenyl | Halo substituted alkyl | Tetrazole | | —$SCH_3$ |
| CO | Phenyl | $OCH_3$ | Tetrazole | | —$SCH_3$ |
| CO | Phenyl | $OCH_2CH_3$ | tetrazole | | —$SCH_3$ |
| CO | Phenyl | $OCH_2CH_2CH_3$ | tetrazole | | —$SCH_3$ |
| CO | Phenyl | $OCH_2CH_2CH_2CH_3$ | Tetrazole | | —$SCH_3$ |
| CO | Phenyl | $OCH_2CH_2CH_2CH_2CH_3$ | Tetrazole | | —$SCH_3$ |
| CO | Phenyl | C5-C8 alkoxy | Tetrazole | | —$SCH_3$ |
| CO | Phenyl | Halo substituted alkoxy | Tetrazole | | —$SCH_3$ |
| CO | Phenyl | $CH_3$ | tetrazole | | —$SCH_3$ |
| CO | Phenyl | $CH_2CH_3$ | tetrazole | | —$SCH_3$ |
| CO | Phenyl | $CH_2CH_2CH_3$ | Tetrazole | | —$SCH_3$ |
| CO | Phenyl | $CH_2CH_2CH_2CH_3$ | Tetrazole | | —$SCH_3$ |
| CO | Phenyl | C5-C8 alkyl | Tetrazole | | —$SCH_3$ |
| CO | Phenyl | F | Tetrazole | | —$SCH_3$ |
| CO | Phenyl | F, F | tetrazole | | —$SCH_3$ |
| CO | Phenyl | F, Cl | tetrazole | | —$SCH_3$ |
| CO | Phenyl | Cl | Tetrazole | | —$SCH_3$ |
| CO | Phenyl | Cl, Cl | Tetrazole | | —$SCH_3$ |
| CO | Phenyl | -(1 to 4 linearly linked atom linker)-optionally subst. aryl | Tetrazole | | —$SCH_3$ |
| CO | Phenyl | -(1 to 4 linearly linked atom linker)-optionally subst. heteroaryl | Tetrazole | | —$SCH_3$ |
| CO | pyridinyl | | tetrazole | | —$SCH_3$ |
| CO | Pyridinyl | $CF_3$ | tetrazole | | —$SCH_3$ |
| CO | Pyridinyl | $CH_2CF_3$ | Tetrazole | | —$SCH_3$ |
| CO | Pyridinyl | Halo substituted alkyl | Tetrazole | | —$SCH_3$ |
| CO | Pyridinyl | $OCH_3$ | Tetrazole | | —$SCH_3$ |
| CO | Pyridinyl | $OCH_2CH_3$ | Tetrazole | | —$SCH_3$ |
| CO | Pyridinyl | $OCH_2CH_2CH_3$ | tetrazole | | —$SCH_3$ |
| CO | Pyridinyl | $OCH_2CH_2CH_2CH_3$ | tetrazole | | —$SCH_3$ |
| CO | Pyridinyl | $OCH_2CH_2CH_2CH_2CH_3$ | Tetrazole | | —$SCH_3$ |
| CO | Pyridinyl | C5-G8 alkoxy | Tetrazole | | —$SCH_3$ |
| CO | Pyridinyl | Halo substituted alkoxy | Tetrazole | | —$SCH_3$ |
| CO | Pyridinyl | $CH_3$ | Tetrazole | | —$SCH_3$ |

TABLE 4-continued

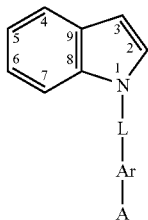

| L¹ | Ar | A | 3 | 5 | 6 |
|---|---|---|---|---|---|
| CO | Pyridinyl | CH₂CH₃ | tetrazole | | —SCH₃ |
| CO | Pyridinyl | CH₂CH₂CH₃ | tetrazole | | —SCH₃ |
| CO | Pyridinyl | CH₂CH₂CH₂CH₃ | Tetrazole | | —SCH₃ |
| CO | Pyridinyl | C5-G8 alkyl | Tetrazole | | —SCH₃ |
| CO | Pyridinyl | F | Tetrazole | | —SCH₃ |
| CO | Pyridinyl | F, F | Tetrazole | | —SCH₃ |
| CO | Pyridinyl | F, Cl | tetrazole | | —SCH₃ |
| CO | Pyridinyl | Cl | tetrazole | | —SCH₃ |
| CO | Pyridinyl | Cl, Cl | Tetrazole | | —SCH₃ |
| CO | Pyridinyl | -(1 to 4 linearly linked atom linker)-optionally subst. aryl | Tetrazole | | —SCH₃ |
| CO | Pyridinyl | -(1 to 4 linearly linked atom linker)-optionally subst. heteroaryl | Tetrazole | | —SCH₃ |
| SO₂ | phenyl | | Tetrazole | | —SCH₂CH₃ |
| SO₂ | phenyl | CF₃ | tetrazole | | —SCH₂CH₃ |
| SO₂ | phenyl | CH₂CF₃ | tetrazole | | —SCH₂CH₃ |
| SO₂ | phenyl | Halo substituted alkyl | Tetrazole | | —SCH₂CH₃ |
| SO₂ | phenyl | OCH₃ | Tetrazole | | —SCH₂CH₃ |
| SO₂ | phenyl | OCH₂CH₃ | Tetrazole | | —SCH₂CH₃ |
| SO₂ | phenyl | OCH₂CH₂CH₃ | Tetrazole | | —SCH₂CH₃ |
| SO₂ | phenyl | OCH₂CH₂CH₂CH₃ | tetrazole | | —SCH₂CH₃ |
| SO₂ | phenyl | OCH₂CH₂CH₂CH₂CH₃ | tetrazole | | —SCH₂CH₃ |
| SO₂ | phenyl | C5-C8 alkoxy | Tetrazole | | —SCH₂CH₃ |
| SO₂ | phenyl | Halo substituted alkoxy | Tetrazole | | —SCH₂CH₃ |
| SO₂ | phenyl | CH₃ | Tetrazole | | —SCH₂CH₃ |
| SO₂ | phenyl | CH₂CH₃ | Tetrazole | | —SCH₂CH₃ |
| SO₂ | phenyl | CH₂CH₂CH₃ | tetrazole | | —SCH₂CH₃ |
| SO₂ | phenyl | CH₂CH₂CH₂CH₃ | tetrazole | | —SCH₂CH₃ |
| SO₂ | phenyl | C5-C8 alkyl | Tetrazole | | —SCH₂CH₃ |
| SO₂ | phenyl | F | Tetrazole | | —SCH₂CH₃ |
| SO₂ | phenyl | F, F | Tetrazole | | —SCH₂CH₃ |
| SO₂ | phenyl | F, Cl | Tetrazole | | —SCH₂CH₃ |
| SO₂ | phenyl | Cl | tetrazole | | —SCH₂CH₃ |
| SO₂ | phenyl | Cl, Cl | tetrazole | | —SCH₂CH₃ |
| SO₂ | phenyl | -(1 to 4 linearly linked atom linker)-optionally subst. aryl | Tetrazole | | —SCH₂CH₃ |
| SO₂ | phenyl | -(1 to 4 linearly linked atom linker)-optionally subst. heteroaryl | Tetrazole | | —SCH₂CH₃ |
| SO₂ | pyridinyl | | Tetrazole | | —SCH₂CH₃ |
| SO₂ | Pyridinyl | CF₃ | Tetrazole | | —SCH₂CH₃ |
| SO₂ | Pyridinyl | CH₂CF₃ | tetrazole | | —SCH₂CH₃ |
| SO₂ | Pyridinyl | Halo substituted alkyl | tetrazole | | —SCH₂CH₃ |
| SO₂ | Pyridinyl | OCH₃ | Tetrazole | | —SCH₂CH₃ |
| SO₂ | Pyridinyl | OCH₂CH₃ | Tetrazole | | —SCH₂CH₃ |
| SO₂ | Pyridinyl | OCH₂CH₂CH₃ | Tetrazole | | —SCH₂CH₃ |
| SO₂ | Pyridinyl | OCH₂CH₂CH₂CH₃ | Tetrazole | | —SCH₂CH₃ |
| SO₂ | Pyridinyl | OCH₂CH₂CH₂CH₂CH₃ | tetrazole | | —SCH₂CH₃ |
| SO₂ | Pyridinyl | C5-C8 alkoxy | tetrazole | | —SCH₂CH₃ |
| SO₂ | Pyridinyl | Halo substituted alkoxy | Tetrazole | | —SCH₂CH₃ |
| SO₂ | Pyridinyl | CH₃ | Tetrazole | | —SCH₂CH₃ |
| SO₂ | Pyridinyl | CH₂CH₃ | Tetrazole | | —SCH₂CH₃ |
| SO₂ | Pyridinyl | CH₂CH₂CH₃ | Tetrazole | | —SCH₂CH₃ |
| SO₂ | Pyridinyl | CH₂CH₂CH₂CH₃ | tetrazole | | —SCH₂CH₃ |
| SO₂ | Pyridinyl | C5-C8 alkyl | tetrazole | | —SCH₂CH₃ |
| SO₂ | Pyridinyl | F | Tetrazole | | —SCH₂CH₃ |
| SO₂ | Pyridinyl | F, F | Tetrazole | | —SCH₂CH₃ |
| SO₂ | Pyridinyl | F, Cl | Tetrazole | | —SCH₂CH₃ |
| SO₂ | Pyridinyl | Cl | Tetrazole | | —SCH₂CH₃ |
| SO₂ | Pyridinyl | Cl, Cl | tetrazole | | —SCH₂CH₃ |

TABLE 4-continued

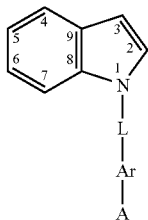

| L¹ | Ar | A | 3 | 5 | 6 |
|---|---|---|---|---|---|
| SO₂ | Pyridinyl | -(1 to 4 linearly linked atom linker)-optionally subst. aryl | tetrazole | | —SCH₂CH₃ |
| SO₂ | Pyridinyl | -(1 to 4 linearly linked atom linker)-optionally subst. heteroaryl | Tetrazole | | —SCH₂CH₃ |
| CO | Phenyl | | Tetrazole | | —SCH₂CH₃ |
| CO | Phenyl | CF₃ | Tetrazole | | —SCH₂CH₃ |
| CO | Phenyl | CH₂CF₃ | Tetrazole | | —SCH₂CH₃ |
| CO | Phenyl | Halo substituted alkyl | tetrazole | | —SCH₂CH₃ |
| CO | Phenyl | OCH₃ | tetrazole | | —SCH₂CH₃ |
| CO | Phenyl | OCH₂CH₃ | Tetrazole | | —SCH₂CH₃ |
| CO | Phenyl | OCH₂CH₂CH₃ | Tetrazole | | —SCH₂CH₃ |
| CO | Phenyl | OCH₂CH₂CH₂CH₃ | Tetrazole | | —SCH₂CH₃ |
| CO | Phenyl | OCH₂CH₂CH₂CH₂CH₃ | Tetrazole | | —SCH₂CH₃ |
| CO | Phenyl | C5-C8 alkoxy | tetrazole | | —SCH₂CH₃ |
| CO | Phenyl | Halo substituted alkoxy | tetrazole | | —SCH₂CH₃ |
| CO | Phenyl | CH₃ | Tetrazole | | —SCH₂CH₃ |
| CO | Phenyl | CH₂CH₃ | Tetrazole | | —SCH₂CH₃ |
| CO | Phenyl | CH₂CH₂CH₃ | Tetrazole | | —SCH₂CH₃ |
| CO | Phenyl | CH₂CH₂CH₂CH₃ | Tetrazole | | —SCH₂CH₃ |
| CO | Phenyl | C5-C8 alkyl | tetrazole | | —SCH₂CH₃ |
| CO | Phenyl | F | tetrazole | | —SCH₂CH₃ |
| CO | Phenyl | F, F | Tetrazole | | —SCH₂CH₃ |
| CO | Phenyl | F, Cl | Tetrazole | | —SCH₂CH₃ |
| CO | Phenyl | Cl | Tetrazole | | —SCH₂CH₃ |
| CO | Phenyl | Cl, Cl | Tetrazole | | —SCH₂CH₃ |
| CO | Phenyl | -(1 to 4 linearly linked atom linker)-optionally subst. aryl | tetrazole | | —SCH₂CH₃ |
| CO | Phenyl | -(1 to 4 linearly linked atom linker)-optionally subst. heteroaryl | tetrazole | | —SCH₂CH₃ |
| CO | pyridinyl | | Tetrazole | | —SCH₂CH₃ |
| CO | Pyridinyl | CF₃ | Tetrazole | | —SCH₂CH₃ |
| CO | Pyridinyl | CH₂CF₃ | Tetrazole | | —SCH₂CH₃ |
| CO | Pyridinyl | Halo substituted alkyl | Tetrazole | | —SCH₂CH₃ |
| CO | Pyridinyl | OCH₃ | tetrazole | | —SCH₂CH₃ |
| CO | Pyridinyl | OCH₂CH₃ | tetrazole | | —SCH₂CH₃ |
| CO | Pyridinyl | OCH₂CH₂CH₃ | Tetrazole | | —SCH₂CH₃ |
| CO | Pyridinyl | OCH₂CH₂CH₂CH₃ | Tetrazole | | —SCH₂CH₃ |
| CO | Pyridinyl | OCH₂CH₂CH₂CH₂CH₃ | Tetrazole | | —SCH₂CH₃ |
| CO | Pyridinyl | C5-G8 alkoxy | Tetrazole | | —SCH₂CH₃ |
| CO | Pyridinyl | Halo substituted alkoxy | tetrazole | | —SCH₂CH₃ |
| CO | Pyridinyl | CH₃ | tetrazole | | —SCH₂CH₃ |
| CO | Pyridinyl | CH₂CH₃ | Tetrazole | | —SCH₂CH₃ |
| CO | Pyridinyl | CH₂CH₂CH₃ | Tetrazole | | —SCH₂CH₃ |
| CO | Pyridinyl | CH₂CH₂CH₂CH₃ | Tetrazole | | —SCH₂CH₃ |
| CO | Pyridinyl | C5-G8 alkyl | Tetrazole | | —SCH₂CH₃ |
| CO | Pyridinyl | F | tetrazole | | —SCH₂CH₃ |
| CO | Pyridinyl | F, F | tetrazole | | —SCH₂CH₃ |
| CO | Pyridinyl | F, Cl | Tetrazole | | —SCH₂CH₃ |
| CO | Pyridinyl | Cl | Tetrazole | | —SCH₂CH₃ |
| CO | Pyridinyl | Cl, Cl | Tetrazole | | —SCH₂CH₃ |
| CO | Pyridinyl | -(1 to 4 linearly linked atom linker)-optionally subst. aryl | Tetrazole | | —SCH₂CH₃ |
| CO | Pyridinyl | -(1 to 4 linearly linked atom linker)-optionally subst. heteroaryl | tetrazole | | —SCH₂CH₃ |
| SO₂ | phenyl | | 3-hydroxy isoxazole | | methoxy |
| SO₂ | phenyl | CF₃ | 3-hydroxy isoxazole | | methoxy |
| SO₂ | phenyl | CH₂CF₃ | 3-hydroxy isoxazole | | methoxy |

TABLE 4-continued

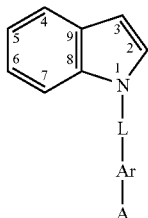

| L¹ | Ar | A | 3 | 5 | 6 |
|---|---|---|---|---|---|
| SO₂ | phenyl | Halo substituted alkyl | 3-hydroxy isoxazole | | methoxy |
| SO₂ | phenyl | OCH₃ | 3-hydroxy isoxazole | | methoxy |
| SO₂ | phenyl | OCH₂CH₃ | 3-hydroxy isoxazole | | methoxy |
| SO₂ | phenyl | OCH₂CH₂CH₃ | 3-hydroxy isoxazole | | methoxy |
| SO₂ | phenyl | OCH₂CH₂CH₂CH₃ | 3-hydroxy isoxazole | | methoxy |
| SO₂ | phenyl | OCH₂CH₂CH₂CH₂CH₃ | 3-hydroxy isoxazole | | methoxy |
| SO₂ | phenyl | C5-C8 alkoxy | 3-hydroxy isoxazole | | methoxy |
| SO₂ | phenyl | Halo substituted alkoxy | 3-hydroxy isoxazole | | methoxy |
| SO₂ | phenyl | CH₃ | 3-hydroxy isoxazole | | methoxy |
| SO₂ | phenyl | CH₂CH₃ | 3-hydroxy isoxazole | | methoxy |
| SO₂ | phenyl | CH₂CH₂CH₃ | 3-hydroxy isoxazole | | methoxy |
| SO₂ | phenyl | CH₂CH₂CH₂CH₃ | 3-hydroxy isoxazole | | methoxy |
| SO₂ | phenyl | C5-C8 alkyl | 3-hydroxy isoxazole | | methoxy |
| SO₂ | phenyl | F | 3-hydroxy isoxazole | | methoxy |
| SO₂ | phenyl | F, F | 3-hydroxy isoxazole | | methoxy |
| SO₂ | phenyl | F, Cl | 3-hydroxy isoxazole | | methoxy |
| SO₂ | phenyl | Cl | 3-hydroxy isoxazole | | methoxy |
| SO₂ | phenyl | Cl, Cl | 3-hydroxy isoxazole | | methoxy |
| SO₂ | phenyl | -(1 to 4 linearly linked atom linker)-optionally subst. aryl | 3-hydroxy isoxazole | | methoxy |
| SO₂ | phenyl | -(1 to 4 linearly linked atom linker)-optionally subst. heteroaryl | 3-hydroxy isoxazole | | methoxy |
| SO₂ | pyridinyl | | 3-hydroxy isoxazole | | methoxy |
| SO₂ | Pyridinyl | CF₃ | 3-hydroxy isoxazole | | methoxy |
| SO₂ | Pyridinyl | CH₂CF₃ | 3-hydroxy isoxazole | | methoxy |
| SO₂ | Pyridinyl | Halo substituted alkyl | 3-hydroxy isoxazole | | methoxy |
| SO₂ | Pyridinyl | OCH₃ | 3-hydroxy isoxazole | | methoxy |
| SO₂ | Pyridinyl | OCH₂CH₃ | 3-hydroxy isoxazole | | methoxy |
| SO₂ | Pyridinyl | OCH₂CH₂CH₃ | 3-hydroxy isoxazole | | methoxy |
| SO₂ | Pyridinyl | OCH₂CH₂CH₂CH₃ | 3-hydroxy isoxazole | | methoxy |
| SO₂ | Pyridinyl | OCH₂CH₂CH₂CH₂CH₃ | 3-hydroxy isoxazole | | methoxy |
| SO₂ | Pyridinyl | C5-C8 alkoxy | 3-hydroxy isoxazole | | methoxy |
| SO₂ | Pyridinyl | Halo substituted alkoxy | 3-hydroxy isoxazole | | methoxy |
| SO₂ | Pyridinyl | CH₃ | 3-hydroxy isoxazole | | methoxy |
| SO₂ | Pyridinyl | CH₂CH₃ | 3-hydroxy isoxazole | | methoxy |
| SO₂ | Pyridinyl | CH₂CH₂CH₃ | 3-hydroxy isoxazole | | methoxy |
| SO₂ | Pyridinyl | CH₂CH₂CH₂CH₃ | 3-hydroxy isoxazole | | methoxy |
| SO₂ | Pyridinyl | C5-C8 alkyl | 3-hydroxy isoxazole | | methoxy |
| SO₂ | Pyridinyl | F | 3-hydroxy isoxazole | | methoxy |
| SO₂ | Pyridinyl | F, F | 3-hydroxy isoxazole | | methoxy |
| SO₂ | Pyridinyl | F, Cl | 3-hydroxy isoxazole | | methoxy |
| SO₂ | Pyridinyl | Cl | 3-hydroxy isoxazole | | methoxy |
| SO₂ | Pyridinyl | Cl, Cl | 3-hydroxy isoxazole | | methoxy |
| SO₂ | Pyridinyl | -(1 to 4 linearly linked atom linker)-optionally subst. aryl | 3-hydroxy isoxazole | | methoxy |
| SO₂ | Pyridinyl | -(1 to 4 linearly linked atom linker)-optionally subst. heteroaryl | 3-hydroxy isoxazole | | methoxy |
| CO | Phenyl | | 3-hydroxy isoxazole | | methoxy |
| CO | Phenyl | CF₃ | 3-hydroxy isoxazole | | methoxy |
| CO | Phenyl | CH₂CF₃ | 3-hydroxy isoxazole | | methoxy |
| CO | Phenyl | Halo substituted alkyl | 3-hydroxy isoxazole | | methoxy |
| CO | Phenyl | OCH₃ | 3-hydroxy isoxazole | | methoxy |
| CO | Phenyl | OCH₂CH₃ | 3-hydroxy isoxazole | | methoxy |
| CO | Phenyl | OCH₂CH₂CH₃ | 3-hydroxy isoxazole | | methoxy |
| CO | Phenyl | OCH₂CH₂CH₂CH₃ | 3-hydroxy isoxazole | | methoxy |
| CO | Phenyl | OCH₂CH₂CH₂CH₂CH₃ | 3-hydroxy isoxazole | | methoxy |
| CO | Phenyl | C5-C8 alkoxy | 3-hydroxy isoxazole | | methoxy |
| CO | Phenyl | Halo substituted alkoxy | 3-hydroxy isoxazole | | methoxy |
| CO | Phenyl | CH₃ | 3-hydroxy isoxazole | | methoxy |

TABLE 4-continued

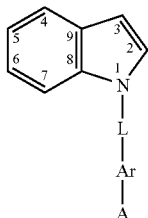

| L¹ | Ar | A | 3 | 5 | 6 |
|---|---|---|---|---|---|
| CO | Phenyl | CH$_2$CH$_3$ | 3-hydroxy isoxazole | | methoxy |
| CO | Phenyl | CH$_2$CH$_2$CH$_3$ | 3-hydroxy isoxazole | | methoxy |
| CO | Phenyl | CH$_2$CH$_2$CH$_2$CH$_3$ | 3-hydroxy isoxazole | | methoxy |
| CO | Phenyl | C5-C8 alkyl | 3-hydroxy isoxazole | | methoxy |
| CO | Phenyl | F | 3-hydroxy isoxazole | | methoxy |
| CO | Phenyl | F, F | 3-hydroxy isoxazole | | methoxy |
| CO | Phenyl | F, Cl | 3-hydroxy isoxazole | | methoxy |
| CO | Phenyl | Cl | 3-hydroxy isoxazole | | methoxy |
| CO | Phenyl | Cl, Cl | 3-hydroxy isoxazole | | methoxy |
| CO | Phenyl | -(1 to 4 linearly linked atom linker)-optionally subst. aryl | 3-hydroxy isoxazole | | methoxy |
| CO | Phenyl | -(1 to 4 linearly linked atom linker)-optionally subst. heteroaryl | 3-hydroxy isoxazole | | methoxy |
| CO | pyridinyl | | 3-hydroxy isoxazole | | methoxy |
| CO | Pyridinyl | CF$_3$ | 3-hydroxy isoxazole | | methoxy |
| CO | Pyridinyl | CH$_2$CF$_3$ | 3-hydroxy isoxazole | | methoxy |
| CO | Pyridinyl | Halo substituted alkyl | 3-hydroxy isoxazole | | methoxy |
| CO | Pyridinyl | OCH$_3$ | 3-hydroxy isoxazole | | methoxy |
| CO | Pyridinyl | OCH$_2$CH$_3$ | 3-hydroxy isoxazole | | methoxy |
| CO | Pyridinyl | OCH$_2$CH$_2$CH$_3$ | 3-hydroxy isoxazole | | methoxy |
| CO | Pyridinyl | OCH$_2$CH$_2$CH$_2$CH$_3$ | 3-hydroxy isoxazole | | methoxy |
| CO | Pyridinyl | OCH$_2$CH$_2$CH$_2$CH$_2$CH$_3$ | 3-hydroxy isoxazole | | methoxy |
| CO | Pyridinyl | C5-G8 alkoxy | 3-hydroxy isoxazole | | methoxy |
| CO | Pyridinyl | Halo substituted alkoxy | 3-hydroxy isoxazole | | methoxy |
| CO | Pyridinyl | CH$_3$ | 3-hydroxy isoxazole | | methoxy |
| CO | Pyridinyl | CH$_2$CH$_3$ | 3-hydroxy isoxazole | | methoxy |
| CO | Pyridinyl | CH$_2$CH$_2$CH$_3$ | 3-hydroxy isoxazole | | methoxy |
| CO | Pyridinyl | CH$_2$CH$_2$CH$_2$CH$_3$ | 3-hydroxy isoxazole | | methoxy |
| CO | Pyridinyl | C5-G8 alkyl | 3-hydroxy isoxazole | | methoxy |
| CO | Pyridinyl | F | 3-hydroxy isoxazole | | methoxy |
| CO | Pyridinyl | F, F | 3-hydroxy isoxazole | | methoxy |
| CO | Pyridinyl | F, Cl | 3-hydroxy isoxazole | | methoxy |
| CO | Pyridinyl | Cl | 3-hydroxy isoxazole | | methoxy |
| CO | Pyridinyl | Cl, Cl | 3-hydroxy isoxazole | | methoxy |
| CO | Pyridinyl | -(1 to 4 linearly linked atom linker)-optionally subst. aryl | 3-hydroxy isoxazole | | methoxy |
| CO | Pyridinyl | -(1 to 4 linearly linked atom linker)-optionally subst. heteroaryl | 3-hydroxy isoxazole | | methoxy |
| SO$_2$ | phenyl | | 3-hydroxy isoxazole | | ethoxy |
| SO$_2$ | phenyl | CF$_3$ | 3-hydroxy isoxazole | | ethoxy |
| SO$_2$ | phenyl | CH$_2$CF$_3$ | 3-hydroxy isoxazole | | ethoxy |
| SO$_2$ | phenyl | Halo substituted alkyl | 3-hydroxy isoxazole | | ethoxy |
| SO$_2$ | phenyl | OCH$_3$ | 3-hydroxy isoxazole | | ethoxy |
| SO$_2$ | phenyl | OCH$_2$CH$_3$ | 3-hydroxy isoxazole | | ethoxy |
| SO$_2$ | phenyl | OCH$_2$CH$_2$CH$_3$ | 3-hydroxy isoxazole | | ethoxy |
| SO$_2$ | phenyl | OCH$_2$CH$_2$CH$_2$CH$_3$ | 3-hydroxy isoxazole | | ethoxy |
| SO$_2$ | phenyl | OCH$_2$CH$_2$CH$_2$CH$_2$CH$_3$ | 3-hydroxy isoxazole | | ethoxy |
| SO$_2$ | phenyl | C5-C8 alkoxy | 3-hydroxy isoxazole | | ethoxy |
| SO$_2$ | phenyl | Halo substituted alkoxy | 3-hydroxy isoxazole | | ethoxy |
| SO$_2$ | phenyl | CH$_3$ | 3-hydroxy isoxazole | | ethoxy |
| SO$_2$ | phenyl | CH$_2$CH$_3$ | 3-hydroxy isoxazole | | ethoxy |
| SO$_2$ | phenyl | CH$_2$CH$_2$CH$_3$ | 3-hydroxy isoxazole | | ethoxy |
| SO$_2$ | phenyl | CH$_2$CH$_2$CH$_2$CH$_3$ | 3-hydroxy isoxazole | | ethoxy |
| SO$_2$ | phenyl | C5-C8 alkyl | 3-hydroxy isoxazole | | ethoxy |
| SO$_2$ | phenyl | F | 3-hydroxy isoxazole | | ethoxy |
| SO$_2$ | phenyl | F, F | 3-hydroxy isoxazole | | ethoxy |
| SO$_2$ | phenyl | F, Cl | 3-hydroxy isoxazole | | ethoxy |
| SO$_2$ | phenyl | Cl | 3-hydroxy isoxazole | | ethoxy |
| SO$_2$ | phenyl | Cl, Cl | 3-hydroxy isoxazole | | ethoxy |

TABLE 4-continued

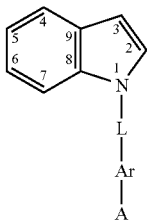

| $L^1$ | Ar | A | 3 | 5 | 6 |
|---|---|---|---|---|---|
| $SO_2$ | phenyl | -(1 to 4 linearly linked atom linker)-optionally subst. aryl | 3-hydroxy isoxazole | | ethoxy |
| $SO_2$ | phenyl | -(1 to 4 linearly linked atom linker)-optionally subst. heteroaryl | 3-hydroxy isoxazole | | ethoxy |
| $SO_2$ | pyridinyl | | 3-hydroxy isoxazole | | ethoxy |
| $SO_2$ | Pyridinyl | $CF_3$ | 3-hydroxy isoxazole | | ethoxy |
| $SO_2$ | Pyridinyl | $CH_2CF_3$ | 3-hydroxy isoxazole | | ethoxy |
| $SO_2$ | Pyridinyl | Halo substituted alkyl | 3-hydroxy isoxazole | | ethoxy |
| $SO_2$ | Pyridinyl | $OCH_3$ | 3-hydroxy isoxazole | | ethoxy |
| $SO_2$ | Pyridinyl | $OCH_2CH_3$ | 3-hydroxy isoxazole | | ethoxy |
| $SO_2$ | Pyridinyl | $OCH_2CH_2CH_3$ | 3-hydroxy isoxazole | | ethoxy |
| $SO_2$ | Pyridinyl | $OCH_2CH_2CH_2CH_3$ | 3-hydroxy isoxazole | | ethoxy |
| $SO_2$ | Pyridinyl | $OCH_2CH_2CH_2CH_2CH_3$ | 3-hydroxy isoxazole | | ethoxy |
| $SO_2$ | Pyridinyl | C5-C8 alkoxy | 3-hydroxy isoxazole | | ethoxy |
| $SO_2$ | Pyridinyl | Halo substituted alkoxy | 3-hydroxy isoxazole | | ethoxy |
| $SO_2$ | Pyridinyl | $CH_3$ | 3-hydroxy isoxazole | | ethoxy |
| $SO_2$ | Pyridinyl | $CH_2CH_3$ | 3-hydroxy isoxazole | | ethoxy |
| $SO_2$ | Pyridinyl | $CH_2CH_2CH_3$ | 3-hydroxy isoxazole | | ethoxy |
| $SO_2$ | Pyridinyl | $CH_2CH_2CH_2CH_3$ | 3-hydroxy isoxazole | | ethoxy |
| $SO_2$ | Pyridinyl | C5-C8 alkyl | 3-hydroxy isoxazole | | ethoxy |
| $SO_2$ | Pyridinyl | F | 3-hydroxy isoxazole | | ethoxy |
| $SO_2$ | Pyridinyl | F, F | 3-hydroxy isoxazole | | ethoxy |
| $SO_2$ | Pyridinyl | F, Cl | 3-hydroxy isoxazole | | ethoxy |
| $SO_2$ | Pyridinyl | Cl | 3-hydroxy isoxazole | | ethoxy |
| $SO_2$ | Pyridinyl | Cl, Cl | 3-hydroxy isoxazole | | ethoxy |
| $SO_2$ | Pyridinyl | -(1 to 4 linearly linked atom linker)-optionally subst. aryl | 3-hydroxy isoxazole | | ethoxy |
| $SO_2$ | Pyridinyl | -(1 to 4 linearly linked atom linker)-optionally subst. heteroaryl | 3-hydroxy isoxazole | | ethoxy |
| CO | Phenyl | | 3-hydroxy isoxazole | | ethoxy |
| CO | Phenyl | $CF_3$ | 3-hydroxy isoxazole | | ethoxy |
| CO | Phenyl | $CH_2CF_3$ | 3-hydroxy isoxazole | | ethoxy |
| CO | Phenyl | Halo substituted alkyl | 3-hydroxy isoxazole | | ethoxy |
| CO | Phenyl | $OCH_3$ | 3-hydroxy isoxazole | | ethoxy |
| CO | Phenyl | $OCH_2CH_3$ | 3-hydroxy isoxazole | | ethoxy |
| CO | Phenyl | $OCH_2CH_2CH_3$ | 3-hydroxy isoxazole | | ethoxy |
| CO | Phenyl | $OCH_2CH_2CH_2CH_3$ | 3-hydroxy isoxazole | | ethoxy |
| CO | Phenyl | $OCH_2CH_2CH_2CH_2CH_3$ | 3-hydroxy isoxazole | | ethoxy |
| CO | Phenyl | C5-C8 alkoxy | 3-hydroxy isoxazole | | ethoxy |
| CO | Phenyl | Halo substituted alkoxy | 3-hydroxy isoxazole | | ethoxy |
| CO | Phenyl | $CH_3$ | 3-hydroxy isoxazole | | ethoxy |
| CO | Phenyl | $CH_2CH_3$ | 3-hydroxy isoxazole | | ethoxy |
| CO | Phenyl | $CH_2CH_2CH_3$ | 3-hydroxy isoxazole | | ethoxy |
| CO | Phenyl | $CH_2CH_2CH_2CH_3$ | 3-hydroxy isoxazole | | ethoxy |
| CO | Phenyl | C5-C8 alkyl | 3-hydroxy isoxazole | | ethoxy |
| CO | Phenyl | F | 3-hydroxy isoxazole | | ethoxy |
| CO | Phenyl | F, F | 3-hydroxy isoxazole | | ethoxy |
| CO | Phenyl | F, Cl | 3-hydroxy isoxazole | | ethoxy |
| CO | Phenyl | Cl | 3-hydroxy isoxazole | | ethoxy |
| CO | Phenyl | Cl, Cl | 3-hydroxy isoxazole | | ethoxy |
| CO | Phenyl | -(1 to 4 linearly linked atom linker)-optionally subst. aryl | 3-hydroxy isoxazole | | ethoxy |
| CO | Phenyl | -(1 to 4 linearly linked atom linker)-optionally subst. heteroaryl | 3-hydroxy isoxazole | | ethoxy |
| CO | pyridinyl | | 3-hydroxy isoxazole | | ethoxy |
| CO | Pyridinyl | $CF_3$ | 3-hydroxy isoxazole | | ethoxy |
| CO | Pyridinyl | $CH_2CF_3$ | 3-hydroxy isoxazole | | ethoxy |

TABLE 4-continued

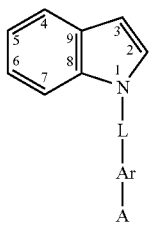

| L[1] | Ar | A | 3 | 5 | 6 |
|---|---|---|---|---|---|
| CO | Pyridinyl | Halo substituted alkyl | 3-hydroxy isoxazole | | ethoxy |
| CO | Pyridinyl | OCH$_3$ | 3-hydroxy isoxazole | | ethoxy |
| CO | Pyridinyl | OCH$_2$CH$_3$ | 3-hydroxy isoxazole | | ethoxy |
| CO | Pyridinyl | OCH$_2$CH$_2$CH$_3$ | 3-hydroxy isoxazole | | ethoxy |
| CO | Pyridinyl | OCH$_2$CH$_2$CH$_2$CH$_3$ | 3-hydroxy isoxazole | | ethoxy |
| CO | Pyridinyl | OCH$_2$CH$_2$CH$_2$CH$_2$CH$_3$ | 3-hydroxy isoxazole | | ethoxy |
| CO | Pyridinyl | C5-G8 alkoxy | 3-hydroxy isoxazole | | ethoxy |
| CO | Pyridinyl | Halo substituted alkoxy | 3-hydroxy isoxazole | | ethoxy |
| CO | Pyridinyl | CH$_3$ | 3-hydroxy isoxazole | | ethoxy |
| CO | Pyridinyl | CH$_2$CH$_3$ | 3-hydroxy isoxazole | | ethoxy |
| CO | Pyridinyl | CH$_2$CH$_2$CH$_3$ | 3-hydroxy isoxazole | | ethoxy |
| CO | Pyridinyl | CH$_2$CH$_2$CH$_2$CH$_3$ | 3-hydroxy isoxazole | | ethoxy |
| CO | Pyridinyl | C5-G8 alkyl | 3-hydroxy isoxazole | | ethoxy |
| CO | Pyridinyl | F | 3-hydroxy isoxazole | | ethoxy |
| CO | Pyridinyl | F, F | 3-hydroxy isoxazole | | ethoxy |
| CO | Pyridinyl | F, Cl | 3-hydroxy isoxazole | | ethoxy |
| CO | Pyridinyl | Cl | 3-hydroxy isoxazole | | ethoxy |
| CO | Pyridinyl | Cl, Cl | 3-hydroxy isoxazole | | ethoxy |
| CO | Pyridinyl | -(1 to 4 linearly linked atom linker)-optionally subst. aryl | 3-hydroxy isoxazole | | ethoxy |
| CO | Pyridinyl | -(1 to 4 linearly linked atom linker)-optionally subst. heteroaryl | 3-hydroxy isoxazole | | ethoxy |
| SO$_2$ | phenyl | | 3-hydroxy isoxazole | | propoxy |
| SO$_2$ | phenyl | CF$_3$ | 3-hydroxy isoxazole | | propoxy |
| SO$_2$ | phenyl | CH$_2$CF$_3$ | 3-hydroxy isoxazole | | propoxy |
| SO$_2$ | phenyl | Halo substituted alkyl | 3-hydroxy isoxazole | | propoxy |
| SO$_2$ | phenyl | OCH$_3$ | 3-hydroxy isoxazole | | propoxy |
| SO$_2$ | phenyl | OCH$_2$CH$_3$ | 3-hydroxy isoxazole | | propoxy |
| SO$_2$ | phenyl | OCH$_2$CH$_2$CH$_3$ | 3-hydroxy isoxazole | | propoxy |
| SO$_2$ | phenyl | OCH$_2$CH$_2$CH$_2$CH$_3$ | 3-hydroxy isoxazole | | propoxy |
| SO$_2$ | phenyl | OCH$_2$CH$_2$CH$_2$CH$_2$CH$_3$ | 3-hydroxy isoxazole | | propoxy |
| SO$_2$ | phenyl | C5-C8 alkoxy | 3-hydroxy isoxazole | | propoxy |
| SO$_2$ | phenyl | Halo substituted alkoxy | 3-hydroxy isoxazole | | propoxy |
| SO$_2$ | phenyl | CH$_3$ | 3-hydroxy isoxazole | | propoxy |
| SO$_2$ | phenyl | CH$_2$CH$_3$ | 3-hydroxy isoxazole | | propoxy |
| SO$_2$ | phenyl | CH$_2$CH$_2$CH$_3$ | 3-hydroxy isoxazole | | propoxy |
| SO$_2$ | phenyl | CH$_2$CH$_2$CH$_2$CH$_3$ | 3-hydroxy isoxazole | | propoxy |
| SO$_2$ | phenyl | C5-C8 alkyl | 3-hydroxy isoxazole | | propoxy |
| SO$_2$ | phenyl | F | 3-hydroxy isoxazole | | propoxy |
| SO$_2$ | phenyl | F, F | 3-hydroxy isoxazole | | propoxy |
| SO$_2$ | phenyl | F, Cl | 3-hydroxy isoxazole | | propoxy |
| SO$_2$ | phenyl | Cl | 3-hydroxy isoxazole | | propoxy |
| SO$_2$ | phenyl | Cl, Cl | 3-hydroxy isoxazole | | propoxy |
| SO$_2$ | phenyl | -(1 to 4 linearly linked atom linker)-optionally subst. aryl | 3-hydroxy isoxazole | | propoxy |
| SO$_2$ | phenyl | -(1 to 4 linearly linked atom linker)-optionally subst. heteroaryl | 3-hydroxy isoxazole | | propoxy |
| SO$_2$ | pyridinyl | | 3-hydroxy isoxazole | | propoxy |
| SO$_2$ | Pyridinyl | CF$_3$ | 3-hydroxy isoxazole | | propoxy |
| SO$_2$ | Pyridinyl | CH$_2$CF$_3$ | 3-hydroxy isoxazole | | propoxy |
| SO$_2$ | Pyridinyl | Halo substituted alkyl | 3-hydroxy isoxazole | | propoxy |
| SO$_2$ | Pyridinyl | OCH$_3$ | 3-hydroxy isoxazole | | propoxy |
| SO$_2$ | Pyridinyl | OCH$_2$CH$_3$ | 3-hydroxy isoxazole | | propoxy |
| SO$_2$ | Pyridinyl | OCH$_2$CH$_2$CH$_3$ | 3-hydroxy isoxazole | | propoxy |
| SO$_2$ | Pyridinyl | OCH$_2$CH$_2$CH$_2$CH$_3$ | 3-hydroxy isoxazole | | propoxy |
| SO$_2$ | Pyridinyl | OCH$_2$CH$_2$CH$_2$CH$_2$CH$_3$ | 3-hydroxy isoxazole | | propoxy |
| SO$_2$ | Pyridinyl | C5-C8 alkoxy | 3-hydroxy isoxazole | | propoxy |
| SO$_2$ | Pyridinyl | Halo substituted alkoxy | 3-hydroxy isoxazole | | propoxy |
| SO$_2$ | Pyridinyl | CH$_3$ | 3-hydroxy isoxazole | | propoxy |

TABLE 4-continued

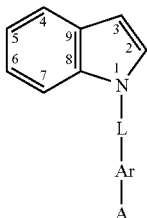

| L¹ | Ar | A | 3 | 5 | 6 |
|---|---|---|---|---|---|
| SO₂ | Pyridinyl | CH₂CH₃ | 3-hydroxy isoxazole | | propoxy |
| SO₂ | Pyridinyl | CH₂CH₂CH₃ | 3-hydroxy isoxazole | | propoxy |
| SO₂ | Pyridinyl | CH₂CH₂CH₂CH₃ | 3-hydroxy isoxazole | | propoxy |
| SO₂ | Pyridinyl | C5-C8 alkyl | 3-hydroxy isoxazole | | propoxy |
| SO₂ | Pyridinyl | F | 3-hydroxy isoxazole | | propoxy |
| SO₂ | Pyridinyl | F, F | 3-hydroxy isoxazole | | propoxy |
| SO₂ | Pyridinyl | F, Cl | 3-hydroxy isoxazole | | propoxy |
| SO₂ | Pyridinyl | Cl | 3-hydroxy isoxazole | | propoxy |
| SO₂ | Pyridinyl | Cl, Cl | 3-hydroxy isoxazole | | propoxy |
| SO₂ | Pyridinyl | -(1 to 4 linearly linked atom linker)-optionally subst. aryl | 3-hydroxy isoxazole | | propoxy |
| SO₂ | Pyridinyl | -(1 to 4 linearly linked atom linker)-optionally subst. heteroaryl | 3-hydroxy isoxazole | | propoxy |
| CO | Phenyl | | 3-hydroxy isoxazole | | propoxy |
| CO | Phenyl | CF₃ | 3-hydroxy isoxazole | | propoxy |
| CO | Phenyl | CH₂CF₃ | 3-hydroxy isoxazole | | propoxy |
| CO | Phenyl | Halo substituted alkyl | 3-hydroxy isoxazole | | propoxy |
| CO | Phenyl | OCH₃ | 3-hydroxy isoxazole | | propoxy |
| CO | Phenyl | OCH₂CH₃ | 3-hydroxy isoxazole | | propoxy |
| CO | Phenyl | OCH₂CH₂CH₃ | 3-hydroxy isoxazole | | propoxy |
| CO | Phenyl | OCH₂CH₂CH₂CH₃ | 3-hydroxy isoxazole | | propoxy |
| CO | Phenyl | OCH₂CH₂CH₂CH₂CH₃ | 3-hydroxy isoxazole | | propoxy |
| CO | Phenyl | C5-C8 alkoxy | 3-hydroxy isoxazole | | propoxy |
| CO | Phenyl | Halo substituted alkoxy | 3-hydroxy isoxazole | | propoxy |
| CO | Phenyl | CH₃ | 3-hydroxy isoxazole | | propoxy |
| CO | Phenyl | CH₂CH₃ | 3-hydroxy isoxazole | | propoxy |
| CO | Phenyl | CH₂CH₂CH₃ | 3-hydroxy isoxazole | | propoxy |
| CO | Phenyl | CH₂CH₂CH₂CH₃ | 3-hydroxy isoxazole | | propoxy |
| CO | Phenyl | C5-C8 alkyl | 3-hydroxy isoxazole | | propoxy |
| CO | Phenyl | F | 3-hydroxy isoxazole | | propoxy |
| CO | Phenyl | F, F | 3-hydroxy isoxazole | | propoxy |
| CO | Phenyl | F, Cl | 3-hydroxy isoxazole | | propoxy |
| CO | Phenyl | Cl | 3-hydroxy isoxazole | | propoxy |
| CO | Phenyl | Cl, Cl | 3-hydroxy isoxazole | | propoxy |
| CO | Phenyl | -(1 to 4 linearly linked atom linker)-optionally subst. aryl | 3-hydroxy isoxazole | | propoxy |
| CO | Phenyl | -(1 to 4 linearly linked atom linker)-optionally subst. heteroaryl | 3-hydroxy isoxazole | | propoxy |
| CO | pyridinyl | | 3-hydroxy isoxazole | | propoxy |
| CO | Pyridinyl | CF₃ | 3-hydroxy isoxazole | | propoxy |
| CO | Pyridinyl | CH₂CF₃ | 3-hydroxy isoxazole | | propoxy |
| CO | Pyridinyl | Halo substituted alkyl | 3-hydroxy isoxazole | | propoxy |
| CO | Pyridinyl | OCH₃ | 3-hydroxy isoxazole | | propoxy |
| CO | Pyridinyl | OCH₂CH₃ | 3-hydroxy isoxazole | | propoxy |
| CO | Pyridinyl | OCH₂CH₂CH₃ | 3-hydroxy isoxazole | | propoxy |
| CO | Pyridinyl | OCH₂CH₂CH₂CH₃ | 3-hydroxy isoxazole | | propoxy |
| CO | Pyridinyl | OCH₂CH₂CH₂CH₂CH₃ | 3-hydroxy isoxazole | | propoxy |
| CO | Pyridinyl | C5-G8 alkoxy | 3-hydroxy isoxazole | | propoxy |
| CO | Pyridinyl | Halo substituted alkoxy | 3-hydroxy isoxazole | | propoxy |
| CO | Pyridinyl | CH₃ | 3-hydroxy isoxazole | | propoxy |
| CO | Pyridinyl | CH₂CH₃ | 3-hydroxy isoxazole | | propoxy |
| CO | Pyridinyl | CH₂CH₂CH₃ | 3-hydroxy isoxazole | | propoxy |
| CO | Pyridinyl | CH₂CH₂CH₂CH₃ | 3-hydroxy isoxazole | | propoxy |
| CO | Pyridinyl | C5-G8 alkyl | 3-hydroxy isoxazole | | propoxy |
| CO | Pyridinyl | F | 3-hydroxy isoxazole | | propoxy |
| CO | Pyridinyl | F, F | 3-hydroxy isoxazole | | propoxy |
| CO | Pyridinyl | F, Cl | 3-hydroxy isoxazole | | propoxy |
| CO | Pyridinyl | Cl | 3-hydroxy isoxazole | | propoxy |
| CO | Pyridinyl | Cl, Cl | 3-hydroxy isoxazole | | propoxy |

TABLE 4-continued

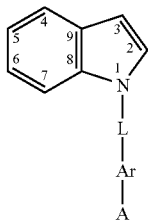

| L¹ | Ar | A | 3 | 5 | 6 |
|---|---|---|---|---|---|
| CO | Pyridinyl | -(1 to 4 linearly linked atom linker)-optionally subst. aryl | 3-hydroxy isoxazole | | propoxy |
| CO | Pyridinyl | -(1 to 4 linearly linked atom linker)-optionally subst. heteroaryl | 3-hydroxy isoxazole | | propoxy |
| SO₂ | phenyl | | 3-hydroxy isoxazole | | —SCH₃ |
| SO₂ | phenyl | CF₃ | 3-hydroxy isoxazole | | —SCH₃ |
| SO₂ | phenyl | CH₂CF₃ | 3-hydroxy isoxazole | | —SCH₃ |
| SO₂ | phenyl | Halo substituted alkyl | 3-hydroxy isoxazole | | —SCH₃ |
| SO₂ | phenyl | OCH₃ | 3-hydroxy isoxazole | | —SCH₃ |
| SO₂ | phenyl | OCH₂CH₃ | 3-hydroxy isoxazole | | —SCH₃ |
| SO₂ | phenyl | OCH₂CH₂CH₃ | 3-hydroxy isoxazole | | —SCH₃ |
| SO₂ | phenyl | OCH₂CH₂CH₂CH₃ | 3-hydroxy isoxazole | | —SCH₃ |
| SO₂ | phenyl | OCH₂CH₂CH₂CH₂CH₃ | 3-hydroxy isoxazole | | —SCH₃ |
| SO₂ | phenyl | C5-C8 alkoxy | 3-hydroxy isoxazole | | —SCH₃ |
| SO₂ | phenyl | Halo substituted alkoxy | 3-hydroxy isoxazole | | —SCH₃ |
| SO₂ | phenyl | CH₃ | 3-hydroxy isoxazole | | —SCH₃ |
| SO₂ | phenyl | CH₂CH₃ | 3-hydroxy isoxazole | | —SCH₃ |
| SO₂ | phenyl | CH₂CH₂CH₃ | 3-hydroxy isoxazole | | —SCH₃ |
| SO₂ | phenyl | CH₂CH₂CH₂CH₃ | 3-hydroxy isoxazole | | —SCH₃ |
| SO₂ | phenyl | C5-C8 alkyl | 3-hydroxy isoxazole | | —SCH₃ |
| SO₂ | phenyl | F | 3-hydroxy isoxazole | | —SCH₃ |
| SO₂ | phenyl | F, F | 3-hydroxy isoxazole | | —SCH₃ |
| SO₂ | phenyl | F, Cl | 3-hydroxy isoxazole | | —SCH₃ |
| SO₂ | phenyl | Cl | 3-hydroxy isoxazole | | —SCH₃ |
| SO₂ | phenyl | Cl, Cl | 3-hydroxy isoxazole | | —SCH₃ |
| SO₂ | phenyl | -(1 to 4 linearly linked atom linker)-optionally subst. aryl | 3-hydroxy isoxazole | | —SCH₃ |
| SO₂ | phenyl | -(1 to 4 linearly linked atom linker)-optionally subst. heteroaryl | 3-hydroxy isoxazole | | —SCH₃ |
| SO₂ | pyridinyl | | 3-hydroxy isoxazole | | —SCH₃ |
| SO₂ | Pyridinyl | CF₃ | 3-hydroxy isoxazole | | —SCH₃ |
| SO₂ | Pyridinyl | CH₂CF₃ | 3-hydroxy isoxazole | | —SCH₃ |
| SO₂ | Pyridinyl | Halo substituted alkyl | 3-hydroxy isoxazole | | —SCH₃ |
| SO₂ | Pyridinyl | OCH₃ | 3-hydroxy isoxazole | | —SCH₃ |
| SO₂ | Pyridinyl | OCH₂CH₃ | 3-hydroxy isoxazole | | —SCH₃ |
| SO₂ | Pyridinyl | OCH₂CH₂CH₃ | 3-hydroxy isoxazole | | —SCH₃ |
| SO₂ | Pyridinyl | OCH₂CH₂CH₂CH₃ | 3-hydroxy isoxazole | | —SCH₃ |
| SO₂ | Pyridinyl | OCH₂CH₂CH₂CH₂CH₃ | 3-hydroxy isoxazole | | —SCH₃ |
| SO₂ | Pyridinyl | C5-C8 alkoxy | 3-hydroxy isoxazole | | —SCH₃ |
| SO₂ | Pyridinyl | Halo substituted alkoxy | 3-hydroxy isoxazole | | —SCH₃ |
| SO₂ | Pyridinyl | CH₃ | 3-hydroxy isoxazole | | —SCH₃ |
| SO₂ | Pyridinyl | CH₂CH₃ | 3-hydroxy isoxazole | | —SCH₃ |
| SO₂ | Pyridinyl | CH₂CH₂CH₃ | 3-hydroxy isoxazole | | —SCH₃ |
| SO₂ | Pyridinyl | CH₂CH₂CH₂CH₃ | 3-hydroxy isoxazole | | —SCH₃ |
| SO₂ | Pyridinyl | C5-C8 alkyl | 3-hydroxy isoxazole | | —SCH₃ |
| SO₂ | Pyridinyl | F | 3-hydroxy isoxazole | | —SCH₃ |
| SO₂ | Pyridinyl | F, F | 3-hydroxy isoxazole | | —SCH₃ |
| SO₂ | Pyridinyl | F, Cl | 3-hydroxy isoxazole | | —SCH₃ |
| SO₂ | Pyridinyl | Cl | 3-hydroxy isoxazole | | —SCH₃ |
| SO₂ | Pyridinyl | Cl, Cl | 3-hydroxy isoxazole | | —SCH₃ |
| SO₂ | Pyridinyl | -(1 to 4 linearly linked atom linker)-optionally subst. aryl | 3-hydroxy isoxazole | | —SCH₃ |
| SO₂ | Pyridinyl | -(1 to 4 linearly linked atom linker)-optionally subst. heteroaryl | 3-hydroxy isoxazole | | —SCH₃ |
| CO | Phenyl | | 3-hydroxy isoxazole | | —SCH₃ |
| CO | Phenyl | CF₃ | 3-hydroxy isoxazole | | —SCH₃ |
| CO | Phenyl | CH₂CF₃ | 3-hydroxy isoxazole | | —SCH₃ |

TABLE 4-continued

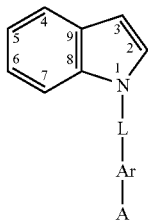

| L¹ | Ar | A | 3 | 5 | 6 |
|---|---|---|---|---|---|
| CO | Phenyl | Halo substituted alkyl | 3-hydroxy isoxazole | | —SCH₃ |
| CO | Phenyl | OCH₃ | 3-hydroxy isoxazole | | —SCH₃ |
| CO | Phenyl | OCH₂CH₃ | 3-hydroxy isoxazole | | —SCH₃ |
| CO | Phenyl | OCH₂CH₂CH₃ | 3-hydroxy isoxazole | | —SCH₃ |
| CO | Phenyl | OCH₂CH₂CH₂CH₃ | 3-hydroxy isoxazole | | —SCH₃ |
| CO | Phenyl | OCH₂CH₂CH₂CH₂CH₃ | 3-hydroxy isoxazole | | —SCH₃ |
| CO | Phenyl | C5-C8 alkoxy | 3-hydroxy isoxazole | | —SCH₃ |
| CO | Phenyl | Halo substituted alkoxy | 3-hydroxy isoxazole | | —SCH₃ |
| CO | Phenyl | CH₃ | 3-hydroxy isoxazole | | —SCH₃ |
| CO | Phenyl | CH₂CH₃ | 3-hydroxy isoxazole | | —SCH₃ |
| CO | Phenyl | CH₂CH₂CH₃ | 3-hydroxy isoxazole | | —SCH₃ |
| CO | Phenyl | CH₂CH₂CH₂CH₃ | 3-hydroxy isoxazole | | —SCH₃ |
| CO | Phenyl | C5-C8 alkyl | 3-hydroxy isoxazole | | —SCH₃ |
| CO | Phenyl | F | 3-hydroxy isoxazole | | —SCH₃ |
| CO | Phenyl | F, F | 3-hydroxy isoxazole | | —SCH₃ |
| CO | Phenyl | F, Cl | 3-hydroxy isoxazole | | —SCH₃ |
| CO | Phenyl | Cl | 3-hydroxy isoxazole | | —SCH₃ |
| CO | Phenyl | Cl, Cl | 3-hydroxy isoxazole | | —SCH₃ |
| CO | Phenyl | -(1 to 4 linearly linked atom linker)-optionally subst. aryl | 3-hydroxy isoxazole | | —SCH₃ |
| CO | Phenyl | -(1 to 4 linearly linked atom linker)-optionally subst. heteroaryl | 3-hydroxy isoxazole | | —SCH₃ |
| CO | pyridinyl | | 3-hydroxy isoxazole | | —SCH₃ |
| CO | Pyridinyl | CF₃ | 3-hydroxy isoxazole | | —SCH₃ |
| CO | Pyridinyl | CH₂CF₃ | 3-hydroxy isoxazole | | —SCH₃ |
| CO | Pyridinyl | Halo substituted alkyl | 3-hydroxy isoxazole | | —SCH₃ |
| CO | Pyridinyl | OCH₃ | 3-hydroxy isoxazole | | —SCH₃ |
| CO | Pyridinyl | OCH₂CH₃ | 3-hydroxy isoxazole | | —SCH₃ |
| CO | Pyridinyl | OCH₂CH₂CH₃ | 3-hydroxy isoxazole | | —SCH₃ |
| CO | Pyridinyl | OCH₂CH₂CH₂CH₃ | 3-hydroxy isoxazole | | —SCH₃ |
| CO | Pyridinyl | OCH₂CH₂CH₂CH₂CH₃ | 3-hydroxy isoxazole | | —SCH₃ |
| CO | Pyridinyl | C5-G8 alkoxy | 3-hydroxy isoxazole | | —SCH₃ |
| CO | Pyridinyl | Halo substituted alkoxy | 3-hydroxy isoxazole | | —SCH₃ |
| CO | Pyridinyl | CH₃ | 3-hydroxy isoxazole | | —SCH₃ |
| CO | Pyridinyl | CH₂CH₃ | 3-hydroxy isoxazole | | —SCH₃ |
| CO | Pyridinyl | CH₂CH₂CH₃ | 3-hydroxy isoxazole | | —SCH₃ |
| CO | Pyridinyl | CH₂CH₂CH₂CH₃ | 3-hydroxy isoxazole | | —SCH₃ |
| CO | Pyridinyl | C5-G8 alkyl | 3-hydroxy isoxazole | | —SCH₃ |
| CO | Pyridinyl | F | 3-hydroxy isoxazole | | —SCH₃ |
| CO | Pyridinyl | F, F | 3-hydroxy isoxazole | | —SCH₃ |
| CO | Pyridinyl | F, Cl | 3-hydroxy isoxazole | | —SCH₃ |
| CO | Pyridinyl | Cl | 3-hydroxy isoxazole | | —SCH₃ |
| CO | Pyridinyl | Cl, Cl | 3-hydroxy isoxazole | | —SCH₃ |
| CO | Pyridinyl | -(1 to 4 linearly linked atom linker)-optionally subst. aryl | 3-hydroxy isoxazole | | —SCH₃ |
| CO | Pyridinyl | -(1 to 4 linearly linked atom linker)-optionally subst. heteroaryl | 3-hydroxy isoxazole | | —SCH₃ |
| SO₂ | phenyl | | 3-hydroxy isoxazole | | —SCH₂CH₃ |
| SO₂ | phenyl | CF₃ | 3-hydroxy isoxazole | | —SCH₂CH₃ |
| SO₂ | phenyl | CH₂CF₃ | 3-hydroxy isoxazole | | —SCH₂CH₃ |
| SO₂ | phenyl | Halo substituted alkyl | 3-hydroxy isoxazole | | —SCH₂CH₃ |
| SO₂ | phenyl | OCH₃ | 3-hydroxy isoxazole | | —SCH₂CH₃ |
| SO₂ | phenyl | OCH₂CH₃ | 3-hydroxy isoxazole | | —SCH₂CH₃ |
| SO₂ | phenyl | OCH₂CH₂CH₃ | 3-hydroxy isoxazole | | —SCH₂CH₃ |
| SO₂ | phenyl | OCH₂CH₂CH₂CH₃ | 3-hydroxy isoxazole | | —SCH₂CH₃ |
| SO₂ | phenyl | OCH₂CH₂CH₂CH₂CH₃ | 3-hydroxy isoxazole | | —SCH₂CH₃ |
| SO₂ | phenyl | C5-C8 alkoxy | 3-hydroxy isoxazole | | —SCH₂CH₃ |
| SO₂ | phenyl | Halo substituted alkoxy | 3-hydroxy isoxazole | | —SCH₂CH₃ |
| SO₂ | phenyl | CH₃ | 3-hydroxy isoxazole | | —SCH₂CH₃ |

TABLE 4-continued

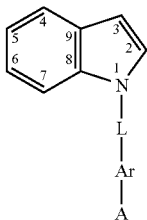

| L¹ | Ar | A | 3 | 5 | 6 |
|---|---|---|---|---|---|
| SO₂ | phenyl | CH₂CH₃ | 3-hydroxy isoxazole | | —SCH₂CH₃ |
| SO₂ | phenyl | CH₂CH₂CH₃ | 3-hydroxy isoxazole | | —SCH₂CH₃ |
| SO₂ | phenyl | CH₂CH₂CH₂CH₃ | 3-hydroxy isoxazole | | —SCH₂CH₃ |
| SO₂ | phenyl | C5-C8 alkyl | 3-hydroxy isoxazole | | —SCH₂CH₃ |
| SO₂ | phenyl | F | 3-hydroxy isoxazole | | —SCH₂CH₃ |
| SO₂ | phenyl | F, F | 3-hydroxy isoxazole | | —SCH₂CH₃ |
| SO₂ | phenyl | F, Cl | 3-hydroxy isoxazole | | —SCH₂CH₃ |
| SO₂ | phenyl | Cl | 3-hydroxy isoxazole | | —SCH₂CH₃ |
| SO₂ | phenyl | Cl, Cl | 3-hydroxy isoxazole | | —SCH₂CH₃ |
| SO₂ | phenyl | -(1 to 4 linearly linked atom linker)-optionally subst. aryl | 3-hydroxy isoxazole | | —SCH₂CH₃ |
| SO₂ | phenyl | -(1 to 4 linearly linked atom linker)-optionally subst. heteroaryl | 3-hydroxy isoxazole | | —SCH₂CH₃ |
| SO₂ | pyridinyl | | 3-hydroxy isoxazole | | —SCH₂CH₃ |
| SO₂ | Pyridinyl | CF₃ | 3-hydroxy isoxazole | | —SCH₂CH₃ |
| SO₂ | Pyridinyl | CH₂CF₃ | 3-hydroxy isoxazole | | —SCH₂CH₃ |
| SO₂ | Pyridinyl | Halo substituted alkyl | 3-hydroxy isoxazole | | —SCH₂CH₃ |
| SO₂ | Pyridinyl | OCH₃ | 3-hydroxy isoxazole | | —SCH₂CH₃ |
| SO₂ | Pyridinyl | OCH₂CH₃ | 3-hydroxy isoxazole | | —SCH₂CH₃ |
| SO₂ | Pyridinyl | OCH₂CH₂CH₃ | 3-hydroxy isoxazole | | —SCH₂CH₃ |
| SO₂ | Pyridinyl | OCH₂CH₂CH₂CH₃ | 3-hydroxy isoxazole | | —SCH₂CH₃ |
| SO₂ | Pyridinyl | OCH₂CH₂CH₂CH₂CH₃ | 3-hydroxy isoxazole | | —SCH₂CH₃ |
| SO₂ | Pyridinyl | C5-C8 alkoxy | 3-hydroxy isoxazole | | —SCH₂CH₃ |
| SO₂ | Pyridinyl | Halo substituted alkoxy | 3-hydroxy isoxazole | | —SCH₂CH₃ |
| SO₂ | Pyridinyl | CH₃ | 3-hydroxy isoxazole | | —SCH₂CH₃ |
| SO₂ | Pyridinyl | CH₂CH₃ | 3-hydroxy isoxazole | | —SCH₂CH₃ |
| SO₂ | Pyridinyl | CH₂CH₂CH₃ | 3-hydroxy isoxazole | | —SCH₂CH₃ |
| SO₂ | Pyridinyl | CH₂CH₂CH₂CH₃ | 3-hydroxy isoxazole | | —SCH₂CH₃ |
| SO₂ | Pyridinyl | C5-C8 alkyl | 3-hydroxy isoxazole | | —SCH₂CH₃ |
| SO₂ | Pyridinyl | F | 3-hydroxy isoxazole | | —SCH₂CH₃ |
| SO₂ | Pyridinyl | F, F | 3-hydroxy isoxazole | | —SCH₂CH₃ |
| SO₂ | Pyridinyl | F, Cl | 3-hydroxy isoxazole | | —SCH₂CH₃ |
| SO₂ | Pyridinyl | Cl | 3-hydroxy isoxazole | | —SCH₂CH₃ |
| SO₂ | Pyridinyl | Cl, Cl | 3-hydroxy isoxazole | | —SCH₂CH₃ |
| SO₂ | Pyridinyl | -(1 to 4 linearly linked atom linker)-optionally subst. aryl | 3-hydroxy isoxazole | | —SCH₂CH₃ |
| SO₂ | Pyridinyl | -(1 to 4 linearly linked atom linker)-optionally subst. heteroaryl | 3-hydroxy isoxazole | | —SCH₂CH₃ |
| CO | Phenyl | | 3-hydroxy isoxazole | | —SCH₂CH₃ |
| CO | Phenyl | CF₃ | 3-hydroxy isoxazole | | —SCH₂CH₃ |
| CO | Phenyl | CH₂CF₃ | 3-hydroxy isoxazole | | —SCH₂CH₃ |
| CO | Phenyl | Halo substituted alkyl | 3-hydroxy isoxazole | | —SCH₂CH₃ |
| CO | Phenyl | OCH₃ | 3-hydroxy isoxazole | | —SCH₂CH₃ |
| CO | Phenyl | OCH₂CH₃ | 3-hydroxy isoxazole | | —SCH₂CH₃ |
| CO | Phenyl | OCH₂CH₂CH₃ | 3-hydroxy isoxazole | | —SCH₂CH₃ |
| CO | Phenyl | OCH₂CH₂CH₂CH₃ | 3-hydroxy isoxazole | | —SCH₂CH₃ |
| CO | Phenyl | OCH₂CH₂CH₂CH₂CH₃ | 3-hydroxy isoxazole | | —SCH₂CH₃ |
| CO | Phenyl | C5-C8 alkoxy | 3-hydroxy isoxazole | | —SCH₂CH₃ |
| CO | Phenyl | Halo substituted alkoxy | 3-hydroxy isoxazole | | —SCH₂CH₃ |
| CO | Phenyl | CH₃ | 3-hydroxy isoxazole | | —SCH₂CH₃ |
| CO | Phenyl | CH₂CH₃ | 3-hydroxy isoxazole | | —SCH₂CH₃ |
| CO | Phenyl | CH₂CH₂CH₃ | 3-hydroxy isoxazole | | —SCH₂CH₃ |
| CO | Phenyl | CH₂CH₂CH₂CH₃ | 3-hydroxy isoxazole | | —SCH₂CH₃ |
| CO | Phenyl | C5-C8 alkyl | 3-hydroxy isoxazole | | —SCH₂CH₃ |
| CO | Phenyl | F | 3-hydroxy isoxazole | | —SCH₂CH₃ |
| CO | Phenyl | F, F | 3-hydroxy isoxazole | | —SCH₂CH₃ |
| CO | Phenyl | F, Cl | 3-hydroxy isoxazole | | —SCH₂CH₃ |
| CO | Phenyl | Cl | 3-hydroxy isoxazole | | —SCH₂CH₃ |
| CO | Phenyl | Cl, Cl | 3-hydroxy isoxazole | | —SCH₂CH₃ |

TABLE 4-continued

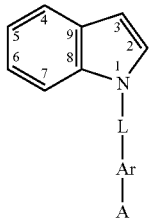

| L¹ | Ar | A | 3 | 5 | 6 |
|---|---|---|---|---|---|
| CO | Phenyl | -(1 to 4 linearly linked atom linker)-optionally subst. aryl | 3-hydroxy isoxazole | | —$SCH_2CH_3$ |
| CO | Phenyl | -(1 to 4 linearly linked atom linker)-optionally subst. heteroaryl | 3-hydroxy isoxazole | | —$SCH_2CH_3$ |
| CO | pyridinyl | | 3-hydroxy isoxazole | | —$SCH_2CH_3$ |
| CO | Pyridinyl | $CF_3$ | 3-hydroxy isoxazole | | —$SCH_2CH_3$ |
| CO | Pyridinyl | $CH_2CF_3$ | 3-hydroxy isoxazole | | —$SCH_2CH_3$ |
| CO | Pyridinyl | Halo substituted alkyl | 3-hydroxy isoxazole | | —$SCH_2CH_3$ |
| CO | Pyridinyl | $OCH_3$ | 3-hydroxy isoxazole | | —$SCH_2CH_3$ |
| CO | Pyridinyl | $OCH_2CH_3$ | 3-hydroxy isoxazole | | —$SCH_2CH_3$ |
| CO | Pyridinyl | $OCH_2CH_2CH_3$ | 3-hydroxy isoxazole | | —$SCH_2CH_3$ |
| CO | Pyridinyl | $OCH_2CH_2CH_2CH_3$ | 3-hydroxy isoxazole | | —$SCH_2CH_3$ |
| CO | Pyridinyl | $OCH_2CH_2CH_2CH_2CH_3$ | 3-hydroxy isoxazole | | —$SCH_2CH_3$ |
| CO | Pyridinyl | C5-G8 alkoxy | 3-hydroxy isoxazole | | —$SCH_2CH_3$ |
| CO | Pyridinyl | Halo substituted alkoxy | 3-hydroxy isoxazole | | —$SCH_2CH_3$ |
| CO | Pyridinyl | $CH_3$ | 3-hydroxy isoxazole | | —$SCH_2CH_3$ |
| CO | Pyridinyl | $CH_2CH_3$ | 3-hydroxy isoxazole | | —$SCH_2CH_3$ |
| CO | Pyridinyl | $CH_2CH_2CH_3$ | 3-hydroxy isoxazole | | —$SCH_2CH_3$ |
| CO | Pyridinyl | $CH_2CH_2CH_2CH_3$ | 3-hydroxy isoxazole | | —$SCH_2CH_3$ |
| CO | Pyridinyl | C5-G8 alkyl | 3-hydroxy isoxazole | | —$SCH_2CH_3$ |
| CO | Pyridinyl | F | 3-hydroxy isoxazole | | —$SCH_2CH_3$ |
| CO | Pyridinyl | F, F | 3-hydroxy isoxazole | | —$SCH_2CH_3$ |
| CO | Pyridinyl | F, Cl | 3-hydroxy isoxazole | | —$SCH_2CH_3$ |
| CO | Pyridinyl | Cl | 3-hydroxy isoxazole | | —$SCH_2CH_3$ |
| CO | Pyridinyl | Cl, Cl | 3-hydroxy isoxazole | | —$SCH_2CH_3$ |
| CO | Pyridinyl | -(1 to 4 linearly linked atom linker)-optionally subst. aryl | 3-hydroxy isoxazole | | —$SCH_2CH_3$ |
| CO | Pyridinyl | -(1 to 4 linearly linked atom linker)-optionally subst. heteroaryl | 3-hydroxy isoxazole | | —$SCH_2CH_3$ |

With reference to the compounds described in Table 4 (and for each of the bicyclic cores), additional compounds are described for each of the substitutent combinations therein where the substituent shown in Table 4 at the 5-position is instead an aryl group; a heteroaryl group; a monocyclic aryl group; a monocyclic heteroaryl group; a bicyclic aryl group; a bicyclic heteroaryl group; a substituted aryl group; a substituted heteroaryl group; a pyridinyl group; a pyrimidinyl group; a pyradazinyl group; a pyrrolyl group; a thiophenyl group.

With reference to the compounds described in Table 4 and the preceding paragraph, additional compounds are described in which L is $CH_2$.

With reference to the compounds described in Table 4 and the preceding two paragraphs, additional compounds are described in which the moiety A is an acyl sulphonamide (—C(=O)—N—$SO_2CH_3$).

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to exemplary compounds of Formula I to provide additional active compounds. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A method for treating a patient suffering from or at risk of a disease or condition for which PPAR modulation provides a therapeutic benefit, comprising
administering to said patient a PPAR modulator having the chemical structure of Formula I, namely

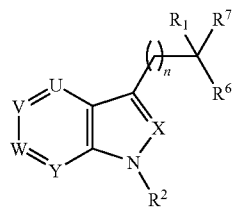

Formula I wherein
U, V, W, X, and Y are independently $CR^8$;
$R^1$ is a carboxyl group or ester thereof or a carboxylic acid isostere;
$R^2$ is —$CH_2$—(optionally substituted phenyl);
$R^6$ and $R^7$ are independently hydrogen, optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl, or $R^6$ and $R^7$ combine to form a mono-carbocyclic or mono-heterocyclic 5- or 6-membered ring system;
$R^8$ is hydrogen, halo, optionally substituted lower alkyl, —$CH_2$—$CR^{12}$=$CR^{13}R^{14}$, optionally substituted cycloalkyl, optionally substituted monofluoroalkyl, optionally substituted difluoroalkyl, optionally substituted trifluoroalkyl, trifluoromethyl, —$CH_2$—C≡$CR^{15}$, optionally substituted heterocycloalkyl, optionally substituted aryl, optionally substituted aralkyl, optionally substituted heteroaryl, optionally substituted heteroaralkyl, —$OR^9$, —$SR^9$, —$NR^{10}R^{11}$, —C(Z)$NR^{10}R^{11}$, —C(Z)$R^{20}$, —S(O)$_2NR^{10}R^{11}$, or —S(O)$_2R^{21}$;
$R^9$ is optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl;
$R^{10}$ and $R^{11}$ are independently hydrogen, optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl, or $R^{10}$ and $R^{11}$ combine to form a mono-carbocyclic or mono-heterocyclic 5- or 6-membered ring system;
$R^{12}$, $R^{13}$, $R^{14}$, and $R^{15}$ are independently optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl;
$R^{20}$ is optionally substituted monofluoroalkyl, trifluoromethyl, optionally substituted difluoroalkyl, —$CH_2$—$CR^{12}$=$CR^{13}R^{14}$, —$CH_2$—C≡$CR^{15}$, optionally substituted lower alkyl, optionally substituted cycloalkyl, optionally substituted heterocycloalkyl, optionally substituted aryl, optionally substituted aralkyl, optionally substituted heteroaryl, or optionally substituted heteroaralkyl;
$R^{21}$ is optionally substituted lower alkoxy, —$CH_2$—$CR^{12}$=$CR^{13}R^{14}$, —$CH_2$—C≡$CR^{15}$, optionally substituted cycloalkyl, optionally substituted heterocycloalkyl, optionally substituted aryl, optionally substituted aralkyl, optionally substituted heteroaryl, or optionally substituted heteroaralkyl;
Z is O or S; and
n=1, or 2;
or pharmaceutically acceptable salt thereof,
wherein said disease or condition is selected from the group consisting of obesity, hyperlipidemia, dyslipidemia, hypertriglyceridemia, hypoalphalipoproteinemia, Syndrome X, Type II diabetes mellitus, Type I diabetes, hyperinsulinemia, impaired glucose tolerance, insulin resistance, diabetic neuropathy, diabetic nephropathy, diabetic retinopathy, diabetic cataracts, hypertension, coronary artery disease, heart failure, atherosclerosis, eczema, psoriasis, colitis, and regulation of appetite and food intake.

2. The method of claim 1, wherein said compound is a compound selected from the group consisting of

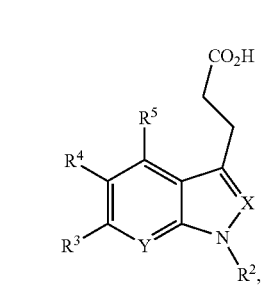

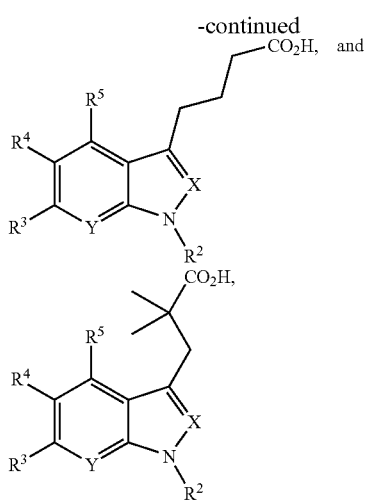

wherein

R³, R⁴, and R⁵ are independently hydrogen, halo, trifluoromethyl, optionally substituted lower alkyl, —CH₂—CR$^{12}$=CR$^{13}$R$^{14}$, —CH₂—C≡CR$^{15}$, optionally substituted cycloalkyl, optionally substituted heterocycloalkyl, optionally substituted aryl, optionally substituted aralkyl, optionally substituted heteroaryl, optionally substituted heteroaralkyl, —OR⁹, —SR⁹, —NR$^{10}$R$^{11}$, —C(Z)NR$^{10}$R$^{11}$, —C(Z)R$^{20}$, —S(O)₂NR$^{10}$R$^{11}$, or —S(O)₂R$^{21}$.

3. The method of claim 1, wherein said compound is a compound selected from the group consisting of
- 3-[5-Methoxy-1-(3-methoxy-benzyl)-1H-indol-3-yl]-propionic acid;
- 3-[1-(3-Chloro-benzyl)-5-methoxy-1H-indol-3-yl]-propionic acid;
- 3-[1-(4-Fluoro-benzyl)-5-methoxy-1H-indol-3-yl]-propionic acid;
- 3-[1-(4-Chloro-benzyl)-5-methoxy-1H-indol-3-yl]-propionic acid;
- 3-[5-Methoxy-1-(2-methoxy-benzyl)-1H-indol-3-yl]-propionic acid;
- 3-[5-Methoxy-1-(2-trifluoromethoxy-benzyl)-1H-indol-3-yl]-propionic acid;
- 3-[5-Methoxy-1-(3-trifluoromethoxy-benzyl)-1H-indol-3-yl]-propionic acid;
- 3-(1-Benzyl-5-methoxy-1H-indol-3-yl)-propionic acid;
- 3-(1-Benzyl-5-methoxy-1H-indol-3-yl)-propionic acid methyl ester; and
- all salts, tautomers, and isomers thereof.

4. The method of claim 1, wherein said compound is approved for administration to a human.

5. The method of claim 1, wherein said disease or condition is selected from the group consisting of congestive heart failure, atherosclerosis, obesity, hyperlipidemia, associated diabetic dyslipidemia, mixed dyslipidemia, hypoalphalipoproteinemia, Syndrome X, Type II diabetes mellitus, Type I diabetes, hyperinsulinemia, impaired glucose tolerance, and insulin resistance.

* * * * *

UNITED STATES PATENT AND TRADEMARK OFFICE
CERTIFICATE OF CORRECTION

PATENT NO. : 7,572,806 B2  
APPLICATION NO. : 12/001026  
DATED : August 11, 2009  
INVENTOR(S) : James Arnold et al.

It is certified that error appears in the above-identified patent and that said Letters Patent is hereby corrected as shown below:

ON THE TITLE PAGE:

Item "(73)   Assignee:   Plexxikon, Inc., Berkeley, CA (US)"

should read

Item --(73)  Assignee:   Plexxikon Inc., Berkeley, CA (US)--

Signed and Sealed this  
Twenty-ninth Day of May, 2012

David J. Kappos  
*Director of the United States Patent and Trademark Office*